(12) United States Patent
Ahn et al.

(10) Patent No.: US 12,332,241 B2
(45) Date of Patent: *Jun. 17, 2025

(54) APOPTOTIC CELL MIMIC

(71) Applicant: Slingshot Biosciences, Inc., Emeryville, CA (US)

(72) Inventors: Keunho Ahn, Pleasanton, CA (US); Zhenyu Deng, Berkeley, CA (US); Martina De Geus, Berkeley, CA (US); Anh Tuan Nguyen, San Francisco, CA (US)

(73) Assignee: Slingshot Biosciences, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/886,396

(22) Filed: Sep. 16, 2024

(65) Prior Publication Data
US 2025/0003960 A1    Jan. 2, 2025

Related U.S. Application Data

(63) Continuation of application No. 18/608,025, filed on Mar. 18, 2024, now Pat. No. 12,130,285, which is a continuation of application No. PCT/US2023/067893, filed on Jun. 2, 2023.

(60) Provisional application No. 63/348,414, filed on Jun. 2, 2022.

(51) Int. Cl.
| | | |
|---|---|---|
| *G01N 33/543* | (2006.01) | |
| *G01N 15/10* | (2024.01) | |
| *G01N 15/14* | (2024.01) | |

(52) U.S. Cl.
CPC ..... *G01N 33/5436* (2013.01); *G01N 15/1012* (2013.01); *G01N 15/14* (2013.01); *G01N 2015/1006* (2013.01)

(58) Field of Classification Search
CPC ............... G01N 33/5436; G01N 15/14; G01N 2015/1006; A61K 31/7088
See application file for complete search history.

(56) References Cited

U.S. PATENT DOCUMENTS

| | | |
|---|---|---|
| 3,822,095 A | 7/1974 | Hirschfeld |
| 3,872,312 A | 3/1975 | Hirschfeld |
| 3,916,205 A | 10/1975 | Kleinerman |

(Continued)

FOREIGN PATENT DOCUMENTS

| | | |
|---|---|---|
| CN | 101214217 A | 7/2008 |
| CN | 101245368 A | 8/2008 |

(Continued)

OTHER PUBLICATIONS

Miltenyi Biotec downloaded from https://www.miltenyibiotec.com/US-en/products/annexin-v-microbead-kit.html Apr. 24, 2025.*

(Continued)

*Primary Examiner* — Terra C Gibbs
(74) *Attorney, Agent, or Firm* — COOLEY LLP

(57) ABSTRACT

Provided herein are hydrogel beads that mimic live, dead, and apoptotic cells. The present disclosure also provides kits and compositions of hydrogel beads. The present disclosure further comprises methods of using the kits, compositions, and hydrogel beads to determine if a target cell sample includes one or more live, dead, or apoptotic cells.

25 Claims, 76 Drawing Sheets
Specification includes a Sequence Listing.

(56) References Cited

U.S. PATENT DOCUMENTS

| | | |
|---|---|---|
| 3,937,799 A | 2/1976 | Lewin et al. |
| 3,947,564 A | 3/1976 | Shannon et al. |
| 3,975,084 A | 8/1976 | Block |
| 4,271,123 A | 6/1981 | Curry et al. |
| 4,295,199 A | 10/1981 | Curry et al. |
| 4,389,491 A | 6/1983 | Hanamoto et al. |
| 4,409,335 A | 10/1983 | Hanamoto et al. |
| 4,448,888 A | 5/1984 | Bleile et al. |
| 4,511,662 A | 4/1985 | Baran et al. |
| 4,704,891 A | 11/1987 | Recktenwald et al. |
| 4,774,189 A | 9/1988 | Schwartz |
| 4,857,451 A | 8/1989 | Schwartz |
| 5,093,234 A | 3/1992 | Schwartz |
| 5,283,079 A | 2/1994 | Wang et al. |
| 5,395,688 A | 3/1995 | Wang et al. |
| 5,820,879 A | 10/1998 | Fernandez et al. |
| 5,841,139 A | 11/1998 | Sostek et al. |
| 5,871,722 A | 2/1999 | Nacht et al. |
| 5,888,823 A | 3/1999 | Matsumoto et al. |
| 6,043,506 A | 3/2000 | Heffelfinger et al. |
| 6,107,365 A | 8/2000 | Bertozzi et al. |
| 6,108,082 A | 8/2000 | Pettipiece et al. |
| 6,214,539 B1 | 4/2001 | Cosand |
| 6,280,618 B2 | 8/2001 | Watkins et al. |
| 6,372,813 B1 | 4/2002 | Johnson et al. |
| 6,586,176 B1 | 7/2003 | Trnovsky et al. |
| 6,657,030 B2 | 12/2003 | Vanderbilt |
| 6,762,055 B2 | 7/2004 | Carver et al. |
| 6,806,058 B2 | 10/2004 | Jesperson et al. |
| 6,872,578 B2 | 3/2005 | Watkins et al. |
| 6,897,072 B1 | 5/2005 | Rich et al. |
| 7,045,366 B2 | 5/2006 | Huang et al. |
| RE39,542 E | 4/2007 | Jain et al. |
| 7,205,156 B2 | 4/2007 | Rich et al. |
| 7,294,503 B2 | 11/2007 | Quake et al. |
| 7,314,584 B2 | 1/2008 | Tsutsui et al. |
| 7,465,538 B2 | 12/2008 | Watkins et al. |
| 7,479,631 B2 | 1/2009 | Rich et al. |
| 7,482,161 B2 | 1/2009 | Carver et al. |
| 7,482,167 B2 | 1/2009 | Sammak et al. |
| 7,531,357 B2 | 5/2009 | Carver et al. |
| 7,569,399 B2 | 8/2009 | Watkins et al. |
| 7,588,942 B2 | 9/2009 | Ho et al. |
| 7,601,539 B2 | 10/2009 | Kawate |
| 7,842,498 B2 | 11/2010 | Um et al. |
| 8,030,095 B2 | 10/2011 | Harriman |
| 8,105,845 B2 | 1/2012 | Notcovich et al. |
| 8,114,580 B2 | 2/2012 | Carver et al. |
| 8,187,885 B2 | 5/2012 | Purvis, Jr. |
| 8,415,161 B2 | 4/2013 | Yan et al. |
| 8,415,173 B2 | 4/2013 | Harriman |
| 8,451,450 B2 | 5/2013 | Heng |
| 8,580,530 B2 | 11/2013 | Buffiere et al. |
| 8,580,531 B2 | 11/2013 | Buffiere et al. |
| 8,603,828 B2 | 12/2013 | Walker et al. |
| 8,609,363 B2 | 12/2013 | Heng et al. |
| 8,704,158 B2 | 4/2014 | Haberstroh et al. |
| 8,748,183 B2 | 6/2014 | Durack et al. |
| 9,012,167 B2 | 4/2015 | Dallenne et al. |
| 9,110,050 B2 | 8/2015 | Likuski et al. |
| 9,175,421 B2 | 11/2015 | Notcovich et al. |
| 9,176,154 B2 | 11/2015 | Darmstadt et al. |
| 9,213,034 B2 | 12/2015 | Walker et al. |
| 9,217,175 B2 | 12/2015 | Regan et al. |
| 9,228,898 B2 | 1/2016 | Kiani et al. |
| 9,417,190 B2 | 8/2016 | Hindson et al. |
| 9,476,101 B2 | 10/2016 | Pregibon et al. |
| 9,658,220 B2 | 5/2017 | King et al. |
| 9,696,257 B2 | 7/2017 | Fox et al. |
| 9,714,897 B2 | 7/2017 | Kim et al. |
| 9,804,149 B2 | 10/2017 | Darmstadt et al. |
| 9,816,931 B2 | 11/2017 | Abate et al. |
| 9,915,598 B2 | 3/2018 | Kim et al. |
| 10,067,135 B2 | 9/2018 | Kaul et al. |
| 10,180,385 B2 | 1/2019 | Fox et al. |
| 10,191,039 B2 | 1/2019 | King et al. |
| 10,328,160 B2 | 6/2019 | Trogler et al. |
| 10,343,167 B2 | 7/2019 | Esmail et al. |
| 10,344,100 B1 | 7/2019 | Vashist et al. |
| 10,392,557 B2 | 8/2019 | Chan |
| 10,416,070 B1 | 9/2019 | Handique |
| 10,429,291 B2 | 10/2019 | Fox et al. |
| 10,481,068 B2 | 11/2019 | Kim et al. |
| 10,508,990 B2 | 12/2019 | Fox et al. |
| 10,732,189 B2 | 8/2020 | Buffiere et al. |
| 10,753,846 B2 | 8/2020 | Kim et al. |
| 10,942,109 B2 | 3/2021 | Kim et al. |
| 11,047,845 B1 | 6/2021 | Barry, Jr. et al. |
| 11,085,036 B2 | 8/2021 | Norberg et al. |
| 11,118,217 B2 | 9/2021 | Xue et al. |
| 11,155,809 B2 | 10/2021 | Lebofsky |
| 11,180,752 B2 | 11/2021 | Wu et al. |
| 11,186,862 B2 | 11/2021 | Lebofsky et al. |
| 11,213,490 B2 | 1/2022 | Shoichet et al. |
| 11,231,355 B2 | 1/2022 | Handique |
| 11,274,337 B2 | 3/2022 | Xue et al. |
| 11,300,496 B2 | 4/2022 | Handique |
| 11,313,782 B2 | 4/2022 | Kim et al. |
| 11,479,816 B2 | 10/2022 | Lebofsky et al. |
| 11,506,655 B2 | 11/2022 | Hunsley et al. |
| 11,598,768 B2 | 3/2023 | Kim |
| 11,603,556 B2 | 3/2023 | Lebofsky |
| 11,663,717 B2 | 5/2023 | Barnes et al. |
| 11,686,661 B2 | 6/2023 | Kim et al. |
| 11,726,023 B2 | 8/2023 | Kim et al. |
| 11,747,261 B2 | 9/2023 | Kim et al. |
| 11,761,877 B2 | 9/2023 | Kim et al. |
| 11,927,519 B2 | 3/2024 | Kim et al. |
| 12,130,285 B2 * | 10/2024 | Ahn ................ G01N 15/14 |
| 2001/0008217 A1 | 7/2001 | Watkins et al. |
| 2001/0054580 A1 | 12/2001 | Watkins et al. |
| 2002/0115116 A1 | 8/2002 | Song et al. |
| 2003/0013116 A1 | 1/2003 | Song et al. |
| 2003/0064403 A1 | 4/2003 | Song et al. |
| 2003/0124371 A1 | 7/2003 | Um et al. |
| 2003/0132538 A1 | 7/2003 | Chandler |
| 2003/0218130 A1 | 11/2003 | Boschetti et al. |
| 2004/0126904 A1 | 7/2004 | Watkins et al. |
| 2005/0059086 A1 | 3/2005 | Huang et al. |
| 2005/0090016 A1 | 4/2005 | Rich et al. |
| 2005/0112650 A1 | 5/2005 | Chang et al. |
| 2005/0118230 A1 | 6/2005 | Hill et al. |
| 2005/0172476 A1 | 8/2005 | Stone et al. |
| 2005/0176056 A1 | 8/2005 | Sammak et al. |
| 2005/0208573 A1 | 9/2005 | Bell et al. |
| 2006/0163385 A1 | 7/2006 | Link et al. |
| 2006/0223187 A1 | 10/2006 | Carver et al. |
| 2006/0240560 A1 | 10/2006 | Bakker et al. |
| 2006/0250616 A1 | 11/2006 | Pettipiece et al. |
| 2006/0269962 A1 | 11/2006 | Watkins et al. |
| 2006/0275820 A1 | 12/2006 | Watkins et al. |
| 2007/0003442 A1 | 1/2007 | Link et al. |
| 2007/0054119 A1 | 3/2007 | Garstecki et al. |
| 2007/0082019 A1 | 4/2007 | Huang et al. |
| 2007/0087348 A1 | 4/2007 | Notcovich et al. |
| 2007/0158547 A1 | 7/2007 | Rich et al. |
| 2007/0178168 A1 | 8/2007 | Ho et al. |
| 2007/0254378 A1 | 11/2007 | Zhang et al. |
| 2007/0259415 A1 | 11/2007 | Zigova et al. |
| 2008/0014589 A1 | 1/2008 | Link et al. |
| 2008/0019921 A1 | 1/2008 | Zhang |
| 2008/0023630 A1 | 1/2008 | Boschetti et al. |
| 2008/0026468 A1 | 1/2008 | Carver et al. |
| 2008/0032405 A1 | 2/2008 | Ho et al. |
| 2008/0044472 A1 | 2/2008 | Garcia et al. |
| 2008/0090737 A1 | 4/2008 | Boschetti |
| 2008/0241262 A1 | 10/2008 | Lee et al. |
| 2009/0148961 A1 | 6/2009 | Luchini et al. |
| 2010/0120059 A1 | 5/2010 | Yan et al. |
| 2010/0178647 A1 | 7/2010 | Carver et al. |
| 2010/0178656 A1 | 7/2010 | Buffiere et al. |
| 2010/0184101 A1 | 7/2010 | Buffiere et al. |
| 2010/0187441 A1 | 7/2010 | Waldbeser et al. |
| 2010/0234252 A1 | 9/2010 | Moradi-Araghi et al. |

(56) References Cited

U.S. PATENT DOCUMENTS

| | | |
|---|---|---|
| 2010/0285594 A1 | 11/2010 | Purvis, Jr. |
| 2011/0117670 A1 | 5/2011 | Walker et al. |
| 2011/0218123 A1 | 9/2011 | Weitz et al. |
| 2011/0222068 A1 | 9/2011 | Heng |
| 2011/0318820 A1 | 12/2011 | Hinz et al. |
| 2012/0129723 A1 | 5/2012 | Notcovich et al. |
| 2012/0295300 A1 | 11/2012 | Heng et al. |
| 2012/0309651 A1 | 12/2012 | Pregibon et al. |
| 2013/0089883 A1 | 4/2013 | Dallenne et al. |
| 2013/0177973 A1 | 7/2013 | Kondo |
| 2013/0274125 A1 | 10/2013 | Binder et al. |
| 2014/0073532 A1 | 3/2014 | Walker et al. |
| 2014/0100791 A1 | 4/2014 | Darmstadt et al. |
| 2014/0157859 A1 | 6/2014 | Darmstadt et al. |
| 2014/0179808 A1 | 6/2014 | Flanagan |
| 2014/0198313 A1 | 7/2014 | Tracy et al. |
| 2014/0221238 A1 | 8/2014 | Regan et al. |
| 2014/0377334 A1 | 12/2014 | Irvine et al. |
| 2015/0027207 A1 | 1/2015 | Likuski et al. |
| 2015/0094232 A1 | 4/2015 | Abate et al. |
| 2015/0177115 A1 | 6/2015 | Kim et al. |
| 2015/0211044 A1 | 7/2015 | Dallenne et al. |
| 2015/0267196 A1 | 9/2015 | Alsberg et al. |
| 2016/0258856 A1 | 9/2016 | Kim et al. |
| 2017/0045436 A1 | 2/2017 | Fox et al. |
| 2017/0159132 A1 | 6/2017 | Okino et al. |
| 2017/0268998 A1 | 9/2017 | Fox et al. |
| 2017/0361322 A1 | 12/2017 | Esmail et al. |
| 2017/0370951 A1 | 12/2017 | Buffiere et al. |
| 2018/0088112 A1 | 3/2018 | Fan et al. |
| 2018/0172687 A1 | 6/2018 | Kaul et al. |
| 2018/0216171 A1 | 8/2018 | Xue et al. |
| 2018/0275040 A1 | 9/2018 | Kim et al. |
| 2018/0371525 A1 | 12/2018 | Lebofsky et al. |
| 2019/0145881 A1 | 5/2019 | Fox et al. |
| 2019/0154707 A1 | 5/2019 | Flamini et al. |
| 2019/0249171 A1 | 8/2019 | Wu et al. |
| 2019/0293546 A1 | 9/2019 | Handique |
| 2020/0056231 A1 | 2/2020 | Lebofsky et al. |
| 2020/0115675 A1 | 4/2020 | Pathak et al. |
| 2020/0150020 A1 | 5/2020 | Kim et al. |
| 2020/0206145 A1 | 7/2020 | Shi et al. |
| 2020/0209064 A1 | 7/2020 | Owsley et al. |
| 2020/0232979 A1 | 7/2020 | Revzin et al. |
| 2020/0249242 A1 | 8/2020 | Batxelli-Molina et al. |
| 2020/0332354 A1 | 10/2020 | Xue et al. |
| 2020/0363434 A1 | 11/2020 | Buffiere et al. |
| 2020/0399428 A1 | 12/2020 | Kleine-Brüggeney et al. |
| 2020/0400546 A1 | 12/2020 | Kim et al. |
| 2020/0408747 A1 | 12/2020 | Zur Megede et al. |
| 2021/0040567 A1 | 2/2021 | Handique et al. |
| 2021/0130880 A1 | 5/2021 | Lebofsky |
| 2021/0190740 A1 | 6/2021 | Scolari et al. |
| 2021/0231552 A1 | 7/2021 | Kim et al. |
| 2021/0247294 A1 | 8/2021 | Handique |
| 2021/0341469 A1 | 11/2021 | Kim et al. |
| 2022/0042077 A1 | 2/2022 | Lebofsky et al. |
| 2022/0065878 A1 | 3/2022 | Lee |
| 2022/0143160 A1 | 5/2022 | Miller et al. |
| 2022/0154266 A1 | 5/2022 | Xue et al. |
| 2022/0178810 A1 | 6/2022 | Kim et al. |
| 2022/0213530 A1 | 7/2022 | Larson et al. |
| 2022/0260476 A1 | 8/2022 | Kim et al. |
| 2022/0364976 A1 | 11/2022 | Kim et al. |
| 2023/0012786 A1 | 1/2023 | Lebofsky et al. |
| 2023/0062518 A1 | 3/2023 | Ebrahim et al. |
| 2023/0067460 A1 | 3/2023 | Nguyen et al. |
| 2023/0152202 A1 | 5/2023 | Kim et al. |
| 2023/0176042 A1 | 6/2023 | Kim et al. |
| 2024/0053248 A1 | 2/2024 | Kim et al. |
| 2024/0060038 A1 | 2/2024 | Nguyen et al. |
| 2024/0219382 A1 | 7/2024 | Ahn et al. |
| 2024/0269185 A1 | 8/2024 | Nguyen et al. |
| 2024/0319067 A1 | 9/2024 | Kim et al. |

FOREIGN PATENT DOCUMENTS

| | | |
|---|---|---|
| CN | 103744185 A | 4/2014 |
| CN | 104641217 A | 5/2015 |
| EP | 3585364 A1 | 1/2020 |
| JP | H07196916 A | 8/1995 |
| JP | 2002510541 A | 4/2002 |
| JP | 2007114026 A | 5/2007 |
| JP | 2012011269 A | 1/2012 |
| JP | 2013520530 A | 6/2013 |
| JP | 2013155358 A | 8/2013 |
| JP | 2014508516 A | 4/2014 |
| JP | 2015530361 A | 10/2015 |
| WO | WO-8910566 A1 | 11/1989 |
| WO | WO-0008212 A1 | 2/2000 |
| WO | WO-0132829 A2 | 5/2001 |
| WO | WO-03000014 A2 | 1/2003 |
| WO | WO-2005013896 A2 | 2/2005 |
| WO | WO-2006003423 A2 | 1/2006 |
| WO | WO-2006078841 A1 | 7/2006 |
| WO | WO-2006096571 A2 | 9/2006 |
| WO | WO-2008115653 A2 | 9/2008 |
| WO | WO-2008121342 A2 | 10/2008 |
| WO | WO-2010025190 A1 | 3/2010 |
| WO | WO-2010025988 A1 | 3/2010 |
| WO | WO-2011098407 A1 | 8/2011 |
| WO | WO-2012033811 A1 | 3/2012 |
| WO | WO-2013113670 A1 | 8/2013 |
| WO | WO-2018108341 A1 | 6/2018 |
| WO | WO-2019048714 A2 | 3/2019 |
| WO | WO-2020037214 A1 | 2/2020 |
| WO | WO-2021154900 A1 | 8/2021 |
| WO | WO-2023215886 A1 | 11/2023 |
| WO | WO-2023235885 A1 | 12/2023 |
| WO | WO-2024044593 A2 | 2/2024 |
| WO | WO-2024064962 A2 | 3/2024 |

OTHER PUBLICATIONS

ThermoFisher/Invitrogen downloaded from https://www.thermofisher.com/order/catalog/product/V13242 on Apr. 24, 2025.*

Atkin-Smith et al., "Isolation of cell type-specific apoptotic bodies by fluorescence-activated cell sorting," Scientific Reports, vol. 7, No. 1, Feb. 1, 2017, pp. 1-7.

Bele, Marjan, Olavi Siiman and Egon Matjevic, "Preparation and flow cytometry of uniform silica-fluorescent dye microspheres." Journal of colloid and interface science 254(2):274-282 (2002).

Chen, M., et al., "Initiator caspases in apoptosis signaling pathways", Apoptosis (London), Aug. 1, 2002, pp. 313-319, DOI: 10.1023/A:1016167228059.

Extended European Search Report for European Application No. EP21744765.5 dated Jan. 29, 2024, 8 pages.

Extended European Search Report issued by the European Patent Office for Application No. 16749674.4, dated Sep. 6, 2018, 12 pages.

Falconnet, et al., "Rapid, Sensitive and Real-Time Multiplexing Platform for the Analysis of Protein and Nucleic-Acid Biomarkers," Analytical Chemistry, pp. 1582-1589 (Jan. 15, 2015).

Gaulding, et al., "Reversible Inter- and Intra-microgel Cross-linking Using Disulfides," Macromolecules, 2012, vol. 45(1), pp. 39-45.

Hasegawa, Urara et al. "Nanogel-quantum dot hybrid nanoparticles for live cell imaging." Biochemical and biophysical research communications 331(4):917-921 (2005).

Higuchi, A., et al., "Design of polymeric materials for culturing human pluripotent stem cells: Progress toward feeder-free and xeno-free culturing," Progress in Polymer Science, Jul. 2014, vol. 39 (7), pp. 1348-1374.

Ibadat, et al., "Synthesis and Characterization of Polymeric Microspheres Template for a Homogeneous and Porous Monolith" Polymers 13, 3639, pp. 1-12 (Oct. 22, 2021).

International Search Report and Written Opinion for International Application No. PCT/US2022/048283 dated Feb. 14, 2023, 14 pages.

International Search Report and Written Opinion for International Application No. PCT/US2023/075041 dated Mar. 8, 2024, 11 pages.

(56) References Cited

OTHER PUBLICATIONS

International Search Report and Written Opinion for International Patent Application No. PCT/US2016/017029, mailed May 19, 2016, 8 pages.
International Search Report and Written Opinion for International Patent Application No. PCT/US21/014538, dated Apr. 8, 2021, 19 pages.
International Search Report and Written Opinion for International Patent Application No. PCT/US21/030590, dated Jul. 26, 2021, 13 pages.
International Search Report and Written Opinion for PCT Application No. PCT/US2023/066684 dated Aug. 7, 2023, 15 pages.
International Search Report and Written Opinion for PCT Application No. PCT/US2023/067893 dated Oct. 10, 2023, 22 pages.
International Search Report and Written Opinion for PCT Application No. PCT/US2023/072659 dated Mar. 14, 2024, 12 pages.
Jain et al. Zwitterionic Hydrogels Based on a Degradable Disulfide Carboxybetaine Cross-Linker, Langmuir 2019, 35, 1864-1871 (Year: 2019).
Jin et al., "Overview of cell death 1-124 signaling pathways", Cancer Biology &G Therapy, vol. 4, No. 2, Feb. 2, 2005, pp. 147-171, DOI: 10.4161/cbt.4.2.1508.
Kim, Jin-Woong et al., "Fabrication of Monodisperse Gel Shells and Functional Microgels in Microfluidic Devices," Angew. Chem. Int. Ed. 46:819-1822 (2007).
Lee, Ki-Chang and Lee, Sang-Yun, "Preparation of Highly Cross-Linked, Monodisperse Poly (methyl methacrylate) Microspheres by Dispersion Polymerization; Part II. Semi-continuation Processes," Macromolecular Research 6(4):293-302 (2008).
Liu, A.L., et al., "Methods for Generating Hydrogel Particles for Protein Delivery," Annals of Biomedical Engineering, Jun. 2016, vol. 44 (6), pp. 1946-1958.
Liu, Z. et al., Recent Advances on Magnetic Sensitive Hydrogels in Tissue Engineering, Frontiers in Chemistry, vol. 8 , Article 124, pp. 1-17, (Mar. 2020).
Luchini, Alessandra et al. "Smart hydrogel particles: biomarker harvesting: one-step affinity purification, size exclusion, and protection against degradation." Nano letters 8(1): 350-361 (2008).
Mani, et al., "Magnetic particles in ultrasensitive biomarker protein measurements for cancer detection and monitoring," Expert Opin Med Diagn. 5(5):381-391 (Sep. 1, 2011).
Patanarut, Alexis et al., "Synthesis and characterization of hydrogel particles containing Cibacron Blue F3G-A." Colloids and Surfaces A: Physicochemical and Engineering Aspects 362(1):8-19 (2010).
Perez-Luna, V.H., et al., "Encapsulation of Biological Agents in Hydrogels for Therapeutic Applications," Gels, vol. 4(61), pp. 1-30, (Jul. 11, 2018).
Petriz et al. Next-generation cell mimics double as apoptosis controls and efficient flow cytometry. Downloaded from https://slingshotbio.com/wp-contenUuploads/2024/05/ Next-generation-cell-mimics-double-as-apoptosis-controls-and-efficient-flow-cytometry-training-tools.pdf on Jul. 1, 2024. Publication date May 2024, 1 page.
Proll, Guenther et al. "Potential of label-free detection in high-content-screening applications." Journal of Chromatography A 1116(1):2-8 (2007).
Salehi-Reyhani, et al., "Artificial cell mimics as simplified models for the study of cell biology," Experimental Biology and Medicine 2017; 242: 1309-1317.
Shastri, V.P., et al., "Non-Degradable Biocompatible Polymers in Medicine: Past, Present and Future", Current Pharmaceutical Biotechnology, Bentham Science Publishers, NL, vol. 4, No. 5, Jan. 1, 2003, pp. 331-337.
Sulaiman et al., "High-Resolution Patterning of Hydrogel Sensing Motifs within Fibrous Substrates for Sensitive and Multiplexed Detection of Biomarkers", ACS Sensors, 2020, vol. 6 No. 1, pp. 203-211.
Tomczak, Nikodem et al., "Designer polymer-quantum dot architectures." Progress in Polymer Science 34:393-430 (2009).
Ugelstad, J. and Mork, P.C., "Swelling of Oligomer-Polymer Particles. New Methods of Preparation of Emulsions and Polymer Dispersions," Advances in Colloid and Interface Sciences, 13:101-140 (1980).
Wallberg et al., "Analysis of Apoptosis and Necroptosis by Fluorescence-Activated Cell Sorting," Cold Spring Harbor Protocol, vol. 2016, No. 4, Apr. 1, 2016, 7 pages.
Ihmels and Otto, "Intercalation of Organic Dye Molecules into Double-Stranded DNA—General Principles and Recent Developments" Top Current Chem 258:161-204 (2005).
Telford, William G. et al., "Multiparametric Analysis of Apoptosis by Flow Cytometry," Methods Mol Biol. 1678:167-202 (2018).

\* cited by examiner

APOPTOTIC CELL MIMIC

CROSS-REFERENCE TO RELATED APPLICATIONS

This application is a continuation of U.S. patent application Ser. No. 18/608,025, filed Mar. 18, 2024, now U.S. Pat. No. 12,130,285, which is a continuation of International Application No. PCT/US2023/067893, filed on Jun. 2, 2023, which claims priority to U.S. Provisional Application No. 63/348,414, filed Jun. 2, 2022. The aforementioned applications are incorporated by reference herein in their entirety for all purposes.

REFERENCE TO AN ELECTRONIC SEQUENCE LISTING

The contents of the electronic sequence listing (SLIN_012_02US_SeqList_ST26.xml; Size: 124,373 bytes; and Date of Creation: Aug. 30, 2024) is herein incorporated by reference in its entirety.

FIELD

The present disclosure generally relates to hydrogel beads that mimic live, dead, and apoptotic cells. The present disclosure also provides kits and compositions of hydrogel beads. The present disclosure further comprises methods of using the kits, compositions, and hydrogel beads to determine if a target cell sample includes one or more live, dead, or apoptotic cells.

BACKGROUND

Flow cytometry is used to analyze and detect the chemical and physical characteristics of cells. Data from this technique allows doctors to diagnose and stage multiple diseases, including cancer. Removing dead and dying cells from flow cytometry data is critical to ensuring the accuracy of the analysis. Dead cells are autofluorescent and are difficult to eliminate from the analysis based solely on forward and side scatter. In flow cytometry viability assays, cells are stained with viability dyes to identify dead and dying cells and evaluated on a flow cytometer. However, the accuracy of these viability assays requires proper controls. Typically, these controls require the use of purified cells of the cell type of interest. Obtaining these purified cells using heat or chemical methods, a process which is wasteful, time-consuming, is not well standardized and is prone to variations from batch to batch. Further, the cells to be used for calibration may be rare or in short supply. Therefore, there is a need in the art for synthetic compositions that can be used as controls for dead, live, and dying cells.

SUMMARY OF THE INVENTION

Provided herein is a hydrogel bead comprising: a) a polymerized monomer and a bifunctional monomer; and b) a pre-apoptotic signal binder.

Provided herein is a hydrogel bead comprising: a) a polymerized monomer and a bifunctional monomer; and b) a pre-apoptotic signal.

Provided herein is a hydrogel bead comprising: a) a polymerized monomer and a bifunctional monomer; b) a pre-apoptotic signal binder; and c) an encapsulated nucleic acid.

Provided herein is a hydrogel bead comprising: a) a polymerized monomer and a bifunctional monomer; b) a pre-apoptotic signal; and c) an encapsulated nucleic acid.

Provided herein is a kit comprising: a) a first population of hydrogel beads, each bead comprising: i) a polymerized monomer; ii) a pre-apoptotic signal binder; and iii) an encapsulated nucleic acid; b) a second population of hydrogel beads, each bead comprising: i) a polymerized monomer; ii) a pre-apoptotic signal binder; but iii) lacking the encapsulated nucleic acid of the first population of hydrogel beads; and c) a third population of hydrogel beads comprising: i) a polymerized monomer; but ii) lacking the pre-apoptotic signal binder of the first population of hydrogel beads; and iii) lacking the encapsulated nucleic acid of the first population of hydrogel beads.

Provided herein is a composition comprising: a) a first population of hydrogel beads, each bead comprising: i) a polymerized monomer; ii) a pre-apoptotic signal binder; and iii) an encapsulated nucleic acid; b) a second population of hydrogel beads, each bead comprising: i) a polymerized monomer; ii) a pre-apoptotic signal binder; but iii) lacking the encapsulated nucleic acid of the first population of hydrogel beads; and c) a third population of hydrogel beads comprising: i) a polymerized monomer; but ii) lacking the pre-apoptotic signal binder of the first population of hydrogel beads; but iii) lacking the encapsulated nucleic acid of the first population of hydrogel beads.

Provided herein is a kit comprising: a) a first population of hydrogel beads, each bead comprising: i) a polymerized monomer; ii) a pre-apoptotic signal; and iii) an encapsulated nucleic acid; b) a second population of hydrogel beads, each bead comprising: i) a polymerized monomer; ii) a pre-apoptotic signal; but iii) lacking the encapsulated nucleic acid of the first population of hydrogel beads; and c) a third population of hydrogel beads comprising: i) a polymerized monomer; but ii) lacking the pre-apoptotic signal of the first population of hydrogel beads; and iii) lacking the encapsulated nucleic acid of the first population of hydrogel beads.

Provided herein is a composition comprising: a) a first population of hydrogel beads, each bead comprising: i) a polymerized monomer; ii) a pre-apoptotic signal; and iii) an encapsulated nucleic acid; b) a second population of hydrogel beads, each bead comprising: i) a polymerized monomer; ii) a pre-apoptotic signal; but iii) lacking the encapsulated nucleic acid of the first population of hydrogel beads; and c) a third population of hydrogel beads comprising: i) a polymerized monomer; but ii) lacking the pre-apoptotic signal of the first population of hydrogel beads; but iii) lacking the encapsulated nucleic acid of the first population of hydrogel beads.

Provided herein is a method of determining if a target cell sample includes one or more dead or pre-apoptotic cells, said method comprising: a) providing a population of hydrogel beads described herein, or from the kits or compositions described herein; b) contacting said population of hydrogel beads with a pre-apoptotic signal and/or a DNA dye; c) measuring concentration of pre-apoptotic signal and/or DNA dye in the population of hydrogel beads; d) measuring concentration of pre-apoptotic signal and/or DNA dye in the target cell sample; and e) comparing the measured concentrations of pre-apoptotic signal and/or DNA dye in the population of hydrogel beads and target cell sample; thereby determining if the target cell sample includes one or more dead or pre-apoptotic cells.

Provided herein is a method of determining if a target cell sample includes one or more dead or pre-apoptotic cells, said method comprising: a) providing a population of hydrogel beads disclosed herein, or from the kits or compositions disclosed herein; b) contacting said population of hydrogel beads with a pre-apoptotic signal and/or a DNA dye; c) measuring concentration of pre-apoptotic signal and/or DNA dye in the population of hydrogel beads in a cytometric device; d) calibrating the cytometric device based on the measured concentration of pre-apoptotic signal and/or DNA dye of the hydrogel beads; e) measuring concentration of pre-apoptotic signal and/or DNA dye in the target cell sample to determine if the target cell sample includes one or more dead or pre-apoptotic cells.

Provided herein is a method of determining if a target cell sample includes one or more dead or pre-apoptotic cells, said method comprising: a) providing a population of hydrogel beads disclosed herein, or from the kits or compositions disclosed herein; wherein at least a subpopulation of hydrogel beads within the population of hydrogel beads, comprises a pre-apoptotic signal and/or a DNA dye; b) measuring concentration of pre-apoptotic signal and/or DNA dye in the population of hydrogel beads; c) measuring concentration of pre-apoptotic signal and/or DNA dye in the target cell sample; and d) comparing the measured concentrations of pre-apoptotic signal and/or DNA dye in the population of hydrogel beads and target cell sample; thereby determining if the target cell sample includes one or more dead or pre-apoptotic cells.

Provided herein is a method of determining if a target cell sample includes one or more dead or pre-apoptotic cells, said method comprising: a) providing a population of hydrogel beads disclosed herein, or from the kits or compositions disclosed herein; wherein at least a subpopulation of hydrogel beads within the population of hydrogel beads, comprises a pre-apoptotic signal and/or a DNA dye; b) measuring concentration of pre-apoptotic signal and/or DNA dye in the population of hydrogel beads in a cytometric device; c) calibrating the cytometric device based on the measured concentration of pre-apoptotic signal and/or DNA dye of the hydrogel beads; d) measuring concentration of pre-apoptotic signal and/or DNA dye in the target cell sample to determine if the target cell sample includes one or more dead or pre-apoptotic cells.

DETAILED DESCRIPTION OF THE INVENTION

Figure 1:
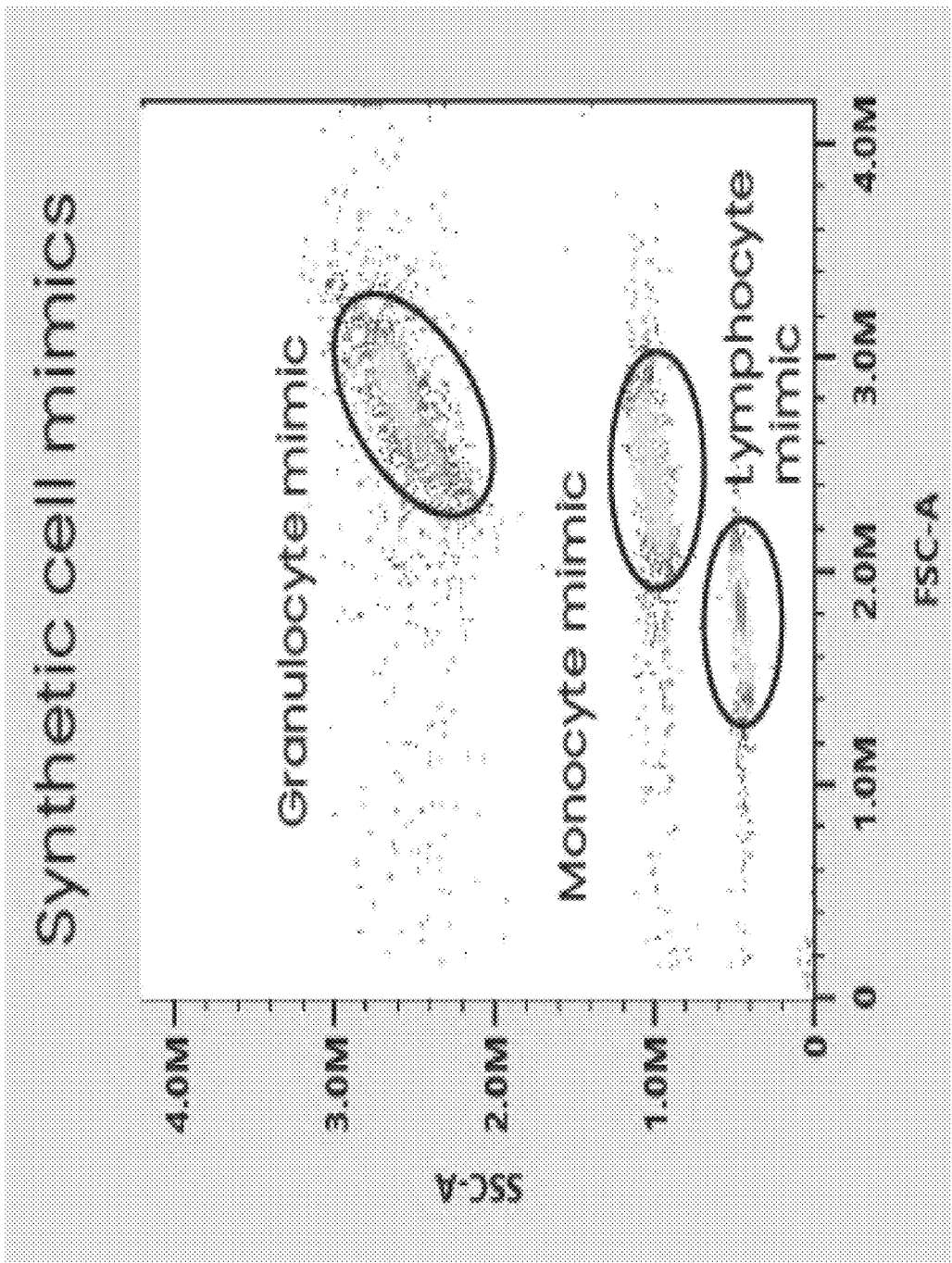
FIG. 1 shows that the hydrogel beads described herein can be modulated to match the forward scatter and side scatter of target cells, such as granulocytes, monocytes, and lymphocytes.
Figure 2:
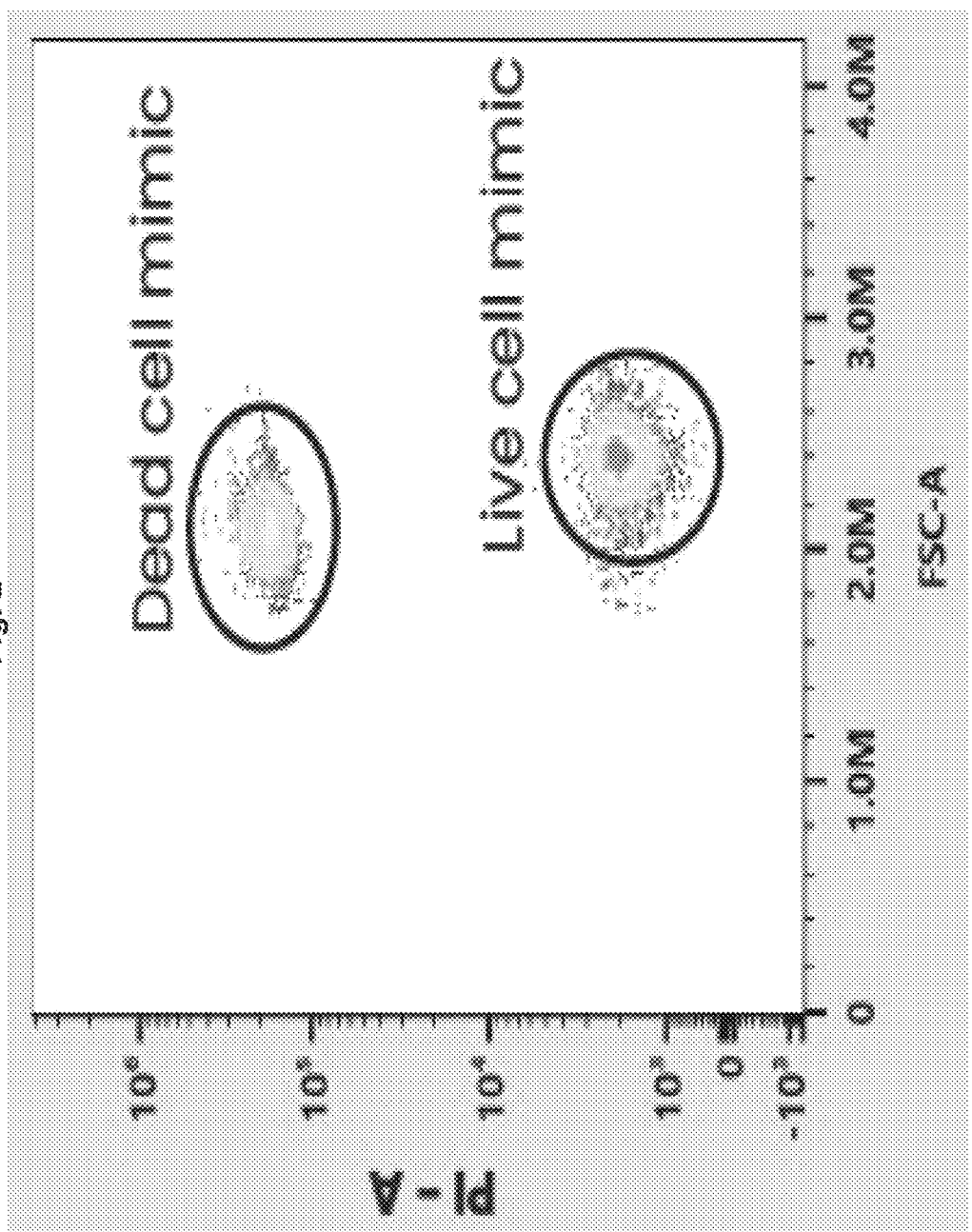
FIG. 2 shows that a hydrogel bead containing a (i) a polymerized monomer and a bifunctional monomer, (ii) an amine dye binder, and (iii) an encapsulated nucleic acid, binds to the DNA-intercalating dye, propidium iodide ("PI").
Figure 3:
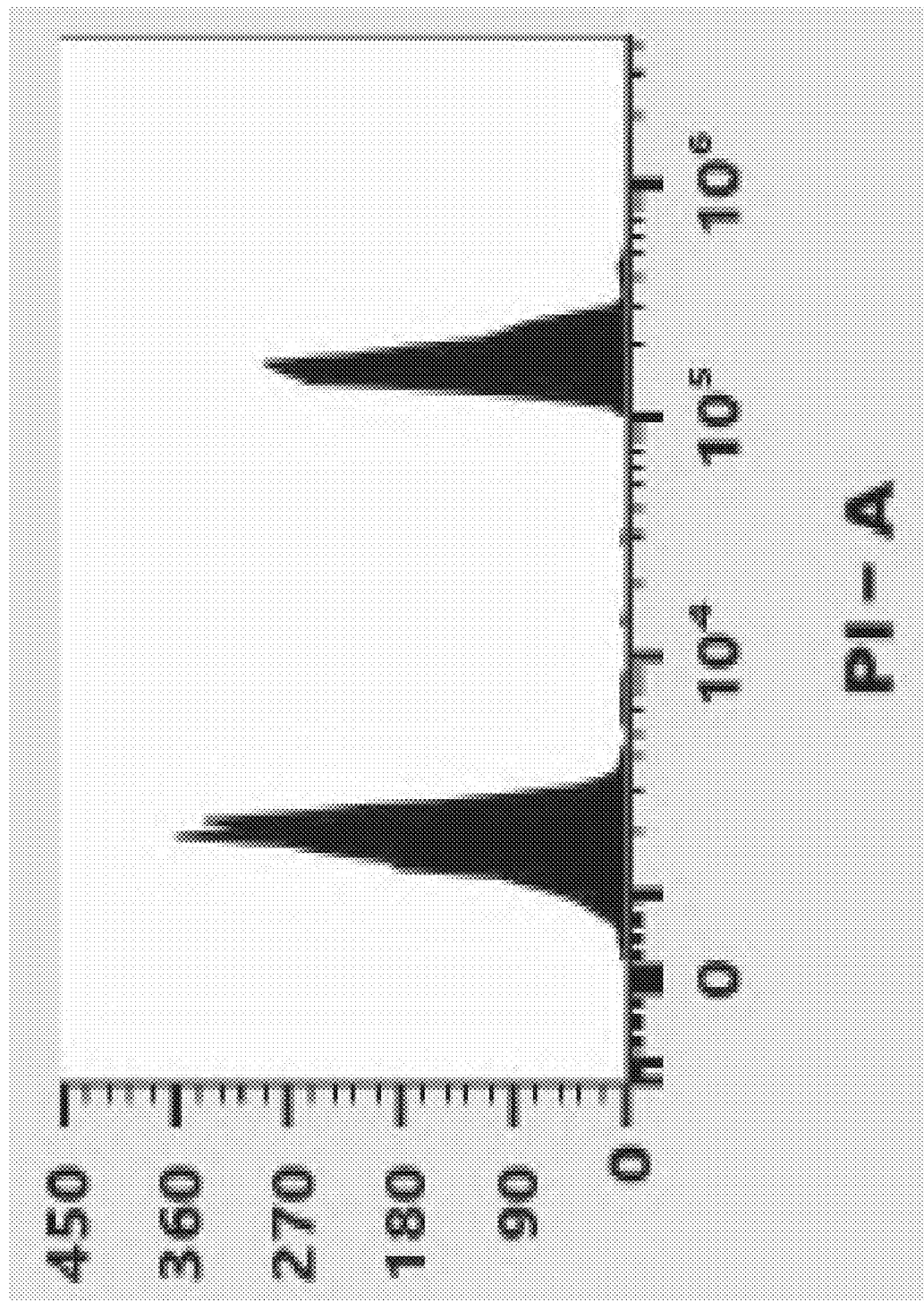
FIG. 3 shows the mean fluorescence intensity of PI binding to the hydrogel bead of FIG. 2.
Figure 4:
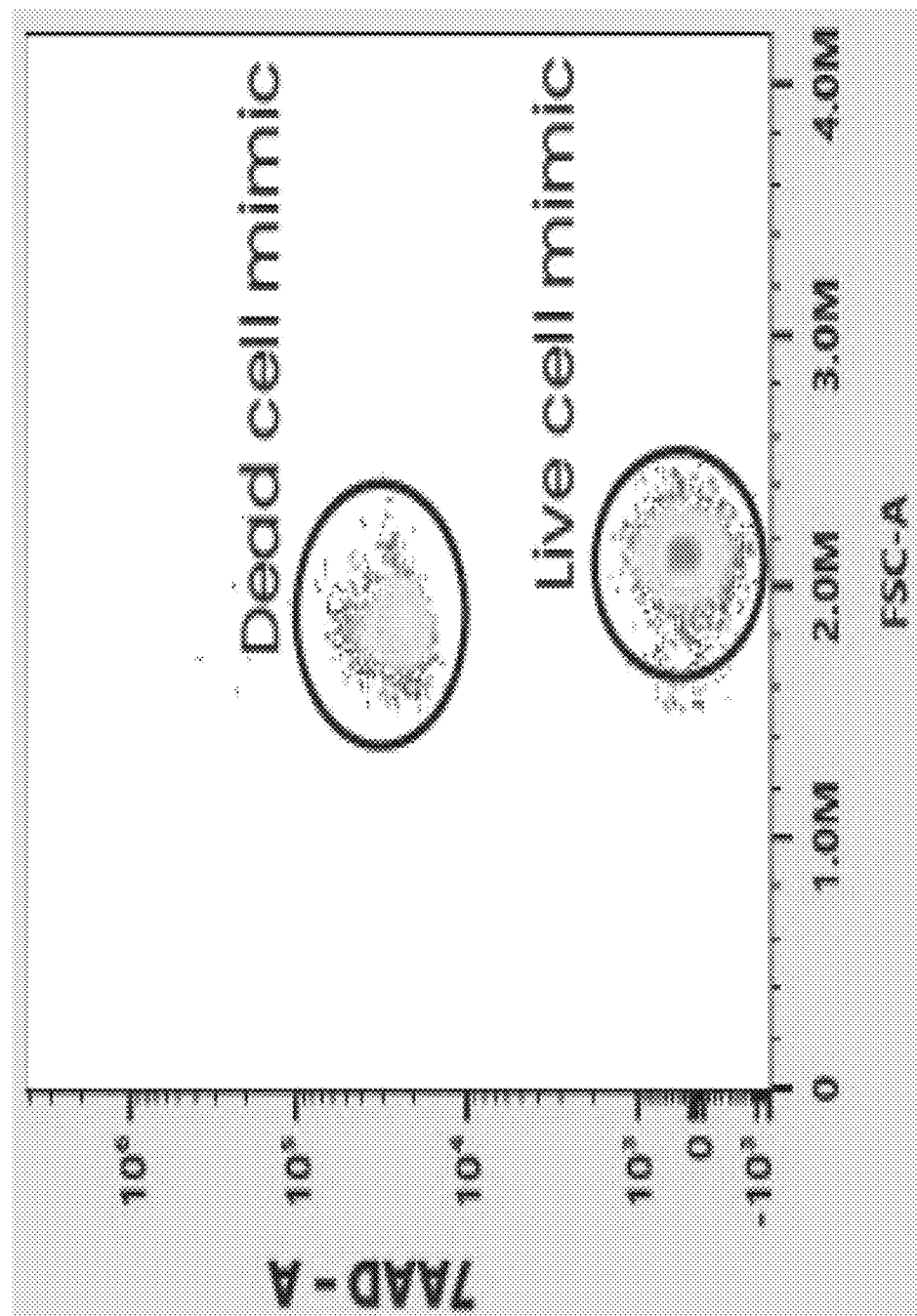
FIG. 4 shows that a hydrogel bead containing a (i) a polymerized monomer and a bifunctional monomer, (ii) an amine dye binder, and (iii) an encapsulated nucleic acid, binds to the DNA-intercalating dye, 7-aminoactinomycin D ("7AAD").
Figure 5:
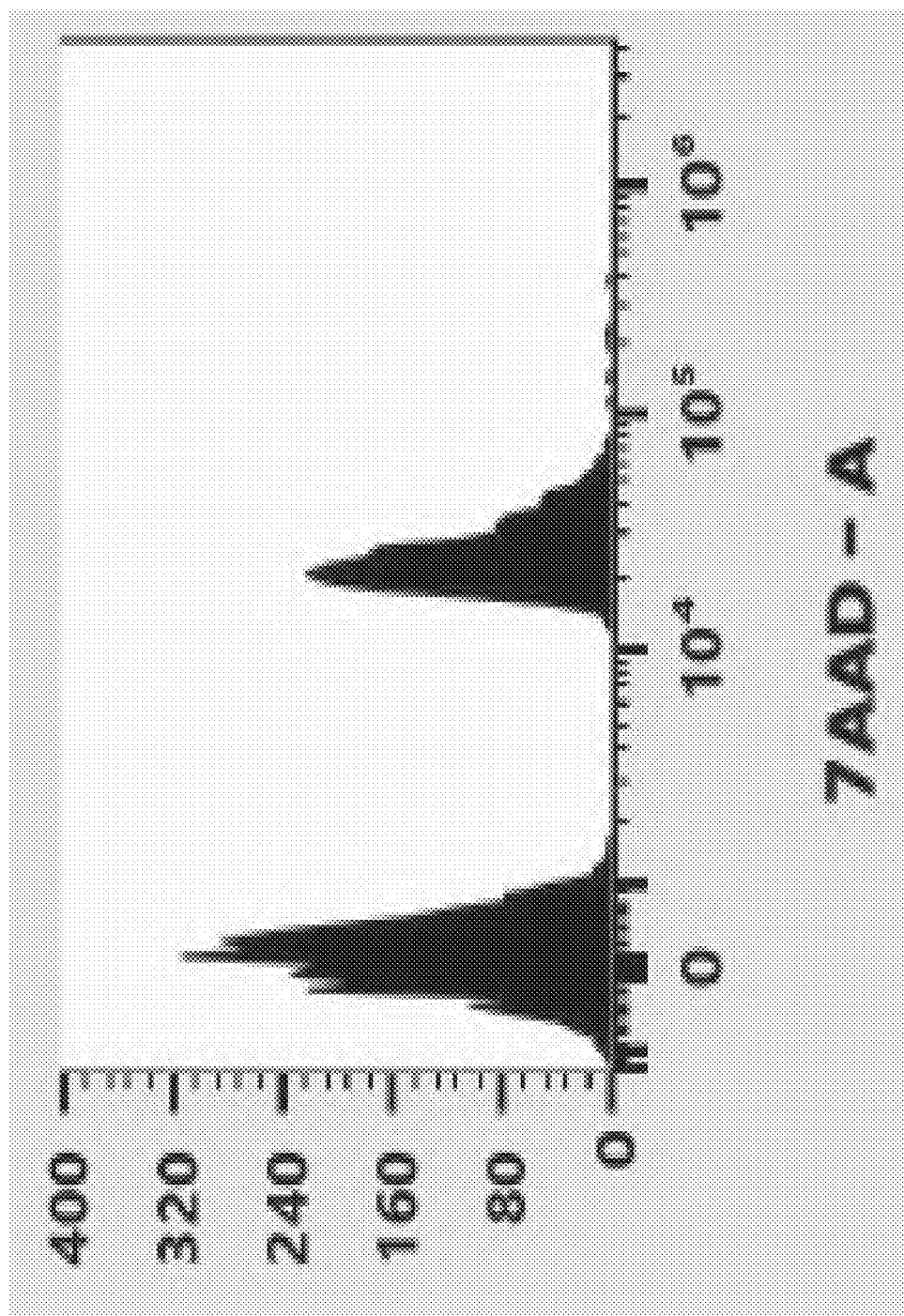
FIG. 5 shows the mean fluorescence intensity of 7AAD binding to the hydrogel bead of FIG. 4.
Figure 6:
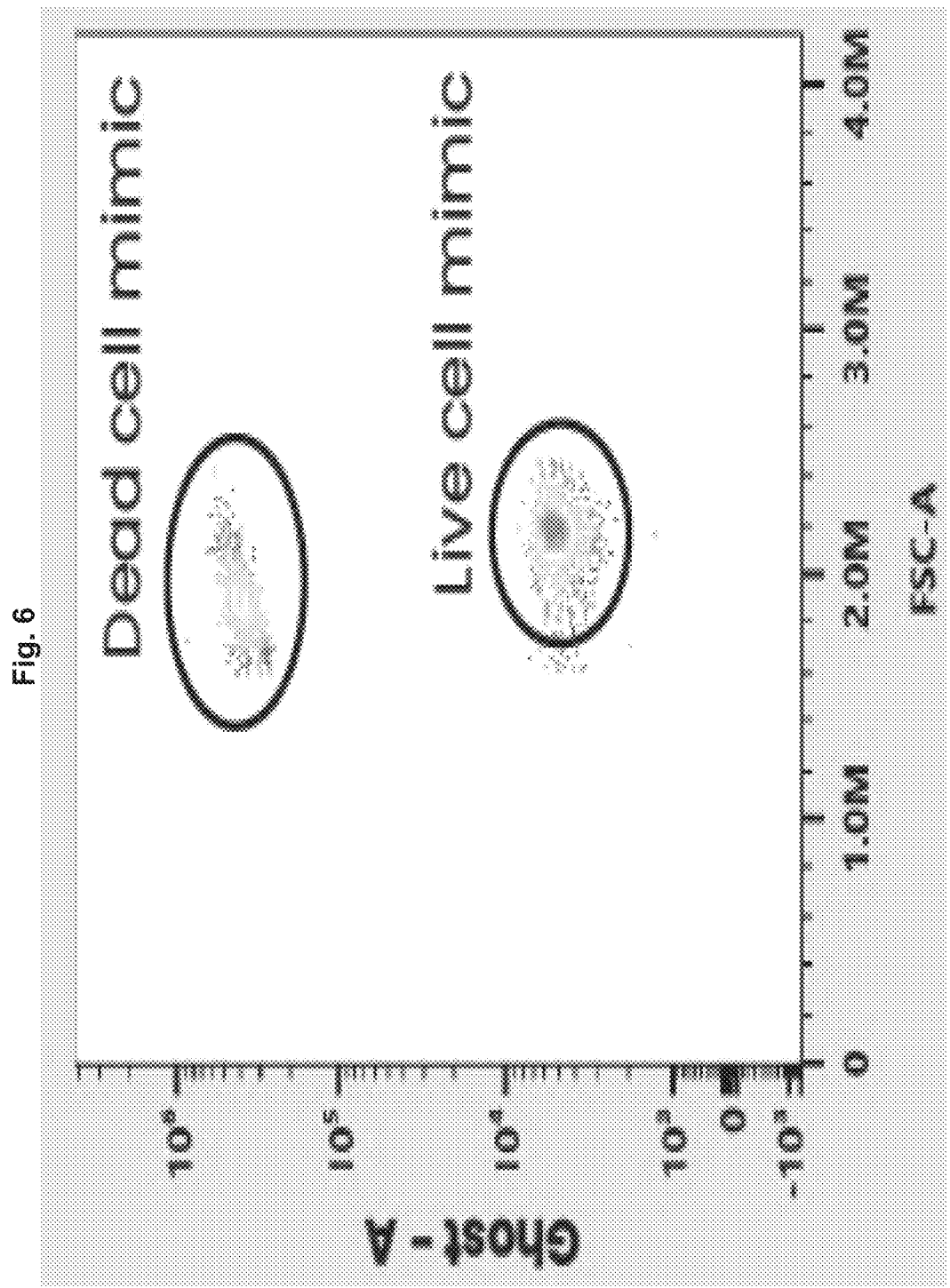
FIG. 6 shows that a hydrogel bead containing a (i) a polymerized monomer and a bifunctional monomer, (ii) an amine dye binder, and (iii) an encapsulated nucleic acid, binds to the amine-reactive viability dye, GHOST DYE™.
Figure 7:
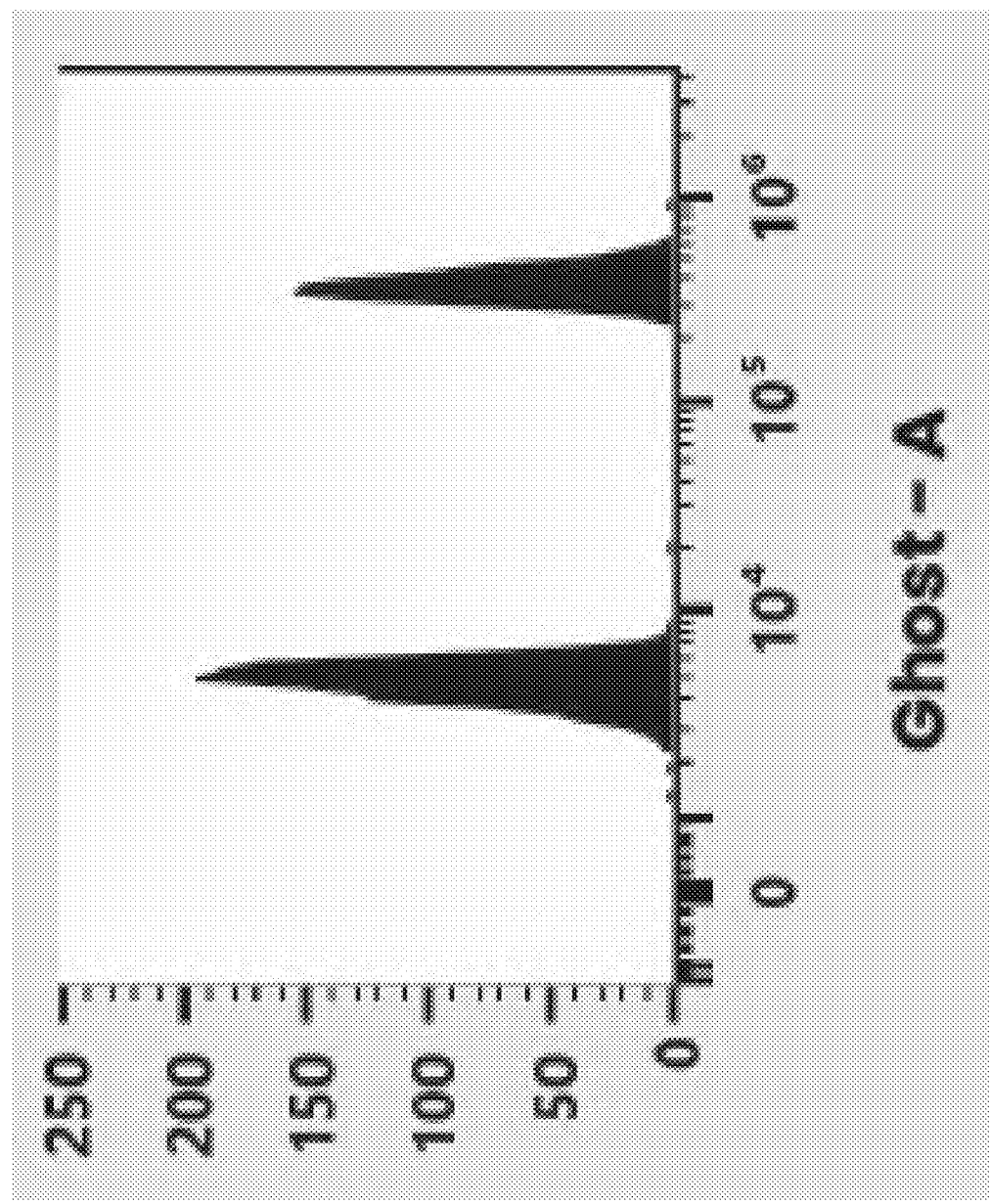
FIG. 7 shows the mean fluorescence intensity of GHOST DYE™ binding to the hydrogel bead of FIG. 6.

The present disclosure provides hydrogel beads (Section IV) and kits (Section VI) and compositions (Section VII) comprising the same. The present disclosure also provides methods (Section VIII) of using the hydrogel beads and kits and compositions comprising the same.

The hydrogel beads provided herein mimic live cells, dead cells, or apoptotic cells. These hydrogel beads have optical-scatter properties (e.g., forward scatter and/or side scatter) that can be tuned to match those of target cell populations. The properties of these beads are further described in Section V.

Advantageously, these hydrogel beads and compositions and kits comprising the same can be used to determine if a target cell population contains live cells, dead cells, and/or cells undergoing apoptosis that are not yet dead. Additionally, the hydrogel beads and compositions and kits comprising the same can be used to quantify the number of live cells, dead cells, and/or apoptotic cells in a target cell population. Compositions comprising hydrogel beads are superior to compositions comprising cells for several reasons. First, the number of hydrogel beads that serve as live cell controls, dead cell controls, and apoptotic cell controls can be modulated. In contrast, the amount of dead, live, and apoptotic cells in cell populations that serve as controls for apoptosis cannot be precisely controlled. Thus, the hydrogel bead compositions can be generated which have 33% each of beads that serve as dead, live, and apoptotic cell mimics. Second, compositions comprising hydrogel beads that are stained with pre-apoptotic signal and viability dyes exhibit clear positive and negative bead populations. In contrast, the separation between positive and negative cell populations is less clear. Third, compositions comprising hydrogel beads exhibit less variability than cells. Different lots of cells may exhibit different properties depending on the age of the cells, whereas hydrogel bead compositions are stable for at least 37 days. Fourth, using hydrogel bead compositions is less time intensive than using cell populations as controls for apoptosis because hydrogel bead compositions do not require cell culture or the induction of apoptosis. In contrast, when cell populations are used as controls for apoptosis, apoptosis must be induced in the control cells using heat or chemical methods. This process is time consuming, wasteful, and not well standardized.

I. Definitions

The indefinite articles "a" and "an" and the definite article "the" are intended to include both the singular and the plural, unless the context in which they are used clearly indicates otherwise.

"At least one" and "one or more" are used interchangeably to mean that the article may include one or more than one of the listed elements.

As used herein, the term "about" refers to plus or minus 10% of the referenced number unless otherwise stated or otherwise evident by the context, and except where such a range would exceed 100% of a possible value, or fall below 0% of a possible value, such as less than 0% content of an ingredient, or more than 100% of the total contents of a composition. For example, reference to the about 10% monomer by weight of the hydrogel means that the monomer can be present in any amount ranging from 9% to 11% by weight of the hydrogel. Unless otherwise indicated, it is to be understood that all numbers expressing quantities, ratios, and numerical properties of ingredients, reaction conditions, and so forth, used in the specification and claims are contemplated to be able to be modified in all instances by the term "about".

The term "scatter-modulating additive" refers to any element capable of modulating the side scatter of a hydrogel bead. Non-limiting examples of scatter-modulating additives include nanoparticles such as those made out of polymethyl methacrylate (PMMA), polystyrene (PS), or silica; and/or high-refractive index molecules added to a hydrogel such as alkyl acrylate, alkyl methacrylate, vinylar, enes such as styrene and methylstyrene, optionally substituted on the aromatic ring with an alkyl group, such as methyl, ethyl or tert-butyl, or with a halogen, such as chlorostyrene, The term "hydrogel bead" refers to particles made out of hydrogel material and optionally containing on or more additional elements for use in described cytometric or coulter assays. In some embodiments, the hydrogels of the present disclosure are generally spherical in shape, and can resemble one or more target cells.

The term "optical-scatter property" refers to a cell or hydrogel's forward scatter (FSC) and side scatter (SSC) properties.

The term "dead cell" refers to a non-viable cell. In some embodiments dead cells have permeable, ruptured, or non-existent membranes, such that the cytoplasm and nucleus are accessible by one or more viability dyes/markers.

The term "pre-apoptotic cell" refers to a cell in which apoptosis has been triggered, but which has not yet died.

The term "hydrogel" refers to a material comprising a macromolecular three-dimensional network that allows it to swell when in the presence of water (i.e., the "hydrated state"), to shrink in the absence of (or by reduction of the amount of) water (i.e., the "dehydrated state"), but not dissolve in water. As used herein, the term "hydrogel" refers to the material in either its hydrated or dehydrated state. The swelling, or absorption of water, is a consequence of the presence of hydrophilic functional groups attached to or dispersed within the macromolecular network. Crosslinks between adjacent macromolecules result in the aqueous insolubility of these hydrogels. The cross-links may be due to chemical (i.e., covalent) or physical (i.e., VanDer Waal forces, hydrogen-bonding, ionic forces, etc.) bonds. These chemical crosslinks may also be hydrolyzed under certain conditions, reversing the insolubility of the hydrogel. Multiple chemical crosslinking chemistries are described in the Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf, the disclosure of which is incorporated by reference in its entirety for all purposes.

The term "bifunctional monomer" refers to a monomer containing a first functional group and a second functional group, wherein the first functional group polymerizes with a monomer to form a hydrogel. In embodiments, the second functional group may be used to conjugate a fluorophore or a cell surface receptor, or domain thereof.

The term "forward scatter" refers to the light scattering properties of a material as measured in the parallel direction of the light travel. Forward scatter is a general measure of size of a particle, and can also be affected by the refractive index of hydrogels of the present disclosure.

The term "side scatter" refers to the light scattering properties of a material as measured in the perpendicular direction of the light travel. Side scatter is a general measure of complexity of a particle, and can also be affected by the refractive index of hydrogels of the present disclosure.

The term "substantially similar" refers to at least 40% similar, at least 50% similar, at least 60% similar, at least 70% similar, at least 80% similar, at least 90% similar, at least 95% similar, at least 96% similar, at least 97% similar, at least 98% similar or at least 99% similar.

The term "cytometric device" refers to a device used in the measurement of number and characteristics of cells. Variables that can be measured by cytometric methods include cell size, cell count, cell morphology (shape and structure), cell cycle phase, DNA content, and the existence or absence of specific proteins on the cell surface or in the cytoplasm. A common cytometric device according to the present disclosure is a flow cytometer. Flow cytometers are well known in the art and typically include a light source, optics, and stream flow.

The term "antigen-binding fragment" refers to a polypeptide fragment that contains at least one complementarity-determining region (CDR) of an immunoglobulin heavy and/or light chain that binds to at least one epitope of the antigen of interest. In this regard, an antigen-binding fragment of an anti-annexin V antibody may comprise 1, 2, 3, 4, 5, or all 6 CDRs of a variable heavy chain (VH) and variable light chain (VL) sequence from an antibody that specifically binds to annexin V. Antigen-binding fragments include proteins that comprise a portion of a full length antibody, generally the antigen binding or variable region thereof, such as Fab, F(ab')2, Fab', Fv fragments, minibodies, diabodies, single domain antibody (dAb), single-chain variable fragments (scFv), and multispecific antibodies formed from antibody fragments.

The term "percent identity" in the context of two or more nucleic acid or polypeptide sequences, refers to two or more sequences or subsequences that have a specified percentage of nucleotides or amino acid residues that are the same, when compared. Unless otherwise indicated, percent identity is determined using the National Center for Biotechnology Information (NCBI)'s Basic Local Alignment Search Tool (BLAST®), available at blast.ncbi.nlm.nih.gov/Blast.cgi, version BLAST+2.13.0.

II. Apoptosis

Apoptosis is a form of programmed cell death that occurs in multicellular organisms. Biochemical events lead to characteristic cell changes (morphology) and cell death. These changes include blebbing, cell shrinkage, nuclear fragmentation, chromatin condensation, DNA fragmentation, and mRNA decay. The average adult human loses between billions of cells each day due to apoptosis.

In contrast to necrosis, which is a form of traumatic cell death that results from acute cellular injury, apoptosis is a highly regulated and controlled process that confers advantages during an organism's life cycle. For example, the separation of fingers and toes in a developing human embryo occurs because cells between the digits undergo apoptosis. Unlike necrosis, apoptosis produces cell fragments called apoptotic bodies that phagocytes are able to engulf and remove before the contents of the cell can spill out onto surrounding cells and cause damage to them.

Apoptosis is a highly regulated process. Apoptosis can be initiated through one of two pathways: intrinsic and extrinsic. In the intrinsic pathway the cell kills itself because it senses cell stress, while in the extrinsic pathway the cell kills itself because of signals from other cells. Weak external signals may also activate the intrinsic pathway of apoptosis. Both pathways induce cell death by activating caspases, which are proteases, or enzymes that degrade proteins. The two pathways both activate initiator caspases, which then activate executioner caspases, which then kill the cell by degrading proteins indiscriminately. A cell's membranes are subject to such degradation, resulting the release of nucleic acids, such as nuclear DNA, mitochondrial DNA and RNA.

The intrinsic pathway is also known as the mitochondrial pathway. Mitochondria are essential to multicellular life. Without them, a cell ceases to respire aerobically and quickly dies. This fact forms the basis for some apoptotic pathways. Apoptotic proteins that target mitochondria affect them in different ways. They may cause mitochondrial swelling through the formation of membrane pores, or they may increase the permeability of the mitochondrial membrane and cause apoptotic effectors to leak out.

During apoptosis, cytochrome c is released from mitochondria through the actions of the proteins Bax and Bak. The mechanism of this release is enigmatic, but appears to stem from a multitude of Bax/Bak homo- and hetero-dimers of Bax/Bak inserted into the outer membrane. Once cytochrome c is released it binds with Apoptotic protease activating factor 1 (Apaf-1) and ATP, which then bind to pro-caspase-9 to create a protein complex known as an apoptosome. The apoptosome cleaves the pro-caspase to its active form of caspase-9, which in turn cleaves and activates pro-caspase into the effector caspase-3.

Mitochondria also release proteins known as SMACs (second mitochondria-derived activator of caspases) into the cell's cytosol following the increase in permeability of the mitochondria membranes. SMAC binds to proteins that inhibit apoptosis (IAPs) thereby deactivating them, and preventing the IAPs from arresting the process and therefore allowing apoptosis to proceed. IAP also normally suppresses the activity of a group of cysteine proteases called caspases, which carry out the degradation of the cell. Thus, the actual degradation enzymes can be seen to be indirectly regulated by mitochondrial permeability.

Two theories of extrinsic direct initiation of apoptotic mechanisms in mammals have been suggested: the TNF-induced (tumor necrosis factor) model and the Fas-Fas ligand-mediated model, both involving receptors of the TNF receptor (TNFR) family coupled to extrinsic signals.

TNF-alpha is a cytokine produced mainly by activated macrophages and is a major extrinsic mediator of apoptosis. Most cells in the human body have two receptors for TNF-alpha: TNFR1 and TNFR2. The binding of TNF-alpha to TNFR1 has been shown to initiate the pathway that leads to caspase activation via the intermediate membrane proteins TNF receptor-associated death domain (TRADD) and Fas-associated death domain protein (FADD). cIAP1/2 can inhibit TNF-α signaling by binding to TRAF2. FLIP inhibits the activation of caspase-8. Binding of this receptor can also indirectly lead to the activation of transcription factors involved in cell survival and inflammatory responses. However, signaling through TNFR1 might also induce apoptosis in a caspase-independent manner.

The fas receptor (First apoptosis signal) (also known as Apo-1 or CD95) is a transmembrane protein of the TNF family which binds the Fas ligand (FasL). The interaction between Fas and FasL results in the formation of the death-inducing signaling complex (DISC), which contains the FADD, caspase-8 and caspase-10. In some types of cells (type 1), processed caspase-8 directly activates other members of the caspase family, and triggers the execution of apoptosis of the cell. In other types of cells (type 11), the Fas-DISC starts a feedback loop that spirals into increasing release of proapoptotic factors from mitochondria and the amplified activation of caspase-8.

Defective apoptotic processes have been implicated in a wide variety of diseases. Excessive apoptosis causes atrophy, whereas an insufficient amount results in uncontrolled cell proliferation, such as cancer. The progression of the human immunodeficiency virus infection into AIDS is due primarily to the depletion of CD4±T-helper lymphocytes in a manner that is too rapid for the body's bone marrow to replenish the cells, leading to a compromised immune system. One of the mechanisms by which T-helper cells are depleted is apoptosis, which results from a series of biochemical pathways.

Inhibition of apoptosis can result in a number of cancers, inflammatory diseases, and viral infections. Interruption of the process can result in a cell that lives past its "use-by date" and is able to replicate and pass on any faulty machinery to its progeny, increasing the likelihood of the cell's becoming cancerous or diseased. It was originally believed that the associated accumulation of cells was due to an increase in cellular proliferation, but it is now believed that it is also due to a decrease in cell death. The most common of these diseases is cancer, the disease of excessive cellular proliferation, which is often characterized by an overexpression of IAP family members. As a result, the malignant cells experience an abnormal response to apoptosis induction: Cycle-regulating genes (such as p53, ras or c-myc) are mutated or inactivated in diseased cells, and further genes (such as bcl-2) also modify their expression in tumors. Some apoptotic factors are vital during mitochondrial respiration e.g. cytochrome C. Pathological inactivation of apoptosis in cancer cells is correlated with frequent respiratory metabolic shifts toward glycolysis (an observation known as the "Warburg hypothesis").

Some factors like Fas receptors and caspases promote apoptosis, while some members of the Bcl-2 family of proteins inhibit apoptosis. Phosphatidylserine (PS) is a commonly used marker of apoptosis. In a normal healthy cell, PS is present on the intracellular side of the cell membrane. However, during apoptosis, PS translocates to the extracellular side of the membrane. The link between TNF-alpha and apoptosis shows why an abnormal production of TNF-alpha plays a fundamental role in several human diseases, especially in autoimmune diseases. Apoptosis is known to be one of the primary mechanisms of targeted cancer therapy. Luminescent iridium complex-peptide hybrids (IPHs) have recently been designed, which mimic TRAIL and bind to death receptors on cancer cells, thereby inducing their apoptosis.

The hydrogel beads and compositions and kits comprising the same are useful for detecting apoptosis, dead cells, and live cells.

III. Detecting Apoptosis Using Viability Staining

Viability staining is the process by which live and dead cell populations within a sample are differentiated. Viability controls are generally a mixture of live and dead cells stained with a differentiating dye. These dyes generally fall into one of two broad categories: DNA-intercalating and primary amine (protein) stains. Despite the fact that several DNA binding dyes are commonly used to identify live cell populations, compensation beads for DNA dyes are rarely available. In addition, existing polystyrene beads used for amine-reactive dyes have fundamentally different properties when compared to cellular material causing difficulties when trying to work with certain major classes of dyes in key fluorescence channels.

To create a staining control, apoptosis must be induced in real cells using heat or chemical methods, a process which is wasteful, time-consuming, and not well standardized. A mixture of live and treated cells are stained with a fluorescent annexin V conjugate, and this is used to differentiate between apoptotic and non-apoptotic populations. In flow cytometry, these controls can be used to set up compensation. Often a live-cell impermeable stain, such as propidium iodide or 7AAD, is used in addition to annexin V to eliminate false positives. In the late stages of apoptosis, the cell membrane will begin to rupture and annexin V enters the cell and can bind to PS on the intracellular part of the membrane. Live-cell impermeable stains are used to detect membrane rupture.

These two dyes are often sold together in "apoptosis detection" kits. There are existing bead products related to annexin V, but they are all meant to be used to deplete or select for apoptotic cells in a population. For example, Miltenyi Biotec sells an annexin V microbead where annexin V is conjugated to the surface of the bead, but this bead is used to enrich populations of apoptotic cells, not as a compensation control in itself.

The ability to identify and measure specific cell types, such as apoptotic cells, relies on proper calibration of the measurement instrument. Calibration has relied on the use of purified cells of the cell type of interest. Obtaining these purified cells using heat or chemical methods, a process which is wasteful, time-consuming, is not well standardized and is prone to variations from batch to batch. Further, the cells to be used for calibration may be rare or in short supply. Therefore, there is a need in the art for synthetic compositions with tunable optical and binding properties that can mimic apoptotic cells.

Flow cytometry is a technique that allows for the rapid separation, counting, and characterization of individual cells, such as potentially apoptotic cells, and is routinely used in clinical and laboratory settings for a variety of applications. Optics-based flow cytometry relies on directing a beam of light onto a hydrodynamically-focused stream of liquid. A number of detectors are then aimed at the point where the stream passes through the light beam: one in line with the light beam (Forward Scatter or FSC) and several perpendicular to it (Side Scatter or SSC). FSC correlates with the cell volume and SSC depends on the inner complexity of the particle (e.g., shape of the nucleus, the amount and type of cytoplasmic granules or the membrane roughness). As a result of these correlations, different specific cell types exhibit different FSC and SSC, allowing cell types to be distinguished.

Using the cells of interest to create calibration controls is time-consuming, wasteful and not well standardized. Using polystyrene beads as a calibration control results in a control that has fundamentally different properties when compared to cellular material of interest, causing difficulties when trying to work with certain major classes of dyes in key fluorescence channels.

Provided herein are calibration controls for flow cytometry that avoid the problems associated with using cells of interest. The calibration controls described herein comprise hydrogel beads.

IV. Hydrogel Beads

Provided herein are hydrogel beads comprising (a) a polymerized monomer and a bifunctional monomer; and in some embodiments (b) a pre-apoptotic signal binder. Also provided herein are hydrogel beads comprising (a) a polymerized monomer and in some embodiments a bifunctional monomer; and (b) a pre-apoptotic signal. In embodiments, the hydrogel beads comprise (c) an encapsulated nucleic acid. In embodiments, the hydrogel beads comprise (d) additional constituents.

IV-A. Polymerized Monomer and Bifunctional Monomers

In embodiments, the polymerized monomer and bifunctional monomer of the hydrogel beads described herein form a hydrogel. Hydrogels are materials comprising a macromolecular three-dimensional network that allow it to swell in the presence of water (i.e., the "hydrated state"), to shrink in the absence of (or by reduction of the amount of) water (i.e., the "dehydrated state"), but not dissolve in water. As used herein, the term "hydrogel" refers to the material in either its hydrated or dehydrated state. The swelling, or absorption of water, is a consequence of the presence of hydrophilic functional groups attached to or dispersed within the macromolecular network. Crosslinks between adjacent macromolecules result in the aqueous insolubility of these hydrogels. The cross-links may be due to chemical (i.e., covalent) or physical (i.e., VanDer Waal forces, hydrogen-bonding, ionic forces, etc.) bonds. These chemical crosslinks may also be hydrolyzed under certain conditions, reversing the insolubility of the hydrogel. Multiple chemical crosslinking chemistries are described in the Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf, the disclosure of which is incorporated by reference in its entirety for all purposes.

In embodiments, the hydrogel comprises greater than about 30%, greater than about 40%, greater than about 50%, greater than about 55%, greater than about 60%, greater than about 65%, greater than about 70%, greater than about 75%, greater than about 80%, greater than about 85%, greater than about 90%, or greater than about 95% water by weight. In embodiments, the hydrogel has a water content of from about 10 percent by weight to about 95 percent by weight, or from about 20 percent by weight to about 95 percent by weight, or from about 30 percent by weight to about 95 percent by weight, or from about 40 percent by weight to about 95 percent by weight, or from about 50 percent by weight to about 95 percent by weight, or from about 60 percent by weight to about 95 percent by weight, or from about 70 percent by weight to about 95 percent by weight, or from about 80 percent by weight to about 95 percent by weight.

In embodiments, the hydrogel retains the same shape in the dehydrated and hydrated conditions. For example, if the hydrogel has an approximately spherical shape in the dehydrated condition, it will be approximately spherical in the hydrated condition.

In embodiments, the hydrogel forms particles. In embodiments, hydrogels are synthesized by polymerizing one or more of the monomers provided herein. In embodiments, any form of polymerization known to those skilled in the art, can be employed to form polymers. In embodiments, polymerization is catalyzed by ultraviolet light-induced radical formation and reaction progression. In embodiments, acrylate is the monomer that is polymerized. In embodiments, acrylamide is the monomer that is polymerized.

In embodiments, the acrylamide is a polymerizable carbohydrate derivatized acrylamide as described in U.S. Pat. No. 6,107,365, the disclosure of which is incorporated by reference in its entirety for all purposes. As described therein and known to those of ordinary skill in the art, specific attachment of acrylamide groups to sugars is readily adapted to a range of monosaccharides and higher order polysaccharides, e.g., synthetic polysaccharides or polysaccharides derived from natural sources, such as glycoproteins found in serum or tissues.

In embodiments, an acrylate-functionalized poly(ethylene) glycol monomer is polymerized. In embodiments, an acrylamide functionalized PEG is polymerized.

In embodiments, the hydrogel bead comprises a monofunctional monomer polymerized with at least one bifunctional monomer. In embodiments, the hydrogel bead comprises a polymer of acrylamide (i.e., poly-acrylamide) and bis-acrylamide (a bifunctional monomer).

In embodiments, a hydrogel bead provided herein comprises a bifunctional monomer polymerized with a second bifunctional monomer. In embodiments, the hydrogel bead that comprises a bifunctional monomer polymerized with a second bifunctional monomer comprises polymers with mixed composition containing compatible chemistries such as acrylamide, bis-acrylamide, and bis-acrylamide structural congeners containing a wide range of additional chemistries. In embodiments, one functional group of the bifunctional monomer is an alkyne and the other functional group is an ester, amide, ketone, aldehyde, azide, alkene, alcohol, amine, or carboxylic acid. In embodiments, one functional group of the bifunctional monomer is an alkyne and the other functional group is an alcohol, amine, or carboxylic acid. In embodiments, one functional group of the bifunctional monomer is an alkene and the other functional group is an amine. In embodiments, one functional group of the bifunctional monomer is an alkene and the other functional group is an alcohol, amine, or carboxylic acid. In embodiments, one functional group of the bifunctional monomer is an alkene and the other functional group is an ester, amide, ketone, aldehyde, azide, alkene, alcohol, amine, or carboxylic acid.

In embodiments, a hydrogel bead provided herein comprises a polymerized monofunctional monomer and is a monofunctional acrylic monomer. Non-limiting examples of monofunctional acrylic monomers for use herein are acrylamide; methacrylamide; N-alkylacrylamides such as N-ethylacrylamide, N-isopropylacrylamide or N-tertbutylacrylamide; N-alkylmethacrylamides such as N-ethylmethacrylamide or Nisopropylmethacrylamide; N,N-dialkylacrylamides such as N,N-dimethylacrylamide and N,N-diethylacrylamide; N-[(dialkylamino)alkyl] acrylamides such as N-[3dimethylamino) propyl]acrylamide or N-[3-(diethylamino)propyl] acrylamide; N-[(dialkylamino) alkyl] methacrylamides such as N-[3-dimethylamino)propyl] methacrylamide or N-[3-(diethylamino) propyl] methacrylamide; (dialkylamino)alkyl acrylates such as 2-(dimethylamino) ethyl acrylate, 2-(dimethylamino)propyl acrylate, or 2-(diethylamino)ethyl acrylates; and (dialkylamino) alkyl methacrylates such as 2-(dimethylamino) ethyl methacrylate.

In embodiments, a bifunctional monomer is selected from the group consisting of: allyl amine, allyl alcohol, allyl isothiocyanate, allyl chloride, and allyl maleimide.

In embodiments, a bifunctional monomer is a bifunctional acrylic monomer. Non-limiting examples of bifunctional acrylic monomers are N,N'-methylenebisacrylamide, N,N'methylene bismethacrylamide, N,N'-ethylene bisacrylamide, N,N'-ethylene bismethacrylamide, N,N'bisacryloylcystamine, N,N'propylenebisacrylamide and N,N'-(1,2-dihydroxyethylene) bisacrylamide.

Higher-order branched chain and linear co-monomers can be substituted in the polymer mix to adjust the refractive index while maintaining polymer density, as described in U.S. Pat. No. 6,657,030, which is incorporated herein by reference in its entirety for all purposes.

The biomonomer, in one embodiment, is functionalized with acrylamide or acrylate. For example, in one embodiment, the polymerizable acrylamide functionalized biomolecule is an acrylamide or acrylate functionalized protein (for example, an acrylamide functionalized collagen or functionalized collagen domain), an acrylamide or acrylate functionalized peptide, or an acrylamide or acrylate functionalized monosaccharide, disaccharide or polysaccharide.

Any monosaccharide, disaccharide or polysaccharide (functionalized or otherwise) can be used as a hydrogel monomer. In one embodiment, an acrylamide or acrylate functionalized monosaccharide, disaccharide or polysaccharide is used as a polymerizable hydrogel monomer. In one embodiment, a structural polysaccharide is used as a polymerizable hydrogel monomer. In a further embodiment, the structural polysaccharide is an arabinoxylan, cellulose, chitin or a pectin. In another embodiment, alginic acid (alginate) is used as a polymerizable hydrogel monomer. In yet another embodiment, a glycosaminoglycan (GAG) is used as a polymerizable monomer in the hydrogels provided herein. In a further embodiment, the GAG is chondroitin sulfate, dermatan sulfate, keratin sulfate, heparin, heparin sulfate or hyaluronic acid (also referred to in the art as hyaluron or hyaluronate) is used as a polymerizable hydrogel monomer. The additional range of compatible biomonomers and their reactive chemistries are known be individuals skilled in the art and follow general chemical reactivity principles.

Biocompatible monomers for use with the hydrogels described herein include in one embodiment, ethyleglycol dimethacrylate (EGDMA), 2-hydroxyethyl methacrylate (HEMA), methylmethacrylte (MMA), methacryloxymethyltrimethylsilane (TMS-MA), N-vinyl-2-pyrrolidon (N-VP), styrene, or a combination thereof.

Naturally occurring hydrogels useful in this disclosure include various polysaccharides available from natural sources such as plants, algae, fungi, yeasts, marine invertebrates and arthropods. Non-limiting examples include agarose, dextrans, chitin, cellulose-based compounds, starch, derivatized starch, and the like. These generally will have repeating glucose units as a major portion of the polysaccharide backbone. Cross-linking chemistries for such polysaccharides are known in the art, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf).

Hyaluronan in one embodiment is used as a hydrogel monomer (either as a single monomer or as a co-monomer). Hyaluronan in one embodiment, is functionalized, for example with acrylate or acrylamide. Hyaluronan is a high molecular weight GAG composed of disaccharide repeating units of N-acetylglucosamine and glucuronic acid linked together through alternating β-1,4 and β-1,3 glycosidic bonds. In the human body, hyaluronate is found in several soft connective tissues, including skin, umbilical cord, synovial fluid, and vitreous humor. Accordingly, in one embodiment, where one or more optical properties of a skin cell, umbilical cord cell or vitreous humor cell is desired to be mimicked, in one embodiment, hyaluronan is used as a hydrogel monomer. Methods for fabricating hydrogel particles are described in Xu et al. (2012). Soft Matter. 8, pp. 3280-3294, the disclosure of which is incorporated herein in its entirety for all purposes. As described therein, hyaluronan can be derivatized with various reactive handles depending on the desired cross-linking chemistry and other monomers used to form a hydrogel particle.

In yet other embodiments, chitosan, a linear polysaccharide composed of randomly distributed β-(1-4)-linked D-glucosamine (deacetylated unit) and N-acetyl-D-glucosamine (acetylated unit), is used as a hydrogel monomer (either as a single monomer or as a co-monomer).

Other polysaccharides for use as a hydrogel monomer or co-monomer include but are not limited to, agar, agarose, alginic acid, alguronic acid, alpha glucan, amylopectin, amylose, arabinoxylan, beta-glucan, callose, capsullan, carrageenan polysaccharides (e.g., kappa, iota or lambda class), cellodextrin, cellulin, cellulose, chitin, chitosan, chrysolaminarin, curdlan, cyclodextrin, alpha-cyclodextrin, dextrin, ficoll, fructan, fucoidan, galactoglucomannan, galactomannan, galactosaminoogalactan, gellan gum, glucan, glucomannan, glucorunoxylan, glycocalyx, glycogen, hemicellulose, homopolysaccharide, hypromellose, icodextrin, inulin, kefiran, laminarin, lentinan, levan polysaccharide, lichenin, mannan, mixed-linkage glucan, paramylon, pectic acid, pectin, pentastarch, phytoglycogen, pleuran, polydextrose, polysaccharide peptide, porphyran, pullulan, schizophyllan, sinistrin, sizofiran, welan gum, xanthan gum, xylan, xyloglucan, zymosan, or a combination thereof. As described throughout, depending on the desired cross-linking chemistry and/or additional co-monomers employed in the hydrogel, the polysaccharide can be further functionalized. For example, one or more of the polysaccharides described herein in one embodiment is functionalized with acrylate or acrylamide.

In one embodiment, an individual hydrogel particle or a plurality thereof comprises a peptide, protein, a protein domain, or a combination thereof as a hydrogel monomer or plurality thereof. In a further embodiment, the protein is a structural protein, or a domain thereof, for example, such as silk, elastin, titin or collagen, or a domain thereof. In one embodiment, the protein is an extracellular matrix (ECM) component (e.g., collagen, elastin, proteoglycan). In even a further embodiment, the structural protein is collagen. In yet a further embodiment, the collagen is collagen type I, collagen type II or collagen type III or a combination thereof. In another embodiment, the hydrogel monomer comprises a proteoglycan. In a further embodiment, the proteoglycan is decorin, biglycan, testican, bikunin, fibromodulin, lumican, or a domain thereof.

In another embodiment, an acrylate-functionalized structural protein hydrogel monomer is used as a component of the hydrogel provided herein (e.g., an acrylate functionalized protein or protein domain, for example, silk, elastin, titin, collagen, proteoglycan, or a functionalized domain thereof). In a further embodiment, the acrylate functionalized structural protein hydrogel monomer comprises a proteoglycan, e.g., decorin, biglycan, testican, bikunin, fibromodulin, lumican, or a domain thereof.

In one embodiment PEG monomers and oligopeptides can be that mimic extracellular matrix proteins are used in the hydrogels provided herein, for example, with vinyl sulfone-functionalized multiarm PEG, integrin binding peptides and bis-cysteine matrix metalloproteinase peptides as described by Lutolf et al. (2003). Proc. Natl. Acad. Sci. U.S.A. 100, 5413-5418, incorporated by reference in its entirety for all purposes. In this particular embodiment, hydrogels are formed by a Michael-type addition reaction between the di-thiolated oligopeptides and vinyl sulfone groups on the PEG. The range of additional compatible chemistries that can be incorporated here are obvious to those skilled in the art and follow general chemical reactivity principles, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf).

Other bioactive domains in natural proteins can also be used as a hydrogel monomer or portion thereof. For example, a cell-adhesive integrin binding domain, a controlled release affinity binding domain or a transglutaminase cross-linking domain can be used in the hydrogels provided herein. Details for producing such hydrogels can be found in Martino et al. (2009). Biomaterials 30, 1089; Martino et al. (2011). Sci. Trans. Med. 3, 100ra89; Hu and Messersmith (2003). J. Am. Chem. Soc. 125, 14298, each of which is incorporated by reference in its entirety for all purposes.

In one embodiment, recombinant DNA methods are used to create proteins, designed to gel in response to changes in pH or temperature, for example, by the methods described by Petka et al. (1998). Science 281, pp. 389-392, incorporated by reference in its entirety for all purposes. Briefly, the proteins consist of terminal leucine zipper domains flanking a water-soluble polyelectrolyte segment. In near-neutral aqueous solutions, coiled-coil aggregates of the terminal domains form a three-dimensional hydrogel polymer network.

An additional range of biocompatible monomers that can be incorporated are known in the art, see, for example the non-degradable biocompatible monomers disclosed in Shastri (2003). Current Pharmaceutical Biotechnology 4, pp. 331-337, incorporated by reference herein in its entirety for all purposes. Other monomers are provided in de Moraes Porto (2012). Polymer Biocompatibility, Polymerization, Dr. Ailton De Souza Gomes (Ed.), ISBN: 978-953-51-0745-3; InTech, DOI: 10.5772/47786; Heller et al. (2010). Journal of Polymer Science Part A: Polymer Chemistry 49, pp. 650-661; Final Report for Biocompatible Materials (2004), The Board of the Biocompatible Materials and the Molecular Engineering in Polymer Science programmes, ISBN 91-631-4985-0, the disclosure of each of which are hereby incorporated by reference in their entirety.

In embodiments, the polymerized monomer is a homopolymer. The term "homopolymer" refers to a polymerized monomer that contains one single repeating monomer unit. In embodiments, the polymerized monomer is a copolymer. The term "copolymer" refers to a polymer made by reaction of two different monomers. The two different monomers are referred to as co-monomers. In embodiments, the monomer is a bifunctional monomer. In embodiments, one of the co-monomers is a bifunctional monomer. In embodiments, both of the co-monomers are bifunctional monomers.

In embodiments, a hydrogel is synthesized in the presence of a crosslinker. In embodiments, the crosslinker is selected from any one of ethylene glycol dimethacrylate (EGDMA), tetraethylene glycol dimethacrylate, and N,N'-15 methylenebisacrylamide.

In embodiments, a hydrogel is synthesized in the presence of a polymerization initiator. In embodiments, the polymerization initiator is persulfate or an equivalent initiator that catalyzes radical formation. In embodiments, the persulfate is any water-soluble persulfate. Non-limiting examples of water soluble persulfates include ammonium persulfate and alkali metal persulfates. In embodiments, the alkali metal persulfate is a lithium, sodium, or potassium alkali metal persulfate. In embodiments, the persulfate is ammonium persulfate or potassium persulfate. In a further embodiment, polymerization of the hydrogel provided herein is initiated by ammonium persulfate.

In embodiments, polymerization of the hydrogel is accelerated by an accelerant which can catalyze the formation of polymerization-labile chemical side groups. In embodiments, the accelerant is a tertiary amine. In embodiments, the tertiary amine is a water-soluble tertiary amine. In embodiments, the accelerant is N,N,N',N'tetramethylethylenediamine, 3-dimethylamino) propionitrile, or N,N,N',N-

'tetramethylethylenediamine (TEMED). In embodiments, the accelerant is isazobis (isobutyronitrile) (AIBN).

In embodiments, the amount of monomer can be varied, for example to obtain a particular optical property or morphological property that is substantially similar to that of a target cell. In embodiments, the monomer is present at about 10 percent by weight to about 95 percent weight of the hydrogel. In embodiments, the monomer is present at about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95% by weight of the hydrogel, including all values and subranges in between inclusive of endpoints.

In embodiments, the polymerized monomer is present at from about 10 percent by weight to about 95 percent weight of the hydrogel. In embodiments, the polymerized monomer is present at from about 15 percent by weight to about 95 percent weight of the hydrogel. In embodiments, the polymerized monomer is present at from about 20 percent by weight to about 95 percent weight of the hydrogel. In embodiments, the polymerized monomer is present at about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95% by weight of the hydrogel, including all values and subranges in between inclusive of endpoints.

In embodiments, the bifunctional monomer is present at from about 10 percent by weight to about 95 percent weight of the hydrogel. In embodiments, the bifunctional monomer is present at from about 15 percent by weight to about 95 percent weight of the hydrogel. In embodiments, the bifunctional monomer is present at from about 20 percent by weight to about 95 percent weight of the hydrogel. In embodiments, the bifunctional monomer is present at about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95% by weight of the hydrogel, including all values and subranges in between inclusive of endpoints.

In embodiments, the co-monomer is present at from about 10 percent by weight to about 95 percent weight of the hydrogel. In embodiments, the co-monomer is present at from about 15 percent by weight to about 95 percent weight of the hydrogel. In embodiments, the co-monomer is present at from about 20 percent by weight to about 95 percent weight of the hydrogel. In embodiments, the co-monomer is present at about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95% by weight of the hydrogel, including all values and subranges in between inclusive of endpoints.

In embodiments, a monomer is selected from any one of: 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly(ethylene glycol) methacrylate, methoxy-poly(ethylene glycol) methacrylate, methacrylic acid, sodium methacrylate, glycerol methacrylate, hydroxypropyl methacrylate, hydroxybutyl methacrylate.

In embodiments, a monomer is selected from any one of lactic acid, glycolic acid, acrylic acid, 1-hydroxyethyl methacrylate, ethyl methacrylate, 2-hydroxyethyl methacrylate (HEMA), propylene glycol methacrylate, acrylamide, N-vinylpyrrolidone (NVP), methyl methacrylate, glycidyl methacrylate, glycerol methacrylate (GMA), glycol methacrylate, ethylene glycol, fumaric acid, a derivatized version thereof, or a combination thereof.

In embodiments, a monomer is selected from any one of: phenyl acrylate, phenyl methacrylate, benzyl acrylate, benzyl methacrylate, 2-phenylethyl acrylate, 2-phenylethyl methacrylate, 2-phenoxyethyl acrylate, 2-phenoxyethyl methacrylate, phenylthioethyl acrylate, phenylthioethyl methacrylate, 2,4,6-tribromophenyl acrylate, 2,4,6-tribromophenyl methacrylate, pentabromophenyl acrylate, pentabromophenyl methacrylate, pentachlorophenyl acrylate, pentachlorophenyl methacrylate, 2,3-dibromopropyl acrylate, 2,3-dibromopropyl methacrylate, 2-naphthyl acrylate, 2-naphthyl methacrylate, 4-methoxybenzyl acrylate, 4-methoxybenzyl methacrylate, 2-benzyloxyethyl acrylate, 2-benzyloxyethyl methacrylate, 4-chlorophenoxyethyl acrylate, 4-chlorophenoxyethyl methacrylate, 2-phenoxyethoxyethyl acrylate, 2-phenoxyethoxyethyl methacrylate, N-phenyl acrylamide, N-phenyl methacrylamide, N-benzyl acrylamide, N-benzyl methacrylamide, N,N-dibenzyl acrylamide, N,N-dibenzyl methacrylamide, N-diphenylmethyl acrylamide N-(4-methylphenyl)methyl acrylamide, N-1-naphthyl acrylamide, N-4-nitrophenyl acrylamide, N-(2-phenylethyl)acrylamide, N-triphenylmethyl acrylamide, N-(4-hydroxyphenyl)acrylamide, N,N-methylphenyl acrylamide, N,N-phenyl phenylethyl acrylamide, N-diphenylmethyl methacrylamide, N-(4-methyl phenyl)methyl methacrylamide, N-1-naphthyl methacrylamide, N-4-nitrophenyl methacrylamide, N-(2-phenylethyl)methacrylamide, N-triphenylmethyl methacrylamide, N-(4-hydroxyphenyl)methacrylamide, N,N-methylphenyl methacrylamide, N,N'-phenyl phenylethyl methacrylamide, N-vinylcarbazole, 4-vinylpyridine, or 2-vinylpyridine.

In embodiments, a monomer is selected from any one of the monomers disclosed in U.S. Pat. No. 6,657,030, which is incorporated by reference in its entirety herein for all purposes.

In embodiments, the monomer is a synthetic monomer. In embodiments, the monomer is a bio-monomer.

In embodiments, a monomer is selected from any one of the monomers in the Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf, the disclosure of which is incorporated by reference in its entirety for all purposes.

In embodiments, the hydrogels are synthetic hydrogels. Synthetic hydrogels comprise synthetic monomers. In embodiments, the hydrogels are bio-hydrogels. Bio-hydrogels comprise a biomolecules, such as a peptide, protein, monosaccharide, disaccharide, polysaccharide, or a carbohydrate. In embodiments, a bio-hydrogel comprises a functional group found on a biomolecule, such as a primary amine, a sulfhydryl, a carbonyl, a carboxylic acid, or a carbohydrate. In embodiments, the hydrogels are hybrid hydrogels. Hybrid hydrogels comprise a synthetic component and a biomolecule and/or a functional group found on a biomolecule. In embodiments, proteins, peptides or carbohydrates can be used as individual monomers to form a hydrogel that includes or does not include a synthetic monomer (or polymer) and in combination with chemically compatible co-monomers and crosslinking chemistries. Compatible crosslinking chemistries include, but are not limited to, amines, carboxyls, and other reactive chemical side groups.

In embodiments, one or more of the monomer, co-monomer, bifunctional monomer is bis/acrylamide in various crosslinking ratios. In embodiments, one or more of the monomer, co-monomer, bifunctional monomer comprises allyl amine. In embodiments, one or more of the monomer, co-monomer, bifunctional monomer provides chemical functionality for secondary labeling/conjugation. In embodiments, one or more of the monomer, co-monomer, bifunctional monomer comprises alginate. For example, hydrazine (e.g., with an NHS ester compound) or EDC coupling reactions (e.g., with a maleimide compound) can be used to construct the hydrogels of the disclosure.

In embodiments, the polymerized monomer is a biodegradable monomer. In embodiments, the biodegradable monomer is a monosaccharide, disaccharide, polysaccharide, peptide, protein, or protein domain. In embodiments, the biodegradable monomer is a structural polysaccharide. In embodiments, the biodegradable monomer is selected from the group consisting of agar, agarose, alginic acid, alguronic acid, alpha glucan, amylopectin, amylose, arabinoxylan, beta-glucan, callose, capsullan, carrageenan polysaccharide, cellodextrin, cellulin, cellulose, chitin, chitosan, chrysolaminarin, curdlan, cyclodextrin, alpha-cyclodextrin, dextrin, dextran, ficoll, fructan, fucoidan, galactoglucomannan, galactomannan, galactosaminoogalactan, gellan gum, glucan, glucomannan, glucorunoxylan, glycocalyx, glycogen, hemicellulose, homopolysaccharide, hypromellose, icodextrin, inulin, kefiran, laminarin, lentinan, levan polysaccharide, lichenin, mannan, mixed-linkage gluxan, paramylon, pectic acid, pectin, pentastarch, phytoglycogen, pleuran, polydextrose, polysaccharide peptide, porphyran, pullulan, schizophyllan, sinistrin, sizofiran, welan gum, xanthan gum, xylan, xyloglucan, zymosan, and a combination thereof.

In embodiments, the hydrogel is biodegradable. In embodiments, the hydrogel comprises a monosaccharide, disaccharide, polysaccharide, peptide, protein, or protein domain. In embodiments, the hydrogel comprises a structural polysaccharide. In embodiments, the hydrogel comprises agar, agarose, alginic acid, alguronic acid, alpha glucan, amylopectin, amylose, arabinoxylan, beta-glucan, callose, capsullan, carrageenan polysaccharide, cellodextrin, cellulin, cellulose, chitin, chitosan, chrysolaminarin, curdlan, cyclodextrin, alpha-cyclodextrin, dextrin, dextran, ficoll, fructan, fucoidan, galactoglucomannan, galactomannan, galactosaminoogalactan, gellan gum, glucan, glucomannan, glucorunoxylan, glycocalyx, glycogen, hemicellulose, homopolysaccharide, hypromellose, icodextrin, inulin, kefiran, laminarin, lentinan, levan polysaccharide, lichenin, mannan, mixed-linkage gluxan, paramylon, pectic acid, pectin, pentastarch, phytoglycogen, pleuran, polydextrose, polysaccharide peptide, porphyran, pullulan, schizophyllan, sinistrin, sizofiran, welan gum, xanthan gum, xylan, xyloglucan, zymosan, or a combination thereof.

In embodiments, a hydrogel bead comprises a biodegradable polymer as a monomer. In embodiments, the biodegradable polymer is a poly(ester) based on polylactide (PLA), polyglycolide (PGA), polycaprolactone (PCL), poly lactic-co-glycolic acid (PLGA) and their copolymers. These polymers can degrade, dissolving a macromolecular particle, through hydrolysis. In embodiments, the biodegradable polymer is a carbohydrate or a protein, or a combination thereof. In one embodiment, a monosaccharide, disaccharide or polysaccharide, (e.g., glucose, sucrose, or maltodextrin) peptide, protein (or domain thereof) is used as a hydrogel monomer. In embodiments, the biodegradable polymers is poly(hydroxyalkanoate)s of the PHB-PHV class, additional poly(ester)s, or natural polymers, for example, modified poly(saccharide)s, e.g., starch, cellulose, and chitosan. In embodiments, the biocompatible polymer is an adhesion protein, cellulose, a carbohydrate, a starch (e.g., maltodextrin, 2-hydroxyethyl starch, alginic acid), a dextran, a lignin, a polyaminoacid, an amino acid, or chitin. Such biodegradable polymers are available commercially, for example, from Sigma Aldrich (St. Louis, MO).

In embodiments, a protein monomer comprises only natural amino acids. In embodiments, a protein monomer comprises non-natural amino acids. For example, self-assembling artificial proteins and proteins with non-natural amino acids (e.g., those incorporated into non-ribosomal peptides or synthetically introduced via synthetic approaches, see for example, Zhang et al. (2013). Current Opinion in Structural Biology 23, pp. 581-587, the disclosure of which is incorporated by reference in its entirety for all purposes), or protein domains thereof, can also be used as hydrogel monomers. The range of non-natural (unnatural) amino acids that can be incorporated into such compositions is well known to those skilled in the art (Zhang et al. (2013). Current Opinion in Structural Biology 23, pp. 581-587; incorporated by reference in its entirety for all purposes). In embodiments, the biodegradable polymer is used as a co-monomer. In embodiments, the biodegradable polymer in one embodiment is a bifunctional monomer.

In embodiments, a hydrogel bead described herein comprises a degradable polymer as a monomer. In embodiments, the degradable polymer is a poly(ester) based on PLA, PGA, PCL, PLGA and their copolymers. In embodiments, the degradable polymer is based on any one of the monomers described herein, which may be degradable by mechanical degradation, chemical degradation, and combinations thereof, or by any other mechanism of degradation. For instance, the monomer may be acrylamide and the degradable polymer formed therefrom may be degraded by exposure to potassium persulfate.

In embodiments, degradation of the individual hydrogel particle or a plurality thereof, whether by biodegradable means, lysis or otherwise, may result in the release of a substance encompassed therein. For instance, when the substance is a biomolecule such as hemoglobin, degradation of the hydrogel particle encompassing the hemoglobin may allow for measurement of the hemoglobin separate from the hydrogel monomer. In another instance, when the substance is a biomolecule such as hemoglobin, degradation of the hydrogel particle encompassing the hemoglobin may be by lysis buffer.

In embodiments, the concentration of bifunctional monomer and/or polymerized monomer may be adjusted to change the refractive index of the hydrogel.

In embodiments, a hydrogel bead described herein may be lysed. A lysable synthetic bead of the present invention allows a user to measure both the intact bead as well as the lysed bead. In embodiments, the hydrogel bead is lysed with a lysis buffer. In embodiments, the lysis buffer is ammonium chloride. Hematological lysis buffers often use ammonium chloride, including the 1×RBC Lysis Buffer and 10×RBC Lysis Buffer from Thermo Fisher Scientific. Hematological lysis buffers used on clinical blood samples are designed to lyse non-nucleated red blood cells and preserve white blood cells in order to perform white blood cell counts and the quantitative measurement of hemoglobin. Other lysis buffers may be designed to dissolve the engineered particle including strong reducing agents such as dithiothreitol (DTT) or betamercaptoethanol (BME). Additional non-limiting examples include divalent ions such as ethylenediaminetetraacetic acid (EDTA) or citrate.

In embodiments, hydrogel beads are formed by precipitation polymerization, as described in Elbert (2011), Acta Biomater. 7, pp. 31-56. This reference is incorporated by reference herein in its entirety for all purposes. Precipitation polymerization is a technique that takes advantage of the differences in the solubility of monomer and polymer to produce microparticles. Specifically, it is known that larger polymer chains generally have lower solubility than smaller ones. Accordingly, above a specific molecular weight, phase separation may be favored. Precipitation polymerization initially begins as solution polymerizations in a single phase, homogenous system. Shortly after the start of the polymerization, in one embodiment, a relatively high concentration of polymer chains is present, favoring phase separation by nucleation. As polymerization proceeds, the concentration of polymer chains is low and existing particles capture the chains before nucleation of new particles can occur. Thus, nucleation of particles occurs only for a brief period of time shortly after the start of the reaction, which in one embodiment, results in a narrow size distribution of particles. In embodiments, hydrogel beads may be formed by one or more methods selected from the group consisting of: lithographic particle formation (Helgeson et al. (2011). Curr. Opin. Colloid. Interface Sci. 16, pp. 106-117, incorporated by reference herein in its entirety for all purposes) membrane emulsification (e.g., by the micosieve emulsification technology techniques described by Nanomi B.V. (Netherlands)), microchannel emulsification (Sugiura et al. (2002). Languimir 18, pp. 5708-5712, incorporated by reference herein in its entirety), or bulk emulsification (SNF Floerger, available at snf.com.au/downloads/Emulsion_Handbook_E.pdf, incorporated by reference herein in its entirety).

In embodiments, hydrogel beads are formed within a microfluidic device having two oil channels that focus on a central stream of aqueous monomer solution. In embodiments, droplets form at the interface of the two channels and central stream to break off droplets in water-in-oil emulsion. In embodiments, after droplets are formed, they are stabilized prior to polymerization. In embodiments, droplets are stabilized by adding a surfactant to the oil phase. In embodiments, droplets are not stabilized prior to polymerization. In embodiments, polymerization of the monomer is triggered by adding an accelerator (e.g., N,N,N',N'tetramethylethylenediamine) to one or both of the oil channels after initial droplets are formed.

In embodiments, the aqueous monomer solution as provided above can include a single monomer species or a plurality of monomer species. In embodiments, the aqueous monomer solution includes co-monomers, a bifunctional monomer, or a combination thereof. In embodiments, the monomer or plurality of monomers includes a bifunctional monomer. In embodiments, the monomer is one of the monomers described above. In embodiments, co-monomers are used to modulate forward scatter or side scatter. In embodiments, co-monomers are used to adjust the refractive index of the hydrogel bead.

In embodiments, the central stream of aqueous monomer solution comprises a cross-linker. In embodiments, the cross-linker is N,N'-bisacrylamide. In embodiments, the central stream of aqueous monomer solution comprises a cross-linker, an accelerator, and the monomer. In embodiments, the aqueous monomer solution comprises an initiator. In embodiments, the initiator is an oxidizing agent. In embodiments, the oxidizing agent is ammonium persulfate.

In embodiments, hydrogel beads are produced by polymerizing droplets. Microfluidic methods of producing a plurality of droplets, including fluidic and rigidified droplets, are described in US Patent Publication No. 2011/0218123 and U.S. Pat. No. 7,294,503, each of which is incorporated herein by reference in their entireties for all purposes. Such methods provide for a plurality of droplets containing a first fluid and being substantially surrounded by a second fluid, where the first fluid and the second fluid are substantially immiscible (e.g., droplets containing an aqueous-based liquid being substantially surrounded by an oil based liquid).

IV-B. Pre-Apoptotic Signals and Pre-Apoptotic Signal Binders

In embodiments, the hydrogel beads described herein comprise a pre-apoptotic signal or a pre-apoptotic signal binder. In embodiments, pre-apoptotic signal binders are present on cells undergoing apoptosis and bind to pre-apoptotic signals. In embodiments, hydrogel beads comprising pre-apoptotic signal binders serve as mimics of apoptotic cells. In some embodiments, pre-apoptotic signal binders are artificially designed to bind to known pre-apoptotic signals (e.g., antibodies targeted at the pre-apoptotic signal).

Table 1A contains pre-apoptotic signal binders and the pre-apoptotic signals that they bind to. In embodiments, the hydrogel beads described herein comprise one, two, three, four, five, six, seven, eight, nine, or ten different pre-apoptotic signal binders, including all ranges and subranges therebetween. In embodiments, the hydrogel beads described herein comprise one, two, three, four, five, six, seven, eight, nine, or ten different pre-apoptotic signals, including all ranges and subranges therebetween.

TABLE 1A

| Pre-apoptotic signal binder | Pre-apoptotic signal |
| --- | --- |
| Phosphatidylserine | Annexin V or a fragment thereof (UniProt Accession No. P08758) |
| Phosphatidylserine | Apo-15 peptide |
| Phosphatidylserine | β2-glycoprotein1 or a fragment thereof (e.g., domain V) (UniProt Accession No. D9IWP9) |
| Phosphatidylserine | milk fat globule-EGF-factor 8 (MFG-E8) (UniProt Accession No. Q08431) |
| Phosphatidylserine | phosphatidylserine receptor or fragment thereof |
| Anti-CD36 antibody or antigen-binding fragment thereof | CD36 (UniProt Accession No. P16671) |
| Thrombospondin-1 (TSP-1) (UniProt Accession No. P07996) | CD36 (UniProt Accession No. P16671) |
| anti-annexin V antibody or antigen-binding fragment thereof | Annexin V or a fragment thereof (UniProt Accession No. P08758) |
| Annexin I (UniProt Accession No. P04083) | phosphatidylserine receptor or fragment thereof |
| calreticulin (UniProt Accession No. Q96L12) | LDL-receptor related protein (UniProt Accession No. P01130) |
| Calreticulin (UniProt Accession No. Q96L12) | Anti-calreticulin antibody or antigen-binding fragment thereof |
| Anti-β2-glycoprotein1 or antigen-binding fragment thereof | β2-glycoprotein1 or a fragment thereof (e.g., domain V) |
| Anti-Milk fat globule-EGF-factor 8 (MFG-E8) or antigen-binding fragment thereof | milk fat globule-EGF-factor 8 (MFG-E8) (UniProt Accession No. Q08431) |
| Anti-Phosphatidylserine receptor or antigen-binding fragment thereof | phosphatidylserine receptor or fragment thereof |
| Anti-LDL-receptor related protein or antigen-binding fragment thereof | LDL-receptor related protein (UniProt Accession No. P01130) |

The following patent documents and publications describe pre-apoptotic signal binders and pre-apoptotic signals and are incorporated by reference herein in their entirety for all purposes: Elmore, Toxicol Pathol. 2007; 35(4): 495-516; Armstrong et al. EMBO Rep. 2011 Apr. 1; 12(4): 287-288; and U.S. Publication No. 2022/0143160.

In embodiments, the pre-apoptotic signal comprises a polypeptide having at least 75%, at least 80%, at least 85%, at least 90%, at least 95%, at least 98%, or 100% identity to annexin V (UniProt Accession No. P08758), a polypeptide having at least 75%, at least 80%, at least 85%, at least 90%, at least 95%, at least 98%, or 100% identity to SEQ ID NO: 103, a polypeptide having at least 75%, at least 80%, at least 85%, at least 90%, at least 95%, at least 98%, or 100% identity to apo-15 peptide, a polypeptide having at least 75%, at least 80%, at least 85%, at least 90%, at least 95%, at least 98%, or 100% identity to β2-glycoprotein1 or a fragment thereof (UniProt Accession No. D91WP9) (e.g., domain V), a polypeptide having at least 75%, at least 80%, at least 85%, at least 90%, at least 95%, at least 98%, or 100% identity to milk fat globule-EGF-factor 8 (MFG-E8) (UniProt Accession No. 008431), a polypeptide having at least 75%, at least 80%, at least 85%, at least 90%, at least 95%, at least 98%, or 100% identity to phosphatidyl serine receptor or fragment thereof, a polypeptide having at least 75%, at least 80%, at least 85%, at least 90%, at least 95%, at least 98%, or 100% identity to SEQ ID NO: 102, a polypeptide having at least 75%, at least 80%, at least 85%, at least 90%, at least 95%, at least 98%, or 100% identity to CD36 (UniProt Accession No. P16671), a polypeptide having at least 75%, at least 80%, at least 85%, at least 90%, at least 95%, at least 98%, or 100% identity to LDL-receptor related protein (UniProt Accession No. P01130), or a polypeptide having at least 75%, at least 80%, at least 85%, at least 90%, at least 95%, at least 98%, or 100% identity to an anti-calreticulin antibody or antigen-binding fragment thereof.

In embodiments, the pre-apoptotic signal comprises annexin V. Annexin V binds to phosphatidylserine that is present on the outer leaflet of the plasma membrane on apoptotic cells. In embodiments, the annexin V is from a species selected from the group consisting of human, rabbit, mouse, *Ailuropoda melanoleuca, Aotus nancymaae, Balaenoptera acutorostrata scammoni, Balaenoptera musculus, Bos indicus, Bos taurus, Bos indicus, Bos mutus, Bos taurus, Bubalus bubalis, Callithrix jacchus, Camelus bactrianus, Canis lupus familiaris, Capra hircus, Carlito syrichta, Castor canadensis, cattle, Cebus imitator, Cervus canadensis, Cervus elaphus, Cervus hanglu yarkandensis, Delphinapterus leucas, Dipodomys ordii, Dipodomys spectabilis, Elephas maximus indicus, Equus przewalskii, Eschrichtius robustus, Felis catus, Gorilla gorilla, Gorilla beringer, Gulo gulo luscus, Halichoerus grypus, Hyaena hyaena, Hylobates moloch, Ictidomys tridecemlineatus, Jaculus jaculus, Lagenorhynchus obliquidens, Lemur catta, Lipotes vexillifer, Loxodonta africana, Macaca fascicularis, Macaca mulatta, Mandrillus leucophaeus, Marmota flaviventris, Marmota marmota marmota, Marmota monax, Moschus berezovskii, Muntiacus muntjak, Mustela putorius furo, Neogale vison, Neomonachus schauinslandi, Nomascus leucogenys, Nycteutes procyonoides, Odobenus rosmarus divergens, Odocoileus virginianus texanus, Orcinus orca, Ovis aries, Pan troglodytes, Papio anubis, Perognathus longimembris pacificus, Phoca vitulina, Physeter catodon, Piliocolobus tephrosceles, Propithecus coquereli, Rangifer tarandus platyrhyncus, Rhinopithecus bieti, Saimiri boliviensis boliviensis, Sciurus carolinensis, Sorex araneus, Sus scrofa, Trachypithecus francoisi, Tupaia chinensis, Tursiops truncatus, Urocitellus parryii, Ursus maritimus, Vulpes lagopus,* and *Zalophus californianus*. In embodiments, the annexin V protein has at least 75%, at least 80%, at least 85%, at least 90%, at least 91%, at least 92%, at least 93%, at least 94%, at least 95%, at least 96%, at least 97%, at least 98%, at least 99%, or 100% identity to an annexin V protein having the amino acid sequence of any one of SEQ ID NOS: 1-101.

In embodiments, the pre-apoptotic signal comprises a polypeptide of SEQ ID NO: 103. In embodiments, the polypeptide of SEQ ID NO: 103 is cyclic. In embodiments, the pre-apoptotic signal comprises the apo-15 peptide. The apo-15 is a cyclic peptide having the amino acid sequence of GRKKWFW (SEQ ID NO: 104). The structure of apo-15 peptide is described in Barth et al. Nat Commun. 2020 Aug. 12; 11(1):4027, which is incorporated by reference herein in its entirety for all purposes. In embodiments, the cyclic apo-15 peptide comprises any fluorescent dye described herein. In embodiments, the dye is conjugated to the one or more of the tryptophan residues of SEQ ID NO: 104. In embodiments, the dye is BODIPY. In embodiments, the fluorescent dye is Trp-BODIPY. The Trp-BODIPY fluorophore is described in Mendive et al. Nat Protocols. 2017; 12:1588-1619, which is incorporated by reference herein in its entirety for all purposes.

In embodiments, the pre-apoptotic signal is a phospholipid-binding protein. In embodiments, the phospholipid-binding protein is β2-glycoprotein1 (β2GPI) or prothrombin. Both of these proteins bind to phosphatidylserine on apoptotic cells. In embodiments, the pre-apoptotic signal is domain V of β2GPI. β2GPI and prothrombin are described in McDonnell et al. Blood Rev. 2020 January; 39:100610 and Houston et al. Mol Cell Biochem. 2011 February; 348(1-2):109-15. These references are incorporated by reference herein in their entirety for all purposes.

In embodiments, the pre-apoptotic signal is milk fat globule-EGF-factor 8 (MFG-E8). MFG-E8 is an anti-inflammatory glycoprotein that mediates the clearance of apoptotic cells. The following references describe MFG-E8 and are incorporated by reference herein in its entirety for all purposes: Lauber et al. Cell Death Differ. 2013 September; 20(9):1230-40 and Borishenko et al. Cell Death Differ. 2004 August; 11(8):943-5.

In embodiments, the pre-apoptotic signal is a phosphatidylserine receptor or a fragment thereof. Phosphatidylserine receptors are expressed by phagocytes. There are multiple phosphatidylserine receptors that have different structures, cell type expressions, and ability to bind to phosphatidylserine. The following reference describes phosphatidylserine receptors and is incorporated by reference herein in its entirety for all purposes: Naeini et al. Cell Mol Biol Lett. 2020 Mar. 26; 25:23. In embodiments, the phosphatidylserine receptor is selected from any one of a brain-specific angiogenesis inhibitor-1 (Bai1), Axl, Tyro3, Mer, TIM-1 (also known as "KIM-1"), TIM-4, lectin-like oxidized low-density lipoprotein receptor-1 (LOX-1), stabilin-1, stabilin-2, CD300a, CD300b, CD300f, receptor for advanced glycosylation end products (RAGE), complement component 1q (C1q), β2-glycoprotein I (β2GPI), annexins, or integrin αVβ3/β35. Table 1B contains the UniProt Accession Nos. of the aforementioned phosphatidylserine receptors. In embodiments, the pre-apoptotic signal is a polypeptide having at least 75%, at least 80%, at least 85%, at least 90%, at least 95%, at least 98%, or 100% identity to any one of the phosphatidylserine receptors of Table 1B.

TABLE 1B

| Phosphatidylserine receptor | UniProt Accession Nos. |
|---|---|
| brain-specific angiogenesis inhibitor-1 (Bai1) | UniProt Accession No. O41514 |
| Axl | UniProt Accession No. P30530 |
| Tyro3 | UniProt Accession No. Q06418 |
| MER | UniProt Accession No. Q12866 or UniProt Accession No. Q50744 |
| TIM-1 | UniProt Accession No. Q96D42 |
| TIM-4 | UniProt Accession No. Q96H15 |
| lectin-like oxidized low-density lipoprotein receptor-1 (LOX-1) | UniProt Accession No. P78380 |
| stabilin-1 | UniProt Accession No. Q9NY15 |
| stabilin-2 | UniProt Accession No. Q8WWQ8 |
| CD300a | UniProt Accession No. Q9UGN4 |
| CD300b | UniProt Accession No. A8K4G0 |
| CD300f | UniProt Accession No. Q8TDQ1 |

TABLE 1B-continued

| Phosphatidylserine receptor | UniProt Accession Nos. |
|---|---|
| receptor for advanced glycosylation end products (RAGE) | UniProt Accession No. Q15109 |
| component 1q (C1q) | UniProt Accession No. P02746; UniProt Accession No. P02745; UniProt Accession No. P02747 |
| integrin αVβ3/β5 | UniProt Accession No. P06756; UniProt Accession No. P05106; UniProt Accession No. P18084 |

In embodiments, the pre-apoptotic signal is CD36. CD36 binds to thrombospondin-1, which is expressed on apoptotic cells. The following article describes CD36's role in apoptosis and is incorporated by reference in its entirety herein for all purposes: Fadok et al. J Immunol. 1998 Dec. 1; 161(11):6250-7.

In embodiments, the pre-apoptotic signal comprises an LDL-receptor related protein. The LDL-receptor related protein binds to calreticulin and initiates clearance of apoptotic cells. The following article describes LDL-receptor related protein's role in apoptosis and is incorporated by reference herein in its entirety: Gardai et al. Cell. 2005 Oct. 21:123(2):321-324. In embodiments, the pre-apoptotic signal is an anti-calreticulin antibody or antigen-binding fragment thereof.

In embodiments, any of the pre-apoptotic signals described herein may comprise a fluorescent dye. In embodiments, the fluorescent dye is any fluorescent dye described herein.

In embodiments, the pre-apoptotic signal binder is selected from a phosphatidylserine, an anti-annexin V antibody or antigen-binding fragment thereof, annexin I, calreticulin, an anti-CD36 antibody or antigen-binding fragment thereof, thrombospondin-1 (TSP-1), anti-β2-glycoprotein I antibody or antigen-binding fragment thereof, anti-milk fat globule-EGF-factor 8 (MFG-E8) or antigen-binding fragment thereof, anti-phosphatidylserine receptor or antigen-binding fragment thereof, or an anti-LDL-receptor related protein or antigen-binding fragment thereof.

In embodiments, the pre-apoptotic signal binder is an anti-annexin V antibody or an antigen-binding fragment thereof. In embodiments, the anti-annexin V antibody or an antigen-binding fragment thereof binds to SRLYDAYELKHALKG (SEQ ID NO: 102) of an annexin V protein or fragment thereof. In embodiments, the anti-annexin V antibody may be purchased from Boster Biological Technology (#PA1008). In embodiments, the anti-annexin V antibody or antigen-binding fragment thereof binds to an annexin V protein with at least 75%, at least 80%, at least 85%, at least 90%, at least 91%, at least 92%, at least 93%, at least 94%, at least 95%, at least 96%, at least 97%, at least 98%, at least 99%, or 100% identity to any one of SEQ ID NOS: 1-101. In embodiments, the anti-annexin V antibody or antigen-binding fragment thereof binds to an annexin V protein from a species selected from any one of human, rabbit, mouse, *Ailuropoda melanoleuca, Aotus nancymaae, Balaenoptera acutorostrata scammoni, Balaenoptera musculus, Bos indicus* x *Bos taurus, Bos indicus, Bos mutus, Bos taurus, Bubalus bubalis, Callithrix jacchus, Camelus bactrianus, Canis lupus familiaris, Capra hircus, Carlito syrichta, Castor canadensis,* cattle, *Cebus imitator, Cervus canadensis, Cervus elaphus, Cervus hanglu yarkandensis, Delphinapterus leucas, Dipodomys ordii, Dipodomys spectabilis, Elephas maximus indicus, Equus przewalskii, Eschrichtius robustus, Felis catus, Gorilla gorilla,*

*Gorilla beringer, Gulo gulo luscus, Halichoerus grypus, Homo sapiens, Hyaena hyaena, Hylobates moloch, Ictidomys tridecemlineatus, Jaculus jaculus, Lagenorhynchus obliquidens, Lemur catta, Lipotes vexillifer, Loxodonta africana, Macaca fascicularis, Macaca mulatta, Mandrillus leucophaeus, Marmota flaviventris, Marmota marmota marmota, Marmota monax, Moschus berezovskii, Muntiacus muntjak, Mustela putorius furo, Neogale vison, Neomonachus schauinslandi, Nomascus leucogenys, Nyctereutes procyonoides, Odobenus rosmarus divergens, Odocoileus virginianus texanus, Orcinus orca, Ovis aries, Pan troglodytes, Papio anubis, Perognathus longimembris pacificus, Phoca vitulina, Physeter catodon, Piliocolobus tephrosceles, Propithecus coquereli, Rangifer tarandus platyrhyncus, Rhinopithecus bieti, Saimiri boliviensis boliviensis, Sciurus carolinensis, Sorex araneus, Sus scrofa, Trachypithecus francoisi, Tupaia chinensis, Tursiops truncatus, Urocitellus parryii, Ursus maritimus, Vulpes lagopus,* and *Zalophus californianus.*

In embodiments, the pre-apoptotic signal binder is phosphatidylserine. The structure of a phosphatidylserine contains a glycerol backbone linked to two fatty acids and a phosphoserine molecule. The structure of phosphatidylserine is below. The R groups in the structure represent fatty acids.

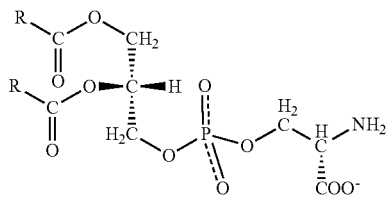

In embodiments, the pre-apoptotic signal binder is annexin I. Annexin I is a glucocorticoid-regulated protein that has been implicated in the regulation of phagocytosis, cell signaling and proliferation, and is postulated to be a mediator of glucocorticoid action in inflammation and in the control of anterior pituitary hormone release. Annexin I expression is elevated in apoptotic cells and appears to play a role in bridging phosphatidylserine on apoptotic cells to phagocytes and to enhancing recognition of apoptotic cells by phagocytes such as macrophages.

In embodiments, any one of the pre-apoptotic signal binders described herein may comprise a fluorescent dye. In embodiments, the fluorescent dye is any fluorescent dye described herein.

In some embodiments the pre-apoptotic signal binder or pre-apoptotic signal are embedded within the hydrogel matrix. In some embodiments the pre-apoptotic signal binder or pre-apoptotic signal are attached at the surface of the hydrogel. In some embodiments the pre-apoptotic signal binder or pre-apoptotic signal are attached to the hydrogel via a functional group (e.g., an amine group or a biotin or a streptavidin).

IV-C. Encapsulated Nucleic Acids

In embodiments, the hydrogel beads described herein further comprise an encapsulated nucleic acid. Hydrogel beads comprising an encapsulated nucleic acid serve as mimics for dead cells. Dead cells typically have compromised cellular membranes and thus exposed DNA.

In embodiments, the hydrogel beads described herein comprise (a) a polymerized monomer and a bifunctional monomer; (b) a pre-apoptotic signal; and (c) an encapsulated nucleic acid.

In embodiments, the hydrogel beads described herein comprise (a) a polymerized monomer and a bifunctional monomer; (b) a pre-apoptotic signal binder; and (c) an encapsulated nucleic acid.

In embodiments, the encapsulated nucleic acid is selected from any one of double stranded DNA, single stranded DNA, complementary DNA (cDNA), and RNA. In embodiments, the encapsulated nucleic acid is double stranded DNA.

In embodiments, hydrogel beads comprising an encapsulated nucleic acid bind to a dye. In embodiments, the dye intercalates between DNA or RNA bases. In embodiments, the dye binds to the major groove of DNA. In embodiments, the dye binds to the minor groove of DNA. In embodiments, the dye is selected from the group consisting of 7-aminoactinomycin D (7AAD), propidium iodide, Hoechst 33258, Hoechst 33342, Hoechst 34580, 4',6-diamidino-2-phenylindole (DAPI), DRAQ5™, DRAQ7™, CytoPhase™ Violet, Helix NP™ Blue, Helix NP™ Green, Helix NP™ NIR, YOYO™-1, TOTO™-1 Iodide (Thermo Fisher Scientific), TO-PRO-3®, SYTOX™ Blue, ethidium bromide, SYBR™ Gold, SYBR™ Green, SYBR™ Safe, EvaGreen®, and crystal violet.

Persons having skill in the art will be familiar with other dyes and detectors of DNA, which in some embodiments, are compatible with the inventions of the instant disclosure.

IV-D. Additional Constituents

In embodiments, a hydrogel bead described herein may comprise one or more additional chemical moieties. In embodiments, a hydrogel bead described herein comprises one or more fluorescent dyes. In embodiments, the fluorescent dye is attached to the hydrogel bead via a covalent bond. In embodiments, the fluorescent dye is attached to the hydrogel bead via noncovalent interactions. In embodiments, the fluorescent dye is selected from one or more of: 6-carboxy-4', 5'-dichloro-2', 7'-dimethoxyfluorescein succinimidylester; 5-(and -6)-carboxyeosin; 5-carboxyfluorescein; 6 carboxyfluorescein; 5-(and -6)-carboxyfluorescein; 5-carboxyfluorescein-bis-(5-carboxymethoxy-2-nitrobenzyl)ether,-alanine-carboxamide, or succinimidyl ester; 5-carboxy fluorescein succinimidyl ester; 6-carboxyfluorescein succinimidyl ester; 5-(and -6)-carboxyfluorescein succinimidyl ester; 5-(4,6-dichlorotriazinyl) amino fluorescein; 2', 7'-difluoro fluorescein; eosin-5-isothiocyanate; erythrosin5-isothiocyanate; 6-(fluorescein-5-carboxamido) hexanoic acid or succinimidyl ester; 6-(fluorescein-5-(and -6)-carboxamido) hexanoic acid or succinimidylester; fluorescein-S-EX succinimidyl ester; fluorescein-5-isothiocyanate; fluorescein-6-isothiocyanate; OregonGreen® 488 carboxylic acid, or succinimidyl ester; Oregon Green® 488 isothiocyanate; Oregon Green® 488-X succinimidyl ester; Oregon Green® 500 carboxylic acid; Oregon Green® 500 carboxylic acid, succinimidylester or triethylammonium salt; Oregon Green® 514 carboxylic acid; Oregon Green® 514 carboxylic acid or succinimidyl ester; Rhodamine-Green™ carboxylic acid, succinimidyl ester or hydrochloride; Rhodamine Green™ carboxylic acid, trifluoroacetamide or succinimidylester; Rhodamine Green™-X succinimidyl ester or hydrochloride; RhodolGreen™ carboxylic acid, N,O-bis-(trifluoroacetyl) or succinimidylester; bis-(4-carboxypiperidinyl) sulfonerhodamine or di(succinimidylester); 5-(and -6)carboxynaphtho fluorescein, 5-(and -6)carboxynaphthofluorescein succinimidyl ester; 5-carboxyrhodamine 6G hydrochloride; 6-carboxyrhodamine6Ghydrochloride, 5-carboxyrhodamine 6G succinimidyl ester; 6-carboxyrhodamine 6G succinimidyl ester; 5-(and -6)-carboxyrhodamine6G succinimidyl ester; 5-carboxy-2',4',5',7'-tetrabromosulfonefluorescein succinimidyl esteror bis-(diisopropylethylammonium) salt; 5-carboxytetramethylrhodamine; 6-carboxytetramethylrhodamine; 5-(and -6)-carboxytetramethylrhodamine; 5-carboxytetramethylrhodamine succinimidyl ester; 6-carboxytetramethylrhodaminesuccinimidyl ester; 5-(and -6)-carboxytetramethylrhodamine succinimidyl ester; 6-carboxy-X-rhodamine; 5-carboxy-X-rhodamine succinimidyl ester; 6-carboxy-Xrhodamine succinimidyl ester; 5-(and -6)-carboxy-Xrhodaminesuccinimidyl ester; 5-carboxy-X-rhodamine triethylammonium salt; Lissamine™ rhodamine B sulfonyl chloride; malachite green; isothiocyanate; NANOGOLD® mono(sulfosuccinimidyl ester); QSY® 21carboxylic acid or succinimidyl ester; QSY® 7 carboxylic acid or succinimidyl ester; Rhodamine Red™-X succinimidyl ester; 6-(tetramethylrhodamine-5-(and -6)-carboxamido) hexanoic acid; succinimidyl ester; tetramethylrhodamine-5-isothiocyanate; tetramethylrhodamine-6-isothiocyanate; tetramethylrhodamine-5-(and -6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; and X-rhodamine-5-(and -6) isothiocyanate, BODIPY® dyes commercially available from Invitrogen, including, but not limited to BODIPY® FL; BODIPY® TMR STP ester; BODIPY® TR-X STP ester; BODIPY® 630/650-X STPester; BODIPY® 650/665-X STP ester; 6-dibromo-4, 4-difluoro-5, 7-dimethyl-4-bora-3 a, 4a-diaza-s-indacene-3-propionic acid succinimidyl ester; 4,4-difluoro-4-bora-3a,4a-diaza-s-indacene-3,5-dipropionic acid; 4,4-difluoro-5,7-dimethyl-4-bora-3a,4a-diaza-s-indacene-3-pentanoicacid; 4,4-difluoro-5,7-dimethyl-4-bora3a,4a-diaza-s-indacene-3-pentanoicacid succinimidyl ester; 4,4-difluoro-5,7-dimefhyl-4-bora-3 a, 4a-diaza-s-indacene-3propionicacid; 4, 4-difluoro-5, 7-dimethyl-4-bora-3 a, 4adiaza-s-indacene-3-propionicacid succinimidyl ester; 4, 4difluoro-5, 7-dimefhyl-4-bora-3a,4a-diaza-s-indacene-3propionic acid; sulfosuccinimidyl ester or sodium salt; 6-((4,4-difluoro-5, 7-dimethyl-4-bora-3a,4a-diaza-s-indacene-3propionyl)amino)hexanoicacid; 6-((4,4-difluoro-5, 7 dimethyl-4-bora-3a,4a-diaza-s-indacene-3-propionyl)amino)hexanoic acid or succinimidyl ester; N-(4, 4-difluoro 5, 7-dimethyl-4-bora-3 a, 4a-diaza-s-indacene-3-propionyl) cysteic acid, succinimidyl ester or triethylammonium salt; 6-4,4-difluoro-1,3-dimethyl-5-(4-methoxyphenyl)-4-bora3a, 4a4, 4-difluoro-5, 7-diphenyl-4-bora-3a,4a-diaza-sindacene-3-propionicacid; 4, 4-difluoro-5, 7-diphenyl-4-bora3 a, 4a-diaza-s-indacene-3-propionicacid succinimidyl ester; 4, 4-difluoro-5-phenyl-4-bora-3 a, 4a-diaza-s-indacene-3-propionic acid; succinimidyl ester; 6-((4, 4-difluoro-5-phenyl-4 bora-3 a, 4a-diaza-s-indacene-3-propionyl)amino) hexanoicacid or succinimidyl ester; 4,4-difluoro-5-(4-phenyl-1,3butadienyl)-4-bora-3 a, 4a-diaza-s-indacene-3-propionicacid succinimidyl ester; 4, 4-difluoro-5-(2-pyrrolyl)-4-bora-3a,4a-diaza-s-indacene-3-propionic acid succinimidyl ester; 6-(((4,4-difluoro-5-(2-pyrrolyl)-4-bora-3a,4a-diaza-s-indacene-3-yl)styryloxy)acetyl)aminohexanoicacid or succinimidyl ester; 4,4-difluoro-5-styryl-4-bora-3a, 4a-diaza-s-indacene-3-propionic acid; 4, 4-difluoro-5-styryl-4-bora-3 a, 4a-diaza-sindacene-3-propionic acid; succinimidyl ester; 4,4-difluoro-1,3,5,7-tetramethyl-4-bora-3a,4adiaza-s-indacene-8-propionicacid; 4,4-difluoro-1,3,5,7-tetramethyl-4bora-3a,4a-diaza-sindacene-8-propionic acid succinimidyl ester; 4,4-difluoro-5-(2-thienyl)-4-bora-3a,4a-diaza-sindacene-3-propionic acid succinimidyl ester; 6-(((4-(4, 4-difluoro-5-(2-thienyl)-4-bora-3 a, 4adiazas-indacene-3-yl)phenoxy)acetyl)amino) hexanoic acid or succinimidyl ester; and 6-(((4,4-difluoro-5-(2-thienyl)-4-bora-3a,4a-diaza-s-indacene-3-yl)styryloxy) acetyl) aminohexanoic acid or succinimidyl ester, Alexa fluor dyes commercially available from Invitrogen, including but not limited to Alexa Fluor® 350 carboxylic acid; Alexa Fluor® 430 carboxylic acid; Alexa Fluor® 488 carboxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 64 7 carboxylic acid; Alexa Fluor® 660 carboxylic acid; and Alexa Fluor® 680 carboxylic acid, cyanine dyes commercially available from Amersham-Pharmacia Biotech, including, but not limited to Cy3 NHS ester; Cy 5 NHS ester; Cy5.5 NHSester; and Cy7 NHS ester.

In embodiments, a hydrogel bead may comprise from 1 to about 20 fluorescent dyes, from 1 to about 10 fluorescent dyes, or from 1 to about 5 fluorescent dyes. In embodiments, a hydrogel bead comprises 1, 2, 3, 4, 5, 6, 7, 8, 9, about 10, about 11, about 12, about 13, about 14, about 15, about 16, about 17, about 18, about 19, or about 20 fluorescent dyes, including all values and subranges in between inclusive of endpoints.

In embodiments, a hydrogel bead comprises a "rainbow particle." Rainbow particles contain a mixture of fluorophores. In embodiments, the rainbow particle comprises from 1 to about 20 fluorophores, from 1 to about 10 fluorophores, or from 1 to about 5 fluorophores. In embodiments, a hydrogel bead comprises a rainbow particle with 1, 2, 3, 4, 5, 6, 7, 8, 9, about 10, about 11, about 12, about 13, about 14, about 15, about 16, about 17, about 18, about 19, or about 20 fluorophores, including all values and subranges in between inclusive of endpoints. In embodiments, a user selects a wavelength with which to excite the rainbow particle with, depending on the fluorophore being interrogated. Rainbow particles are commercially available, for example, from BD Biosciences (catalog nos. 556298 (mid range FL1 fluorescence), 556286 (6 color, 3.0-3.4 µm), 556288 (6 color, 6.0-6.4 µm), 559123 (8 color)) and Spherotech in various diameters (e.g., catalog nos. RCP20-5 (4 color), RCP-30-5 (6 peaks), RCP-30-5A (8 peaks).

In embodiments, the hydrogel bead comprises a scatter-modulating additive. In embodiments, the scatter-modulating additive comprises polymer nanoparticles. In embodiments, the polymer nanoparticles comprise polystyrene. In embodiments, the scatter-modulating additive includes a co-monomer. In embodiments, the scatter-modulating additive includes a suspension of nanoparticles.

In embodiments, the hydrogel bead is a chemically functionalized hydrogel particle. In embodiments, the hydrogel comprises a free amine group. In embodiments, the pre-apoptotic signal binder is attached to the free amine group. In embodiments, the pre-apoptotic signal is attached to the free amine group. In embodiments, the hydrogel bead comprises allylamine. In embodiments, the hydrogel bead comprises biotin. In embodiments, the hydrogel bead comprises streptavidin. In embodiments, the hydrogel bead comprises avidin. In embodiments, the chemically functionalized hydrogel particle comprises an amine group, a carboxyl group, a hydroxyl group, or a combination thereof. In embodiments, the hydrogel bead comprises multiple bifunctional monomers to functionalize the hydrogel bead with different chemistries and/or molecules.

In embodiments, the hydrogel bead is functionalized to mimic one or more optical properties of a target cell or labeled target cell. In embodiments, the hydrogel bead comprises one or more high-refractive index molecules. In embodiments, the hydrogel bead comprises a plurality of high-refractive index molecules. In embodiments, the high-refractive index molecule enables for mimicking of the SSC of a target cell. In embodiments, the high-refractive index molecule is selected from one or more of colloidal silica, alkyl acrylate, alkyl methacrylate or a combination thereof. In embodiments, the high-refractive index molecule is alkyl acrylate, alkyl methacrylate, or both. In embodiments, alkyl acrylates or alkyl methacrylates contain 1 to 18, 1 to 8, or 2 to 8, carbon atoms in the alkyl group. In embodiments, the alkyl group is methyl, ethyl, n-propyl, isopropyl, n-butyl, isobutyl or tertbutyl, 2-ethylhexyl, heptyl or octyl. In embodiments, the alkyl group is branched. In embodiments, the alkyl group is linear.

In embodiments, the hydrogel bead comprises a cell surface marker, an epitope binding region of a cell surface marker, or a combination thereof.

V. Properties of Hydrogel Beads

In embodiments, the hydrogel beads described herein comprise an artificial optical scatter property that is substantially similar to a corresponding optical-scatter property of a target cell.

In embodiments, the target cell is a lymphocyte, a monocyte, or a granulocyte. In embodiments, the target cell is a prokaryotic cell. In embodiments, the target cell is a eukaryotic cell. In embodiments, the target cell is a white blood cell. In embodiments, the target cell is a platelet. In embodiments, the target cell is a red blood cell. In embodiments, the target cell is an immune cell. In embodiments, the immune cell is a T cell, a B cell, an NK cell, a lymphocyte, a monocyte, a granulocyte, a neutrophil, an eosinophil, a basophil, a mast cell, a macrophage, or a dendritic cell.

In embodiments, the optical scatter property is selected from side scatter (SSC), forward scatter (FSC), an angled light scattering profile, or a secondary marker profile, such as a fluorescence marker profile, absorption profile, fluorescence profile or emissions profile.

In embodiments, the artificial optical scatter property is provided by a co-monomer, a chemical side-group, an encapsulated material, a colloidal silica, or a ratio of acrylamide to bis-acrylamide.

In embodiments, the optical-scatter property that is substantially similar to the corresponding optical-scatter property of the target cell is SSC. In embodiments, a hydrogel bead has a SSC within 30%, within 25%, within 20%, within 15%, within 10%, within 5%, or within 1% that of a target cell, as measured by a cytometric device. In embodiments, side scattering of the a hydrogel bead is tuned by adding a colloidal suspension of silica nanoparticles and/or PMMA (poly(methyl methacrylate)) particles (~100 nm) to the central aqueous phase prior to polymerization.

In embodiments, the optical-scatter property that is substantially similar to the corresponding optical-scatter property of the target cell is FSC. In embodiments, the forward scatter of a hydrogel bead may be modulated by adjusting the refractive index of the hydrogel. In embodiments, the refractive index of a hydrogel bead described herein may be measured using interferometry, the deviation method, the Brewster Angle method, or by using a refractometer. In embodiments, the refractive index of the hydrogel may be adjusted by adding co-monomers. In embodiments, the co-monomers are allyl acrylate, allyl methacrylate, or a combination thereof. Forward scatter can also be modulated with side scattering nanoparticles containing sufficient optical resolution/size/density including, but not limited to, higher density colloidal suspensions of silica and/or PMMA particles.

In embodiments, the refractive index (RI) of a hydrogel bead provided herein is greater than about 1.10, greater than about 1.15, greater than about 1.20, greater than about 1.25, greater than about 1.30, greater than about 1.35, greater than about 1.40, greater than about 1.45, greater than about 1.50, greater than about 1.55, greater than about 1.60, greater than about 1.65, greater than about 1.70, greater than about 1.75, greater than about 1.80, greater than about 1.85, greater than about 1.90, greater than about 1.95, greater than about 2.00, greater than about 2.10, greater than about 2.20, greater than about 2.30, greater than about 2.40, greater than about 2.50, greater than about 2.60, greater than about 2.70, greater than about 2.80, or greater than about 2.90.

In embodiments, the refractive index (RI) of a hydrogel bead provided herein is from about 1.10 to about 3.0, or from about 1.15 to about 3.0, or from about 1.20 to about 3.0, or from about 1.25 to about 3.0, or from about 1.30 to about 3.0, or from about 1.35 to about 3.0, or from about 1.4 to about 3.0, or from about 1.45 to about 3.0, or from about 1.50 to about 3.0, or from about 1.6 to about 3.0, or from about 1.7 to about 3.0, or from about 1.8 to about 3.0, or from about 1.9 to about 3.0, or from about 2.0 to about 3.0.

In embodiments, the refractive index (RI) of a hydrogel bead provided herein is less than about 1.10, less than about 1.15, less than about 1.20, less than about 1.25, less than about 1.30, less than about 1.35, less than about 1.40, less than about 1.45, less than about 1.50, less than about 1.55, less than about 1.60, less than about 1.65, less than about 1.70, less than about 1.75, less than about 1.80, less than about 1.85, less than about 1.90, less than about 1.95, less than about 2.00, less than about 2.10, less than about 2.20, less than about 2.30, less than about 2.40, less than about 2.50, less than about 2.60, less than about 2.70, less than about 2.80, or less than about 2.90.

In embodiments, the hydrogel bead has a refractive index of greater than about 1.15. In embodiments, the hydrogel bead has a refractive index of greater than about 1.3. In embodiments, the hydrogel bead has a refractive index of greater than about 1.7.

In some embodiments, a hydrogel particle of the disclosure has material modulus properties (e.g., elasticity) more closely resembling that of a target cell as compared to a polystyrene bead of the same diameter.

In embodiments, the dimensions (e.g., diameter, width, thickness) of a hydrogel bead of the present disclosure are substantially similar to a target cell. In embodiments, a hydrogel bead has a diameter of less than about 1 μm, about 2 μm, about 5 μm, about 10 μm, about 15 μm, about 20 μm, about 25 μm, about 30 μm, about 35 μm, about 40 μm, about 45 μm, about 50 μm, about 60 μm, about 70 μm, about 80 μm, about 90 μm, about 100 μm, about 120 μm, about 150 μm, about 200 μm, about 250 μm, about 300 μm, about 350 μm, about 400 μm, about 450 μm, about 500 μm, about 600 μm, about 800 μm, or less than about 1000 μm in diameter. In some embodiments, a hydrogel particle has a diameter of more than about 1 μm, 2, 5, 10, 15, 20, 25, 30, 35, 40, 45, 50, 60, 70, 80, 90, 100, 120, 150, 200, 250, 300, 350, 400, 450, 500, 600, 800, or greater than 1000 μm in diameter. In some embodiments, a hydrogel particle has a diameter in the range of 2.5 μm to 100 μm. In some embodiments, a hydrogel particle has a diameter of from about 2.5 μm to about 25 μm, from about 3 μm to about 20 μm, from about 3.5 μm to about 15 μm, from about 4 μm to about 12 μm, from about 5 μm to about 10 μm, from about 6 μm to about 9 μm, from about 7 μm to about 8 μm, or from about 10 μm to about 20 μm. In embodiments, the hydrogel bead has a diameter of less than about 100 μm. In embodiments, the hydrogel bead has a diameter of less than about 10 μm. In embodiments, the hydrogel bead has a diameter of more than about 10 μm. In embodiments, the hydrogel bead has a diameter from about 10 μm to about 20 μm. In embodiments, a hydrogel bead has a diameter of less than about 1 μm. In embodiments, a hydrogel bead has a diameter of more than about 1 μm. In embodiments, the diameter of a hydrogel bead is measured using dynamic light scattering.

In embodiments, a hydrogel bead has a width of less than about 1 μm, about 2 μm, about 5 μm, about 10 μm, about 15 μm, about 20 μm, about 25 μm, about 30 μm, about 35 μm, about 40 μm, about 45 μm, about 50 μm, about 60 μm, about 70 μm, about 80 μm, about 90 μm, about 100 μm, about 120 μm, about 150 μm, about 200 μm, about 250 μm, about 300 μm, about 350 μm, about 400 μm, about 450 μm, about 500 μm, about 600 μm, about 800 μm, or less than about 1000 μm. In some embodiments, a hydrogel particle has a width of more than about 1 μm, about 2 μm, about 5 μm, about 10 μm, about 15 μm, about 20 μm, about 25 μm, about 30 μm, about 35 μm, about 40 μm, about 45 μm, about 50 μm, about 60 μm, about 70 μm, about 80 μm, about 90 μm, about 100 μm, about 120 μm, about 150 μm, about 200 μm, about 250 μm, about 300 μm, about 350 μm, about 400 μm, about 450 μm, about 500 μm, about 600 μm, about 800 μm, or about 1000 μm. In some embodiments, a hydrogel particle has a width in the range of 2.5 μm to 100 μm. In some embodiments, a hydrogel particle has a width of from about 2.5 μm to about 25 μm, from about 3 μm to about 20 μm, from about 3.5 μm to about 15 μm, from about 4 μm to about 12 μm, from about 5 μm to about 10 μm, from about 6 μm to about 9 μm, or from about 7 μm to about 8 μm.

In embodiments, a hydrogel particle has a thickness of less than about 1 μm, about 2 μm, about 5 μm, about 10 μm, about 15 μm, about 20 μm, about 25 μm, about 30 μm, about 35 μm, about 40 μm, about 45 μm, about 50 μm, about 60 μm, about 70 μm, about 80 μm, about 90 μm, about 100 μm, about 120 μm, about 150 μm, about 200 μm, about 250 μm, about 300 μm, about 350 μm, about 400 μm, about 450 μm, about 500 μm, about 600 μm, about 800 μm, or less than about 1000 μm. In some embodiments, a hydrogel particle has a thickness of more than about 1 μm, about 2 μm, about 5 μm, about 10 μm, about 15 μm, about 20 μm, about 25 μm, about 30 μm, about 35 μm, about 40 μm, about 45 μm, about 50 μm, about 60 μm, about 70 μm, about 80 μm, about 90 μm, about 100 μm, about 120 μm, about 150 μm, about 200 μm, about 250 μm, about 300 μm, about 350 μm, about 400 μm, about 450 μm, about 500 μm, about 600 μm, about 800 μm, or less than about 1000 μm, including all ranges and subranges therebetween. In some embodiments, a hydrogel particle has a thickness in the range of 2.5 μm to 100 μm. In some embodiments, a hydrogel particle has a thickness of from about 2.5 μm to about 25 μm, from about 3 μm to about 20 μm, from about 3.5 μm to about 15 μm, from about 4 μm to about 12 μm, from about 5 μm to about 10 μm, from about 6 μm to about 9 μm, or from about 7 μm to about 8

In embodiments, the hydrogel bead exhibits a mean fluorescence intensity (MFI) when labeled with the pre-apoptotic signal that is at least as high as the MFI of a target cell labeled with the same pre-apoptotic signal.

In embodiments, the hydrogel bead exhibits a mean fluorescence intensity (MFI) when labeled with the pre-apoptotic signal that is substantially the same as the MFI of a target cell labeled with the same pre-apoptotic signal.

In embodiments, the MFI of the hydrogel bead and the MFI of the target cell are within 10% to within 50%. In embodiments, the MFI of the hydrogel bead and the MFI of the target cell are within 10%, within 11%, within 12%, within 13%, within 14%, within 15%, within 16%, within 17%, within 18%, within 19%, within 20%, within 21%, within 22%, within 23%, within 24%, within 25%, within 26%, within 27%, within 28%, within 29%, within 30%, within 31%, within 32%, within 33%, within 34%, within 35%, within 36%, within 37%, within 38%, within 39%, within 40%, within 41%, within 42%, within 43%, within 44%, within 45%, within 46%, within 47%, within 48%, within 49%, or within 50%, including all values and subranges in between inclusive of endpoints.

In embodiments, the MFI of the hydrogel bead and the MFI of the target cell is within 50%, 40%, 30%, 20%, or 10%.

In embodiments, the hydrogel bead exhibits a mean fluorescence intensity (MFI) when labeled with a DNA binding dye that is at least as high as the MFI of a target cell labeled with the same DNA binding dye. In embodiments, the hydrogel bead exhibits a mean fluorescence intensity (MFI) when labeled with a DNA binding dye that is substantially the same as the MFI of a target cell labeled with the same DNA binding dye.

VI. Kits Comprising Hydrogel Beads

In embodiments, kits comprising the hydrogel beads of Section IV described herein are provided.

In embodiments provided herein is a kit comprising: a) a first population of hydrogel beads, each bead comprising: i) a polymerized monomer; ii) a pre-apoptotic signal binder; and iii) an encapsulated nucleic acid; b) a second population of hydrogel beads, each bead comprising: i) a polymerized monomer; ii) a pre-apoptotic signal binder; but iii) lacking the encapsulated nucleic acid of the first population of hydrogel beads; and c) a third population of hydrogel beads comprising: i) a polymerized monomer; but ii) lacking the pre-apoptotic signal binder of the first population of hydrogel beads. iii) lacking the encapsulated nucleic acid of the first population of hydrogel beads.

In embodiments, the second and third populations of the hydrogels do not contain any nucleic acids. In embodiments, the second and third populations of the hydrogels do not contain any double stranded DNA. In embodiments, the first, second, and third, population of hydrogel beads are at a w/w ratio of about 1:1:1. In embodiments, the first, second, and third, population of hydrogel beads are at a ratio of about 1:1:1 by number of beads.

In embodiments, the first, second, and third, population of hydrogel beads are at a w/w ratio of about 1:1:8, about 1:2:7, about 1:3:6, about 1:4:5, about 1:5:4, about 1:6:3, about 1:7:2, about 1:8:1, about 2:1:7, about 2:2:6, about 2:3:5, about 2:4:4, about 2:5:3, about 2:6:2, about 2:7:1, about 3:1:6, about 3:2:5, about 3:3:4, about 3:4:3, about 3:5:2, about 3:6:1, about 4:1:5, about 4:2:4, about 4:3:3, about 4:4:2, about 4:5:1, about 5:1:4, about 5:2:3, about 5:3:2, about 5:4:1, about 6:1:3, about 6:2:2, about 6:3:1, about 7:1:2, about 7:2:1, or about 8:1:1. In embodiments, In embodiments, the first, second, and third, population of hydrogel beads are at a ratio of about 1:1:8, about 1:2:7, about 1:3:6, about 1:4:5, about 1:5:4, about 1:6:3, about 1:7:2, about 1:8:1, about 2:1:7, about 2:2:6, about 2:3:5, about 2:4:4, about 2:5:3, about 2:6:2, about 2:7:1, about 3:1:6, about 3:2:5, about 3:3:4, about 3:4:3, about 3:5:2, about 3:6:1, about 4:1:5, about 4:2:4, about 4:3:3, about 4:4:2, about 4:5:1, about 5:1:4, about 5:2:3, about 5:3:2, about 5:4:1, about 6:1:3, about 6:2:2, about 6:3:1, about 7:1:2, about 7:2:1, or about 8:1:1 by number of beads.

In embodiments, each of the first, second, and third, population of hydrogel beads represents about 10-50% of the total amount of hydrogel beads in the kit or composition by weight. In embodiments, each of the first, second, and third, population of hydrogel beads represents about 10-50% of total amount of hydrogel beads in the kit or composition by number of beads.

VII. Compositions Comprising Hydrogel Beads

In embodiments, compositions comprising the hydrogel beads of Section IV described herein are provided.

In embodiments, the compositions comprise a) a first population of hydrogel beads, each bead comprising: i) a polymerized monomer; ii) a pre-apoptotic signal binder; and iii) an encapsulated nucleic acid; b) a second population of hydrogel beads, each bead comprising: i) a polymerized monomer; ii) a pre-apoptotic signal binder; but iii) lacking the encapsulated nucleic acid of the first population of hydrogel beads; and c) a third population of hydrogel beads comprising: i) a polymerized monomer; but ii) lacking the pre-apoptotic signal binder of the first population of hydrogel beads; but iii) lacking the encapsulated nucleic acid of the first population of hydrogel beads.

In embodiments, the compositions comprise a) a first population of hydrogel beads, each bead comprising: i) a polymerized monomer; ii) a pre-apoptotic signal binder; and iii) an encapsulated nucleic acid; b) a second population of hydrogel beads, each bead comprising: i) a polymerized monomer; ii) a pre-apoptotic signal binder; but iii) lacking the encapsulated nucleic acid of the first population of hydrogel beads; and c) a third population of hydrogel beads comprising: i) a polymerized monomer; but ii) lacking the pre-apoptotic signal binder of the first population of hydrogel beads; but iii) lacking the encapsulated nucleic acid of the first population of hydrogel beads.

In embodiments, the compositions comprise a) a first population of hydrogel beads, each bead comprising: i) a polymerized monomer; ii) a pre-apoptotic signal; and iii) an encapsulated nucleic acid; b) a second population of hydrogel beads, each bead comprising: i) a polymerized monomer; ii) a pre-apoptotic signal; but iii) lacking the encapsulated nucleic acid of the first population of hydrogel beads; and c) a third population of hydrogel beads comprising: i) a polymerized monomer; but ii) lacking the pre-apoptotic signal of the first population of hydrogel beads; but iii) lacking the encapsulated nucleic acid of the first population of hydrogel beads.

In embodiments, the second and third populations of the hydrogels do not contain any nucleic acids. In embodiments, the second and third populations of the hydrogels do not contain any double stranded DNA. In embodiments, the first, second, and third, population of hydrogel beads are at a w/w ratio of about 1:1:1. In embodiments, the first, second, and third, population of hydrogel beads are at a ratio of about 1:1:1 by number of beads. In embodiments, each of the first, second, and third, population of hydrogel beads represents about 10-50% of total amount of hydrogel beads in the kit or composition by weight. In embodiments, each of the first, second, and third, population of hydrogel beads represents about 10-50% of total amount of hydrogel beads in the kit or composition by number of beads.

In embodiments, the first, second, and third, population of hydrogel beads are at a w/w ratio of about 1:1:8, about 1:2:7, about 1:3:6, about 1:4:5, about 1:5:4, about 1:6:3, about 1:7:2, about 1:8:1, about 2:1:7, about 2:2:6, about 2:3:5, about 2:4:4, about 2:5:3, about 2:6:2, about 2:7:1, about 3:1:6, about 3:2:5, about 3:3:4, about 3:4:3, about 3:5:2, about 3:6:1, about 4:1:5, about 4:2:4, about 4:3:3, about 4:4:2, about 4:5:1, about 5:1:4, about 5:2:3, about 5:3:2, about 5:4:1, about 6:1:3, about 6:2:2, about 6:3:1, about 7:1:2, about 7:2:1, or about 8:1:1. In embodiments, the first, second, and third, population of hydrogel beads are at a ratio of about 1:1:8, about 1:2:7, about 1:3:6, about 1:4:5, about 1:5:4, about 1:6:3, about 1:7:2, about 1:8:1, about 2:1:7, about 2:2:6, about 2:3:5, about 2:4:4, about 2:5:3, about 2:6:2, about 2:7:1, about 3:1:6, about 3:2:5, about 3:3:4, about 3:4:3, about 3:5:2, about 3:6:1, about 4:1:5, about 4:2:4, about 4:3:3, about 4:4:2, about 4:5:1, about 5:1:4, about 5:2:3, about 5:3:2, about 5:4:1, about 6:1:3, about 6:2:2, about 6:3:1, about 7:1:2, about 7:2:1, or about 8:1:1 by number of beads.

VIII. Methods of Utilizing Hydrogel Beads

In embodiments, provided herein are methods of determining if a target cell sample includes one or more dead or pre-apoptotic cells. In embodiments, the method comprises: a) providing a population of hydrogel beads described herein, or a kit or composition provided herein; b) contacting said population of hydrogel beads with a pre-apoptotic signal and/or a DNA dye; c) measuring concentration of pre-apoptotic signal and/or DNA dye in the population of hydrogel beads; d) measuring concentration of pre-apoptotic signal and/or DNA dye in the target cell sample; and e) comparing the measured concentrations of pre-apoptotic signal and/or DNA dye in the population of hydrogel beads and target cell sample; thereby determining if the target cell sample includes one or more dead or pre-apoptotic cells.

In embodiments, provided herein is a method of determining if a target cell sample includes one or more dead or pre-apoptotic cells, said method comprising: a) providing a population of hydrogel beads, kit, or composition described herein, b) contacting said population of hydrogel beads with a pre-apoptotic signal and/or a DNA dye; c) measuring concentration of pre-apoptotic signal and/or DNA dye in the population of hydrogel beads in a cytometric device; d) calibrating the cytometric device based on the measured concentration of pre-apoptotic signal and/or DNA dye of the hydrogel beads; and e) measuring concentration of pre-apoptotic signal and/or DNA dye in the target cell sample to determine if the target cell sample includes one or more dead or pre-apoptotic cells.

In embodiments, provided herein is a method of determining if a target cell sample includes one or more dead or pre-apoptotic cells, said method comprising: a) providing a population of hydrogel beads described herein, or a population of hydrogel beads from the kits or compositions described herein; wherein at least a subpopulation of hydrogel beads within the population of hydrogel beads, comprises a pre-apoptotic signal and/or a DNA dye; b) measuring concentration of pre-apoptotic signal and/or DNA dye in the population of hydrogel beads; c) measuring concentration of pre-apoptotic signal and/or DNA dye in the target cell sample; and d) comparing the measured concentrations of pre-apoptotic signal and/or DNA dye in the population of hydrogel beads and target cell sample; thereby determining if the target cell sample includes one or more dead or pre-apoptotic cells.

In embodiments, provided herein is a method of determining if a target cell sample includes one or more dead or pre-apoptotic cells, said method comprising: a) providing a population of hydrogel beads described herein, or a population of hydrogel beads from the kits or compositions described herein; wherein at least a subpopulation of hydrogel beads within the population of hydrogel beads, comprises a pre-apoptotic signal and/or a DNA dye; b) measuring concentration of pre-apoptotic signal and/or DNA dye in the population of hydrogel beads in a cytometric device; c) calibrating the cytometric device based on the measured concentration of pre-apoptotic signal and/or DNA dye of the hydrogel beads; d) measuring concentration of pre-apoptotic signal and/or DNA dye in the target cell sample to determine if the target cell sample includes one or more dead or pre-apoptotic cells.

In embodiments, the hydrogel beads provided herein may be used to determine the dynamic range and/or sensitivity of detection of a particular cell surface marker or combination thereof on a population of target cells. In embodiments, the hydrogel beads can be tuned to have substantially the same side scatter and/or forward scatter of the target cell. In embodiments, subpopulations of the hydrogel particle are derivatized with a specific number of copies of a cell surface marker. In embodiments, the cell surface marker is a cell surface receptor or domain thereof. In embodiments, the cell surface receptor or domain thereof is an epitope binding region thereof. In embodiments, individual subpopulations of hydrogel beads can each be derivatized to have a unique number of copies of a cell surface marker, e.g., one subpopulation will contain 100 copies of a cell surface marker, a second subpopulation will contain 1,000 copies of the same cell surface marker, and a third subpopulation will contain 10,000 copies of the same cell surface. In embodiments, the populations of hydrogel beads are fluorescently stained for the respective cell surface marker and fluorescence is detected for hydrogel beads in each subpopulation. In this regard, the subpopulations of hydrogel particles can be used to generate a standard curve of fluorescence emission for target cells with the respective cell marker. The cell surface marker can be any of the cell surface markers provided thereof, or binding regions thereof, or a cell surface marker known to one of ordinary skill in the art.

IX. Instrumentation

The hydrogel beads of the present disclosure can be used in a variety of cytometric applications. A non-limiting list of cytometric devices compatible with the presently disclosed hydrogels and methods is provided in Table 2, below.

TABLE 2

Instruments for use with embodiments described herein

| Instrument | Manufacturer |
|---|---|
| MACSQuant ® Analyzer 10 | Miltenyi |
| MACSQuant ® VYB | Miltenyi |
| BD FACSCalibur ™ | BD Biosciences |
| BD FACSCanto ™ High Throughput Sampler | BD Biosciences |
| BD FACSCanto II | BD Biosciences |
| BD FACSCanto ™ | BD Biosciences |
| BD FACSCount ™ | BD Biosciences |
| BD Accuri ™ C6 | BD Biosciences |
| BD LSRFortessa ™ X-20 | BD Biosciences |
| BD FACSCanto ™ II | BD Biosciences |
| BD LSR II | BD Biosciences |
| BD LSRFortessa ™ | BD Biosciences |
| BD FACSVerse ™ | BD Biosciences |
| BD FACSAria ™ Fusion | BD Biosciences |
| BD FACSAria ™ | BD Biosciences |

TABLE 2-continued

Instruments for use with embodiments described herein

| Instrument | Manufacturer |
|---|---|
| BD FACSAria ™ III | BD Biosciences |
| BD FACSJazz ™ | BD Biosciences |
| BD Influx ™ | BD Biosciences |
| Fortessa X50. | BD Biosciences |
| FlowSight Flow Cytometer | Millipore |
| Guava easyCyte 6-2L Benchtop Flow Cytometer | Millipore |
| guava easyCyte 5HT Benchtop Flow Cytometer | Millipore |
| guava easyCyte 8 Benchtop Flow Cytometer | Millipore |
| guava easyCyte 5 Benchtop Flow Cytometer | Millipore |
| guava easyCyte 8HT Benchtop Flow Cytometer | Millipore |
| guava easyCyte 6HT-2L Benchtop Flow Cytometer | Millipore |
| ImageStreamX Mark II Imaging Flow Cytometer | Millipore |
| Muse Cell Analyzer | Millipore |
| guava easyCyte 12HT Benchtop Flow Cytometer | Millipore |
| guava easyCyte 12 Benchtop Flow Cytometer | Millipore |
| S3e ™ Cell Sorter | Bio-Rad |
| S3 ™ Cell Sorter | Bio-Rad |
| Avalon Cell Sorter | Bio-Rad/Propel Labs |
| CytoFLEX | Beckman Coulter |
| FP 1000 Cell Preparation System | Beckman Coulter |
| Vi-CELL ® XR Cell Viability Analyzer | Beckman Coulter |
| FC 500 Series | Beckman Coulter |
| MoFlo ® Astrios ™ | Beckman Coulter |
| Coulter Epics XL ™ and XL-MCL ™ | Beckman Coulter |
| Gallios ™ | Beckman Coulter |
| CyAn ™ ADP Analyzer | Beckman Coulter |
| Attune ™ Acoustic Focusing Cytometer | Life Technologies |
| Attune ® NxT Acoustic Focusing Cytometer | Life Technologies |
| EVOS | Life Technologies |
| Countess II FL | Life Technologies |
| EC800 Cell Analyzer | Sony |
| SH800 Cell Sorter | Sony |
| SP6800 Spectral Analyzer | Sony |
| SY3200 Cell Sorter | Sony |
| A50-Micro' | Apogee Flow Systems |
| A50-Universal | Apogee Flow Systems |
| Auto40 | Apogee Flow Systems |
| FlowSight | Amnis |
| ImageStream$^X$ Mark II | Amnis |
| JSAN | Bay Bioscience |
| CytoSense | CytoBuoy |
| CytoSub | CytoBuoy |
| CytoSense | CytoBuoy |
| CytoBuoy | CytoBuoy |
| Cytonome Viva ™ G1 | CYTONOME |
| GigaSort ™ | CYTONOME |
| Hydris | CYTONOME |
| Agilent 2100 Bioanalyzer | Agilent Technologies |
| NovoCyte | ACEA Biosciences |
| CyFlow ® Space | Partec technology |
| CyFlow ® Cube 8 | Partec technology |
| CyFlow ® Cube 6 | Partec technology |
| CyFlow ® Ploidy Analyser | Partec technology |
| CyFlow ® Counter | Partec technology |
| CyFlow ® miniPOC | Partec technology |
| CyFlow ® SL | Partec technology |
| CyFlow ® Sorter | Partec technology |
| CyFlow ® CCA | Partec technology |
| CyFlow ® Oenolyser | Partec technology |
| NucleoCounter ® NC-3000 ™ | Chemometec |
| NucleoCounter ® NC-250 ™ | Chemometec |
| NucleoCounter ® NC-200 ™-High Precision Cell Counter | Chemometec |
| Cytek ® Aurora | Cytek Biosciences |
| HPC-100 Portable Flow Cytometer | Cronus Technologies Ltd |
| Cytell Cell Imaging System | GE Healthcare |
| MAGPIX | Luminex |
| Luminex ® 100/200 ™ System | Luminex |
| FLEXMAP 3D ® | Luminex |
| ImageXpress ® Velos Laser Scanning Cytometer | molecular devices |
| ClonePix ™ 2 | molecular devices |
| SpectraMax ® i3 | molecular devices |
| AQ1 Discrete Analyzer | SEAL Analytical Ltd. |

TABLE 2-continued

Instruments for use with embodiments described herein

| Instrument | Manufacturer |
|---|---|
| AQ2 Discrete Analyzer | SEAL Analytical Ltd. |
| AQ400 Discrete Analyzer | SEAL Analytical Ltd. |
| AQUA 900 | SEAL Analytical Ltd. |
| AA3 HR AutoAnalyzer | SEAL Analytical Ltd. |
| AA1 AutoAnalyzer | SEAL Analytical Ltd. |
| QuAAtro39 | SEAL Analytical Ltd. |
| Infralyzer 2000 | SEAL Analytical Ltd. |
| Technicon AutoAnalyzer II (AAII) | SEAL Analytical Ltd. |
| Technicon/Bran + Luebbe TrAAcs 800-2000 | SEAL Analytical Ltd. |
| Bran + Luebbe FIA Analyzer | SEAL Analytical Ltd. |
| BioSorter ® Large Particle Flow Cytometer | Union Biometrica, Inc. |
| COPAS ™ Large Particle Flow Cytometers | Union Biometrica, Inc. |
| Cellometer Mini Cell Counter | Nexcelom |
| Cellometer Auto T4 Cell Viability Counter | Nexcelom |
| Cellometer Auto X4 Cell Viability Counter | Nexcelom |
| Cellometer Auto 1000 Cell Viability Counter | Nexcelom |
| Cellometer Auto 2000 Cell Viability Counter | Nexcelom |
| Cellometer Vision CBA | Nexcelom |
| Celigo S | Nexcelom |
| NovoCyte ™ 1000 | ACEA |
| NovoCyte ™ 2000 | ACEA |
| NovoCyte ™ 2060 | ACEA |
| NovoCyte ™ 3000 | ACEA |
| HPC-100 | Handyem |
| S1000EXi | Stratedigm |
| SE520Xi | Stratedigm |
| Sysmex ® DI-60 | Sysmex |
| CellaVision ® DM96 | Sysmex |
| CellaVision ® DM1200 | Sysmex |
| Cytation | BioTek |
| EasyCell Assistant | Medica |
| IN Cell Analyzer | GE Healthcare |
| Big Blue | BD Biosciences |
| Kermit | Miltenyi |
| ac6 | BD Biosciences |
| srDAs | BD Biosciences |
| a | BD Biosciences |
| FACSCanto II Immunology | BD Biosciences |
| Test Cyt | Millipore |
| milt | Miltenyi |
| ac | BD Biosciences |
| ietest | BD Biosciences |
| Curiel's Aria | BD Biosciences |
| AttuneÂ ® Acoustic Focusing Cytometer Blue/Violet | Life Technologies |
| Medawar LSRII | BD Biosciences |
| Medawar Calibur | BD Biosciences |
| FACSAria INER | BD Biosciences |
| Attune R/A | Life Technologies |
| Fortessa | BD Biosciences |
| Aria | BD Biosciences |
| SORTER | BD Biosciences |
| Cyan | Beckman Coulter |
| LSR II | BD Biosciences |
| ARIA | BD Biosciences |
| Canto II | BD Biosciences |
| F09-LSR Fortessa 1 | BD Biosciences |
| "The Hoff" | BD Biosciences |
| 6th Floor Hess Fortessa A | BD Biosciences |
| Cerebro BDFACSAriaII | BD Biosciences |
| Mystique BDFACSAriaIII | BD Biosciences |
| Godzilla BDFACSAriaII | BD Biosciences |
| Wolverine BDFACSAriaII | BD Biosciences |
| Megatron BDFACSAriaII | BD Biosciences |
| Megatron BDFACSAriaII | BD Biosciences |
| Fortessa B | BD Biosciences |
| 6 colour Canto II | BD Biosciences |
| 10 colour LSR II | BD Biosciences |
| 4 laser 13 colour Influx sorter | BD Biosciences |
| 14 colour X20 | BD Biosciences |
| SORP | BD Biosciences |
| FACSAria INER | BD Biosciences |
| LSR561 | BD Biosciences |
| Fortessa FCF UZH | BD Biosciences |
| LSR 2 B | BD Biosciences |
| LSRII-C | BD Biosciences |
| Cal 3 | BD Biosciences |
| Aria II A | BD Biosciences |
| LSR 16 | BD Biosciences |
| LSB Fortessa | BD Biosciences |
| IMMUN LSRII | BD Biosciences |
| IRC | BD Biosciences |
| UV LSR | BD Biosciences |
| 5 Laser Aria | BD Biosciences |
| Curiel's LSR II | BD Biosciences |
| LSR Fortessa | BD Biosciences |
| Mauzeroll Aria | BD Biosciences |
| Frenette | BD Biosciences |
| Fallon | Beckman Coulter |
| Galios | Beckman Coulter |
| LSRIIFortessa | BD Biosciences |
| FACSCanto II CLSB | BD Biosciences |
| LSR II SC | BD Biosciences |
| UNCA Fortessa | BD Biosciences |
| VERSE | BD Biosciences |
| ARIAII | BD Biosciences |
| ARIAIII | BD Biosciences |
| F09 - BD LSRFortessa | BD Biosciences |
| HMRI FACSCanto II A | BD Biosciences |
| HMRI FACSCantoll B (HTS) | BD Biosciences |
| HMRI Aria III | BD Biosciences |
| L2 | BD Biosciences |
| UoN Canto | BD Biosciences |
| LSRII M902 | BD Biosciences |
| Fortessa 1 | BD Biosciences |
| F05-FACSAria | BD Biosciences |
| F02-FACSAria III | BD Biosciences |
| F10-BD FACSAria III | BD Biosciences |
| BD FACSLyric ™ | BD Biosciences |
| F03-Guava | Millipore |
| Aria Blue 11 Color | BD Biosciences |
| Aria Red | BD Biosciences |
| Aria Orange | BD Biosciences |
| Aria Cyan | BD Biosciences |
| Aria Emerald | BD Biosciences |
| Aria Silver BSL3 | BD Biosciences |
| LSR Fortessa | BD Biosciences |
| LSR II Bldg 4 | BD Biosciences |
| LSR Fortessa bldg 4 | BD Biosciences |
| CANTO II Bldg 50 | BD Biosciences |
| 4 Laser LSR II | BD Biosciences |
| 5 Laser LSR II | BD Biosciences |
| FACSArray BL-2 | BD Biosciences |
| FACSCalibur | BD Biosciences |
| DUAL for long term studies | BD Biosciences |
| MoFlo 1095 Production only | Beckman Coulter |
| BL-2 FACSAria III sorter | BD Biosciences |
| Astrios BL-2 sorter | Beckman Coulter |
| Tessy | BD Biosciences |
| LSR II-1 | BD Biosciences |
| Fortessa | BD Biosciences |
| 4 laser AriaIII | BD Biosciences |
| LSRFortessa | BD Biosciences |
| UoN FACSAria II cell sorter | BD Biosciences |
| Door | Beckman Coulter |
| Fortessa | BD Biosciences |
| WCI-FACSAria I | BD Biosciences |
| LSRII Karp8 | BD Biosciences |
| Karp 8 | BD Biosciences |
| Canto | BD Biosciences |
| Aria sorter | BD Biosciences |
| DI lab | BD Biosciences |
| DI FACSAria | BD Biosciences |
| Constance | BD Biosciences |
| DI FACSAria III | BD Biosciences |
| WCI_FACS Canto | BD Biosciences |
| MACSQuant 10 | Miltenyi |
| VAMC Memphis LSR | BD Biosciences |
| VAMC Memphis S3 | Bio-Rad |
| ARIA INER | BD Biosciences |
| Uhura | BD Biosciences |
| Kirk | BD Biosciences |

TABLE 2-continued

Instruments for use with embodiments described herein

| Instrument | Manufacturer |
|---|---|
| Data | Millipore |
| Spock | BD Biosciences |
| McCoy | BD Biosciences |

EXAMPLES

The following examples are given for the purpose of illustrating various embodiments of the disclosure and are not meant to limit the present disclosure in any fashion. Changes therein and other uses which are encompassed within the spirit of the disclosure, as defined by the scope of the claims, will be recognized by those skilled in the art.

Example 1. Generation of Hydrogel Beads

Photomasks for UV lithography were sourced from CADart Services Inc. and were designed using AutoCad (AutoDesk, Inc.). SU-8 photo resist (Microchem, Inc.) was photo crosslinked on 4" silicon wafers using a collimated UV light source (OAI, Inc.) to create masters for microfluidic device fabrication. PDMS (polydimethylsiloxane, Sigma Aldrich, Inc.) was prepared and formed using standard published methods for soft lithography and microfluidic device fabrication (See, McDonald J C, et al., 2000, Electrophoresis 21:27-40).

Droplets were formed using flow-focusing geometry where two oil channels focus a central stream of aqueous monomer solution to break off droplets in a water-in-oil emulsion. A fluorocarbon-oil (Novec 7500 3M, Inc.) was used as the outer, continuous phase liquid for droplet formation. To stabilize droplets before polymerization, a surfactant was added at 0.5% w/w to the oil phase (ammonium carboxylate salt of Krytox 157 FSH, Dupont). To make the basic polyacrylamide gel bead, a central phase of an aqueous monomer solution containing N-acrylamide (1-20% w/v), a cross-linker that allows for the hydrogel to be lysed (N,N'-bis(acryloyl)cystamine, bis(2-methacryloyl)oxyethyl disulfide, allyl disulfide, polyethylene glycol (PEG)N-hydroxysuccinimide (NHS) ester disulfide, acryloyl-PEG-disulfide-PEG-acryloyl, or succinimidyl 3-(2-pyridyldithio) propionate, dicumyl alcohol dimethacrylate, dicumyl alcohol diacrylate, 2,5-dimethyl-2,5-hexanediol dimethacrylate, acylhydrazone, or 3,9-divinyl-2,4,8,10-tetraoxaspiro[5.5]undecane), an accelerator, and ammonium persulfate (1% w/v) was used. An accelerator, (N,N,N',N' tetramethylethylenediamine (2% vol %) was added to the oil-phase in order to trigger hydrogel bead polymerization after droplet formation.

Co-monomers may be added to the basic gel formulation to add functionality. Allyl-amine provided primary amine groups for secondary labeling after gel formation. Forward scatter may be modulated by adjusting the refractive index of the gel by adding co-monomers allyl acrylate and allyl methacrylate. Side scattering of the droplets may be tuned by adding a colloidal suspension of silica nanoparticles and/or PMMA (poly(methyl methacrylate)) particles (~100 nm) to the central aqueous phase prior to polymerization.

Stoichiometric multiplexing of the hydrogel beads was achieved by utilizing co-monomers containing chemically orthogonal side groups (amine, carboxyl, maleimide, epoxide, alkyne, etc.) for secondary labeling.

Droplets were formed at an average rate of 5 kHz and were collected in the fluorocarbon oil phase. Polymerization was completed at 50° C. for 30 minutes, and the resulting hydrogel beads were washed from the oil into an aqueous solution.

Three different populations of hydrogel beads were prepared according to the methods above. The first hydrogel bead population contained (i) a polymerized monomer and a bifunctional monomer, (ii) a phosphatidylserine or an anti-annexin V antibody or antigen-binding fragment thereof (a pre-apoptotic signal binder), and (iii) an encapsulated nucleic acid. This first population of hydrogel beads can bind to both pre-apoptotic signals and DNA-intercalating dyes, and thus serves as mimics of dead cells.

The second hydrogel bead population contained (i) a polymerized monomer and a bifunctional monomer, and (ii) a pre-apoptotic signal binder (e.g., phosphatidylserine or an anti-annexin V antibody or antigen-binding fragment thereof), but lacked the encapsulated nucleic acid of the first hydrogel bead population. This second population of hydrogel beads can bind to pre-apoptotic signals, but cannot bind to DNA-intercalating dyes and thus serves as mimics of cells undergoing apoptosis, but not yet dead.

The third hydrogel bead population contained (i) a polymerized monomer and a bifunctional monomer, but lacked the pre-apoptotic signal binder and encapsulated nucleic acid of the first and second population of hydrogel beads. This third population of hydrogel beads cannot bind to pre-apoptotic signals or DNA-intercalating dyes and thus serves as mimics of live cells.

A fourth hydrogel bead population was produced for live/dead assays. This fourth population of hydrogel beads comprised an amine-reactive dye binder, and an encapsulated nucleic acid, but did not include the pre-apoptotic signal binder of the first population of hydrogel beads. This fourth population of beads served as a dual signal control for dead cells in the cases where either a signal for DNA or amines would implicate a dead population.

Figure 74:
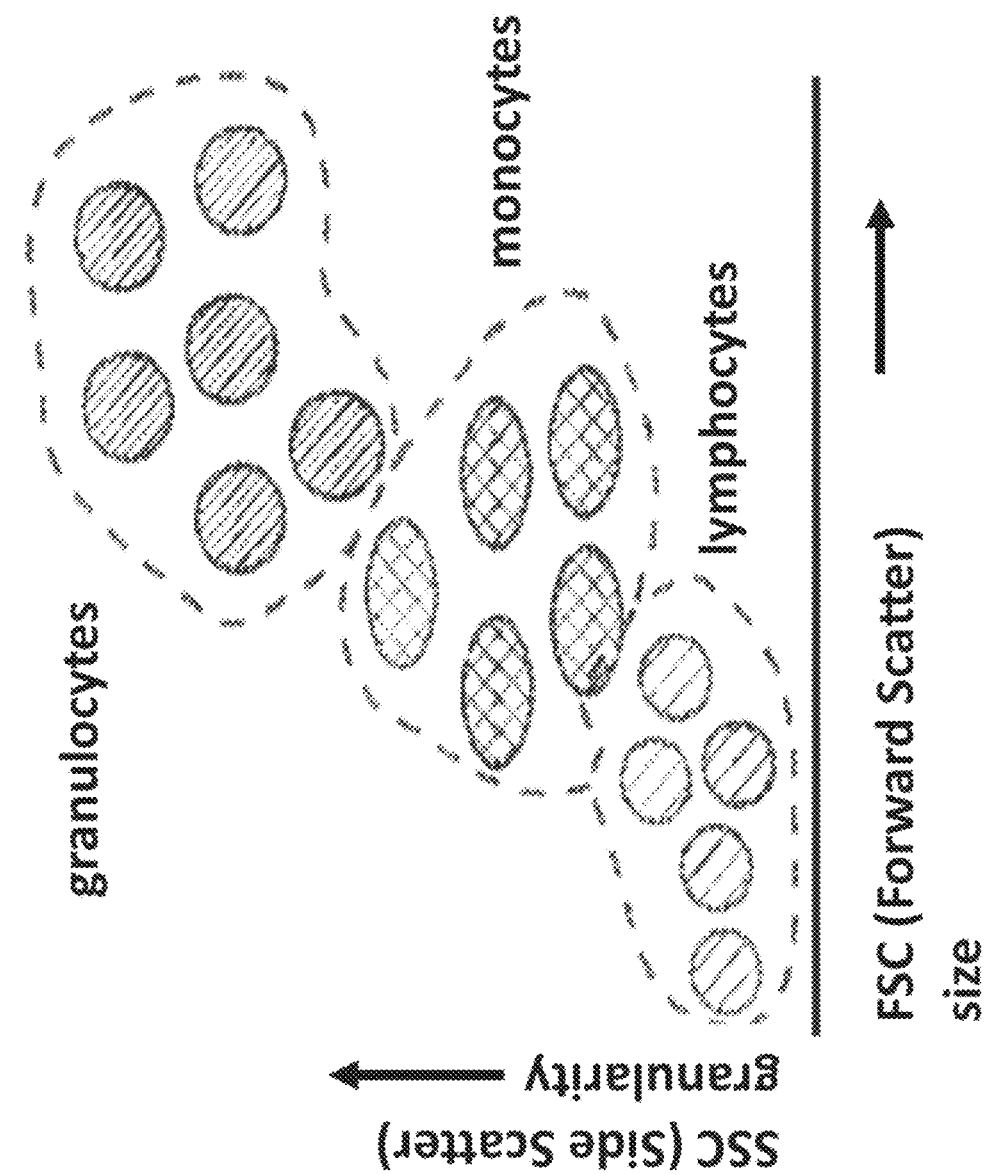
FIGS. 74-76 illustrate the tuning of the optical properties of hydrogel beads to match the optical properties of a target cell.
Figure 75:
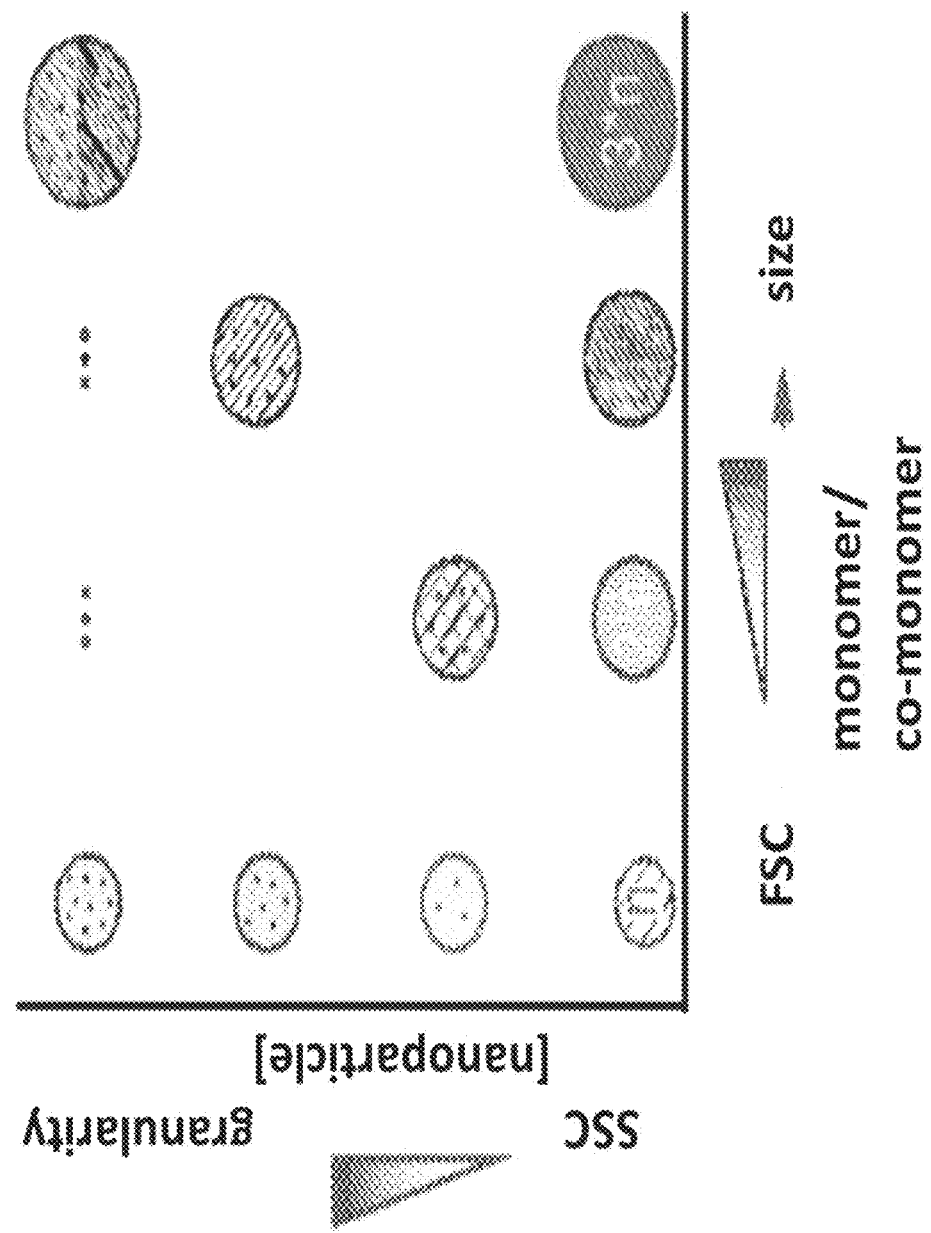
Figure 76:
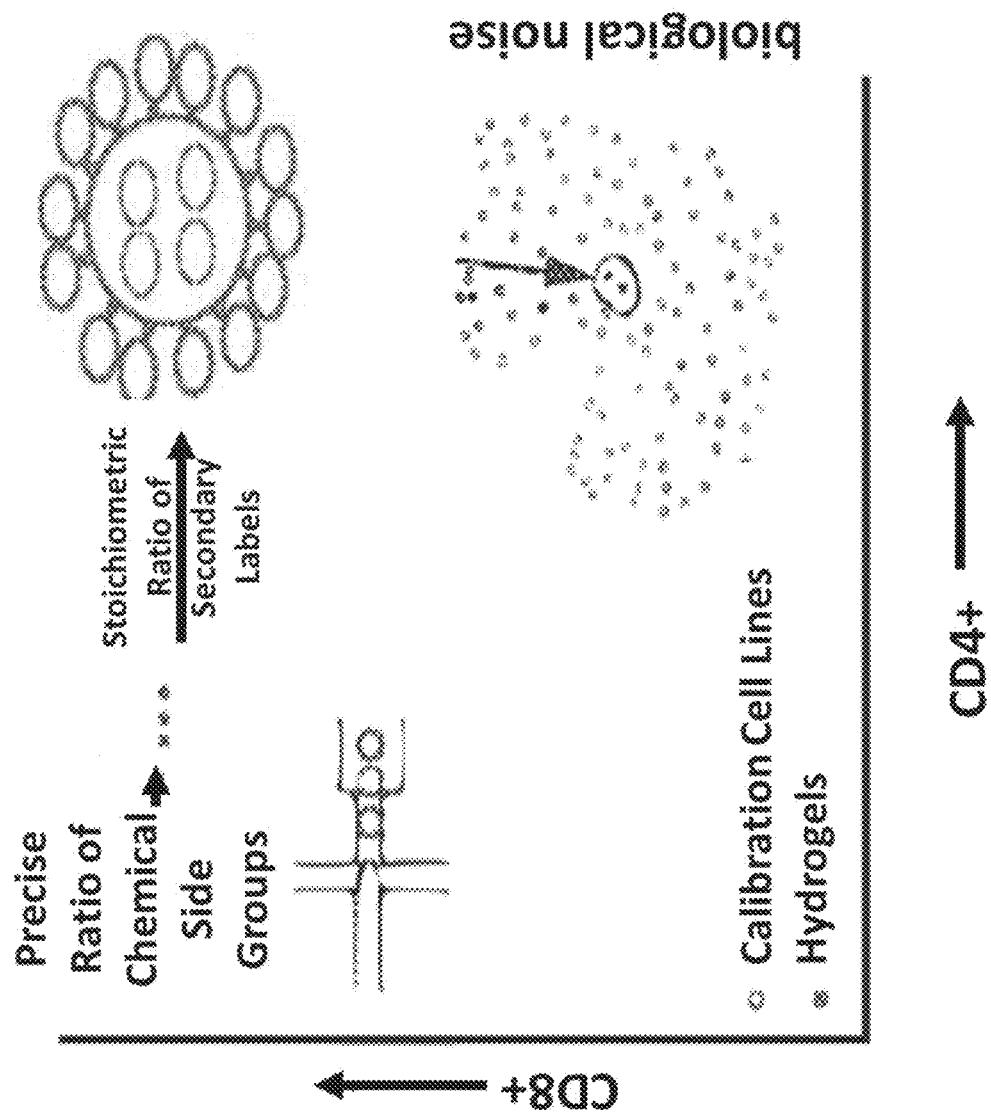

Example 2. Hydrogel Beads Mimic the Forward and Side Scatter Profiles of Various Cell Types This example describes the optional tuning of hydrogel beads to match the optical properties of one or more target cells. Different types of cells (e.g., granulocytes, monocytes, and lymphocytes) exhibit different optical-scatter properties (e.g., forward scatter and side scatter). In some embodiments, the optical properties of the hydrogel beads are tuned to mimic specific cell types. Tuning of hydrogels can be carried out via methods described in U.S. Pat. No. 10,753, 846. Briefly, as depicted in FIGS. 74-76, hydrogel beads are tuned in multiple dimensions to match specific cell types. Cells are deconvolved using combinations of optical parameters such as FSC and SSC (FIG. 75), and/or secondary markers. Hydrogel beads are further functionalized with stoichiometrically tuned ratios of specific chemical side-groups and secondary labels allowing the bead to precisely match the target cell without suffering from the biological noise associated with fixed cell lines. (FIG. 76). FIG. 1 shows that the hydrogel beads described herein can be modulated to match the forward scatter and side scatter of various cell populations.

Figure 8:
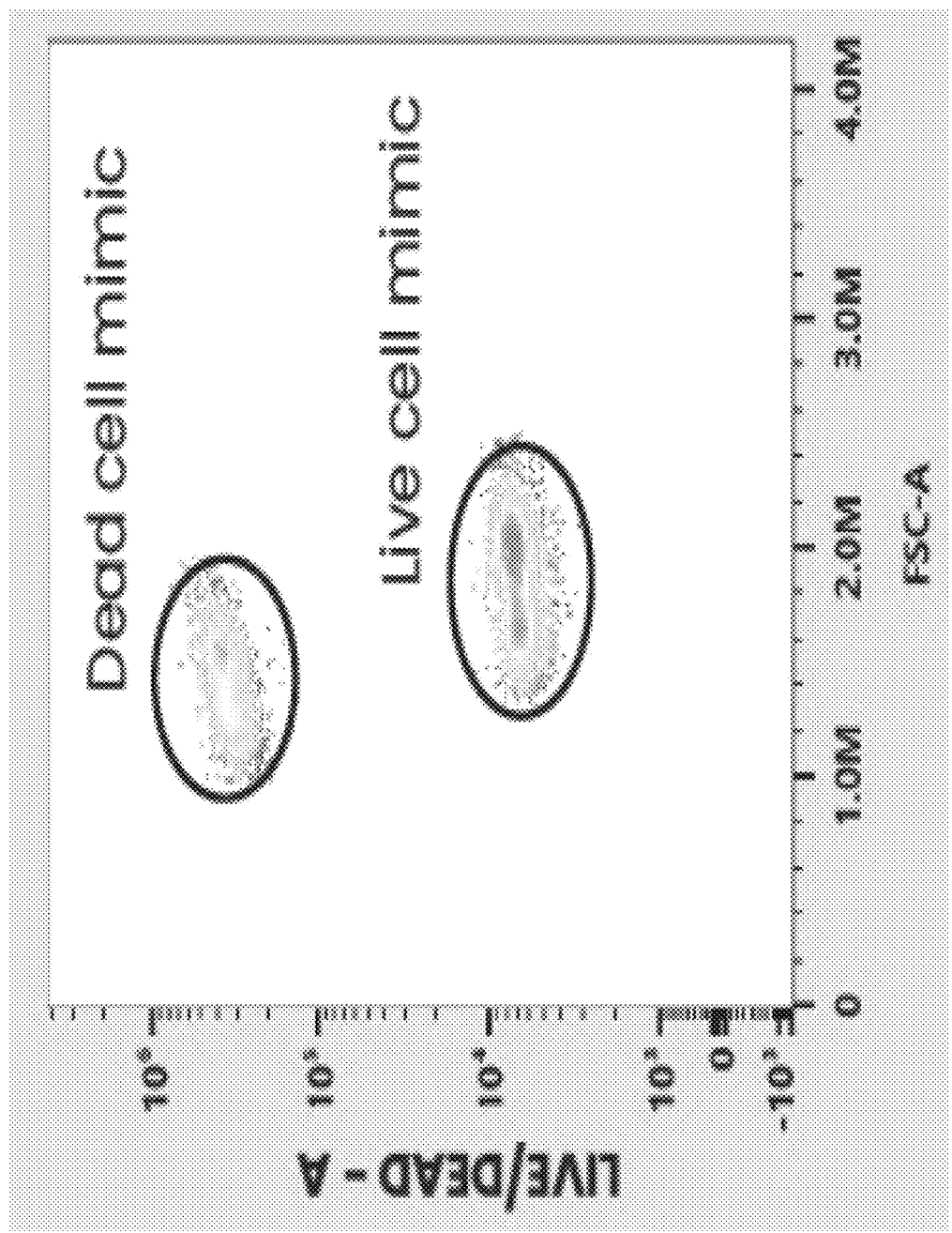
FIG. 8 shows that a hydrogel bead containing a (i) a polymerized monomer and a bifunctional monomer, (ii) an amine dye binder, and (iii) an encapsulated nucleic acid, binds to the amine-reactive viability dye, LIVE/DEAD™ Fixable Blue.
Figure 9:
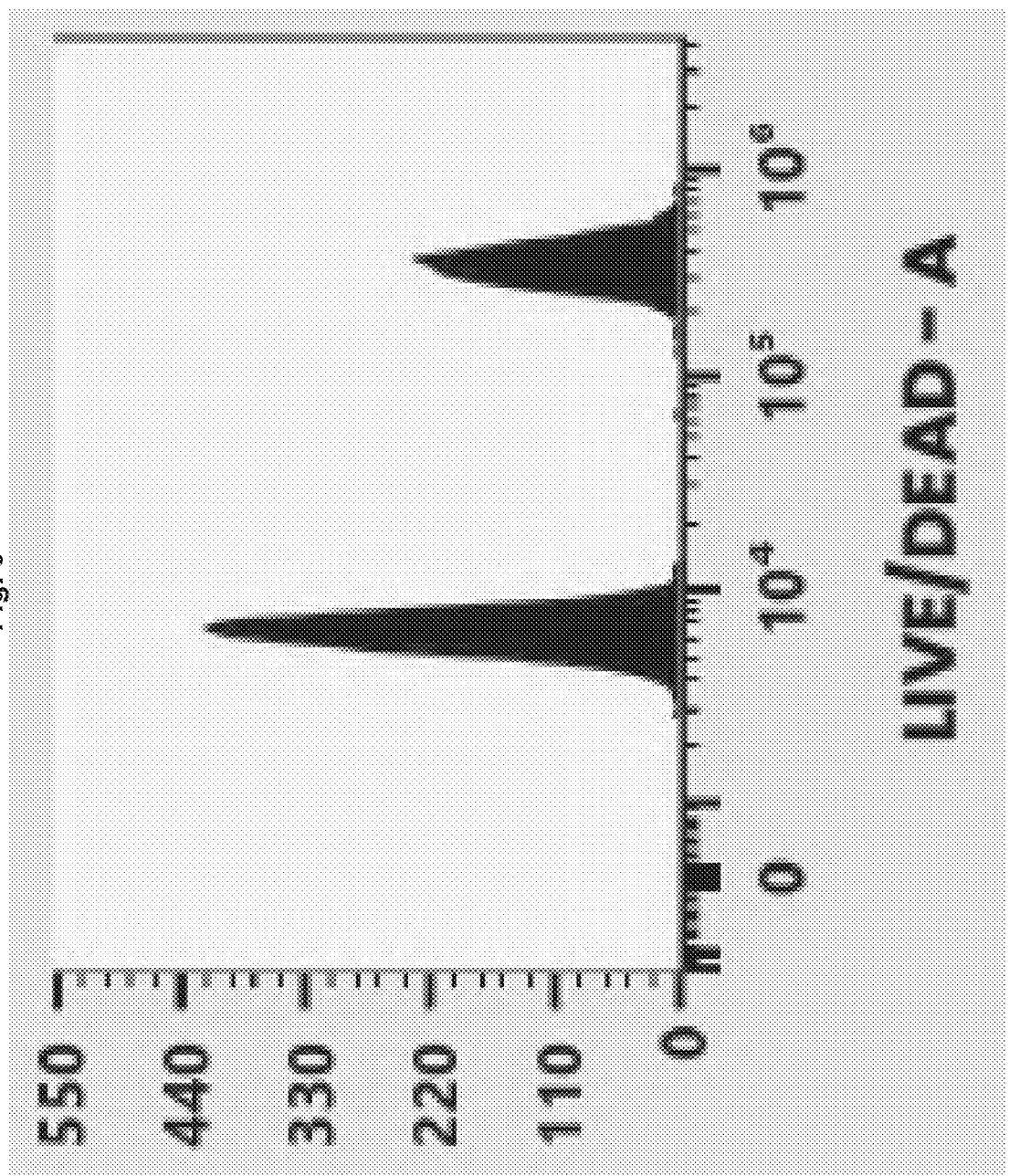
FIG. 9 shows the mean fluorescence intensity of LIVE/DEAD™ Fixable Blue binding to the hydrogel bead of FIG. 8.
Figure 10:
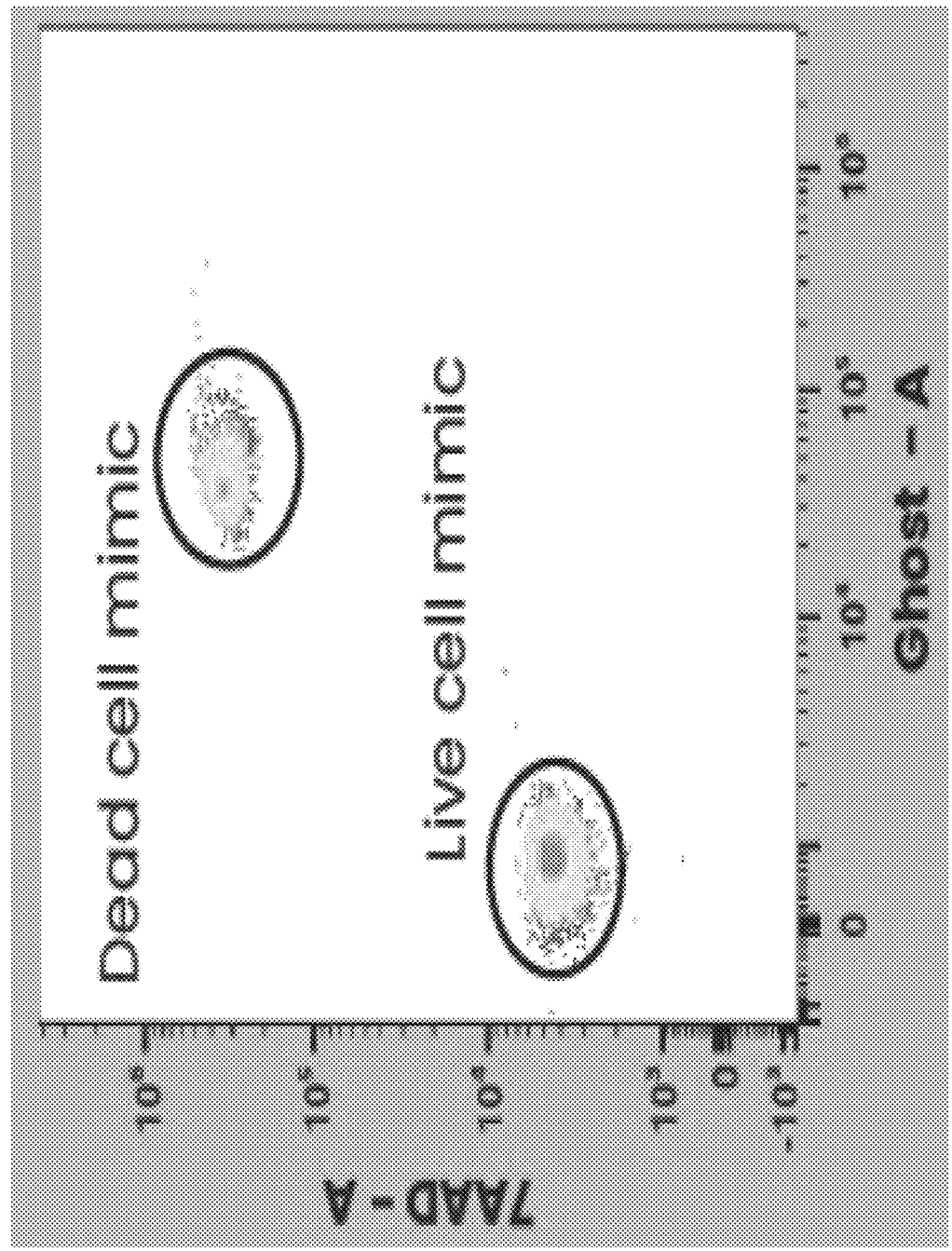
FIG. 10 shows that a hydrogel bead containing a (i) a polymerized monomer and a bifunctional monomer, (ii) an amine dye binder, and (iii) an encapsulated nucleic acid, binds to both the amine-reactive viability dye, GHOST DYE™ and the DNA-intercalating dye, 7-aminoactinomycin D ("7AAD").
Figure 11:
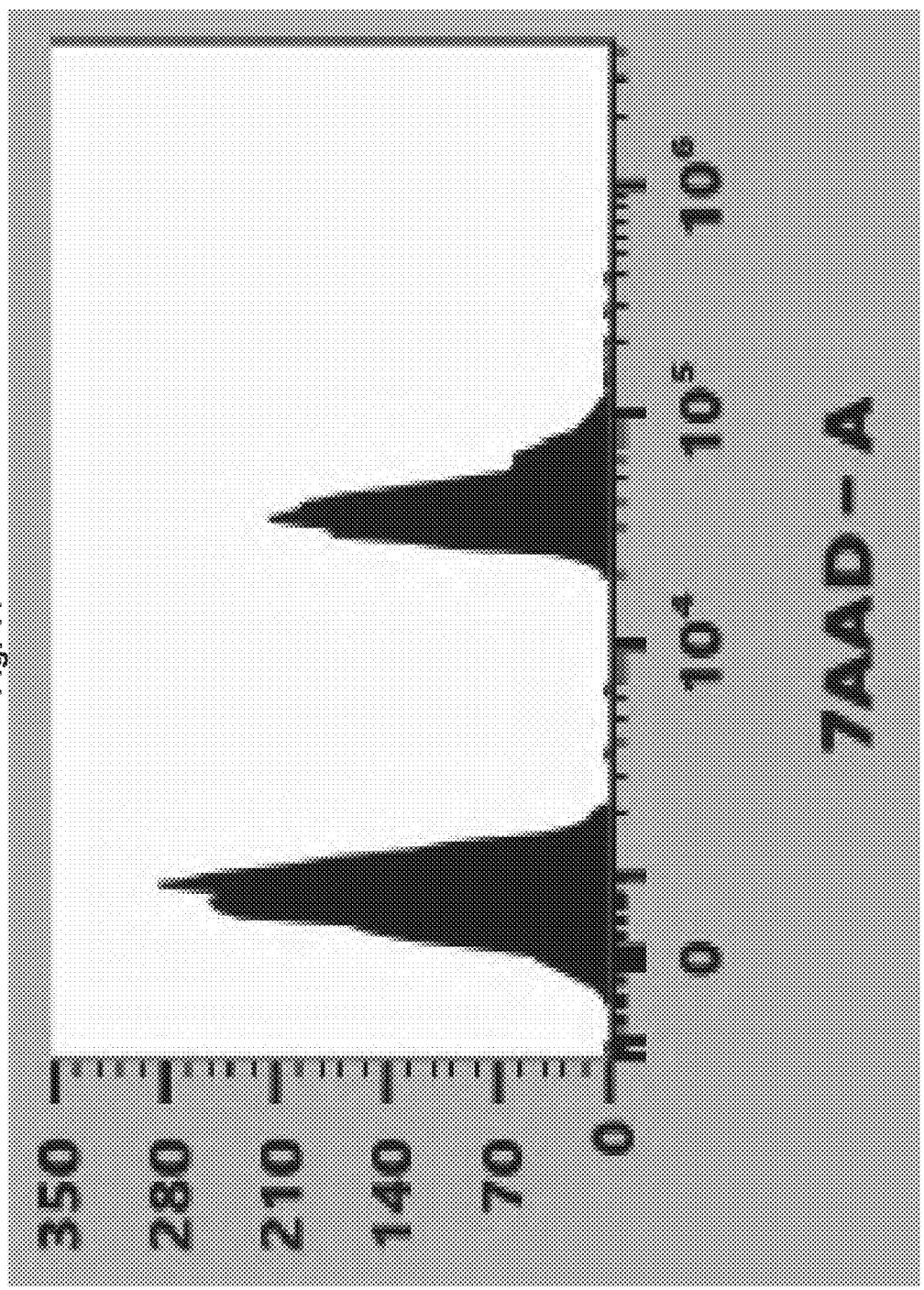
FIG. 11 shows the mean fluorescence intensity of DNA-intercalating dye, 7AAD, binding to the hydrogel bead of FIG. 10.
Figure 12:
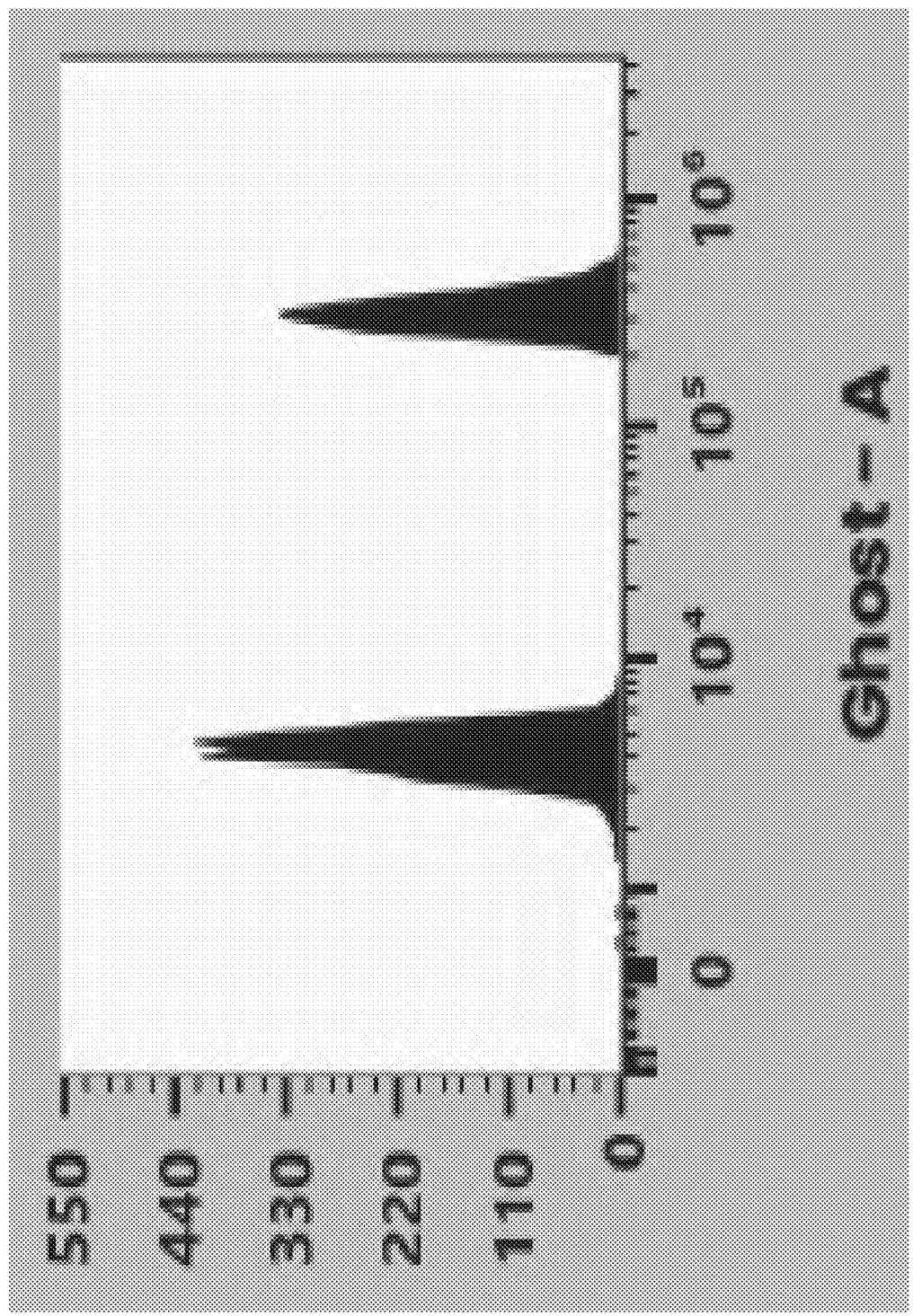
FIG. 12 shows the mean fluorescence intensity of the amine-reactive viability dye, GHOST DYE™ binding to the hydrogel bead of FIG. 10.

Example 3. Hydrogel Beads can be Stained with Both DNA-Intercalating Dyes and Amine Reactive Dyes This example demonstrates the use of the hydrogel beads of the present disclosure as controls for DNA and other amine-binding dyes. The "fourth" population of hydrogel beads of Example 1, which contains (i) a polymerized monomer and a bifunctional monomer, (ii) an amine dye binder, and (iii) an encapsulated nucleic acid, binds to both DNA-intercalating dyes (FIGS. 2-5) and amine-reactive dyes (FIGS. 6-9). FIGS. 2-5 show that the fourth population of hydrogel beads binds to multiple DNA-intercalating dyes. For example, the fourth hydrogel bead binds to propidium iodide ("PI," FIGS. 2-3) and 7-aminoactinomycin D ("7AAD," FIGS. 4-5). FIGS. 6-9 show that the fourth hydrogel bead binds to the amine-reactive dyes, GHOST DYE™ (FIGS. 6-7) and LIVE/DEAD™ Fixable Blue (FIGS. 8-9). FIGS. 10-12 show that the fourth hydrogel bead can simultaneously bind to a DNA-intercalating dye (e.g., 7AAD) and an amine-reactive dye (e.g., GHOST DYE™)

The ability of the hydrogel beads to bind both amine-reactive dyes and DNA-intercalating dyes allows the beads to serve as controls for dead cells depending on the requirements of the assay.

Example 4. Hydrogel Beads are Superior to Heat-Killed Cells and Polystyrene Beads as Viability Controls Viability controls are utilized in flow cytometry to differentiate between live, dead, and apoptotic cells. The ability of (i) the hydrogel beads of Example 1 (comprising the fourth, second, and third hydrogel beads populations); (ii) a mixture of heat-killed and live lymphocytes, (iii) and amine-reactive polystyrene beads to serve as viability controls was compared. Each of (i), (ii), (iii) was stained with both the DNA-intercalating dye 7AAD and the amine-reactive dye, GHOST DYE™. The concentration of DNA-intercalating dye and GHOST DYE™ in each sample was evaluated on a cytometric device.

Figure 13:
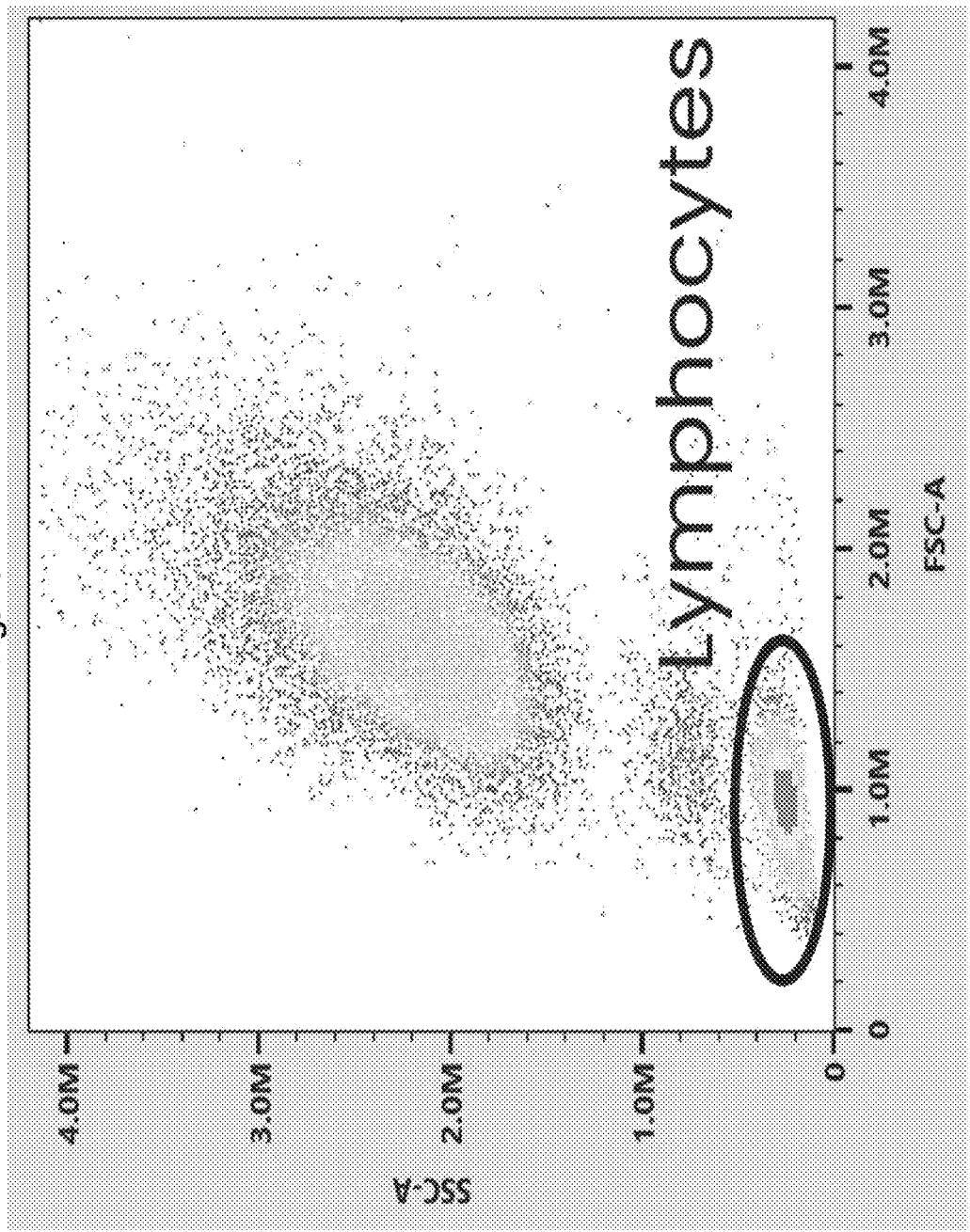
FIG. 13 shows the forward scatter and side scatter of lymphocytes.
Figure 14:
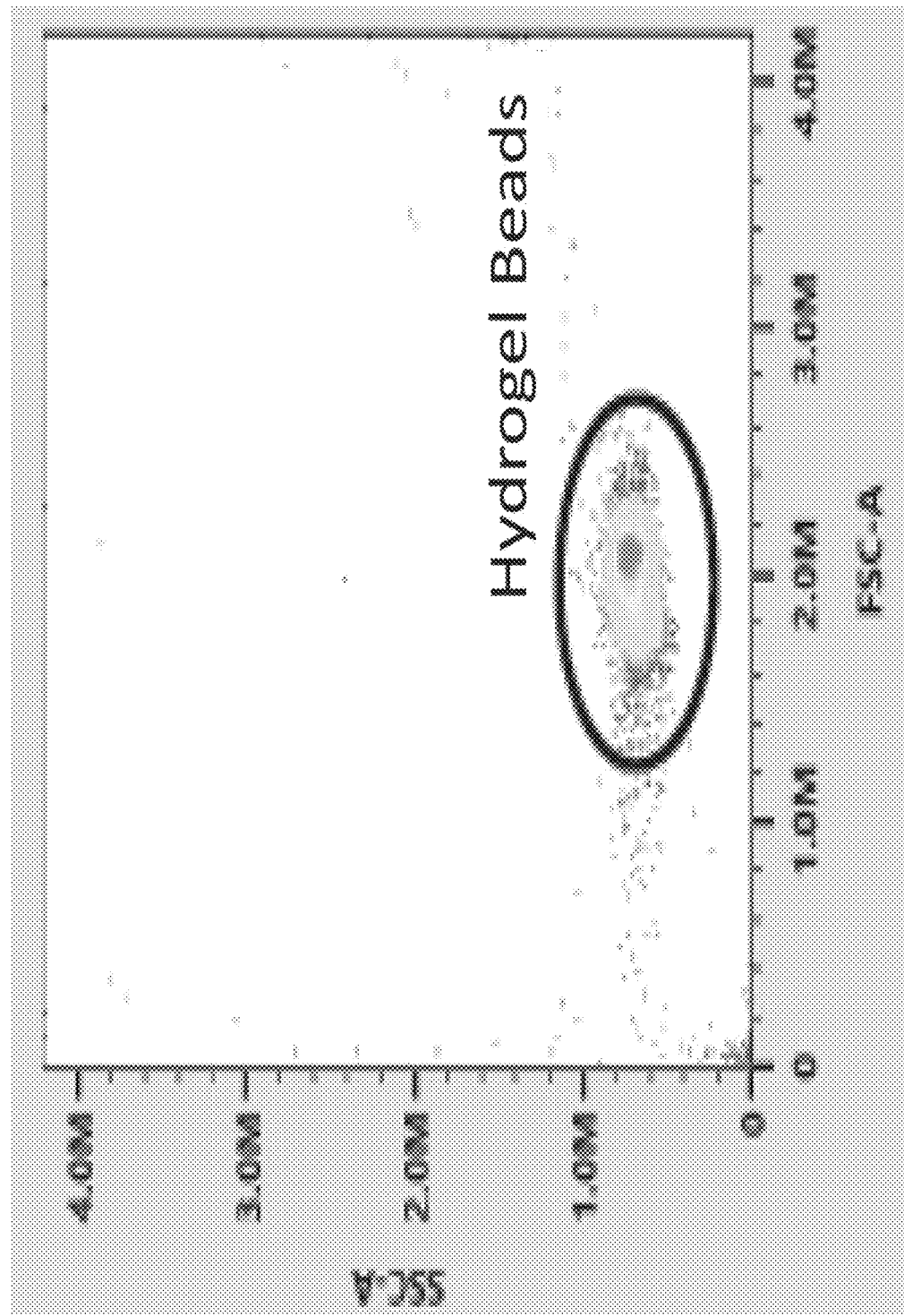
FIG. 14 shows the forward scatter and side scatter of the hydrogel beads of Example 4.
Figure 15:
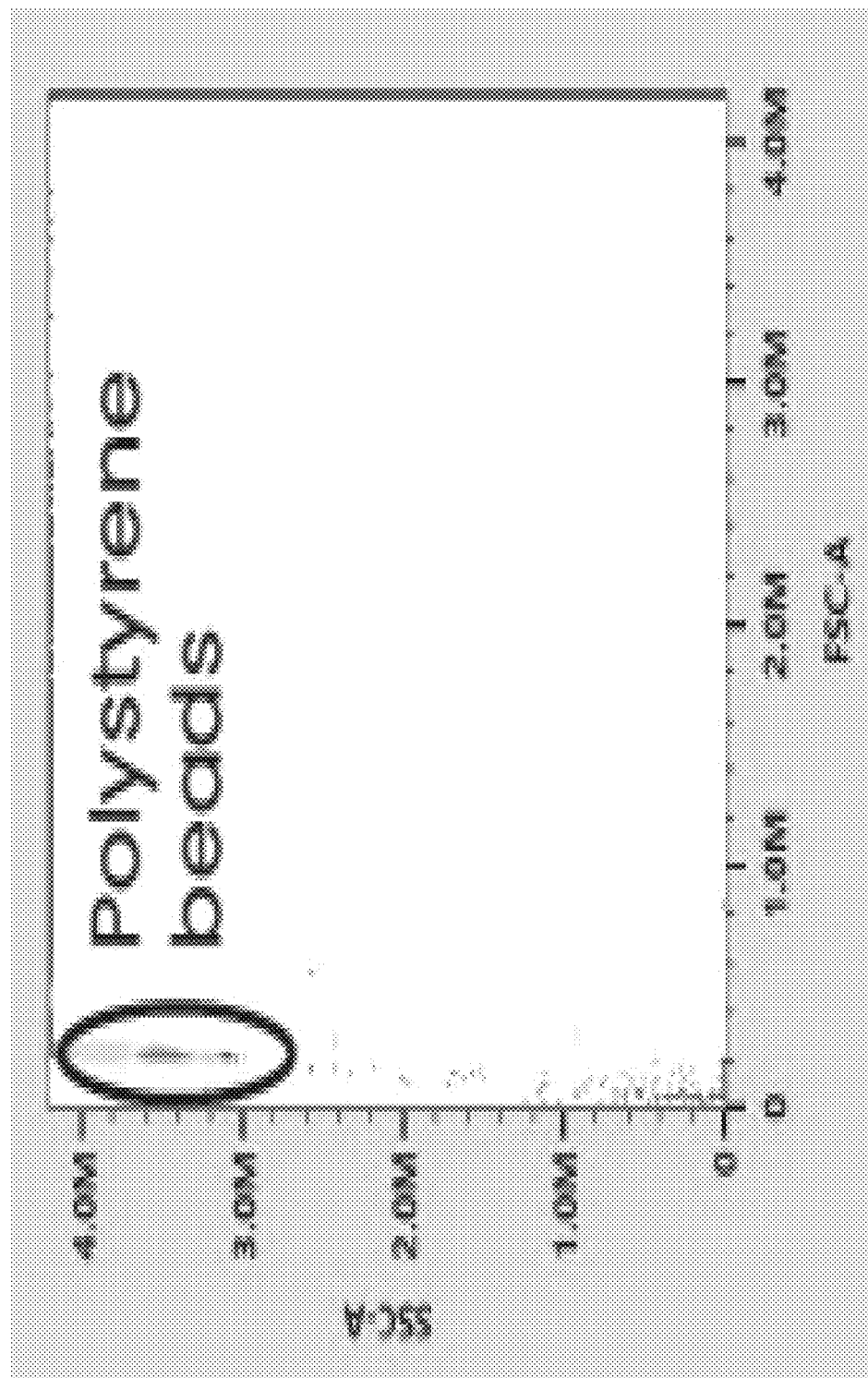
FIG. 15 shows the forward scatter and side scatter of amine-reactive polystyrene beads.

FIGS. 13-15 show the forward scatter and side scatter of (i) the hydrogel beads of Example 1 (FIG. 14, labeled "Hydrogel Beads"), (ii) the mixture of heat-killed and live lymphocytes (FIG. 13), and (iii) the amine-reactive polystyrene beads (FIG. 15). The (i) hydrogel beads of Example 1 exhibited substantially the same side scatter as lymphocytes. (compare FIG. 14 to FIG. 13). In contrast, the side scatter of (iii) amine-reactive polystyrene beads is different than that of lymphocytes (compare FIG. 15 to FIG. 13).

Figure 16:
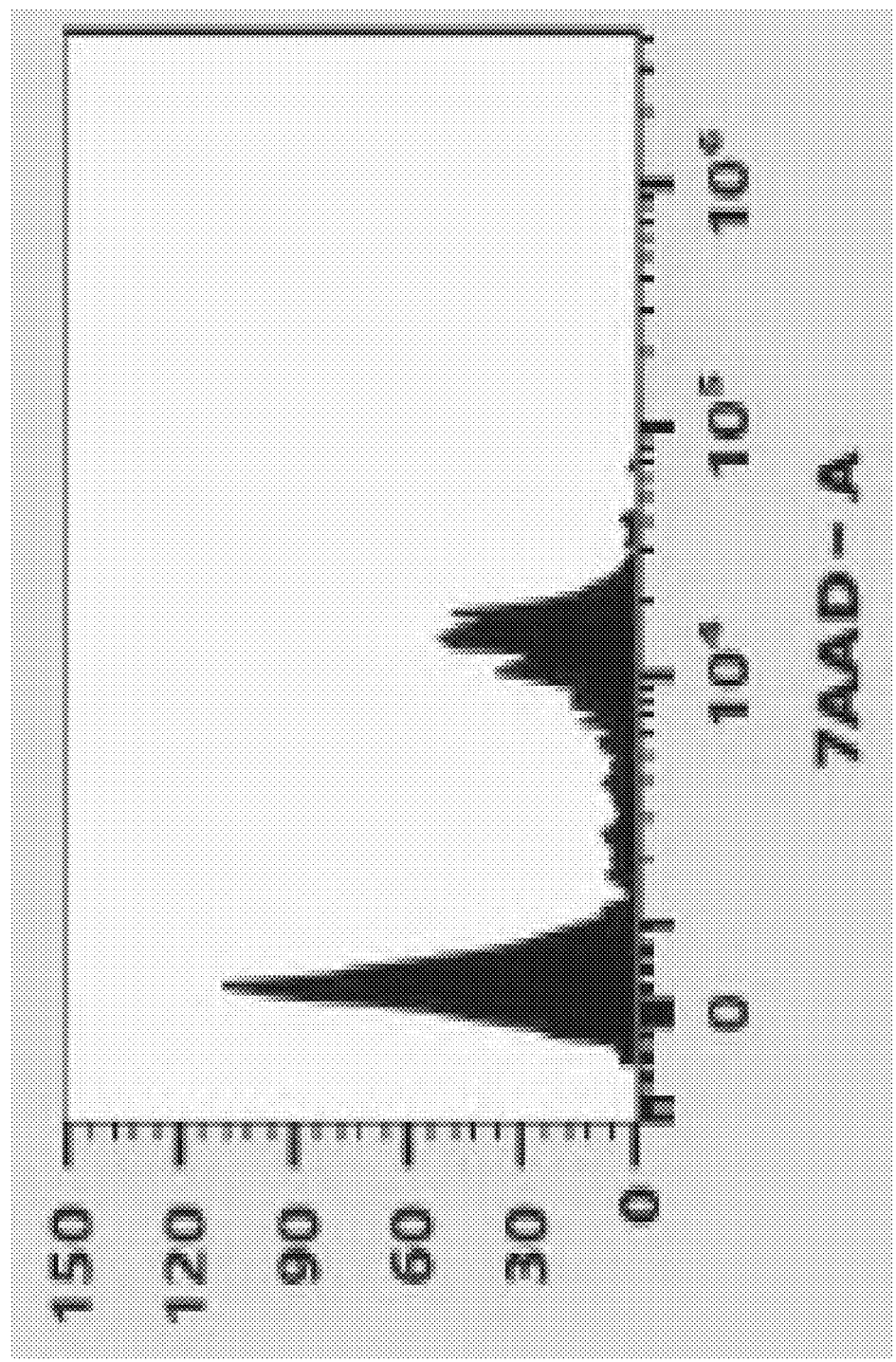
FIG. 16 shows the mean fluorescence intensity of DNA-intercalating dye, 7AAD, binding to the mixture of live and heat-killed lymphocytes of Example 4.
Figure 17:
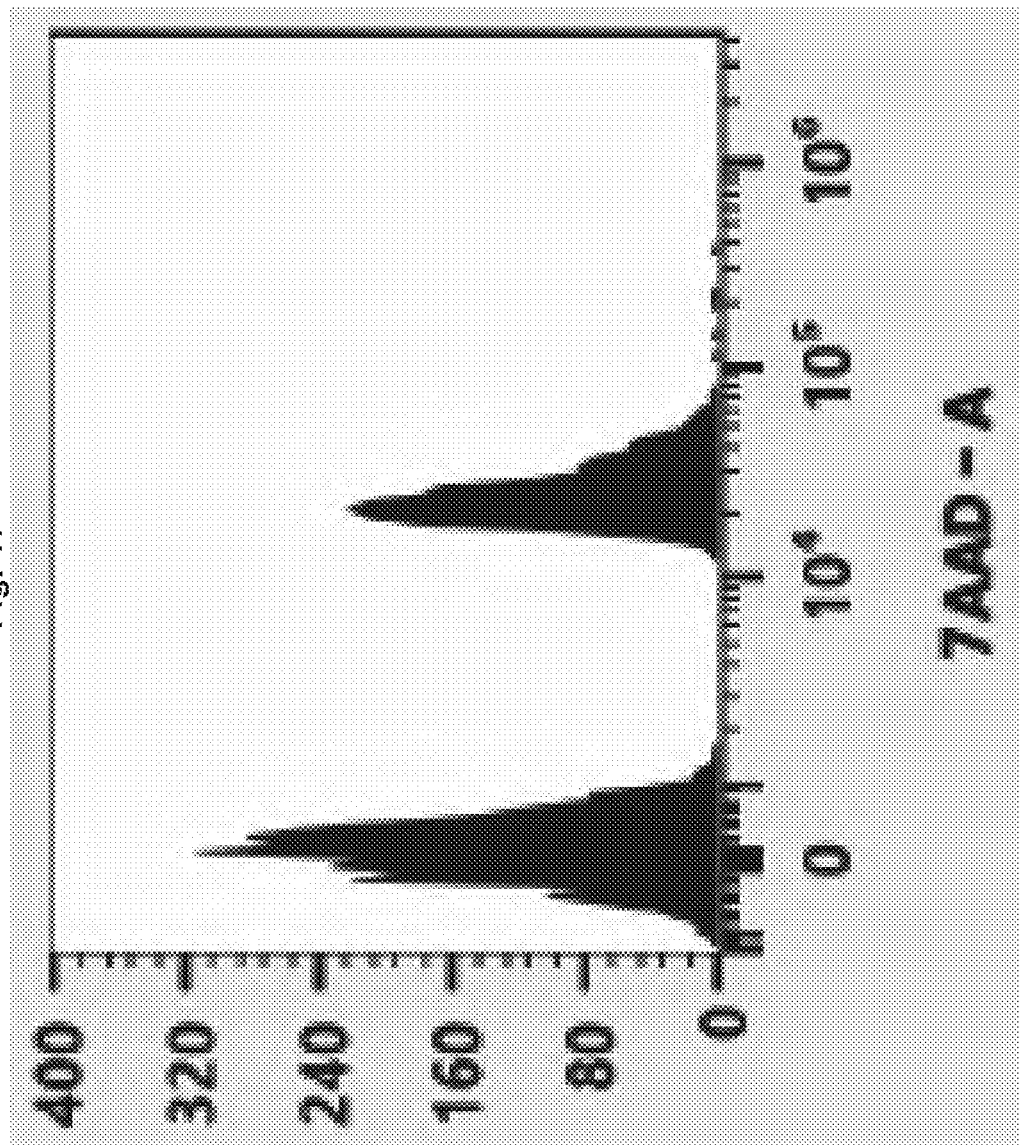
FIG. 17 shows the mean fluorescence intensity of DNA-intercalating dye, 7AAD, binding to the hydrogel beads of Example 4.

FIGS. 16-17 show that the DNA-intercalating dye, 7AAD, binds to (i) the hydrogel beads of Example 1 (FIG. 17) and (ii) the mixture of heat-killed and live lymphocytes (FIG. 16). However, the (iii) amine-reactive polystyrene beads do not bind to 7AAD.

Figure 18:
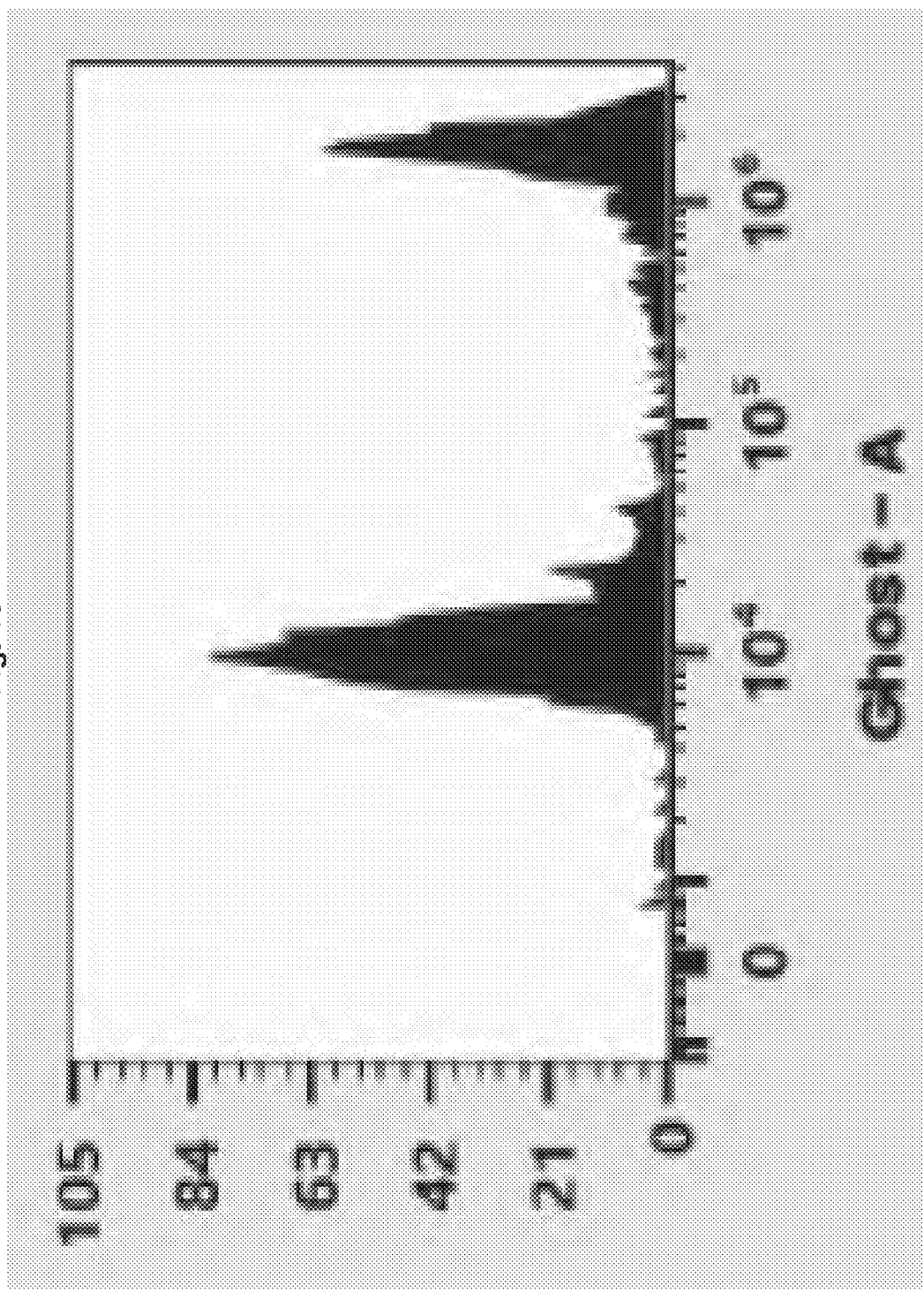
FIG. 18 shows the mean fluorescence intensity of the amine-reactive viability dye, GHOST DYE™, binding to the mixture of live and heat-killed lymphocytes of Example 4.
Figure 19:
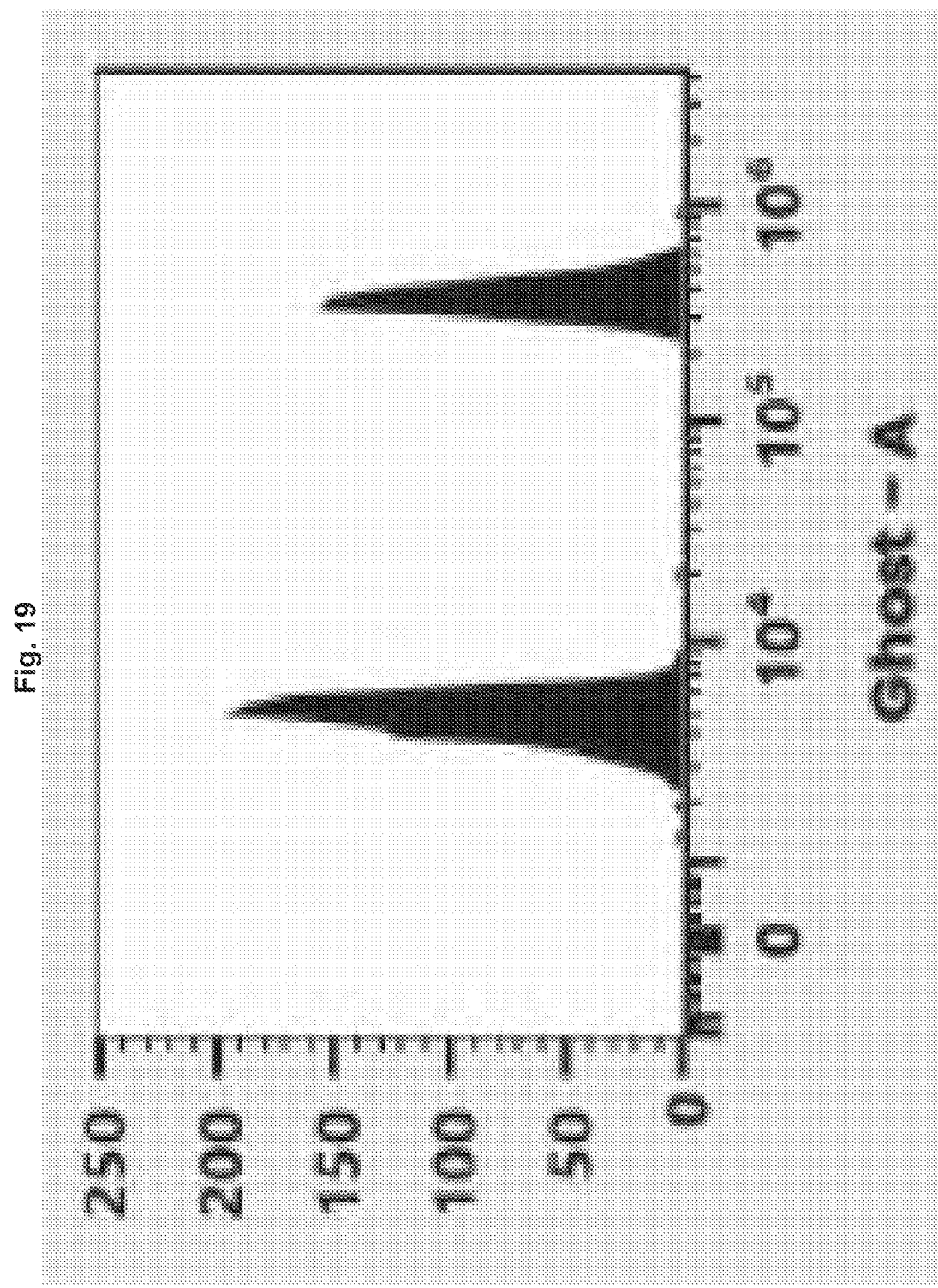
FIG. 19 shows the mean fluorescence intensity of the amine-reactive viability dye, GHOST DYE™, binding to the hydrogel beads of Example 4.
Figure 20:
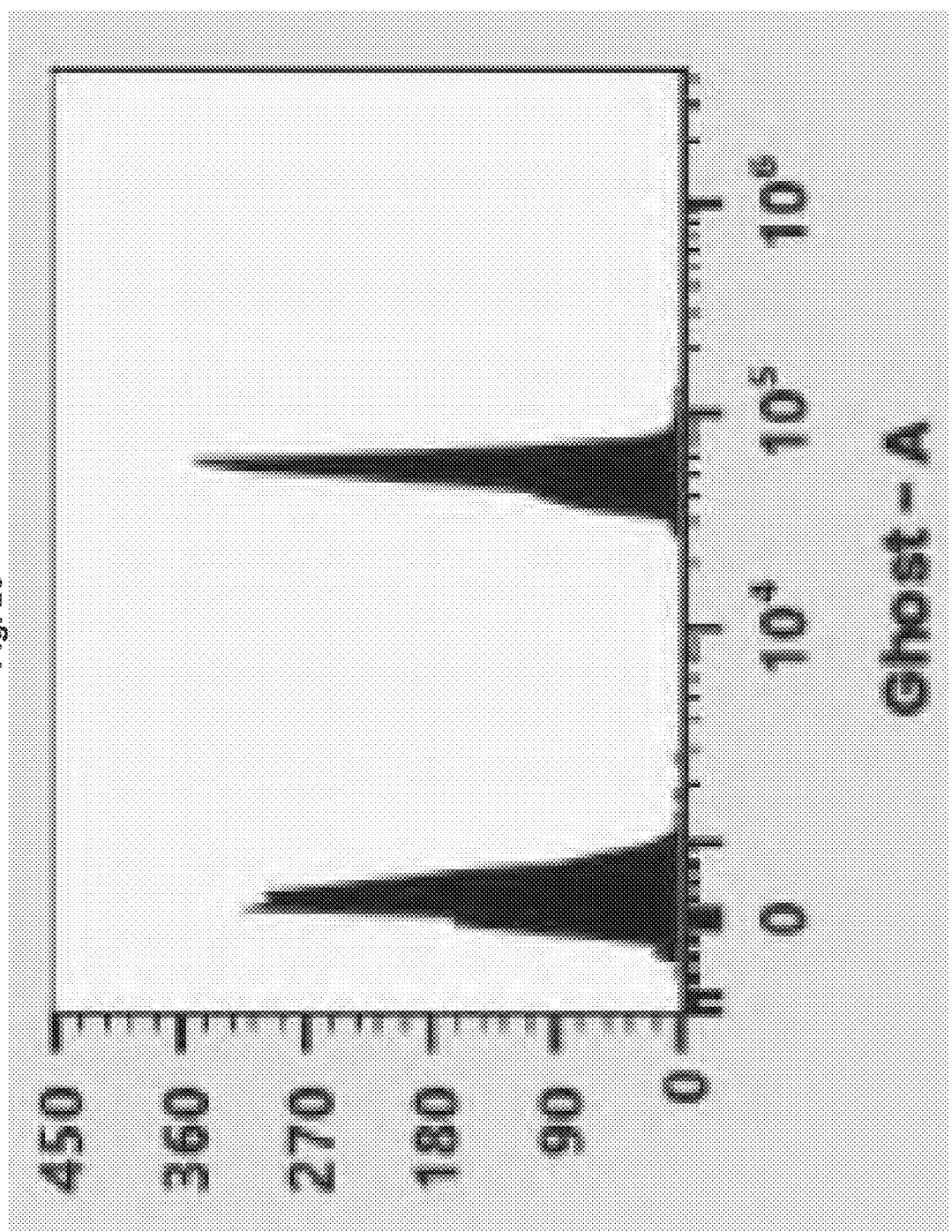
FIG. 20 shows the mean fluorescence intensity of the amine-reactive viability dye, GHOST DYE™, binding to the polystyrene beads of Example 4.

FIGS. 18-20 show that the amine-reactive dye, GHOST DYE™ binds to (i) the hydrogel beads of Example 1 (FIG. 19), (ii) the mixture of heat-killed and live lymphocytes (FIG. 18), and (iii) the amine-reactive polystyrene beads (FIG. 20).

Unlike the amine-reactive polystyrene beads, which only bound to the amine-reactive dye, the fourth population of hydrogel beads of Example 1 bound to both DNA-intercalating dyes and amine-reactive dyes. Thus, the hydrogel beads of Example 1 are superior to the polystyrene beads as viability controls and offer versatility and a range of choices for scientists.

The hydrogel beads of Example 1 are also superior to the mixture of heat-killed and live lymphocytes as a viability control. Production of the heat-killed and live lymphocyte control is time-consuming because it requires heat killing a portion of the lymphocytes. Additionally, dead lymphocytes emit higher autofluorescence compared to live cells and experience higher levels of non-specific binding. Using hydrogel beads mitigates these issues and thereby improves consistency between experiments.

Example 5. Hydrogel Beads of Example 1 Mimic Target Cell Populations Containing Live Cells, Dead Cells, and Cells Undergoing Apoptosis A composition containing populations of the first, second, and third hydrogel beads of Example 1 allowed for identification of live cells, dead cells, and cells undergoing apoptosis. The first hydrogel bead population contained both a pre-apoptotic signal binder (e.g., phosphatidylserine ("PS")), and an encapsulated nucleic acid. The second hydrogel bead population contained a pre-apoptotic signal binder, but did not contain an encapsulated nucleic acid. The third hydrogel bead population contained neither a pre-apoptotic signal binder, nor an encapsulated nucleic acid.

The first second and third populations of hydrogel beads were stained with an annexin V that was tagged with a fluorescein isothiocyanate (FITC) dye. This annexin V binds to PS. The hydrogel beads were also stained with a DNA-intercalating dye, 7AAD, which intercalates between DNA bases, and exhibits fluorescence. The three populations of hydrogels were subsequently evaluated on a flow cytometric device.

Figure 21:
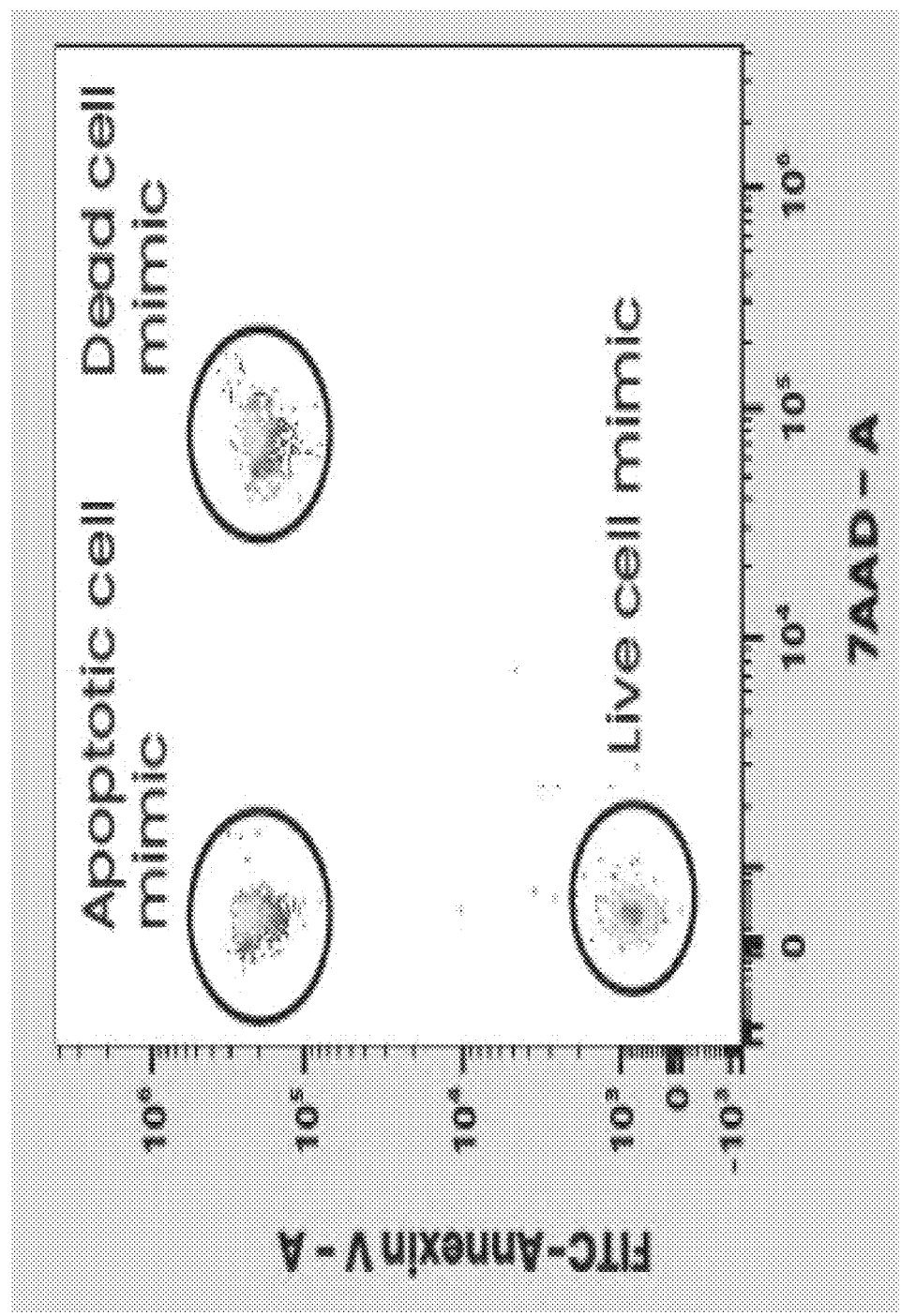
FIG. 21 shows binding of a hydrogel bead composition containing three populations of hydrogel beads to annexin V labeled with a fluorescein isothiocyanate ("FITC") dye (y-axis) and the DNA-intercalating dye, 7AAD (x-axis). The first hydrogel bead population contained both a pre-apoptotic signal binder and an encapsulated nucleic acid. The second nucleic bead population contained a pre-apoptotic signal binder, but did not contain an encapsulated amino acid. The third hydrogel bead population contained neither a pre-apoptotic signal binder (e.g., phosphatidylserine ("PS")), nor an encapsulated nucleic acid. The first population of hydrogel beads bound to both annexin V and 7AAD and served as dead cell mimics. The second population of hydrogel beads bound to annexin V, but not to 7AAD, and served as apoptotic cell mimics. The third population of hydrogel beads bound to neither annexin V nor 7AAD and served as live cell mimics.
Figure 22:
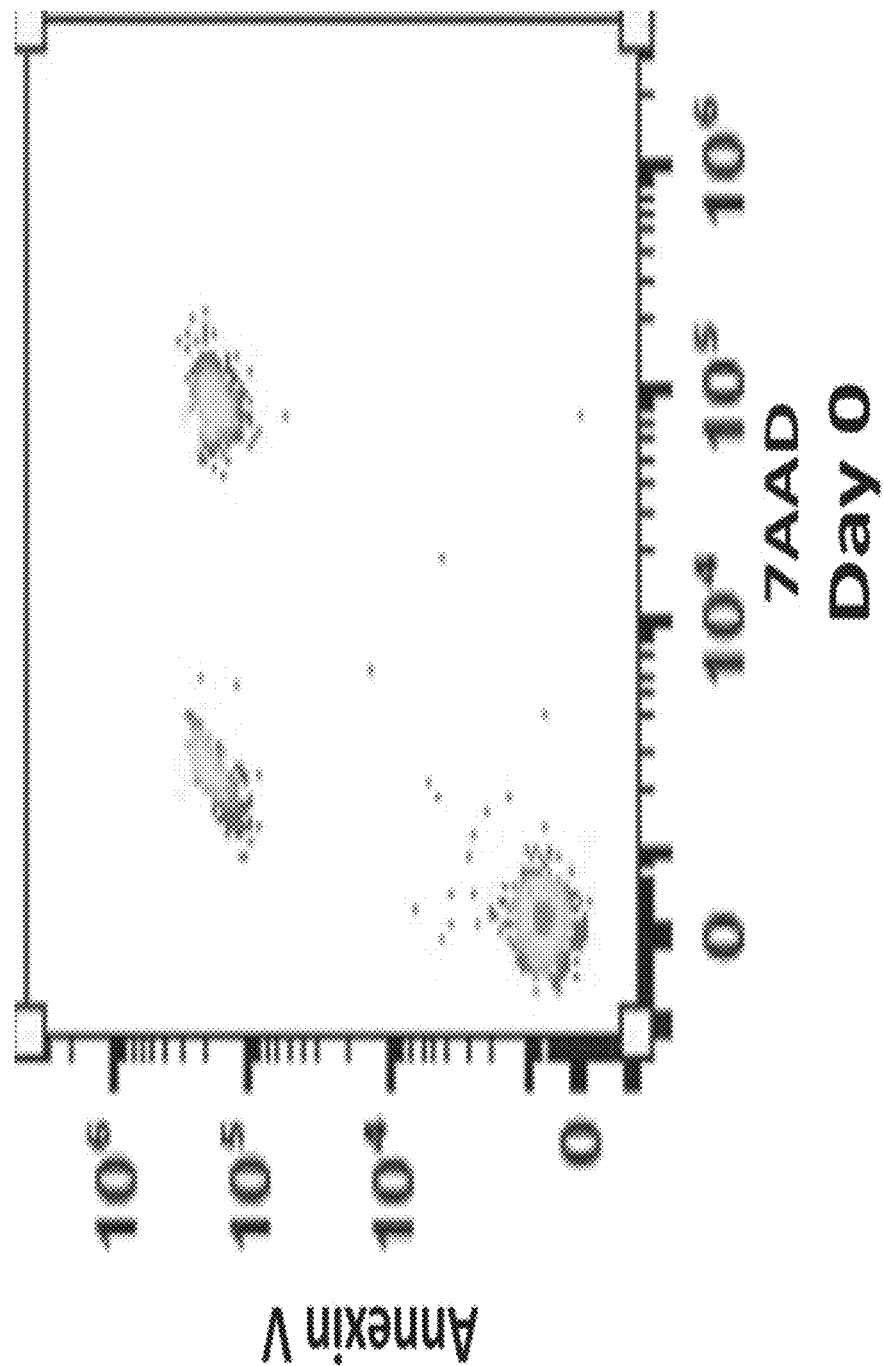
FIGS. 22-26 shows binding of a hydrogel bead composition to annexin V and 7AAD at day 0 (FIG. 22) and one day (FIG. 23), seven days (FIG. 24), fourteen days (FIG. 25), and thirty seven days (FIG. 26) after storage. The first hydrogel bead population contained both a pre-apoptotic signal binder (e.g., an anti-annexin V antibody or antigen-binding fragment thereof) and an encapsulated nucleic acid. The second hydrogel bead population contained a pre-apoptotic signal binder (e.g., an anti-annexin V antibody or antigen-binding fragment thereof), but did not contain an encapsulated nucleic acid. The third hydrogel bead population contained neither a pre-apoptotic signal binder (e.g., phosphatidylserine ("PS")), nor an encapsulated nucleic acid.
Figure 23:
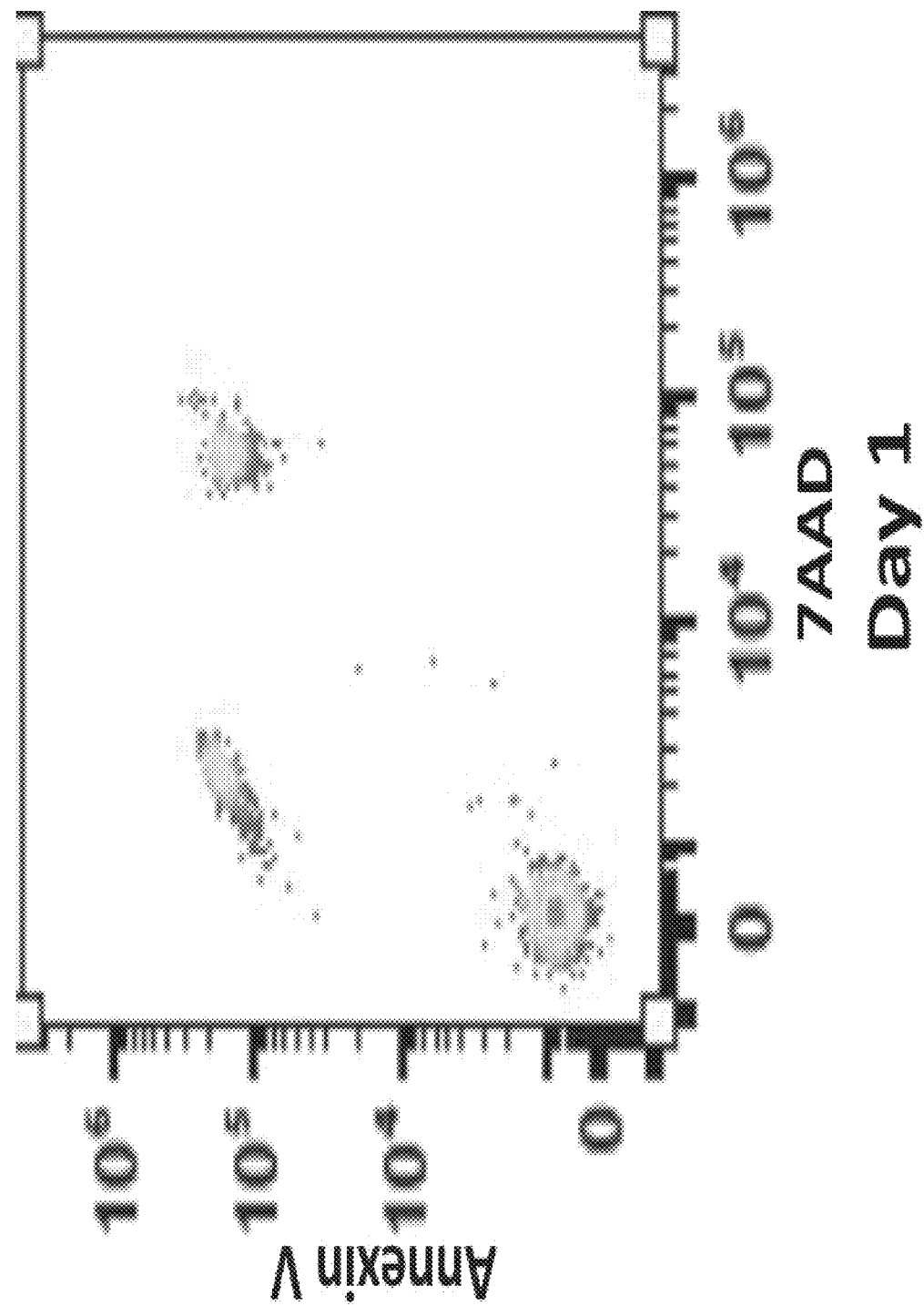
Figure 24:
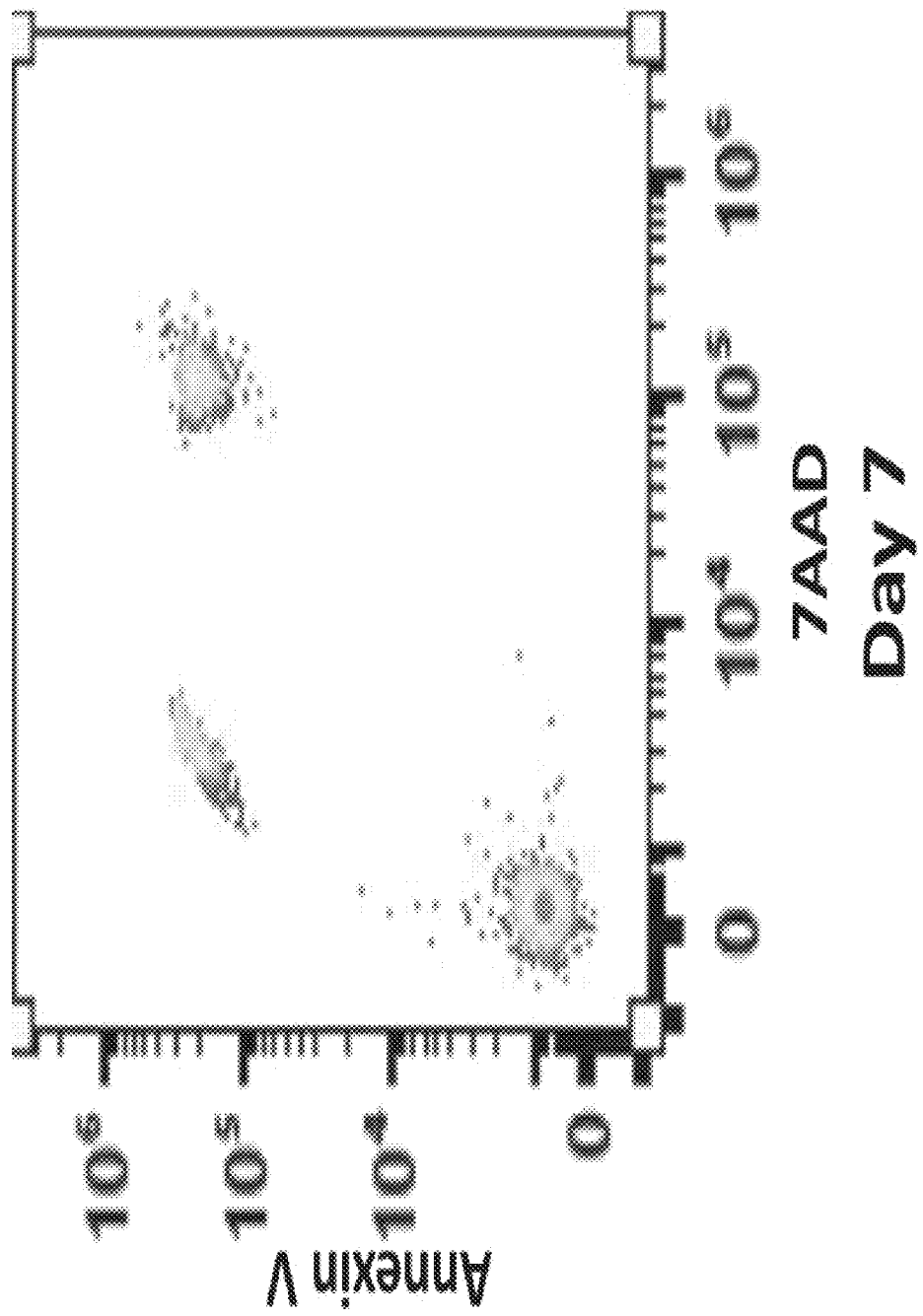
Figure 25:
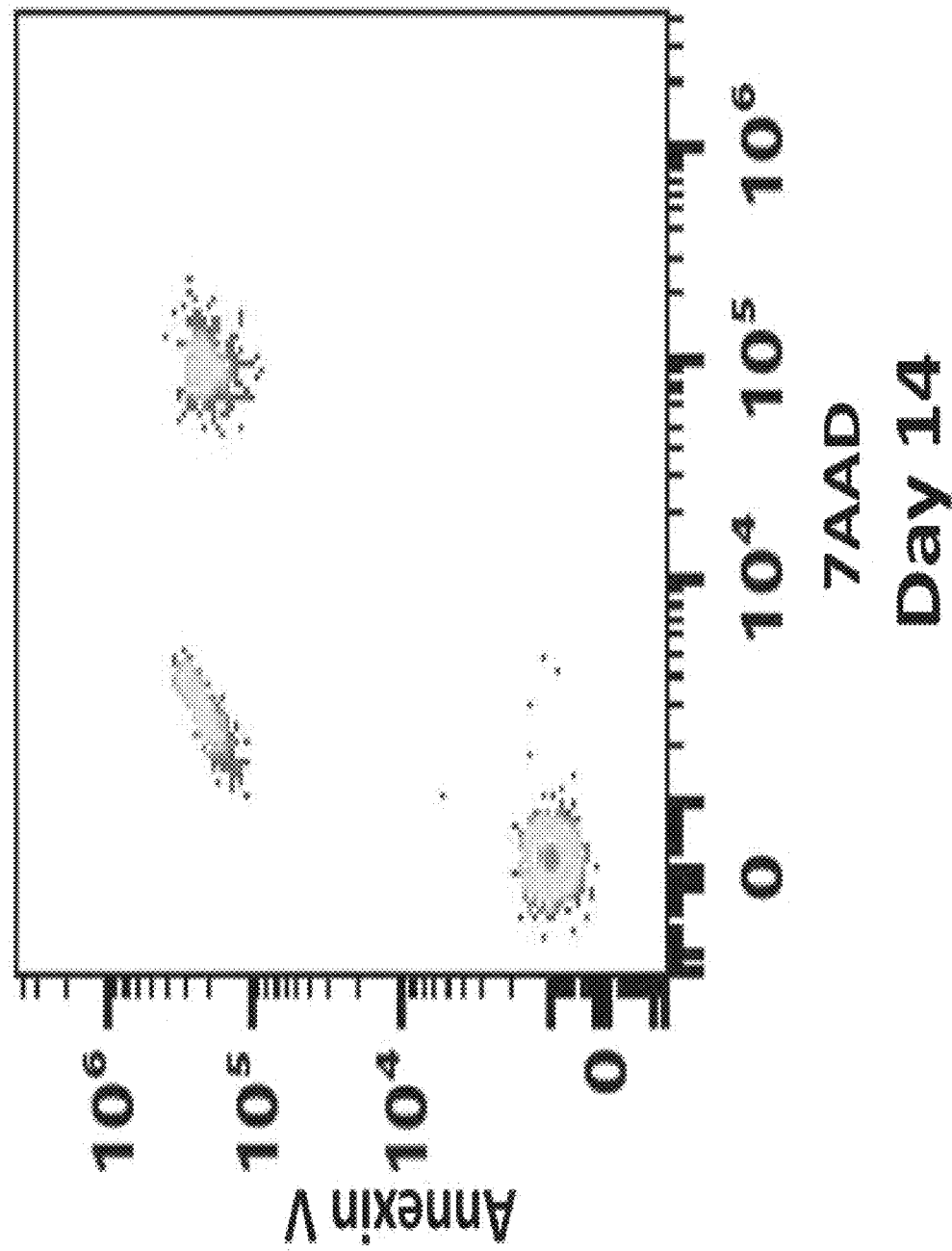
Figure 26:
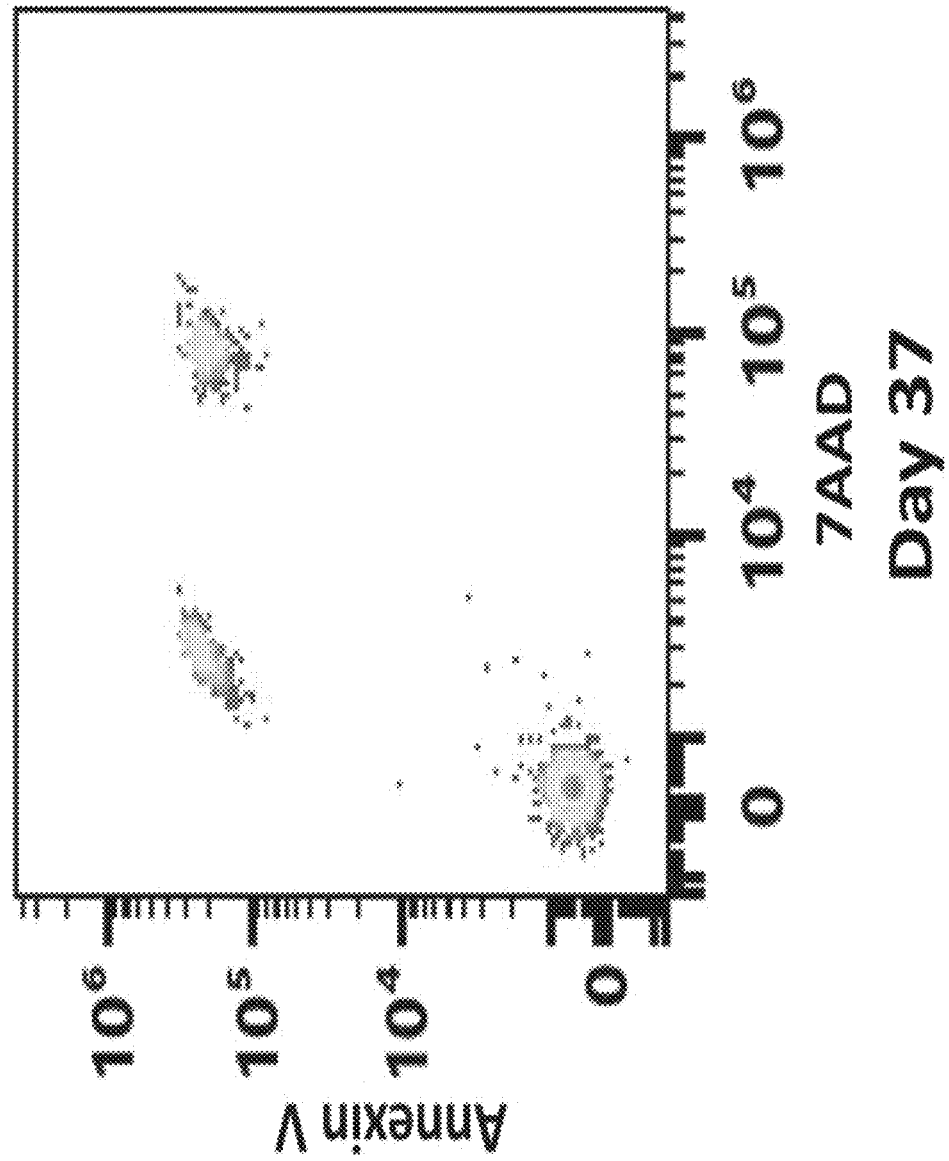
Figure 27:
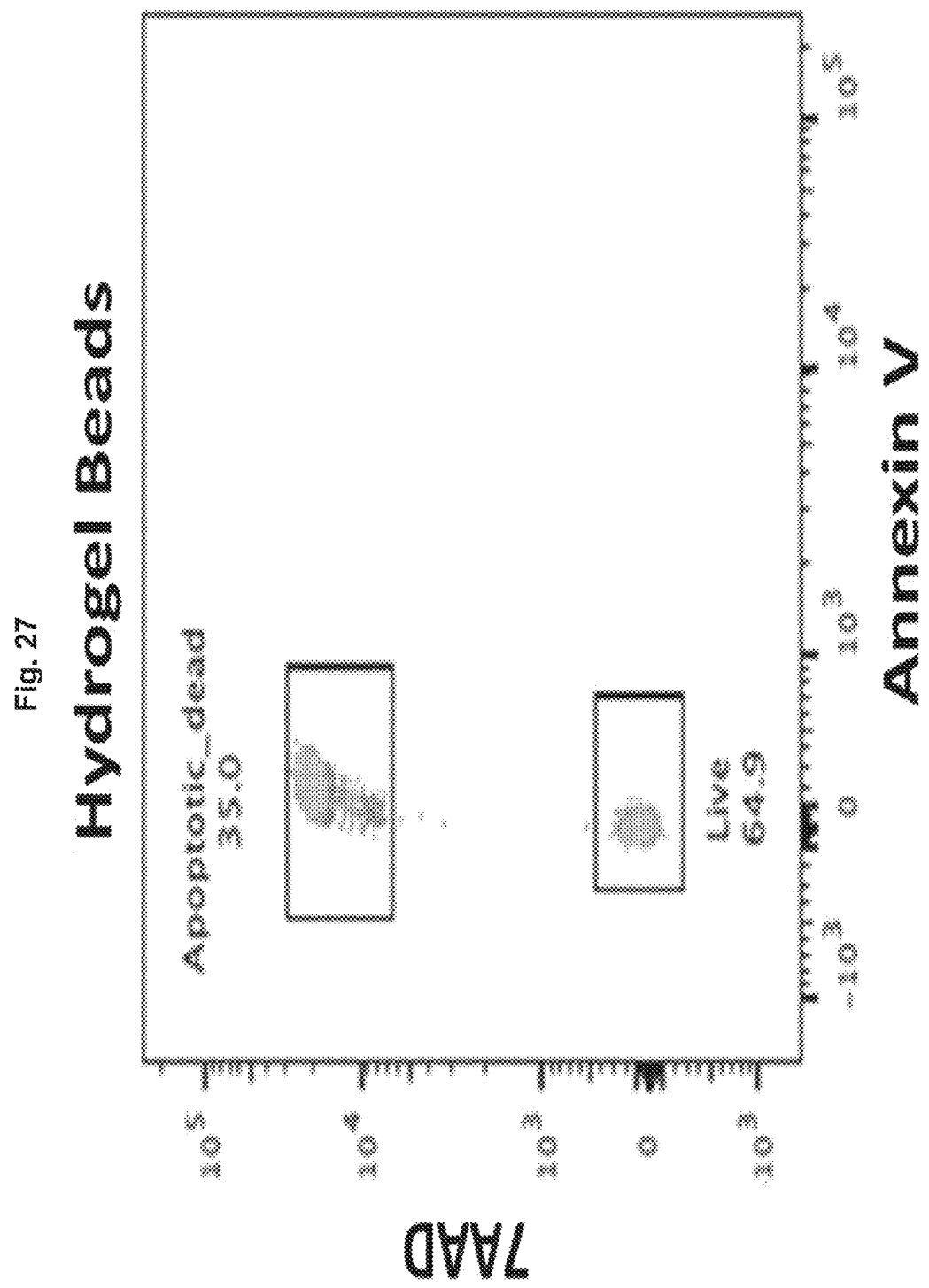
FIGS. 27-29 show binding of 7AAD to the following samples, which were stained with 7AAD only, on a BD FACSLyric™ cytometric device: a hydrogel bead composition (FIG. 27), Jurkat cells (FIG. 28), and PBMC (FIG. 29). The hydrogel bead composition contained three populations of hydrogel beads. The first hydrogel bead population contained both a pre-apoptotic signal binder (e.g., a phosphatidylserine or an anti-annexin V antibody or antigen-binding fragment thereof) and an encapsulated nucleic acid. The second hydrogel bead population contained a pre-apoptotic signal binder (e.g., a phosphatidylserine or an anti-annexin V antibody or antigen-binding fragment thereof), but did not contain an encapsulated nucleic acid. The third hydrogel bead population contained neither a pre-apoptotic signal binder (e.g., phosphatidylserine or an anti-annexin V antibody or antigen-binding fragment thereof), nor an encapsulated nucleic acid.
Figure 28:
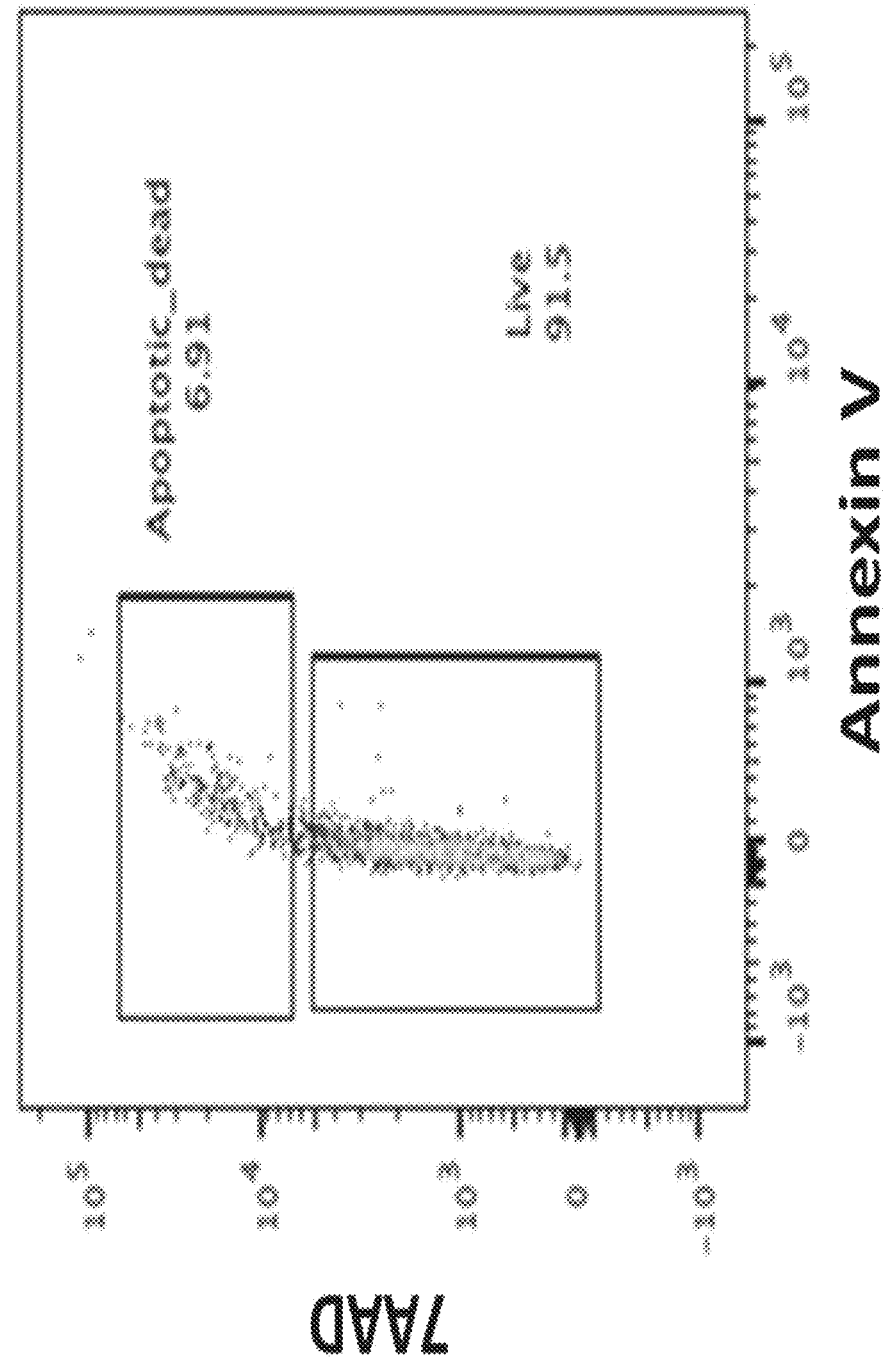

FIG. 21 shows binding of the three hydrogel bead populations to annexin V and 7AAD. The third hydrogel bead population bound to neither annexin V nor 7AAD, and is labeled "Live cell mimic." The second hydrogel bead population bound to annexin V, but not to 7AAD, and is labeled "Apoptotic cell mimic." The first hydrogel bead population bound to both annexin V and 7AAD, and is labeled "Dead cell mimic."

Use of the first, second, and third population of hydrogel beads provides an improvement over the live/dead assay of Example 4, which used the second, third and fourth populations of hydrogel beads. The hydrogel beads in Example 4 were capable of distinguishing between dead cells (beads containing an amine-dye binder and encapsulated nucleic acid), and live cells (lacking the amine-dye binder and encapsulated nucleic acid of the fourth population).

Advantageously, the first, second, and third population of hydrogels tested in this Example, serve as a mimic for a cell population that contains live cells, dead cells, and cells undergoing apoptosis. Cells that are live do not contain DNA that is accessible to a DNA-intercalating dyes and also do not have an exposed PS apoptosis signal binder. Thus, the third hydrogel bead population that bound to neither annexin V nor 7AAD served as live cell mimics. Cells that are undergoing apoptosis have exposed phosphatidylserine and thus can bind to annexin V. Thus, the second hydrogel bead population that bound to annexin V, but not to 7AAD, served as a mimic for cells undergoing apoptosis. Cells that are dead have ruptured cell membranes and thus have exposed PS and DNA. Thus, the first hydrogel bead population that bound to both annexin V and DNA served as a mimic for dead cells.

Example 6. Hydrogel Beads are Stable for at Least 37 Days

The stability of hydrogel beads of the present disclosure. A composition comprising equal amounts of three different hydrogel bead populations was prepared.

The first hydrogel bead population contained (i) a polymerized monomer and a bifunctional monomer, (ii) an anti-annexin V antibody or antigen-binding fragment thereof (a pre-apoptotic signal binder), and (iii) an encapsulated nucleic acid. This first population of hydrogel beads can bind to both pre-apoptotic signals and DNA-intercalating dyes, and thus serve as mimics of dead cells.

The second hydrogel bead population contained (i) a polymerized monomer and a bifunctional monomer, and (ii) a pre-apoptotic signal binder (e.g., an anti-annexin V antibody or antigen-binding fragment thereof), but lacked the encapsulated nucleic acid of the first hydrogel bead population. This second population of hydrogel beads can bind to pre-apoptotic signals, but cannot bind to DNA-intercalating dyes and thus serve as mimics of cells undergoing apoptosis, but not yet dead.

The third hydrogel bead population contained (i) a polymerized monomer and a bifunctional monomer, but lacked the pre-apoptotic signal binder and encapsulated nucleic acid of the first population of hydrogel beads. This third population of hydrogel beads cannot bind to pre-apoptotic signals or DNA-intercalating dyes and thus serve as mimics of live cells.

The composition was stored at 4° C. for 37 days. The composition was stained with an annexin V dye tagged with the FITC dye, which binds to the anti-annexin V antibody, and the DNA-intercalating dye, 7AAD, before storage ("day 0") and one day, seven days, fourteen days, and thirty-seven days after storage. The composition was subsequently evaluated on a flow cytometric device.

FIGS. 22-26 shows binding of the composition to annexin V and 7AAD at day 0 (FIG. 22); one day (FIG. 23); seven days (FIG. 24); fourteen days (FIG. 25); and thirty seven days (FIG. 26) after storage. The third hydrogel bead population bound to neither annexin V nor 7AAD for 37 days of storage at 4° C., demonstrating stability and avoidance of non-specific binding. The second hydrogel bead population bound to annexin V, but not to 7AAD for 37 days of storage at 4° C. The first hydrogel bead population bound to both annexin V and 7AAD for 37 days of storage at 4° C.

This experiment showed that the hydrogel bead populations remain stable and thus can serve as mimics for live cell, dead cell, and apoptotic cells for at least 37 days when the hydrogel beads are stored at 4° C.

Example 7. Hydrogel Bead Populations Stained with a Single Dye are Superior to Live Cells Stained with a Single Dye as Compensation Controls The ability of the following compositions, which were each stained with a single dye, to serve as compensation controls was evaluated: (a) a composition containing first, second and third hydrogel bead populations of Example 1; (b) Jurkat cells; and (c) peripheral blood mononuclear cells (PBMCs)).

The composition containing the three hydrogel bead populations was prepared by combining the first hydrogel bead population, second hydrogel bead population, and third hydrogel bead population in equal ratios.

Each of the following samples: (a) the composition containing the three hydrogel bead populations, (b) the PBMCs, and (c) the Jurkat cells were stained with either annexin V labeled with an ALEXA FLUOR® 647 dye or 7AAD. The composition was subsequently evaluated on a CYTEK® Aurora cytometric device or a BD FACSLyric™.

Figure 29:
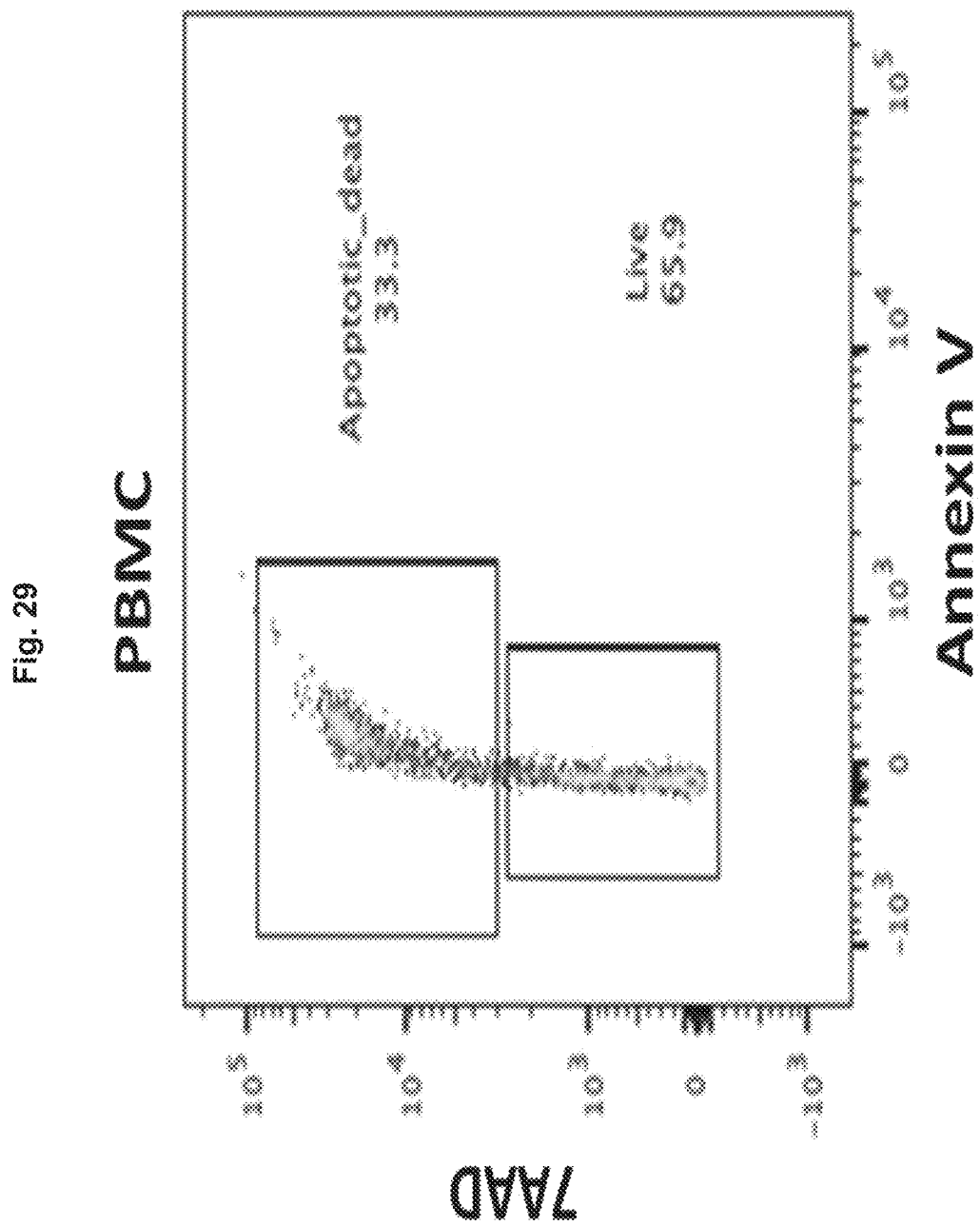
Figure 30:
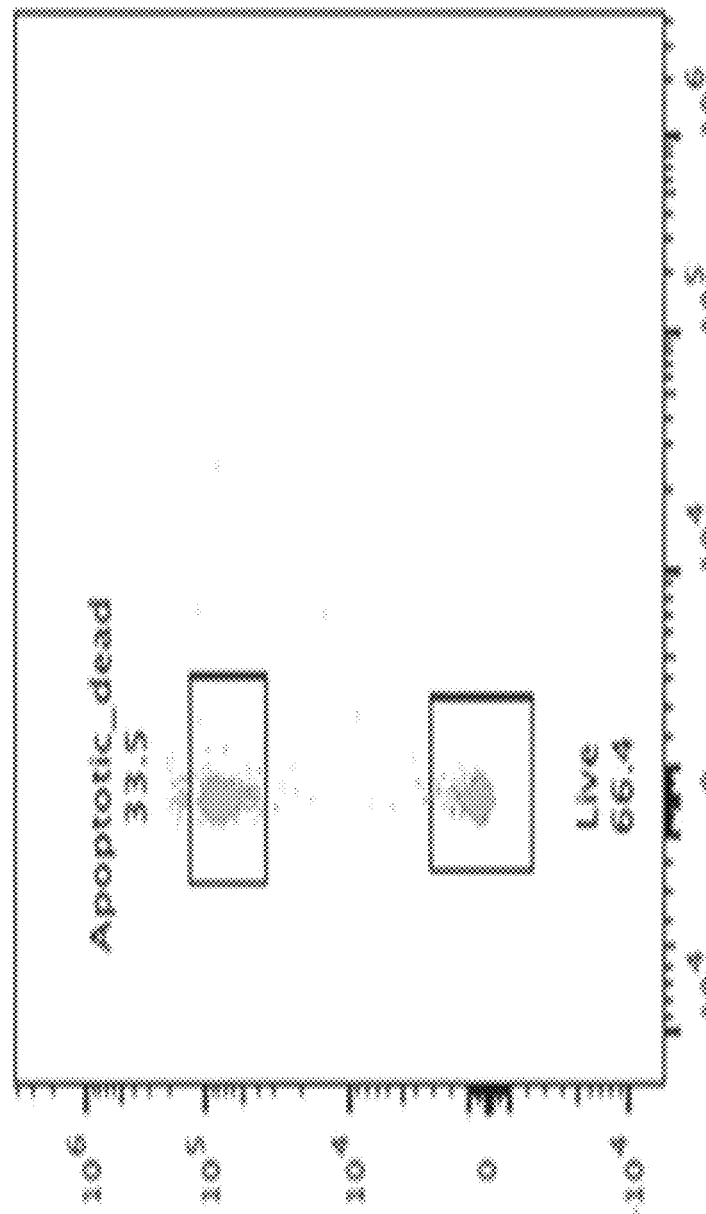
FIGS. 30-31 show binding of 7AAD to the following samples, which were stained with 7AAD only, on a CYTEK® Aurora cytometric device: a hydrogel bead composition (FIG. 30) and Jurkat cells (FIG. 31). The hydrogel bead composition contained three populations of hydrogel beads. The first hydrogel bead population contained both a pre-apoptotic signal binder (e.g., a phosphatidylserine or an anti-annexin V antibody or antigen-binding fragment thereof) and an encapsulated nucleic acid. The second hydrogel bead population contained a pre-apoptotic signal binder (e.g., a phosphatidylserine or an anti-annexin V antibody or antigen-binding fragment thereof), but did not contain an encapsulated nucleic acid. The third hydrogel bead population contained neither a pre-apoptotic signal binder (e.g., phosphatidylserine or an anti-annexin V antibody or antigen-binding fragment thereof), nor an encapsulated nucleic acid.
Figure 31:
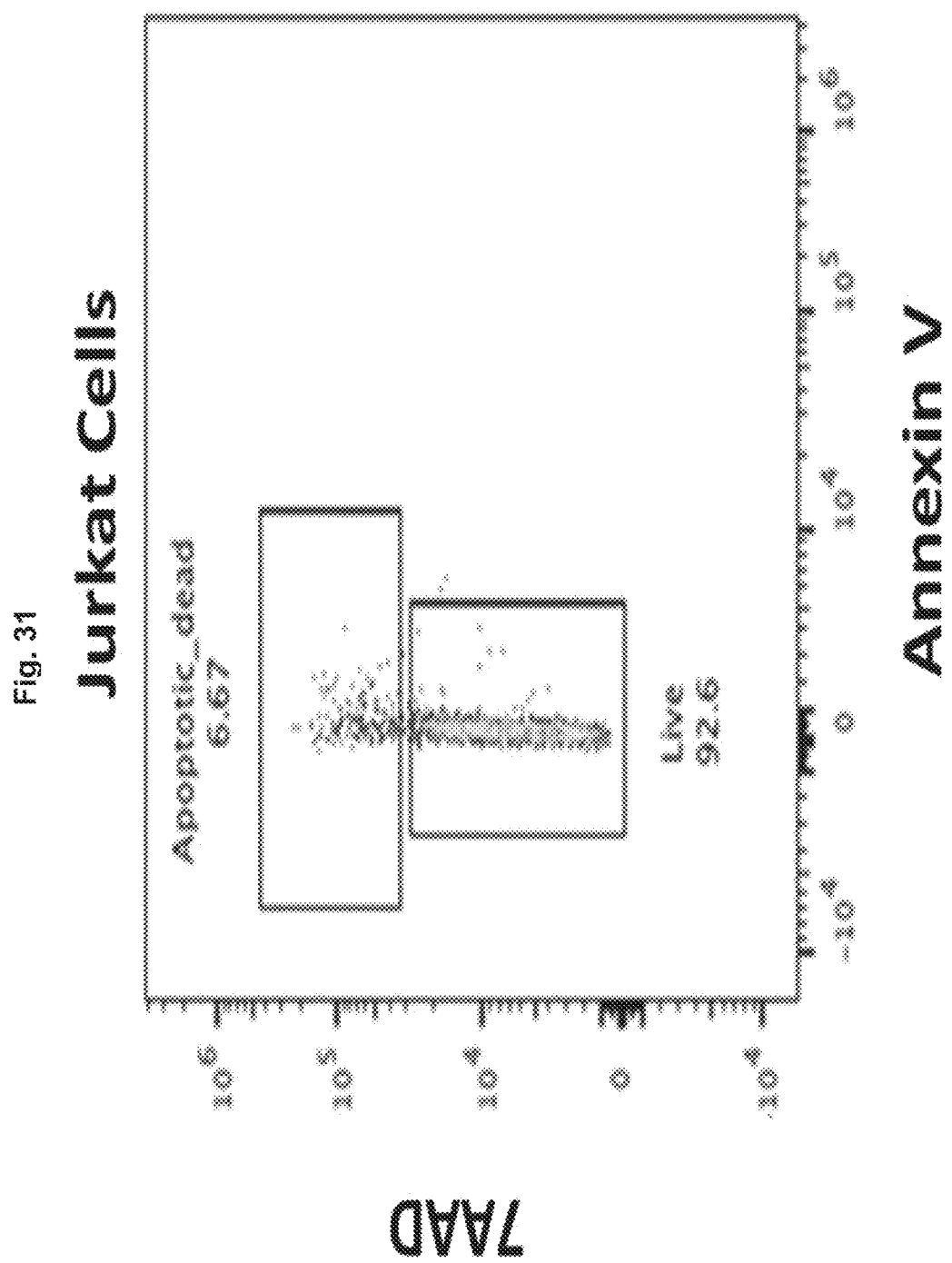
Figure 32:
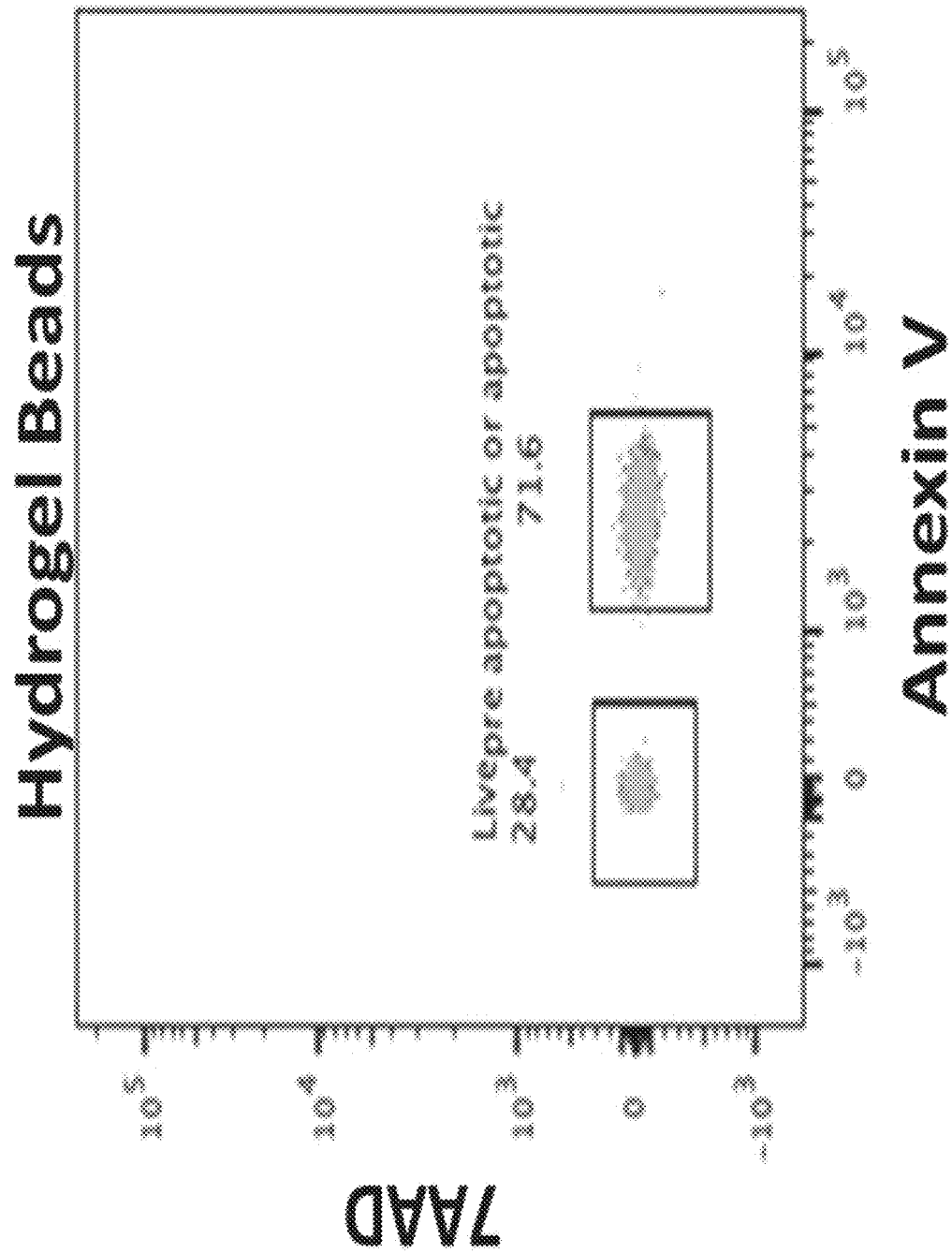
FIGS. 32-34 show binding of annexin V to the following compositions on a BD FACSLyric™ cytometric device: a composition containing the three hydrogel bead populations (FIG. 32), Jurkat cells (FIG. 33), or PBMC (FIG. 34). The first hydrogel bead population contained both a pre-apoptotic signal binder (e.g., a phosphatidylserine or an anti-annexin V antibody or antigen-binding fragment thereof) and an encapsulated nucleic acid. The second hydrogel bead population contained a pre-apoptotic signal binder (e.g., a phosphatidylserine or an anti-annexin V antibody or antigen-binding fragment thereof), but did not contain an encapsulated nucleic acid. The third hydrogel bead population contained neither a pre-apoptotic signal binder (e.g., phosphatidylserine or an anti-annexin V antibody or antigen-binding fragment thereof), nor an encapsulated nucleic acid.
Figure 33:
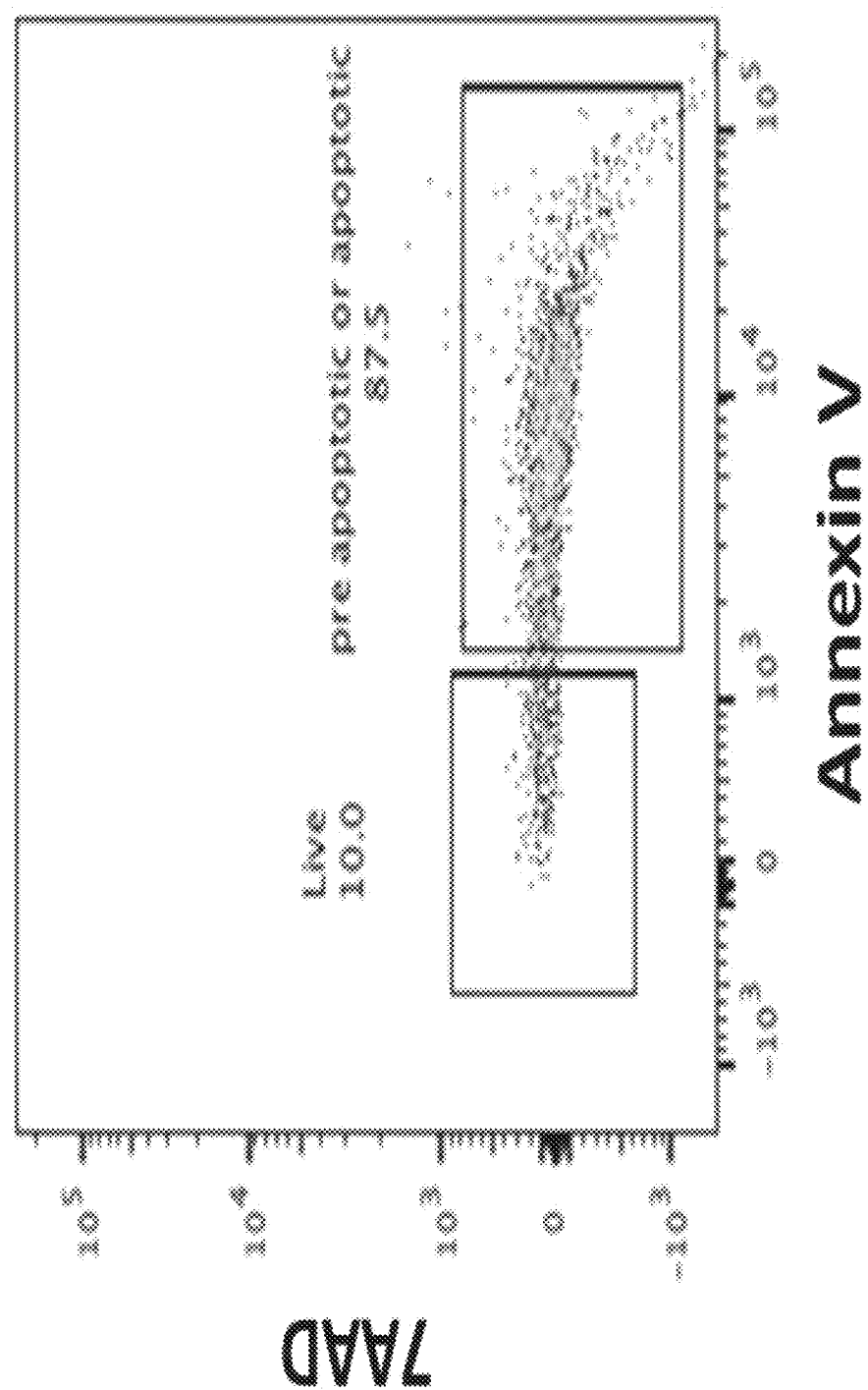

FIGS. 27-31 show binding of 7AAD to the following samples, which were stained with 7AAD only, on a BD FACSLyric™ cytometric device (FIGS. 27-29) or a CYTEK® Aurora cytometric device (FIGS. 30-31): (a) a composition containing the three hydrogel bead populations (FIG. 27, FIG. 30), (b) Jurkat cells (FIG. 28, FIG. 31), and (c) PBMC (FIG. 29).

Figure 34:
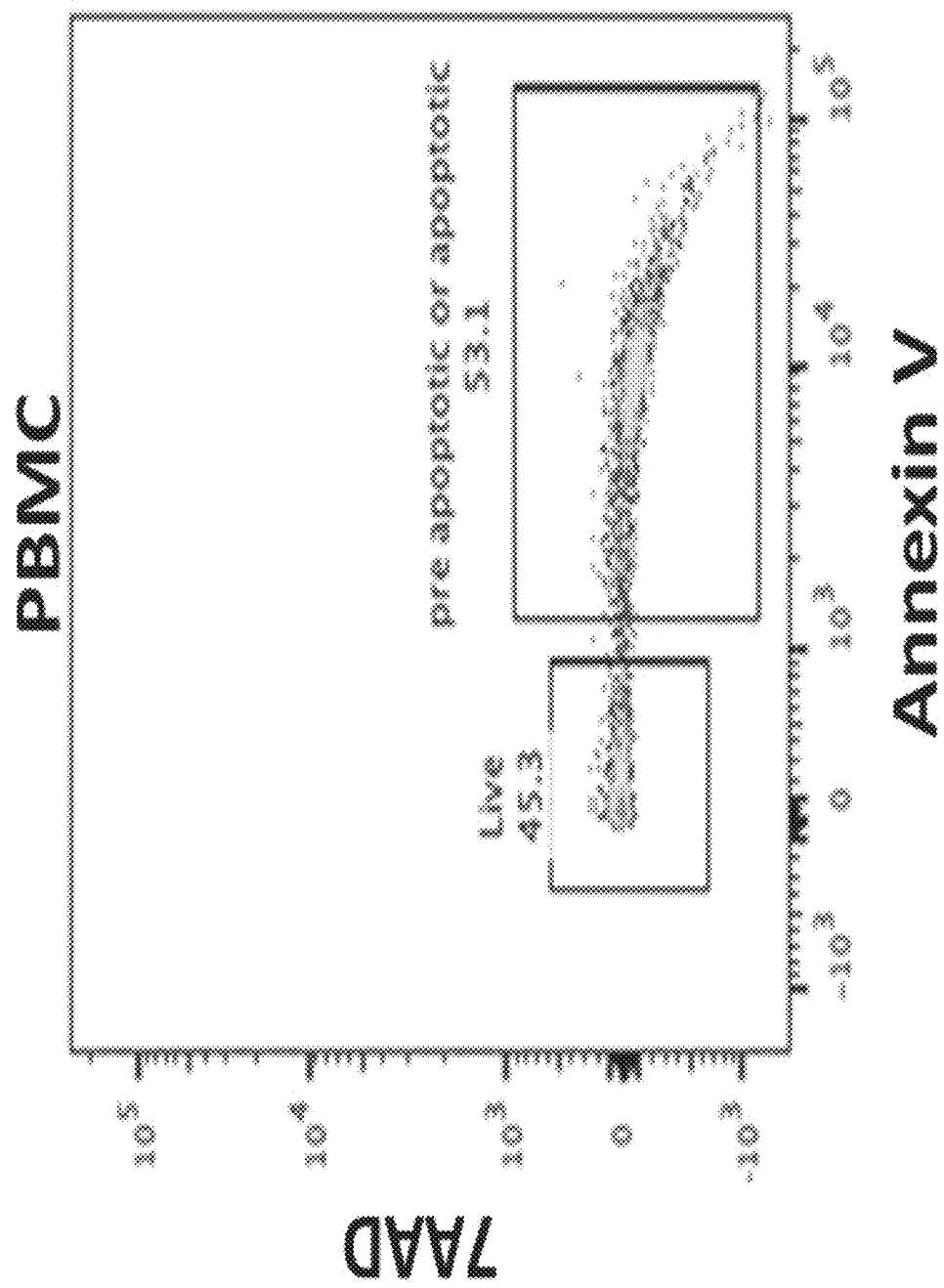
Figure 35:
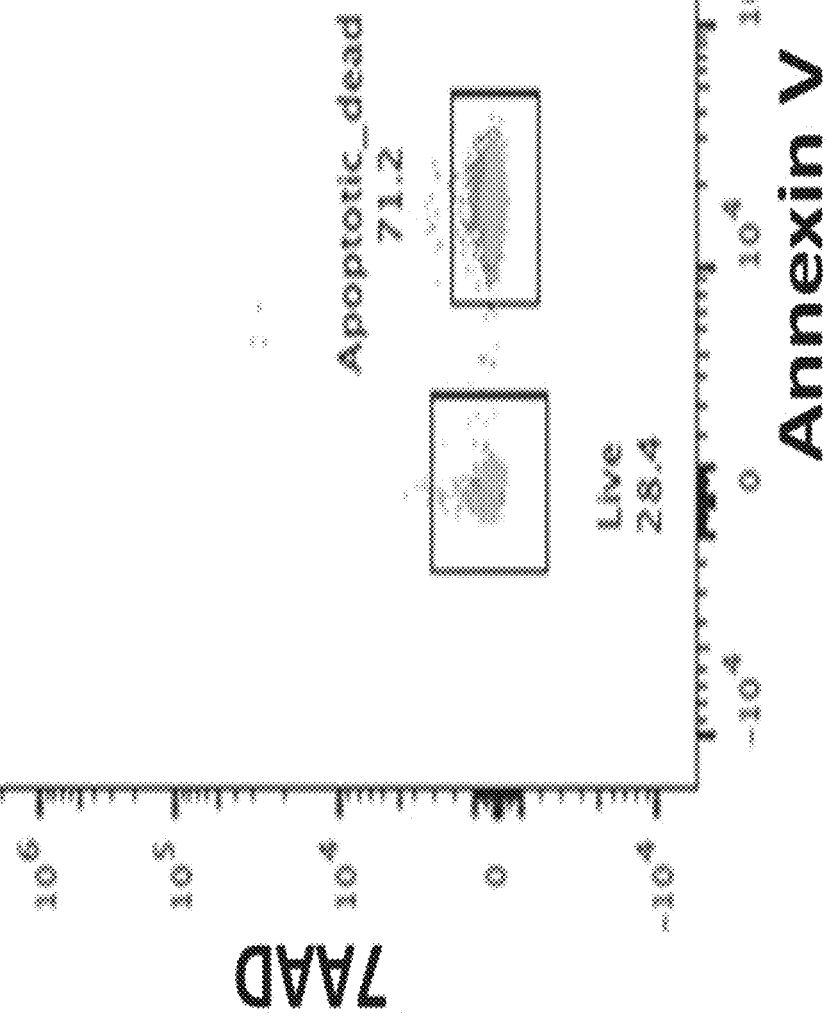
FIGS. 35-36 show binding of annexin V to a composition containing the three hydrogel bead populations (FIG. 35) and Jurkat cells (FIG. 36) on a CYTEK® Aurora cytometric device. The first hydrogel bead population contained both a pre-apoptotic signal binder (e.g., a phosphatidylserine or an anti-annexin V antibody or antigen-binding fragment thereof) and an encapsulated nucleic acid. The second hydrogel bead population contained a pre-apoptotic signal binder (e.g., a phosphatidylserine or an anti-annexin V antibody or antigen-binding fragment thereof), but did not contain an encapsulated nucleic acid. The third hydrogel bead population contained neither a pre-apoptotic signal binder (e.g., phosphatidylserine or an anti-annexin V antibody or antigen-binding fragment thereof), nor an encapsulated nucleic acid.
Figure 36:
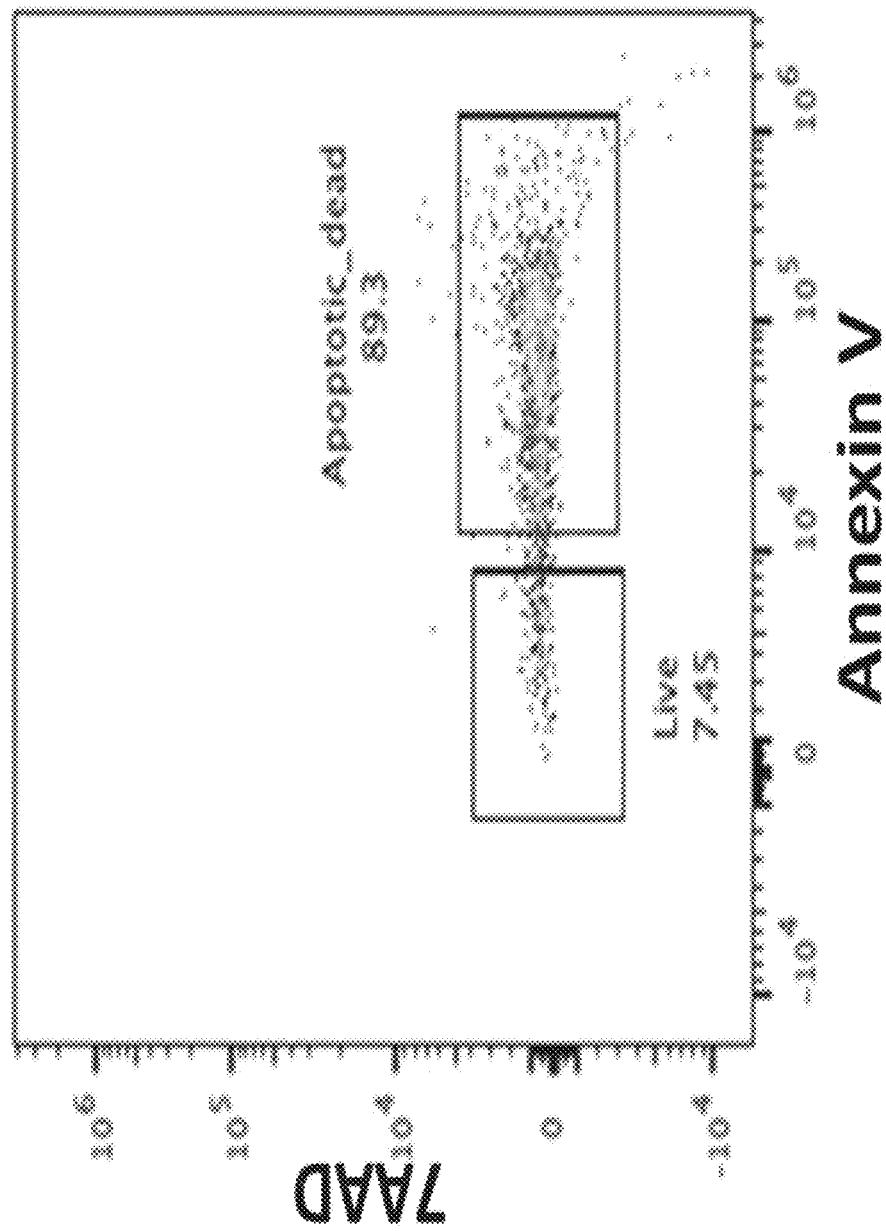

FIGS. 32-36 show binding of annexin V to the following samples, which were stained with annexin V only, on a BD FACSLyric™ cytometric device (FIGS. 32-34) or a CYTEK® Aurora cytometric device (FIGS. 35-36): (a) composition containing the three hydrogel bead populations (FIG. 32, FIG. 35), (b) Jurkat cells (FIG. 33, FIG. 36), and (c) PBMC (FIG. 34).

When the hydrogel bead composition was stained with a single dye (either 7AAD or annexin V), the flow cytometry scatter plot showed clear positive (populations that bound to 7AAD or annexin V) and negative (populations that did not bind to 7AAD or annexin V) populations. In contrast, the scatter plots of cells stained with single dyes did not show clear positive or negative populations. (compare FIG. 30 with FIG. 31). This trend was independent of cytometry device. This shows that hydrogel bead compositions stained with a single dye are superior controls to cells stained with a single dye.

Example 8. Hydrogel Bead Populations Stained with a Single Dye are Superior to Live Cells Stained with a Single Dye as Gating Controls, Compensation Controls, and for Spectral Unmixing The ability of the following compositions to serve as gating controls, compensation controls, and as tools for spectral unmixing was evaluated: (a) a composition containing the first, second, and third hydrogel bead populations of Example 1; (b) Jurkat cells; and (c) peripheral blood mononuclear cells (PBMCs).

The composition containing three hydrogel bead populations was prepared by combining the first hydrogel bead population, second hydrogel bead population, and third hydrogel bead population in equal ratios.

Composition (a) was aliquoted into a 96-well plate (100 μL of hydrogel beads suspended in Annexin V buffer per well) and stained with 7AAD and/or Annexin V labeled with an ALEXA FLUOR® 647 dye.

Composition (b) was prepared by suspending Jurkat cells in Annexin V buffer at a concentration of ten million cells per milliliter. Composition (b) was aliquoted into a 96-well plate (100 μL of composition (b) per well). Composition (b) was treated with CD95 (0.0625 μg/mL) for one hour at 37° C. and subsequently washed three times with Annexin V buffer by centrifugation at 400×g for five minutes. Composition (b) was then stained with 7AAD and/or Annexin V labeled with an ALEXA FLUOR® 647 dye for thirty minutes.

Composition (c) was prepared by suspending PBMCs that were previously cryo-preserved in Annexin V buffer at a concentration of five million cells per milliliter. Composition (c) was aliquoted into a 96-well plate (100 μL of composition (c) per well). Composition (c) was treated with CD95 (0.0625 μg/mL) for one hour at 37° C. and subsequently washed three times with Annexin V buffer by centrifugation at 400×g for five minutes. Composition (c) was then stained with 7AAD and/or Annexin V labeled with an ALEXA FLUOR® 647 dye for thirty minutes.

After staining, each of compositions (a), (b), and (c) was washed three times with Annexin V buffer by centrifugation at 400×g for five minutes.

The samples were resuspended in Annexin V buffer. 500,000 cells from each sample were evaluated on a CYTEK® Aurora cytometric device or a BD FACSLyric™ cytometric device. Fluorescence spillover on the BD FACSLyric™ cytometric device was corrected via automated compensation. The fluorescence spectra information of compositions (a), (b), and (c) labeled with a single dye (either 7AAD or Annexin V labeled with an ALEXA FLUOR® 647 dye) was used to perform spectral unmixing on the CYTEK® Aurora cytometric device.

Figure 37:
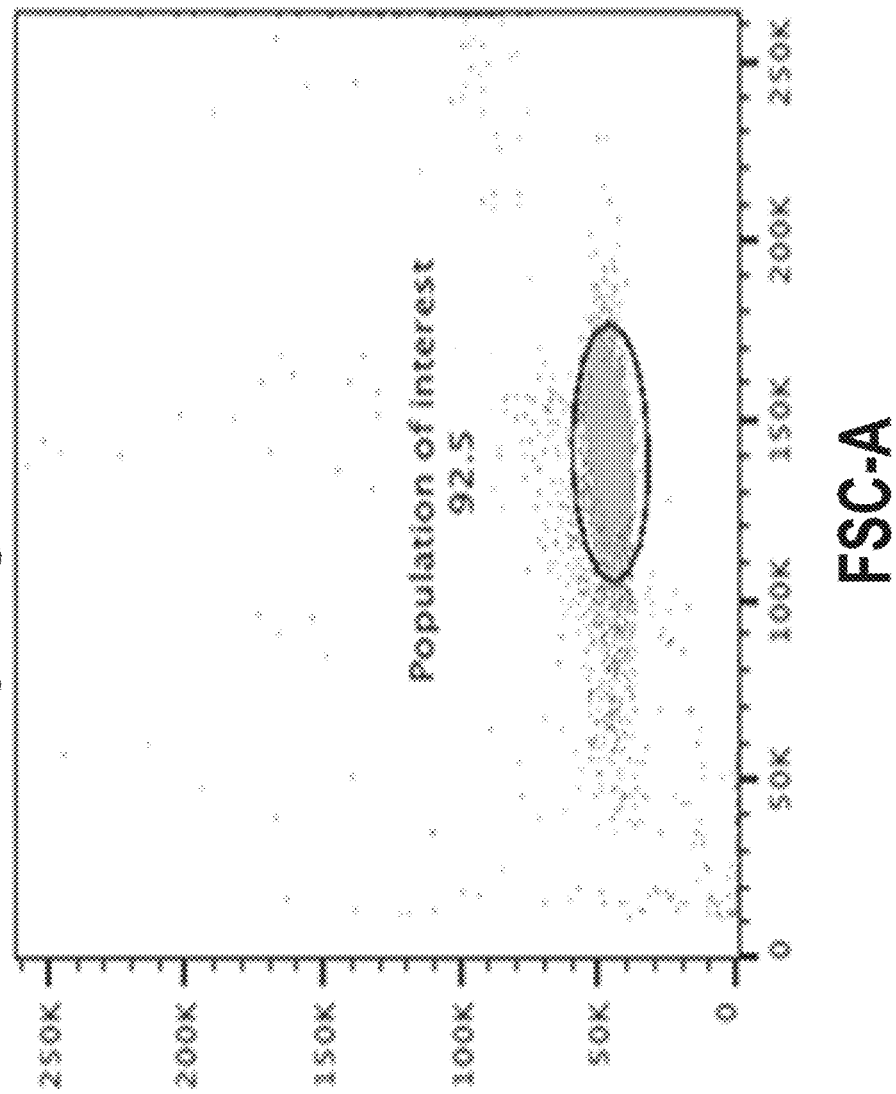
FIGS. 37-39 show the forward scatter and side scatter of a composition containing three hydrogel bead populations (FIG. 37); Jurkat cells (FIG. 38); or peripheral blood mononuclear cells (PBMCs) (FIG. 39) as measured on a BD FACSLyric™ cytometric device. Each composition was gated to exclude debris (see circle on FIGS. 37-39). Each of these compositions is described in detail in Example 8.
Figure 38:
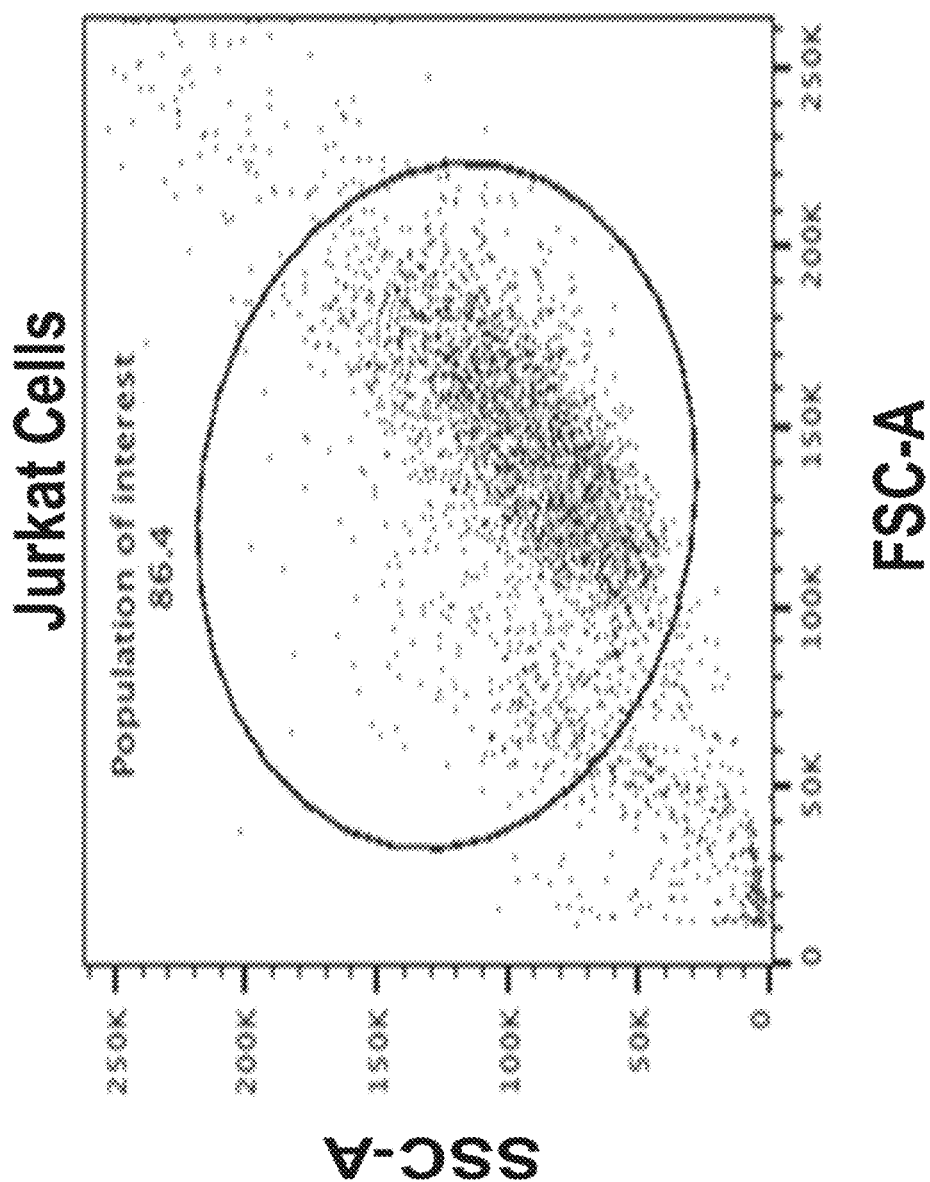
Figure 39:
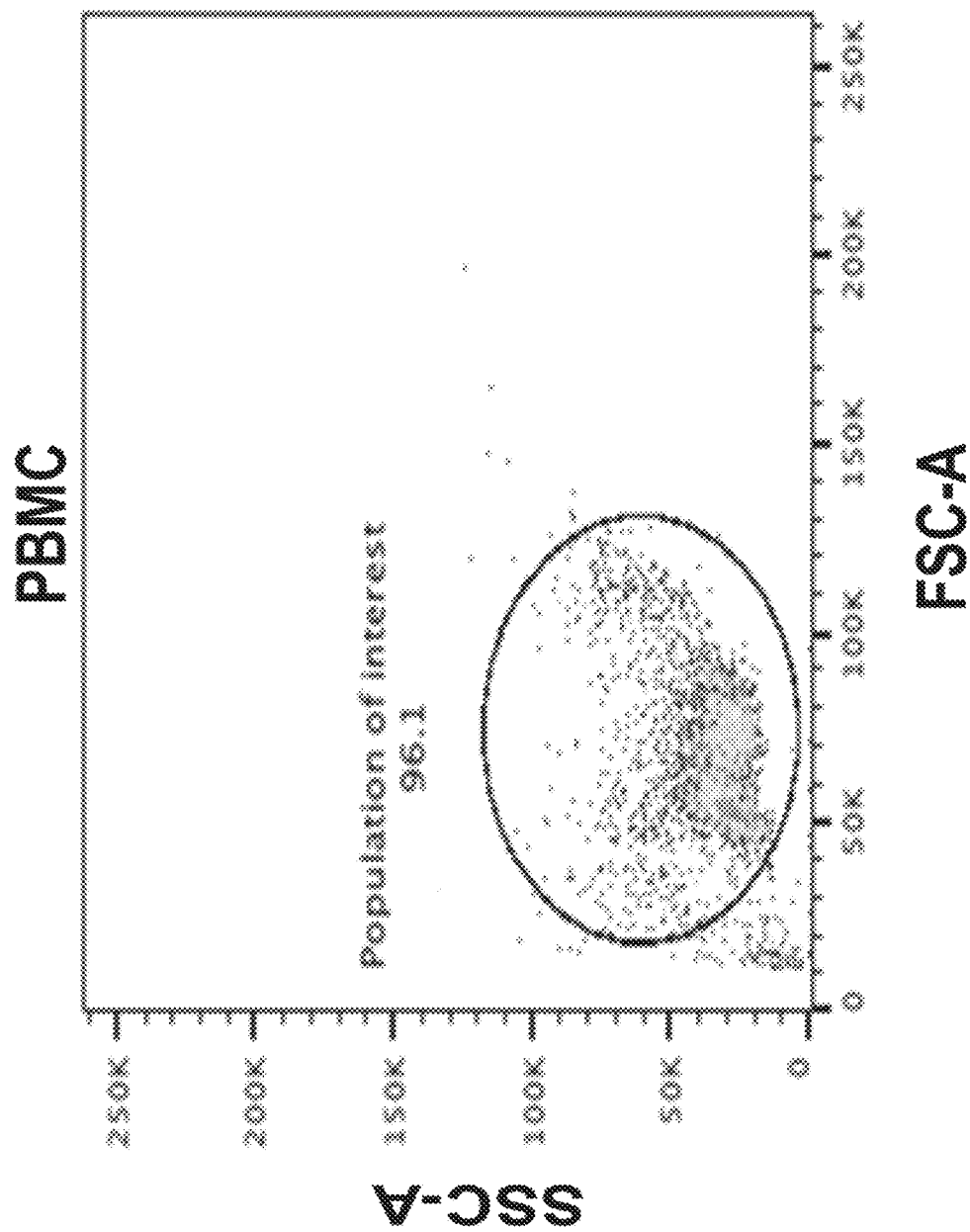
Figure 40:
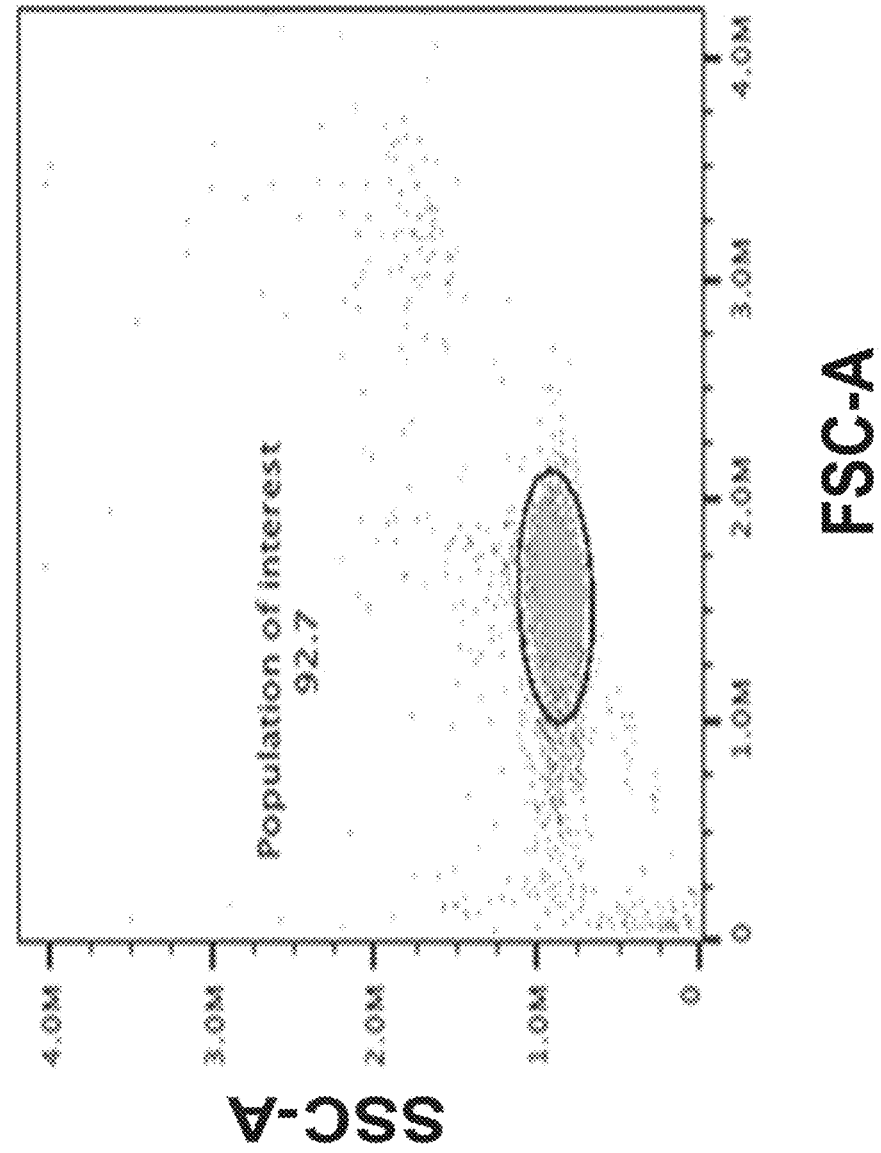
FIGS. 40-42 show the forward scatter and side scatter of a composition containing three hydrogel bead populations (FIG. 40); Jurkat cells (FIG. 41); or peripheral blood mononuclear cells (PBMCs) (FIG. 42) as measured on a BD FACSLyric™ cytometric device. Each composition was gated to exclude debris (see circle on FIGS. 40-42). Each of these compositions is described in detail in Example 8.
Figure 41:
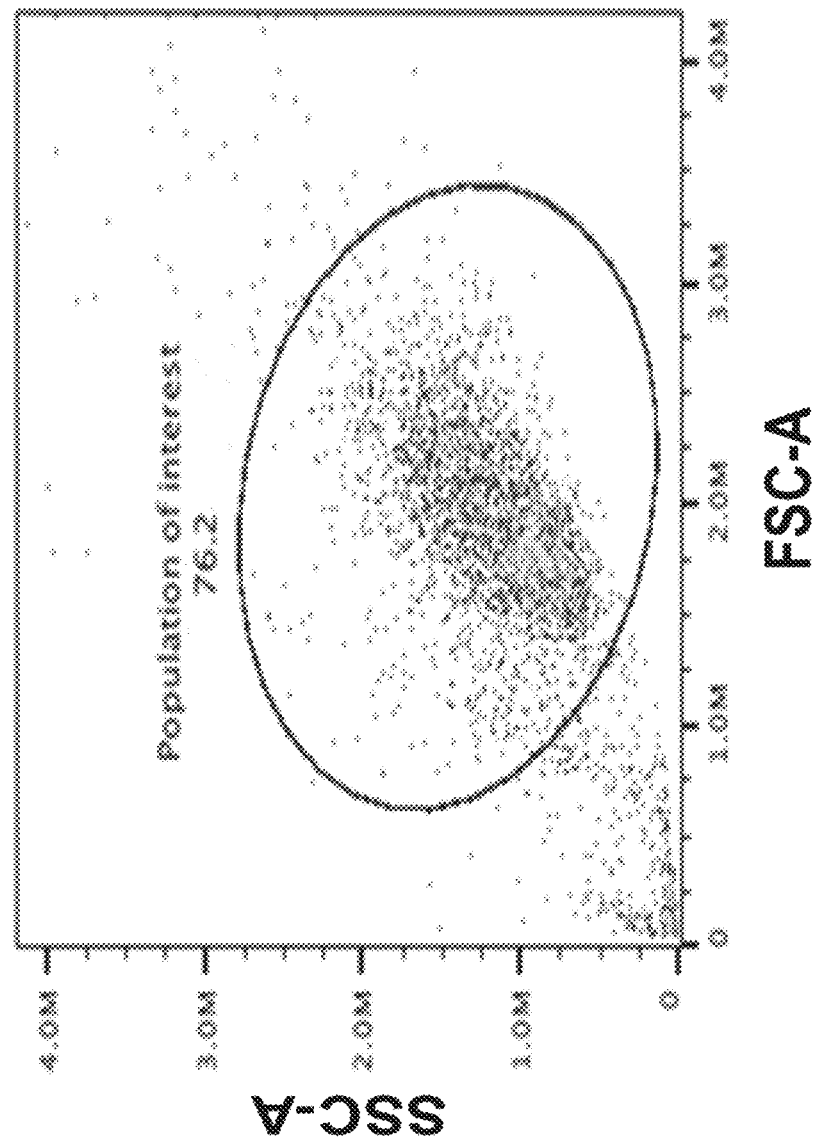
Figure 42:
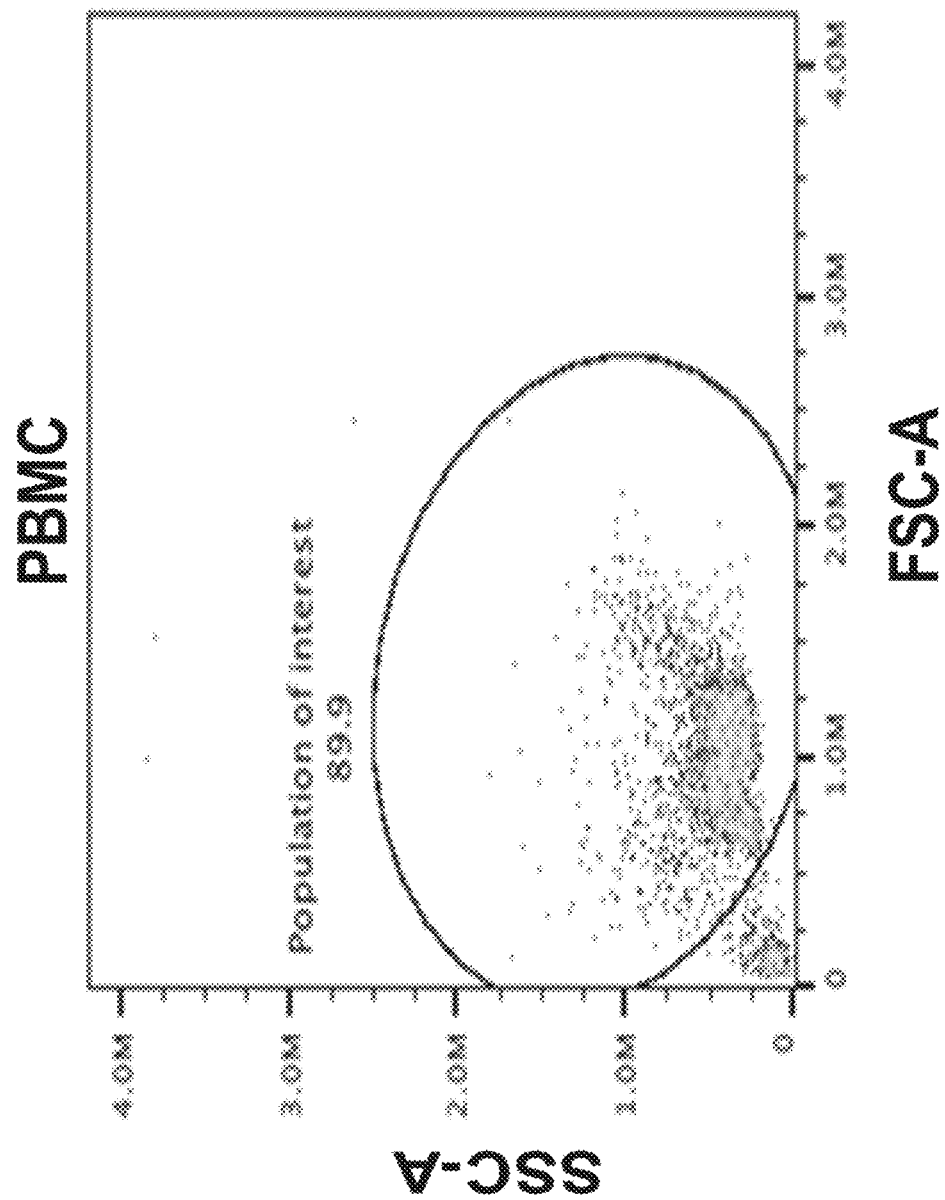

FIGS. 37-39 show the forward scatter ("FSC") and side scatter ("SSC") of (a) a composition containing three hydrogel bead populations (FIG. 37); (b) Jurkat cells (FIG. 38); or (c) peripheral blood mononuclear cells (PBMCs) (FIG. 39) as measured on a BD FACSLyric™ cytometric device. FIGS. 40-42 show the forward scatter and side scatter of (a) a composition containing three hydrogel bead populations (FIG. 40); (b) Jurkat cells (FIG. 41); or (c) peripheral blood mononuclear cells (PBMCs) (FIG. 42) as measured on a BD FACSLyric™ cytometric device. Each composition was gated to exclude debris (see circle on FIGS. 37-42).

The gated cells and/or beads were analyzed on each cytometric device to determine what beads or cells bound to 7AAD and/or Annexin V.

Results on BD FACSLyric™ Cytometric Device

Cells or beads from each of composition (a), (b), and (c) bound to 7AAD and/or Annexin V labeled with an ALEXA FLUOR® 647 dye, as detected on the BD FACSLyric™ cytometric device. Composition (a), which contained the three hydrogel bead populations, was more compatible with the automated compensation algorithms on the BD FACSLyric™ cytometric device than composition (b) Jurkat cells or composition (c) PBMCs. Additionally, the distinction between positive populations and negative populations was clearer in composition (a) than in the two cell populations (b) and (c).

Figure 43:
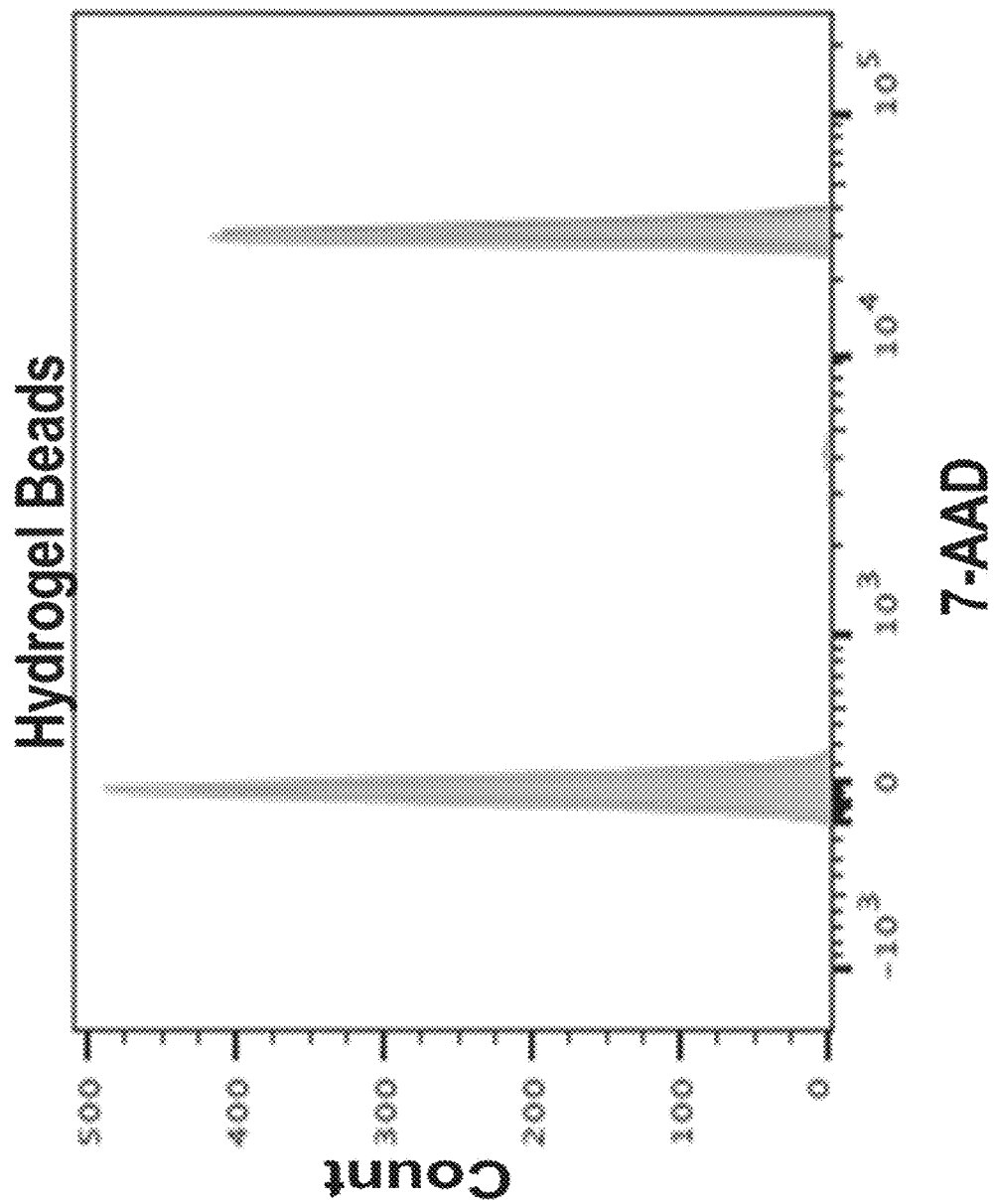
FIGS. 43-45 are histograms that show the mean fluorescence intensity of 7AAD in a composition containing three hydrogel bead populations (FIG. 43); Jurkat cells (FIG. 44); or peripheral blood mononuclear cells (PBMCs) (FIG. 45), as measured on a BD FACSLyric™ cytometric device. Each of these compositions is described in detail in Example 8.
Figure 44:
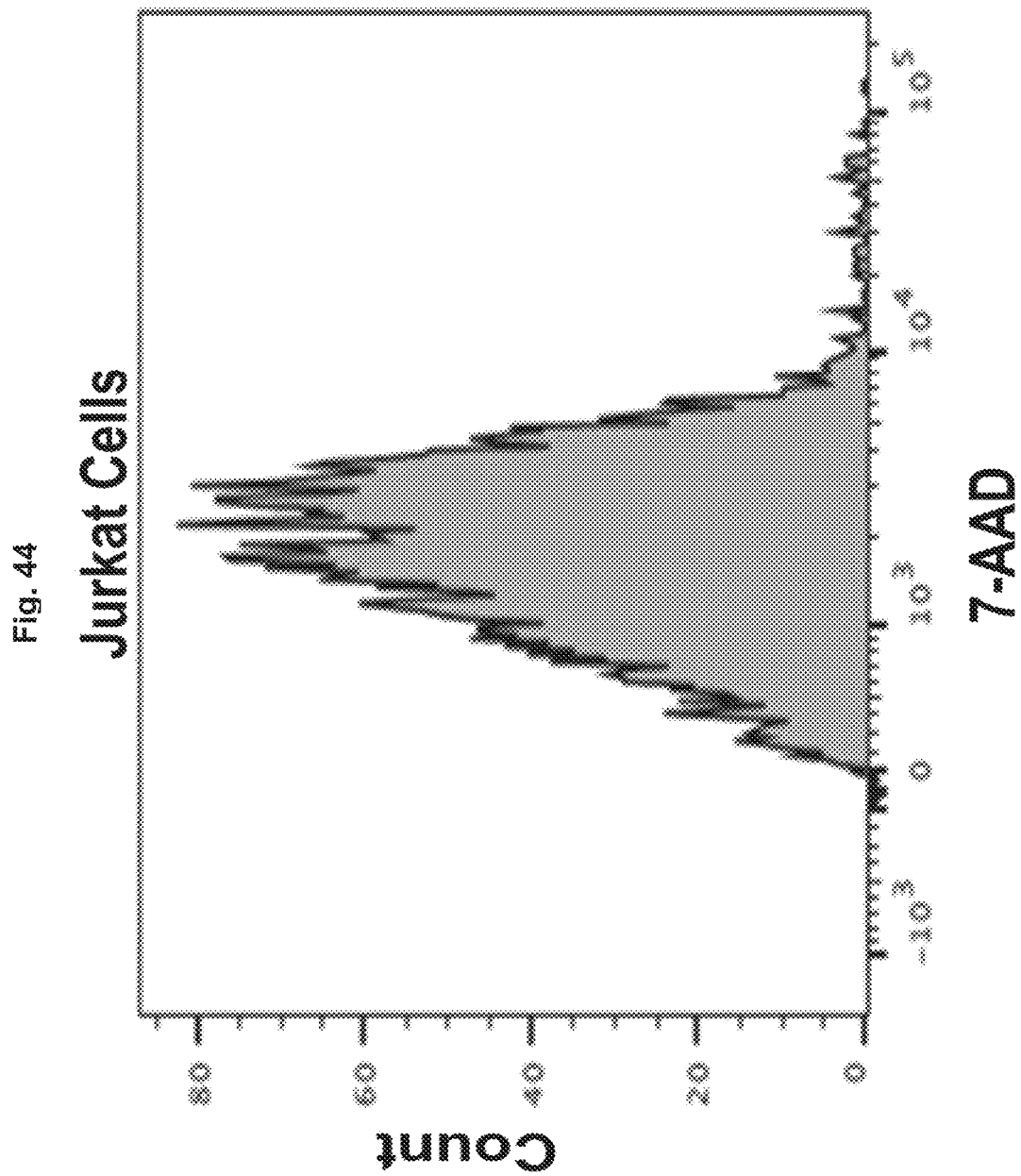
Figure 45:
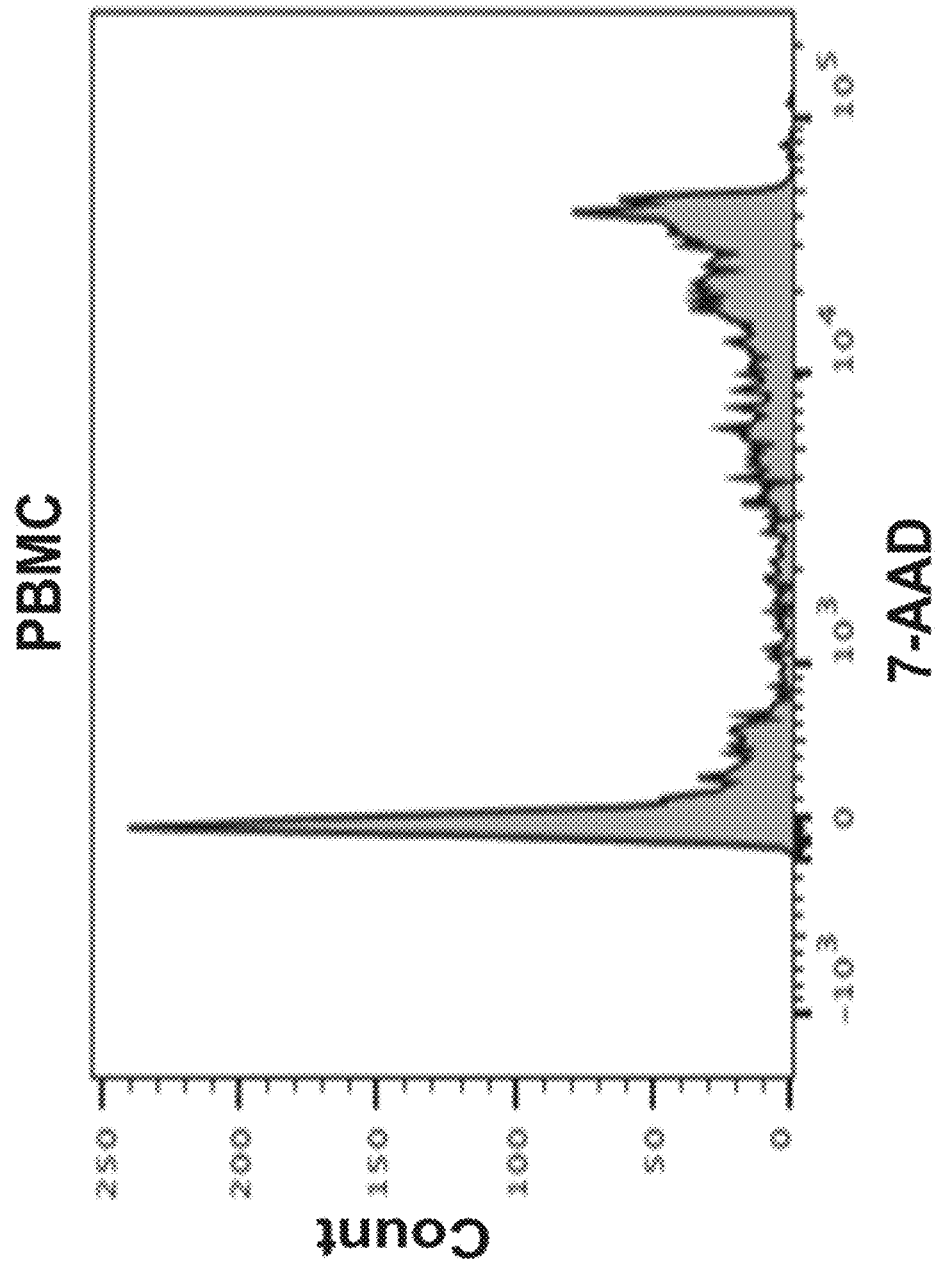

FIGS. 43-45 are histograms that show the mean fluorescence intensity of 7AAD in (a) a composition containing three hydrogel bead populations (FIG. 43); (b) Jurkat cells (FIG. 44); or (c) peripheral blood mononuclear cells (PBMCs) (FIG. 45), as measured on a BD FACSLyric™ cytometric device.

Figure 52:
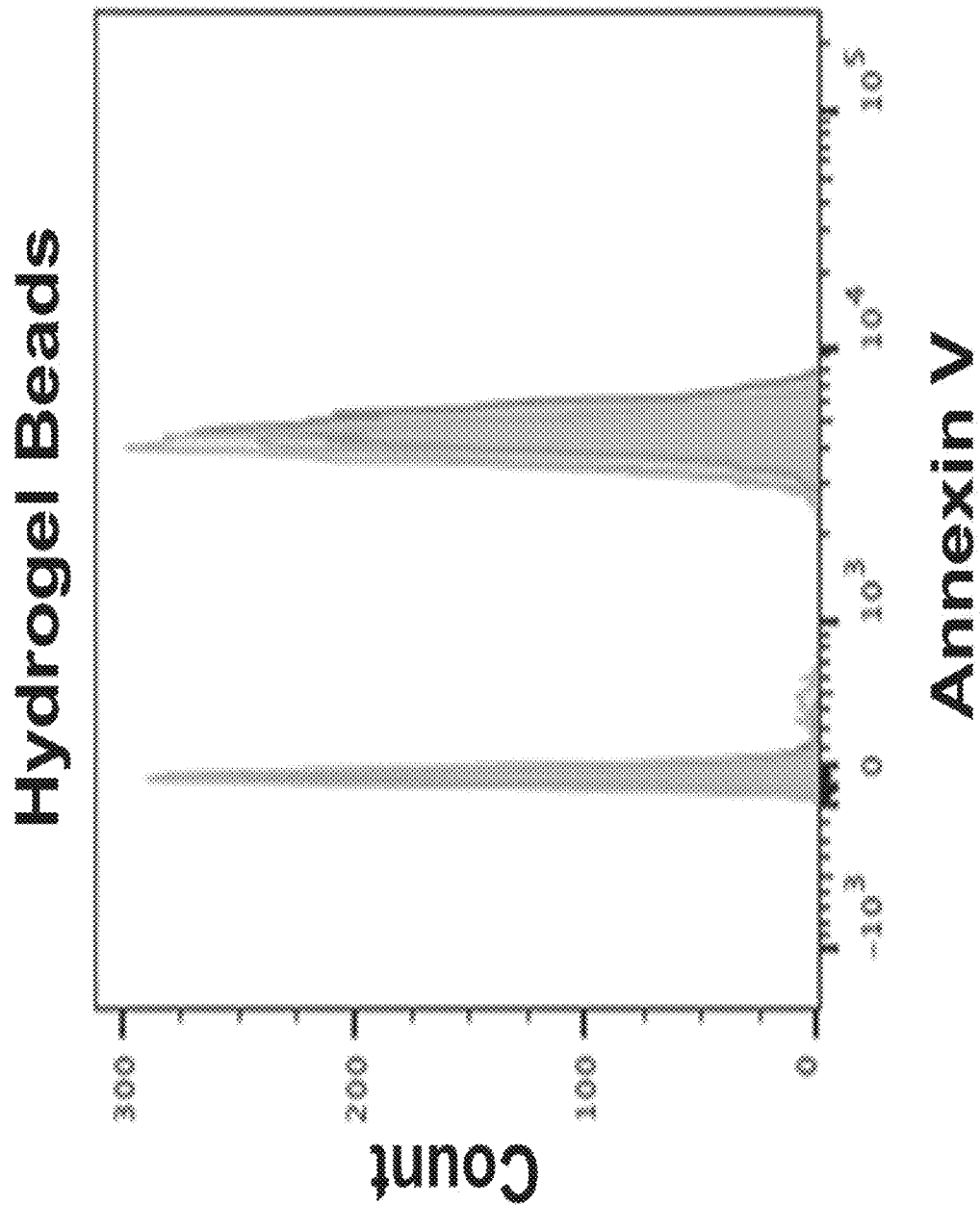
FIGS. 52-54 are histograms that show the mean fluorescence intensity of Annexin V labeled with an ALEXA FLUOR® 647 dye in a composition containing three hydrogel bead populations (FIG. 52); Jurkat cells (FIG. 53); or peripheral blood mononuclear cells (PBMCs) (FIG. 54), as measured on a BD FACSLyric™ cytometric device. Each of these compositions is described in detail in Example 8.
Figure 53:
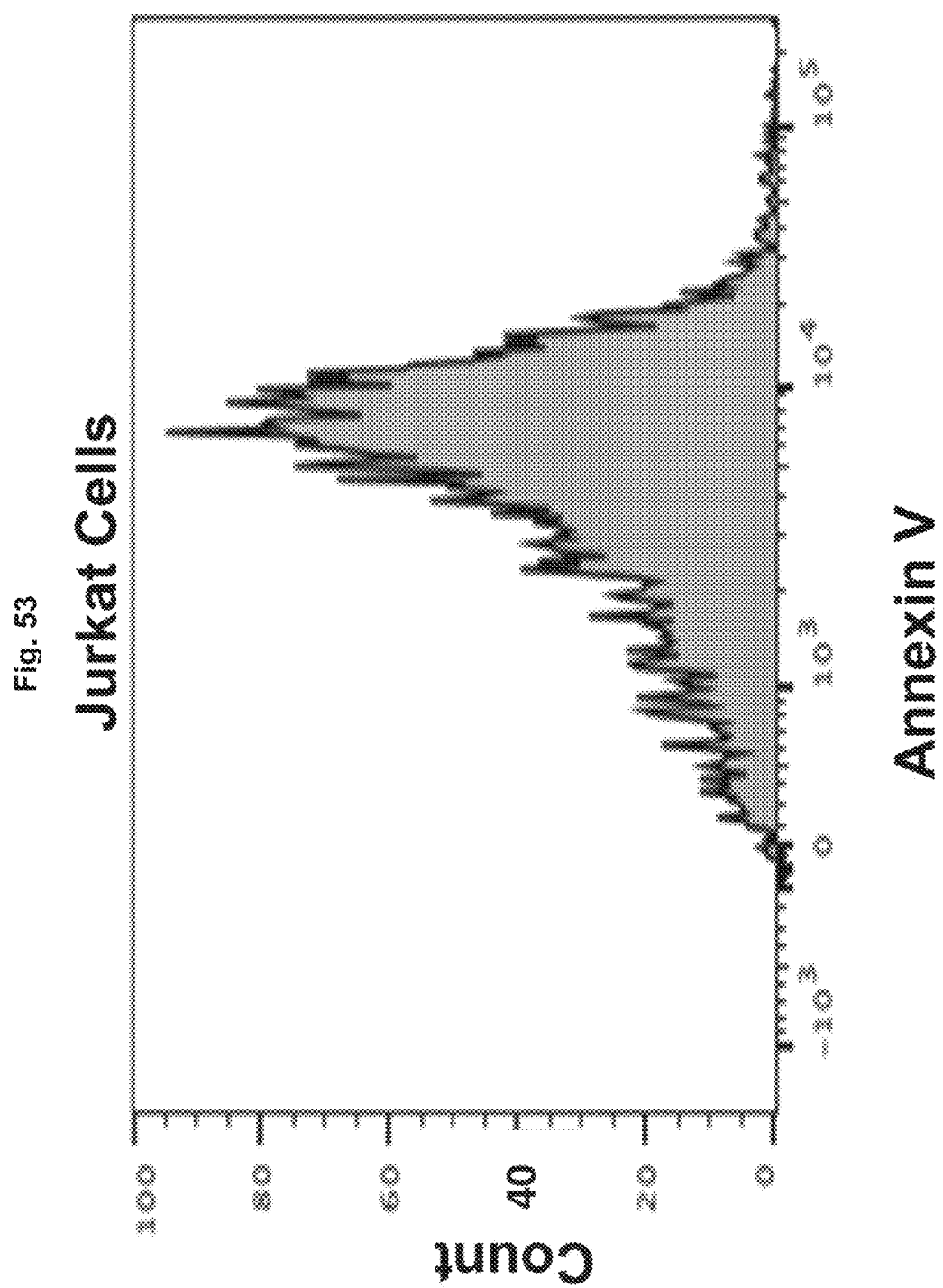
Figure 54:
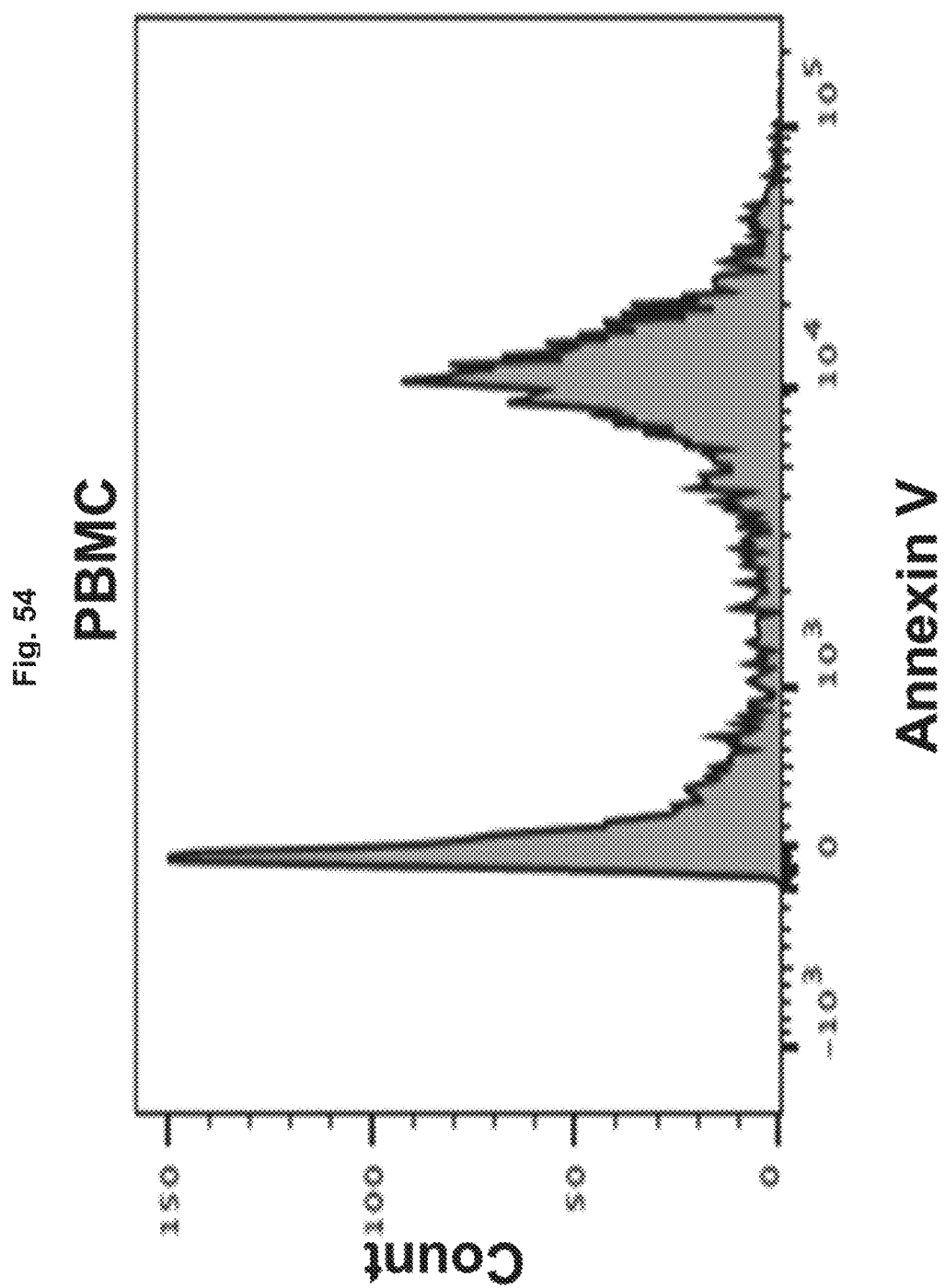

FIGS. 52-54 are histograms that show the mean fluorescence intensity of Annexin V labeled with an ALEXA FLUOR® 647 dye in (a) a composition containing three hydrogel bead populations (FIG. 52); (b) Jurkat cells (FIG. 53); or (c) peripheral blood mononuclear cells (PBMCs) (FIG. 54), as measured on a BD FACSLyric™ cytometric device.

Figure 61:
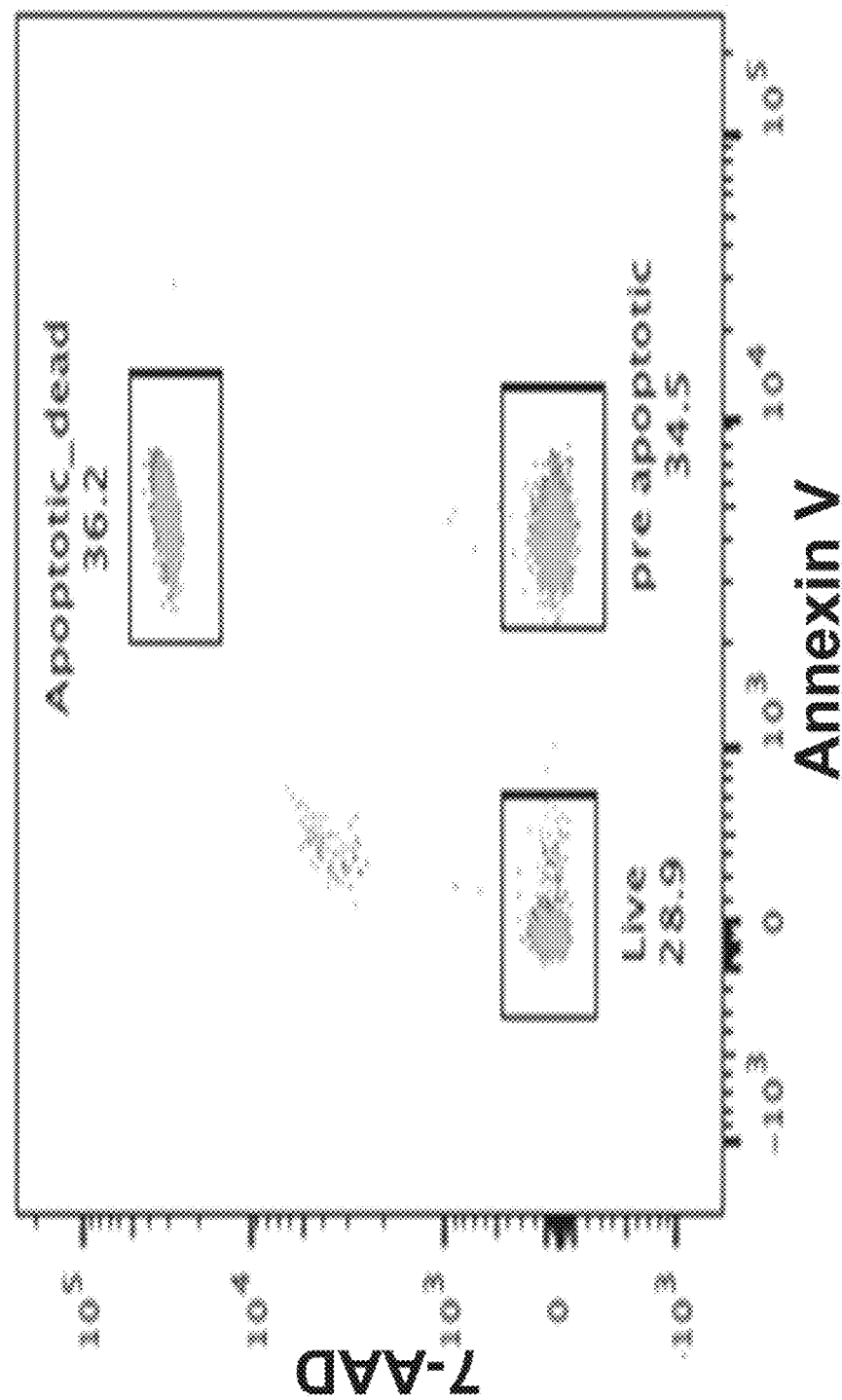
FIGS. 61-63 show binding of 7AAD and Annexin V labeled with an ALEXA FLUOR® 647 dye to a composition containing three hydrogel bead populations (FIG. 61); Jurkat cells (FIG. 62); or peripheral blood mononuclear cells (PBMCs) (FIG. 63), as measured on a BD FACSLyric™ cytometric device. The live cells, dead cells, and apoptotic cells (labeled "pre-apoptotic") are labeled in each figure. Fluorescence spillover on the BD FACSLyric™ cytometric device was corrected via automated compensation. Each of these compositions is described in detail in Example 8.
Figure 62:
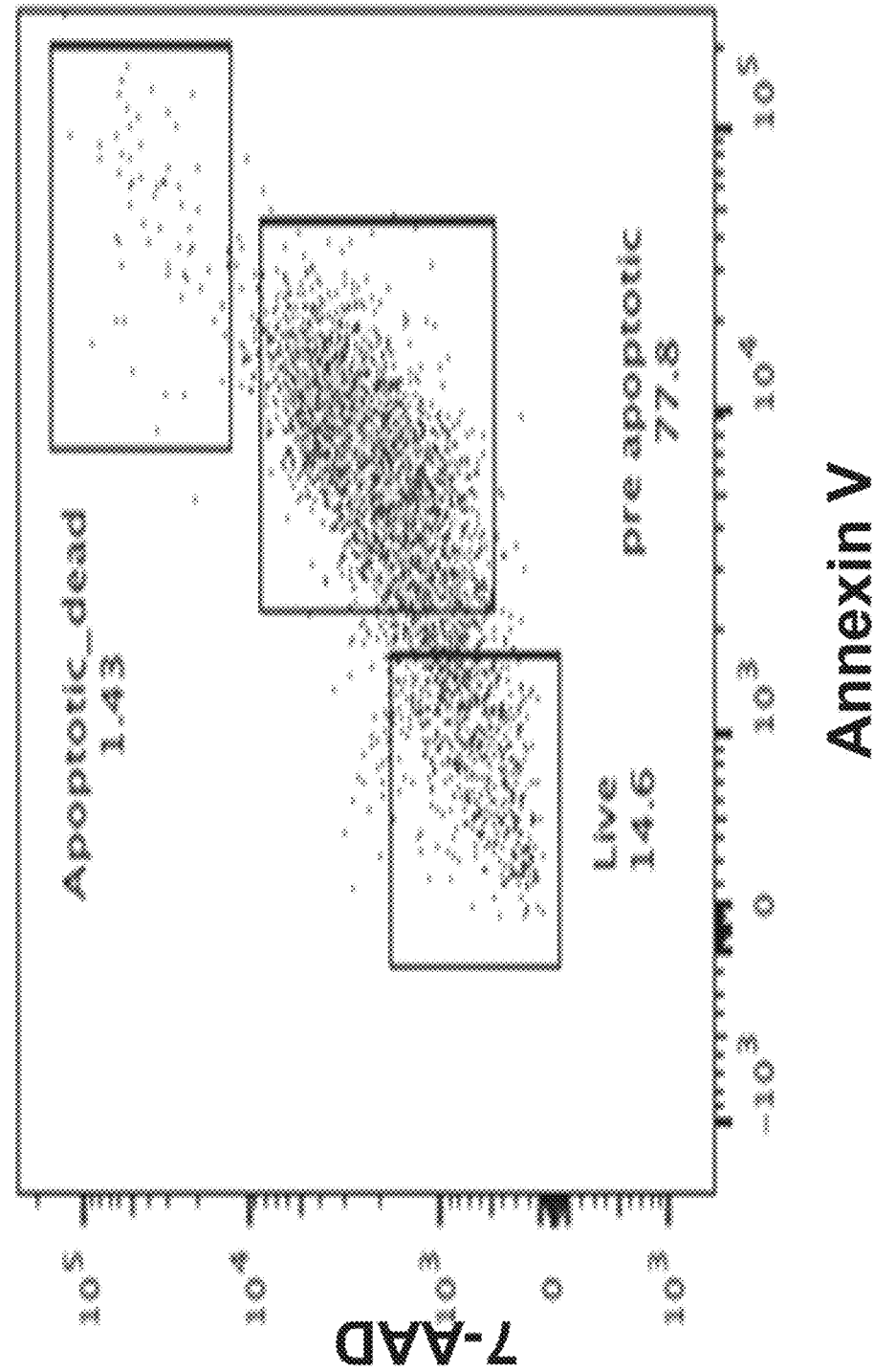
Figure 63:
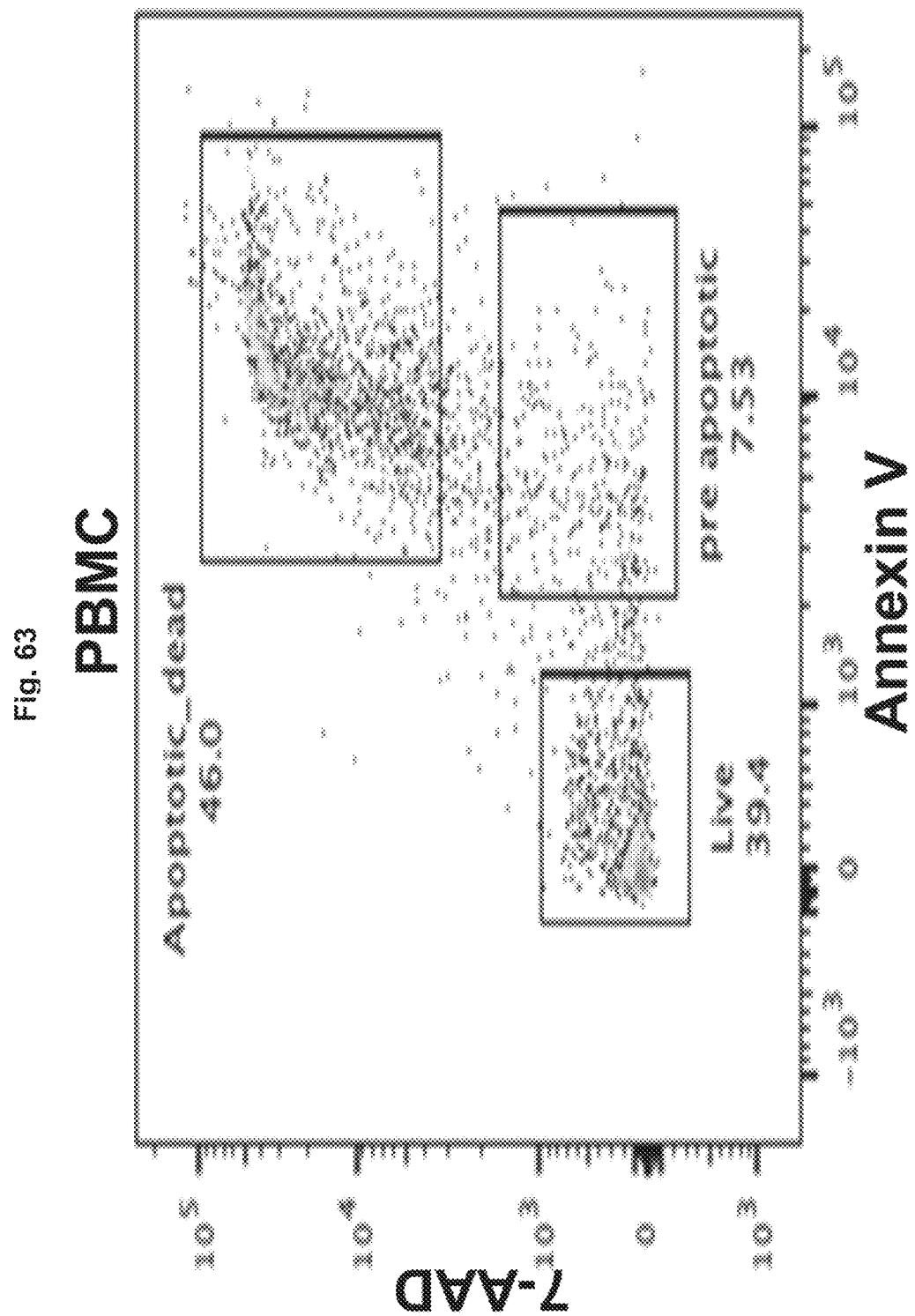

FIGS. 61-63 show binding of 7AAD and Annexin V labeled with an ALEXA FLUOR® 647 dye to (a) a composition containing three hydrogel bead populations (FIG. 61); (b) Jurkat cells (FIG. 62); or (c) peripheral blood mononuclear cells (PBMCs) (FIG. 63), as measured on a BD FACSLyric™ cytometric device. The live cells, dead cells, and apoptotic cells (labeled "pre-apoptotic") are labeled in each figure. Fluorescence spillover on the BD FACSLyric™ cytometric device was corrected via automated compensation.

Results on CYTEK® Aurora Cytometric Device

Cells or beads from each of compositions (a), (b), and (c) bound to 7AAD and/or Annexin V labeled with an ALEXA FLUOR® 647 dye, as detected on the CYTEK® Aurora cytometric device.

Figure 46:
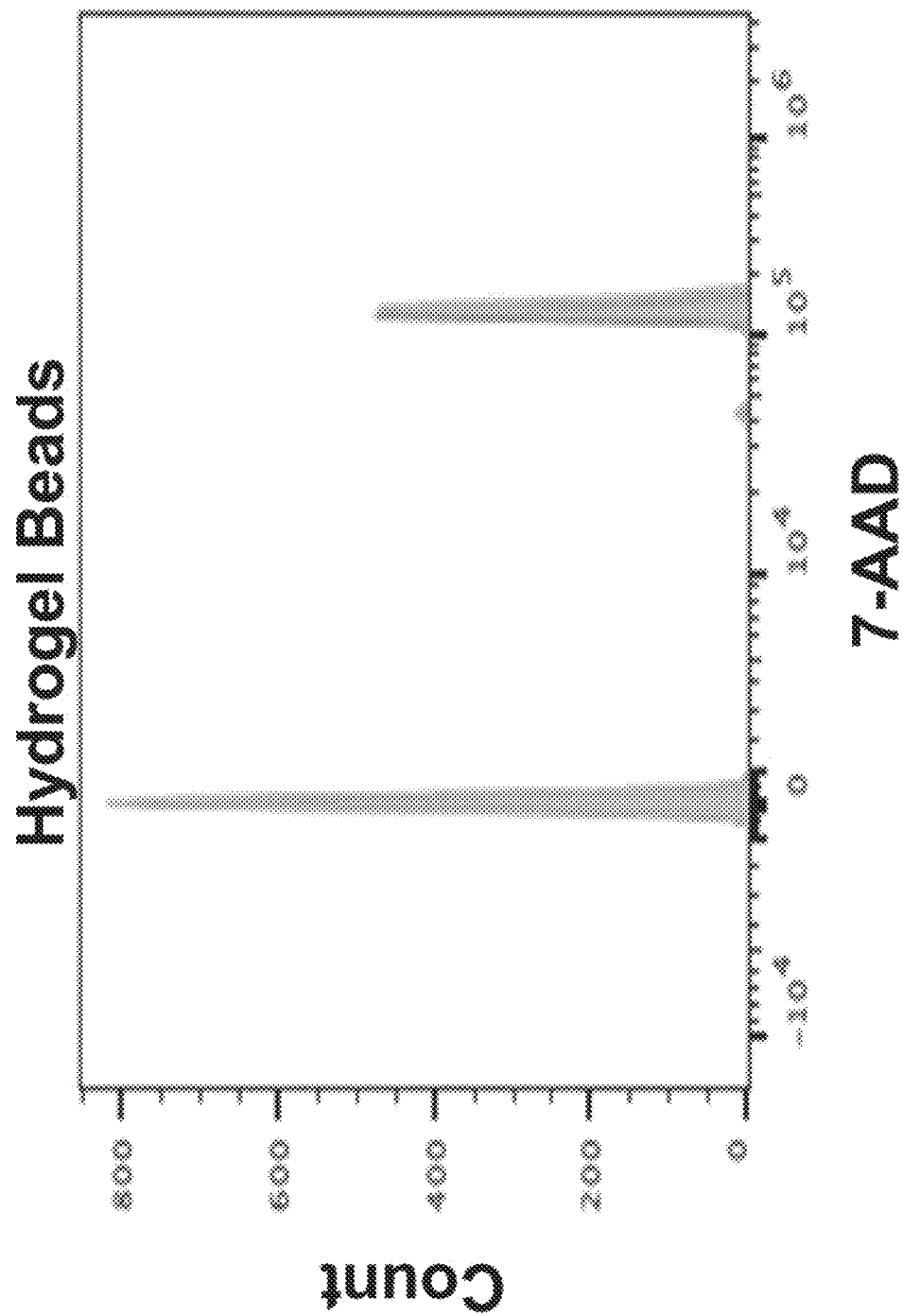
FIGS. 46-48 are histograms that show the mean fluorescence intensity of 7AAD in a composition containing three hydrogel bead populations (FIG. 46); Jurkat cells (FIG. 47); or peripheral blood mononuclear cells (PBMCs) (FIG. 48), as measured on a CYTEK® Aurora cytometric device. The fluorescence spectra information of Jurkat cells labeled with a single dye (either 7AAD or Annexin V labeled with an ALEXA FLUOR® 647 dye) was used to perform spectral unmixing. Each of these compositions is described in detail in Example 8.
Figure 47:
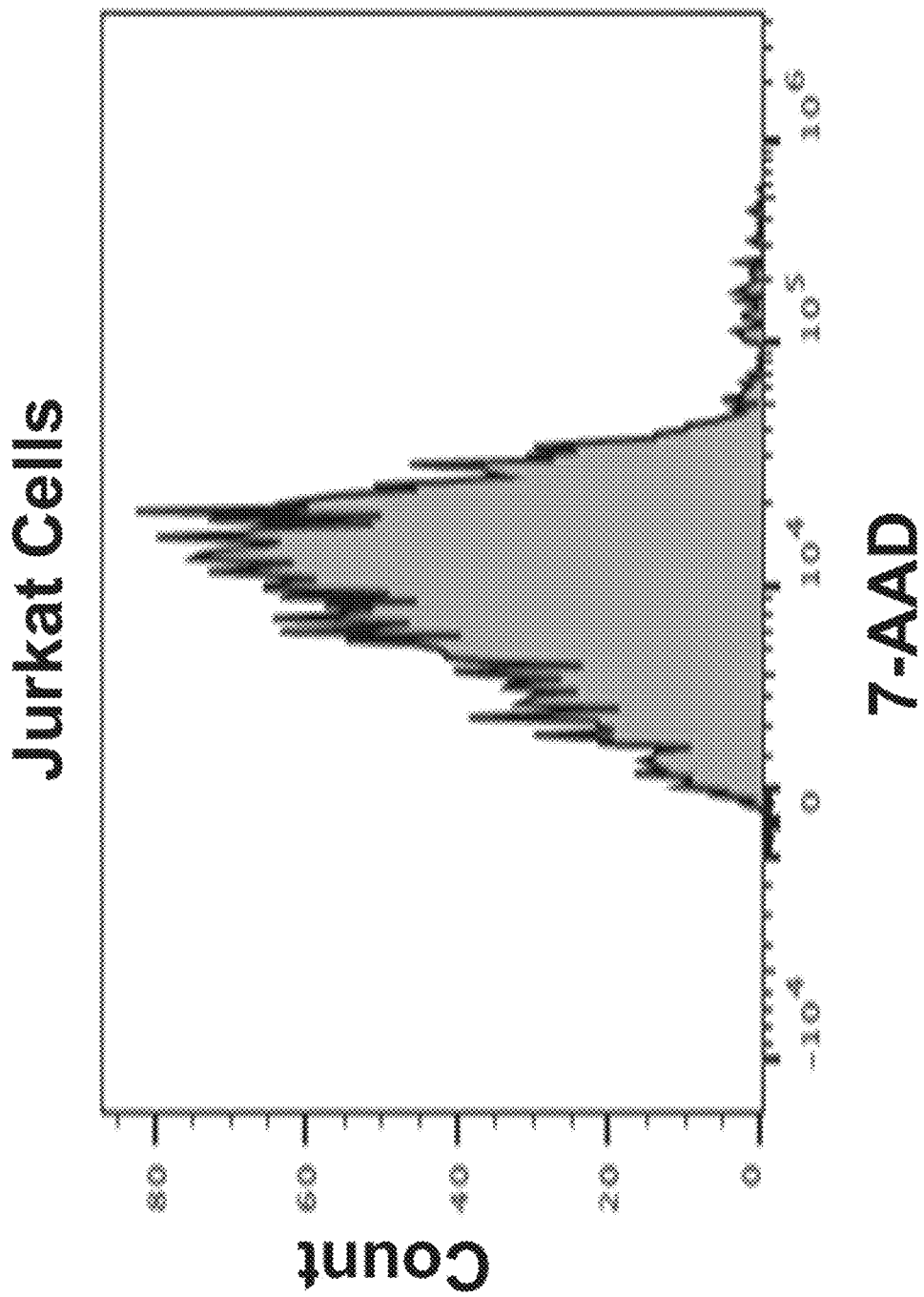
Figure 48:
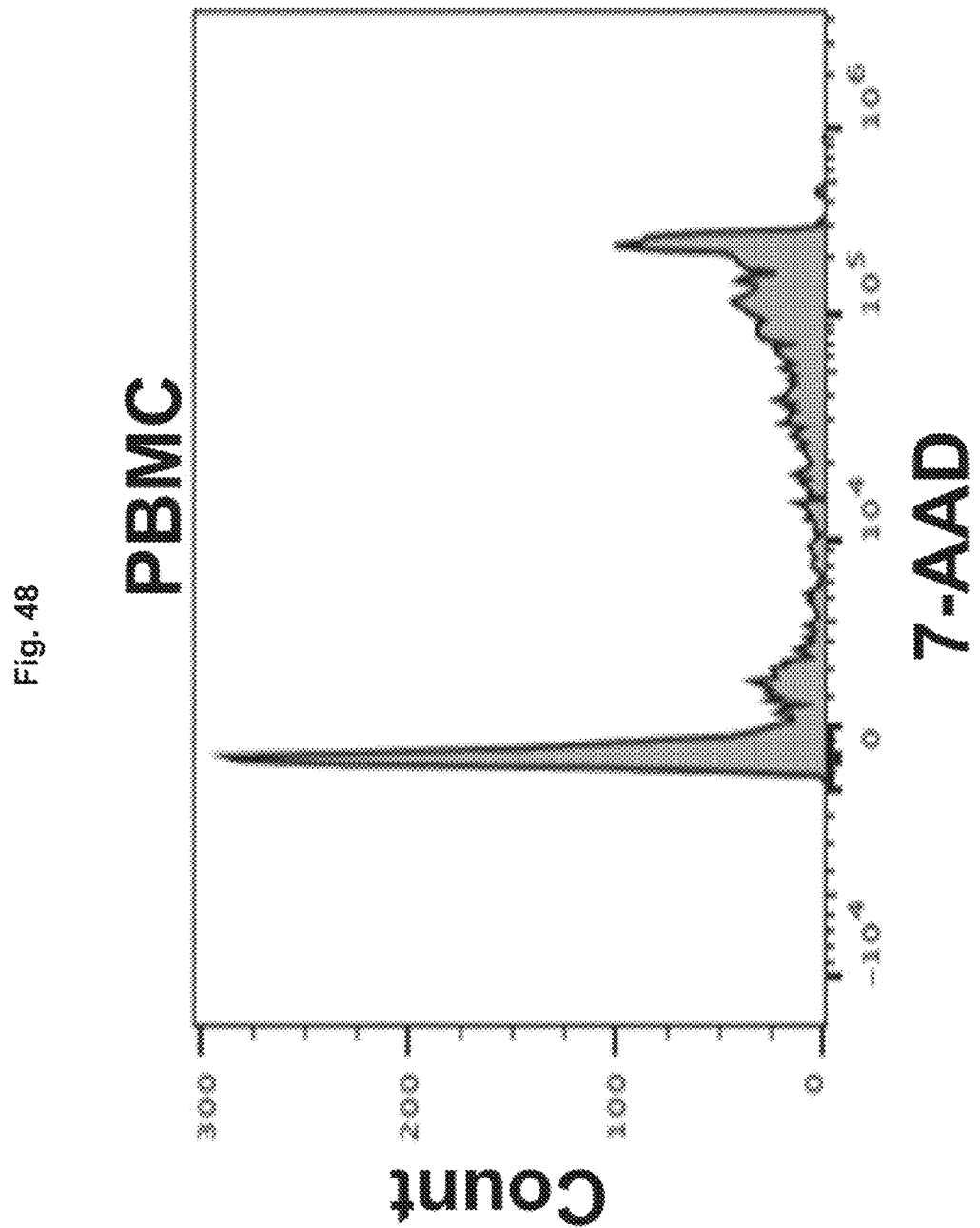
Figure 49:
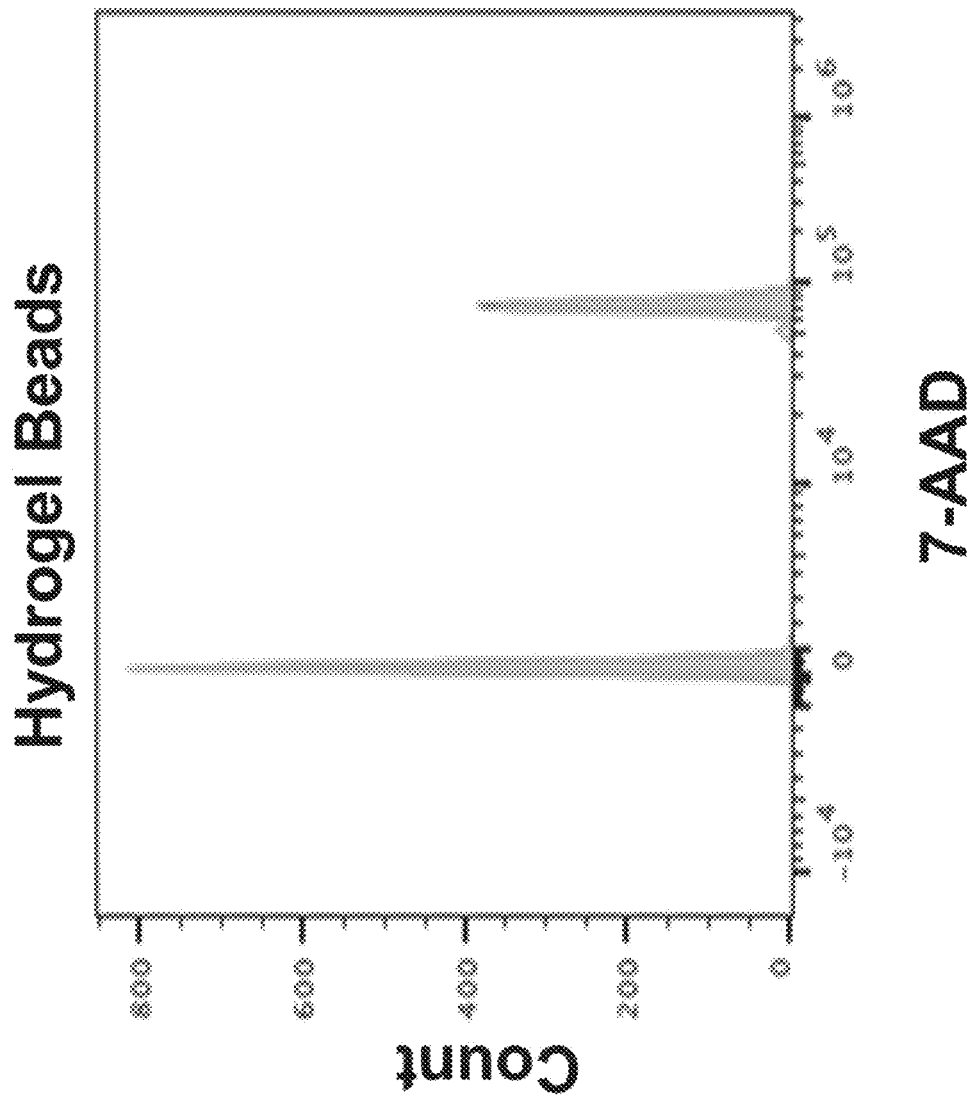
FIGS. 49-51 are histograms that show the mean fluorescence intensity of 7AAD in a composition containing three hydrogel bead populations (FIG. 49); Jurkat cells (FIG. 50); or peripheral blood mononuclear cells (PBMCs) (FIG. 51), as measured on a CYTEK® Aurora cytometric device. The fluorescence spectra information of PBMCs labeled with a single dye (either 7AAD or Annexin V labeled with an ALEXA FLUOR® 647 dye) was used to perform spectral unmixing. Each of these compositions is described in detail in Example 8.
Figure 50:
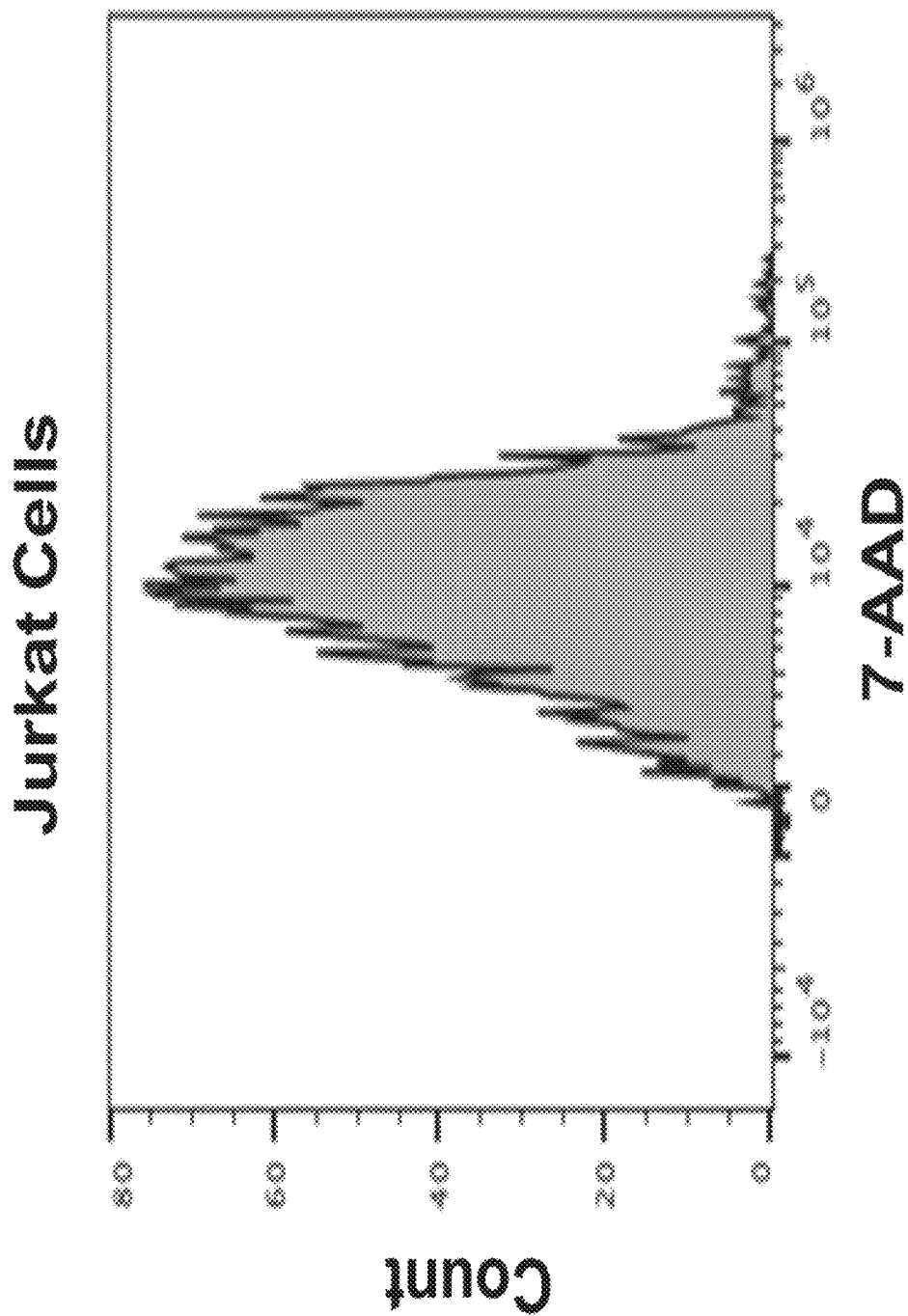
Figure 51:
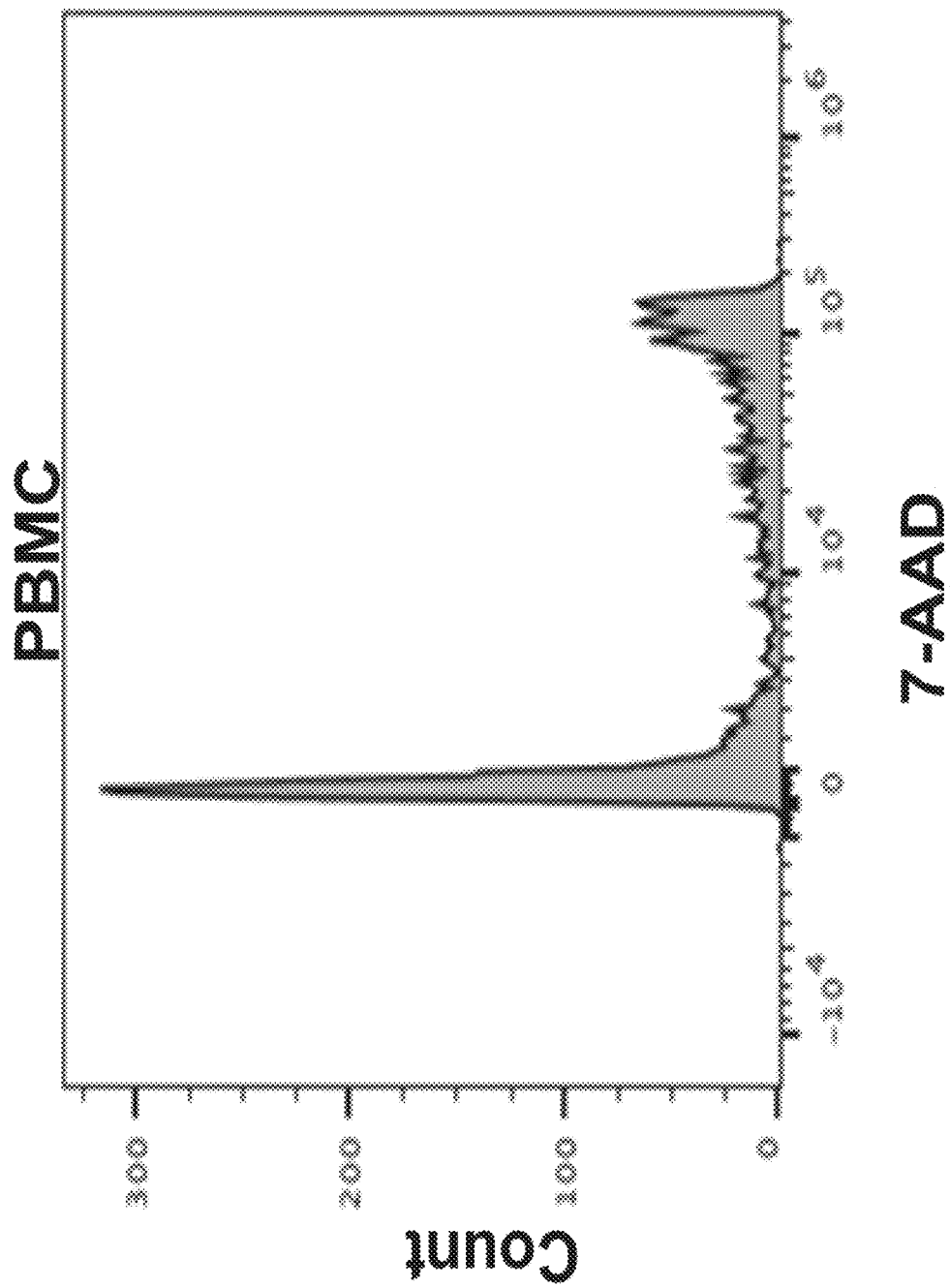

FIGS. 46-51 are histograms that show the mean fluorescence intensity of 7AAD in (a) a composition containing three hydrogel bead populations (FIG. 46, FIG. 49); (b) Jurkat cells (FIG. 47, FIG. 50); or (c) peripheral blood mononuclear cells (PBMCs) (FIG. 48, FIG. 51), as measured on a CYTEK® Aurora cytometric device. In FIGS. 46-48, the fluorescence spectra of Jurkat cells bound to Annexin V labeled with an ALEXA FLUOR® 647 dye was used to perform spectral unmixing. In FIGS. 49-51, the fluorescence spectra of PBMCs bound to Annexin V labeled with an ALEXA FLUOR® 647 dye was used to perform spectral unmixing.

Figure 55:
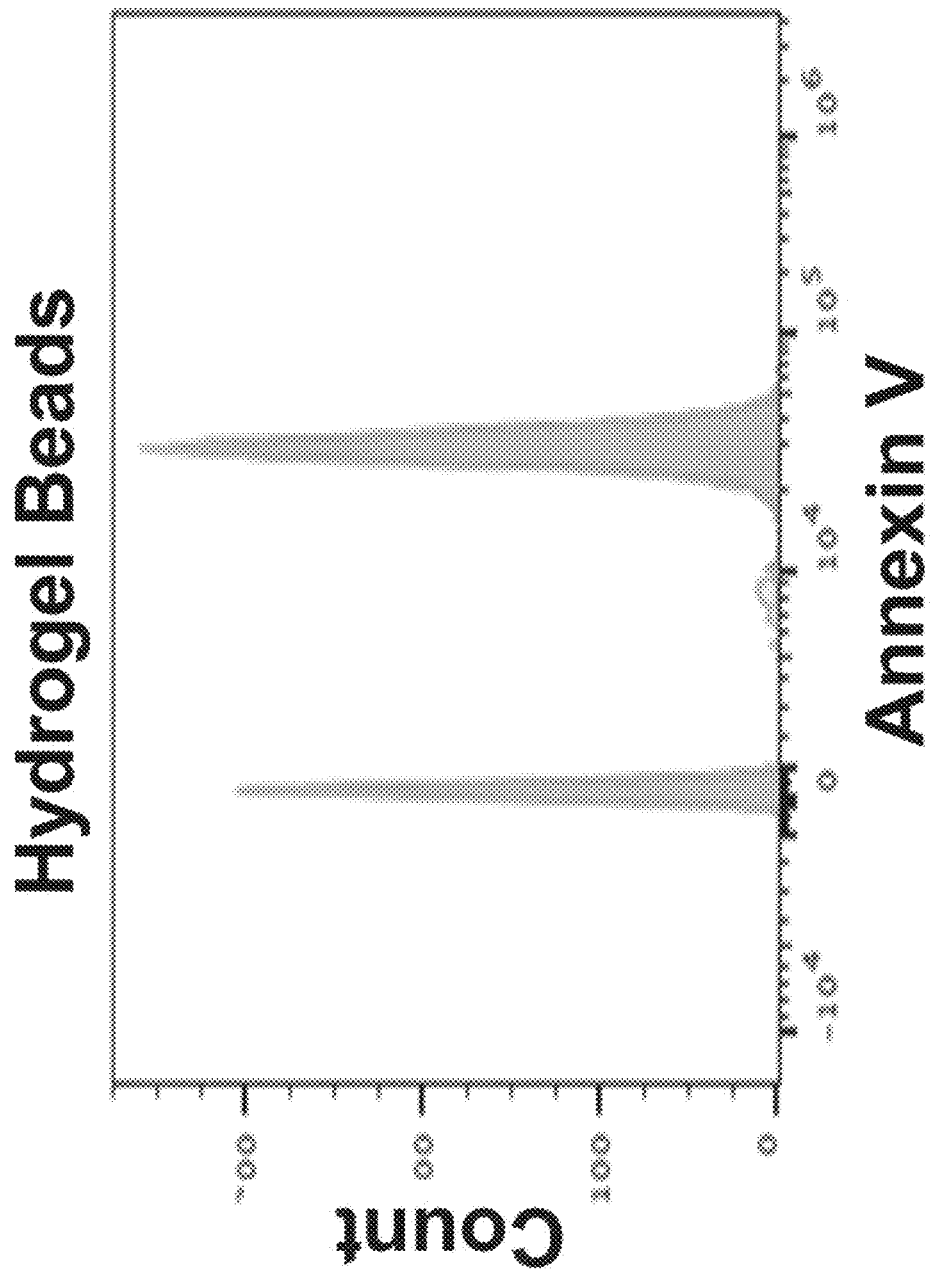
FIGS. 55-57 are histograms that show the mean fluorescence intensity of Annexin V labeled with an ALEXA FLUOR® 647 dye in a composition containing three hydrogel bead populations (FIG. 55); Jurkat cells (FIG. 56); or peripheral blood mononuclear cells (PBMCs) (FIG. 57), as measured on a CYTEK® Aurora cytometric device. The fluorescence spectra information of Jurkat cells bound to Annexin V labeled with an ALEXA FLUOR® 647 dye was used to perform spectral unmixing. Each of these compositions is described in detail in Example 8.
Figure 56:
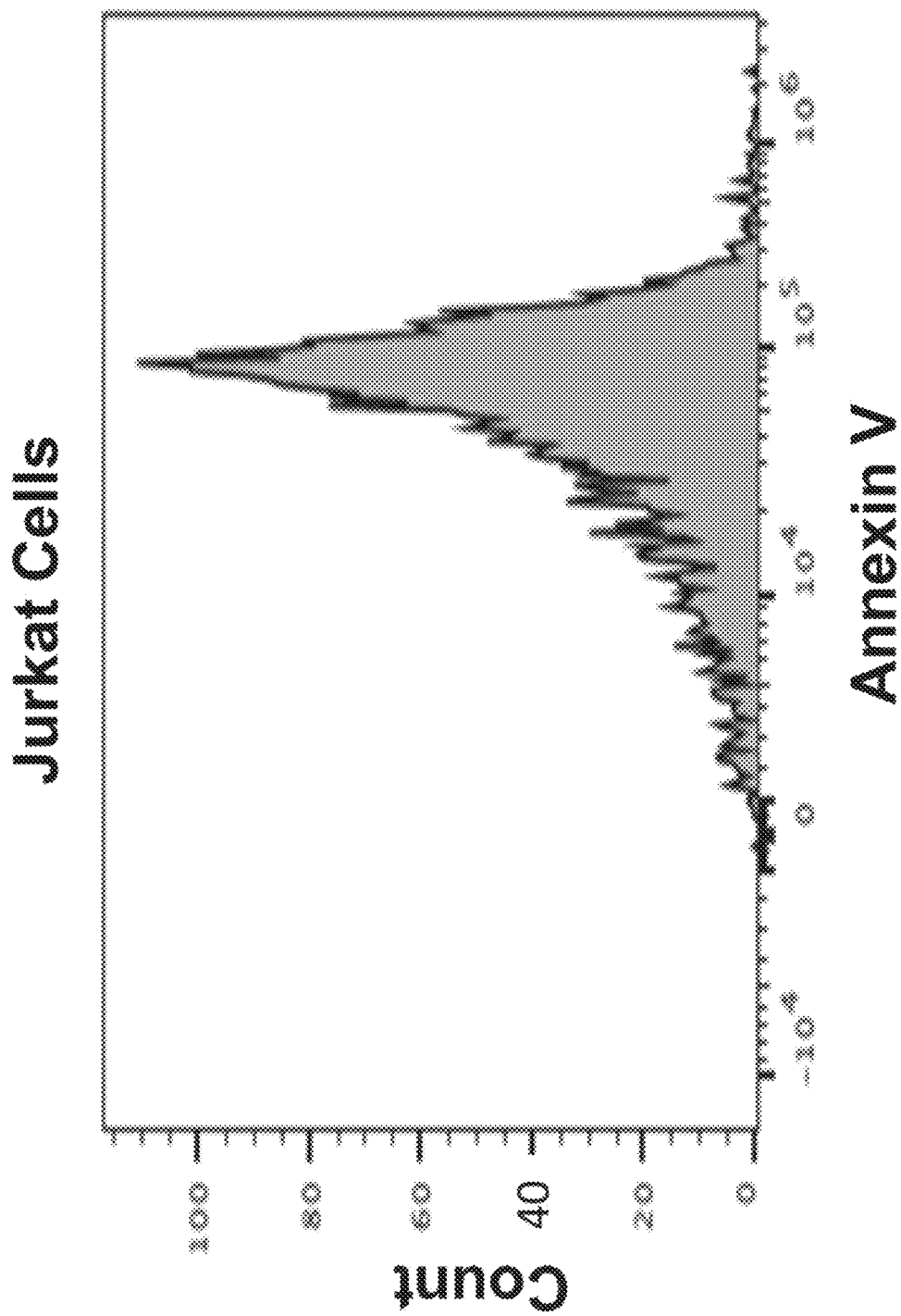
Figure 57:
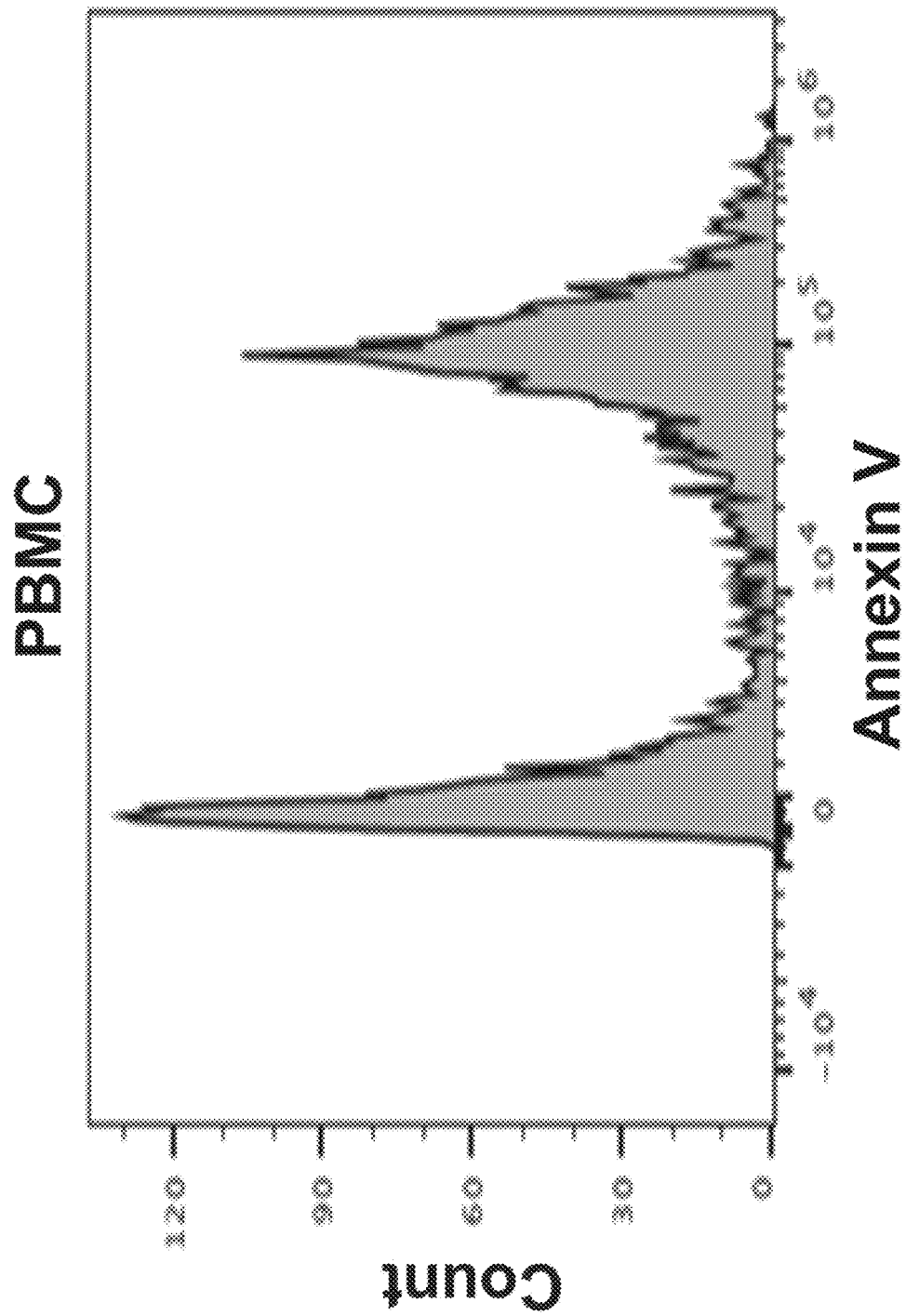
Figure 58:
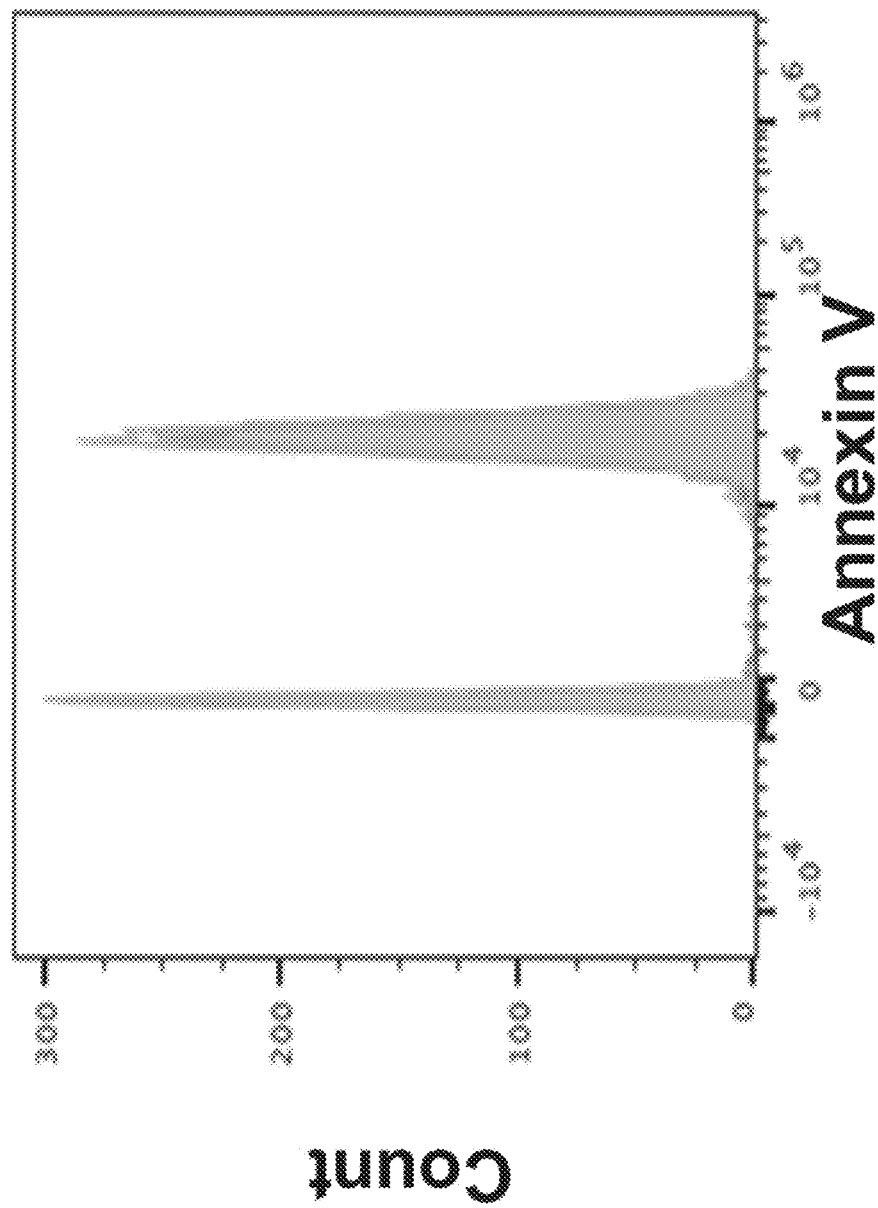
FIGS. 58-60 are histograms that show the mean fluorescence intensity of Annexin V labeled with an ALEXA FLUOR® 647 dye in a composition containing three hydrogel bead populations (FIG. 58); Jurkat cells (FIG. 59); or peripheral blood mononuclear cells (PBMCs) (FIG. 60), as measured on a CYTEK® Aurora cytometric device. The fluorescence spectra information of PBMCs bound to Annexin V labeled with an ALEXA FLUOR® 647 dye was used to perform spectral unmixing. Each of these compositions is described in detail in Example 8.
Figure 59:
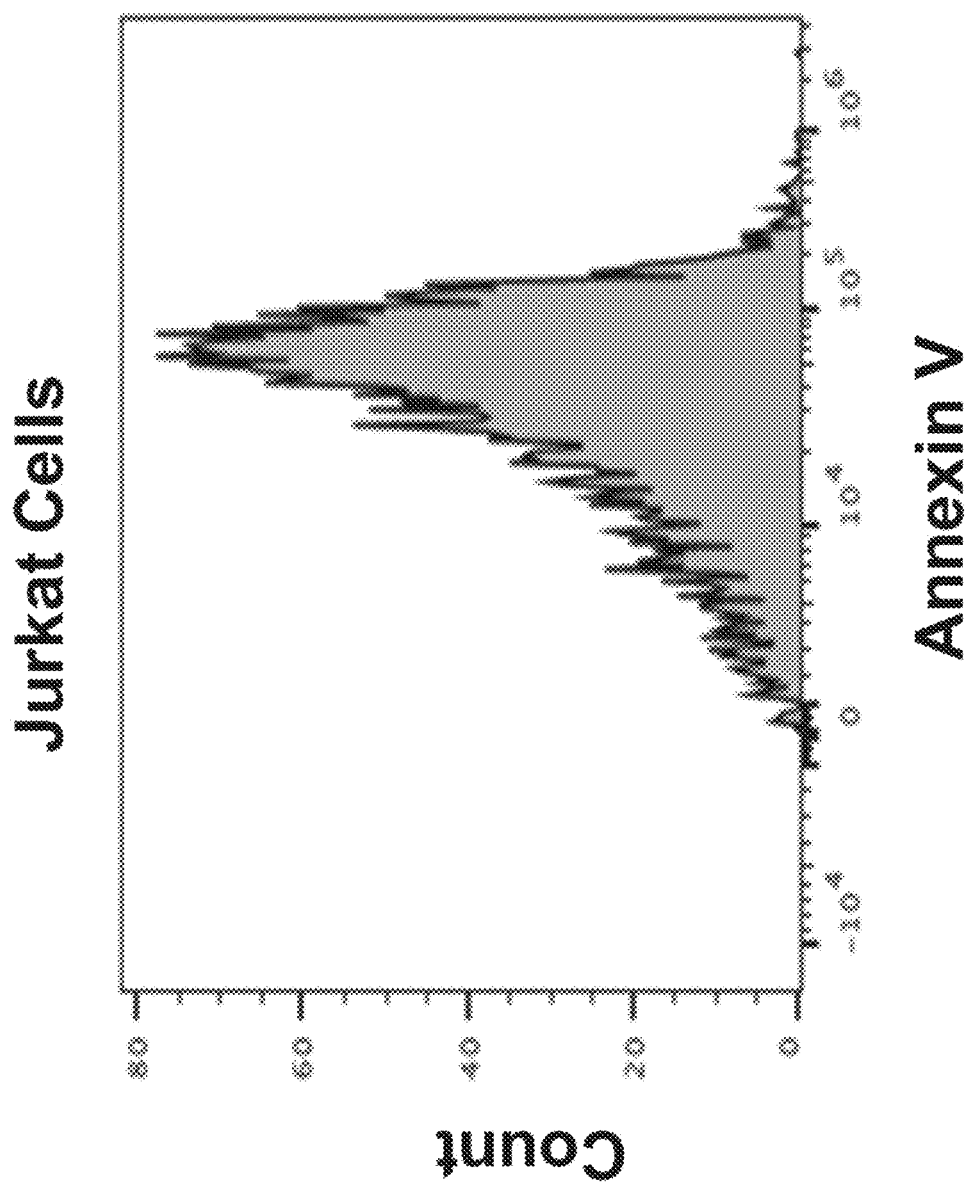
Figure 60:
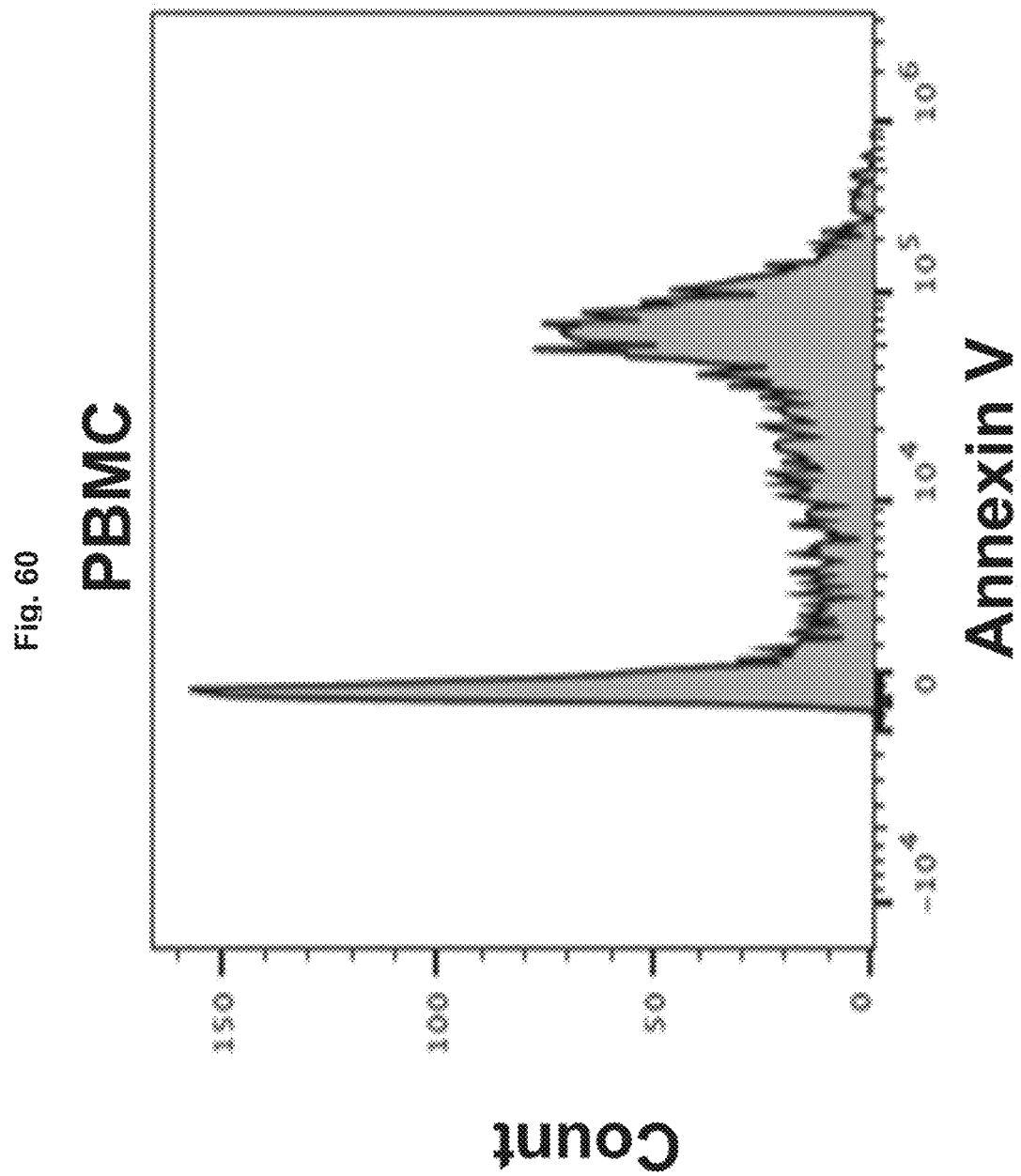

FIGS. 55-60 are histograms that show the mean fluorescence intensity of Annexin V labeled with an ALEXA FLUOR® 647 dye in (a) a composition containing three hydrogel bead populations (FIG. 55, FIG. 58); (b) Jurkat cells (FIG. 56, FIG. 59); or (c) peripheral blood mononuclear cells (PBMCs) (FIG. 57, FIG. 60), as measured on a CYTEK® Aurora cytometric device. In FIGS. 55-57, the fluorescence spectra of Jurkat cells bound to Annexin V labeled with an ALEXA FLUOR® 647 dye was used to perform spectral unmixing. In FIGS. 58-60, the fluorescence spectra of PBMCs bound to Annexin V labeled with an ALEXA FLUOR® 647 dye was used to perform spectral unmixing.

Figure 64:
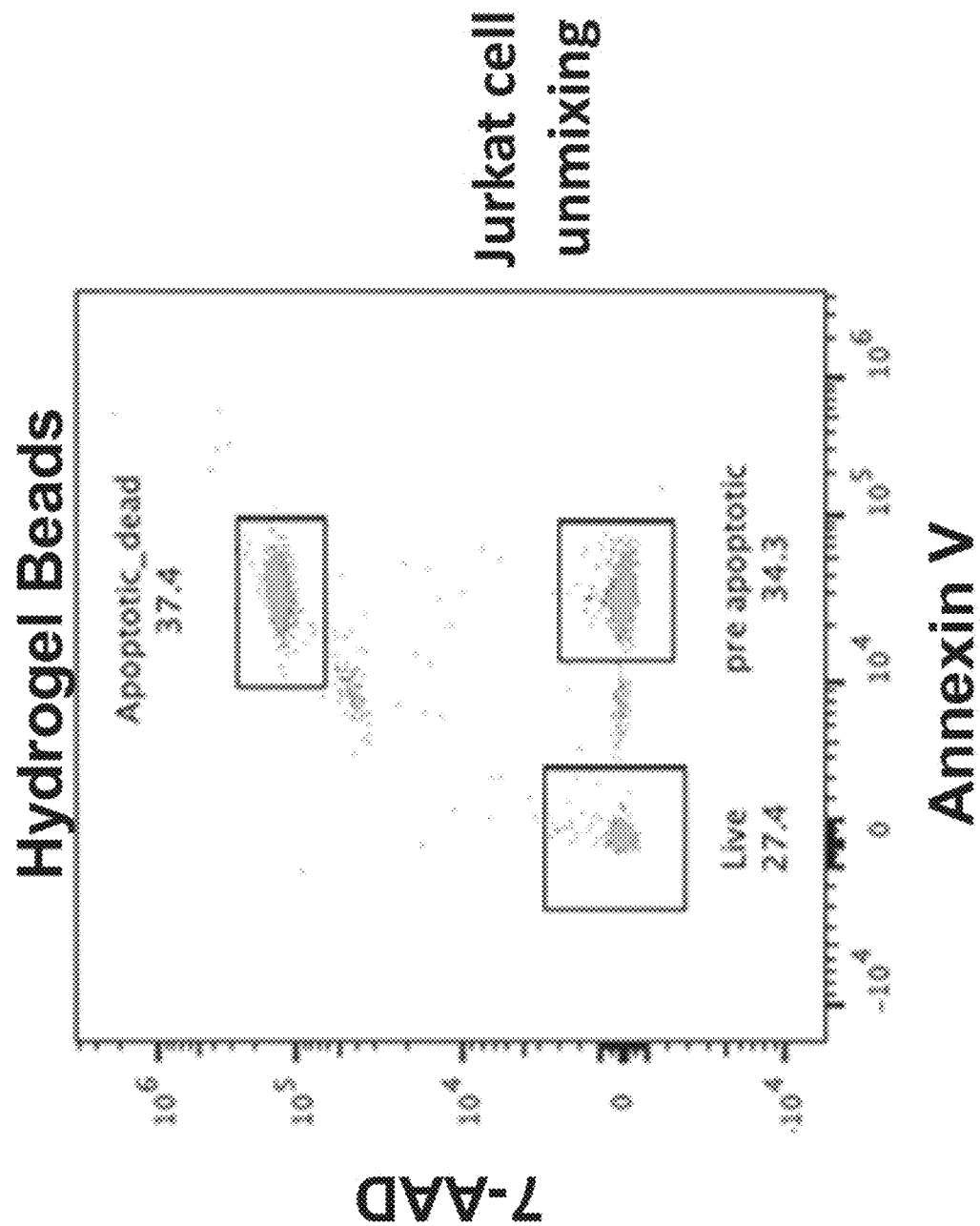
FIGS. 64-66 show binding of 7AAD and Annexin V labeled with an ALEXA FLUOR® 647 dye to a composition containing three hydrogel bead populations (FIG. 64); Jurkat cells (FIG. 65); or peripheral blood mononuclear cells (PBMCs) (FIG. 66), as measured on a CYTEK® Aurora cytometric device. Each of these compositions is described in detail in Example 8. The live cells, dead cells, and apoptotic cells (labeled "pre-apoptotic") are labeled in each figure. The fluorescence spectra of Jurkat cells bound to Annexin V labeled with an ALEXA FLUOR® 647 dye and/or 7AAD was used to perform spectral unmixing.
Figure 65:
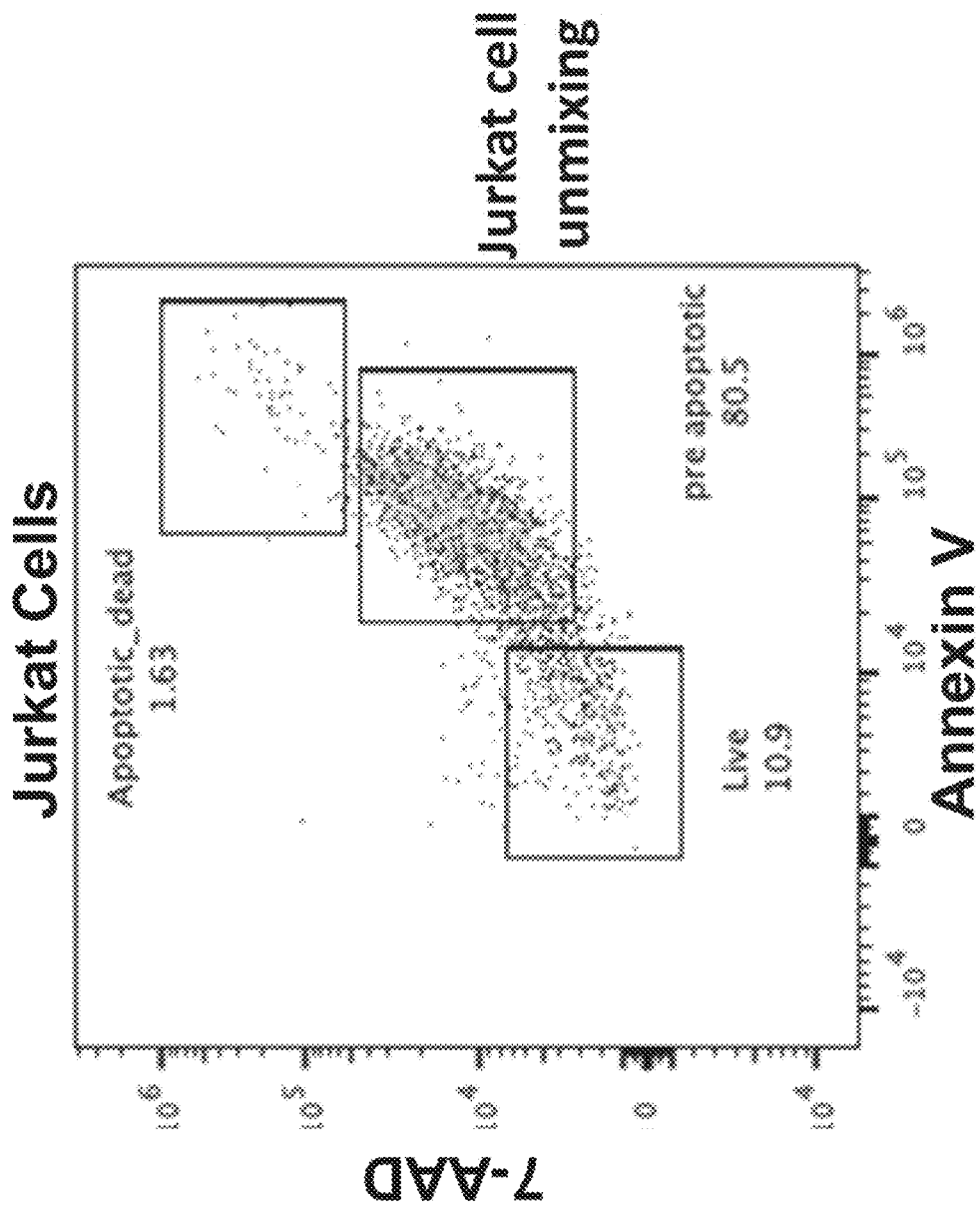
Figure 66:
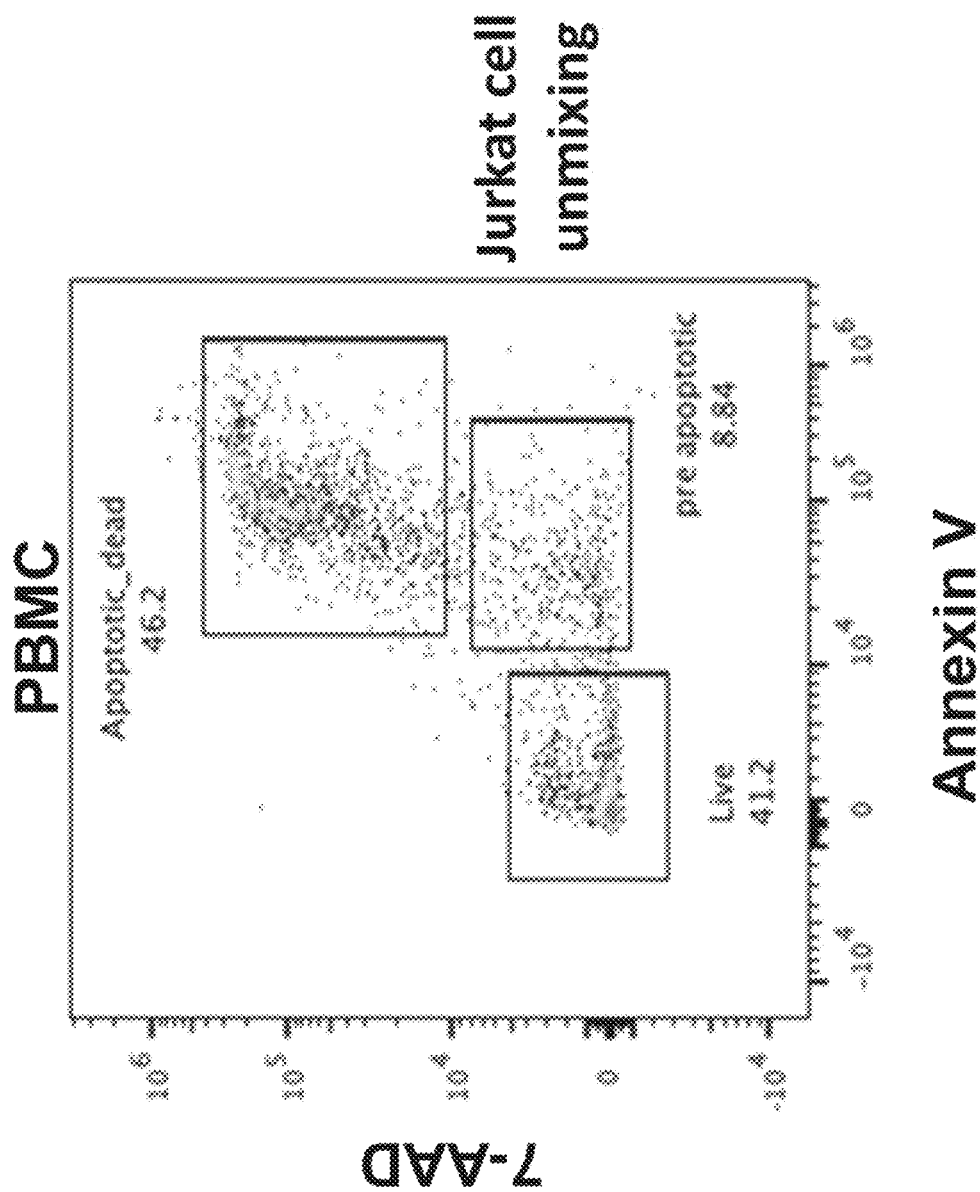
Figure 67:
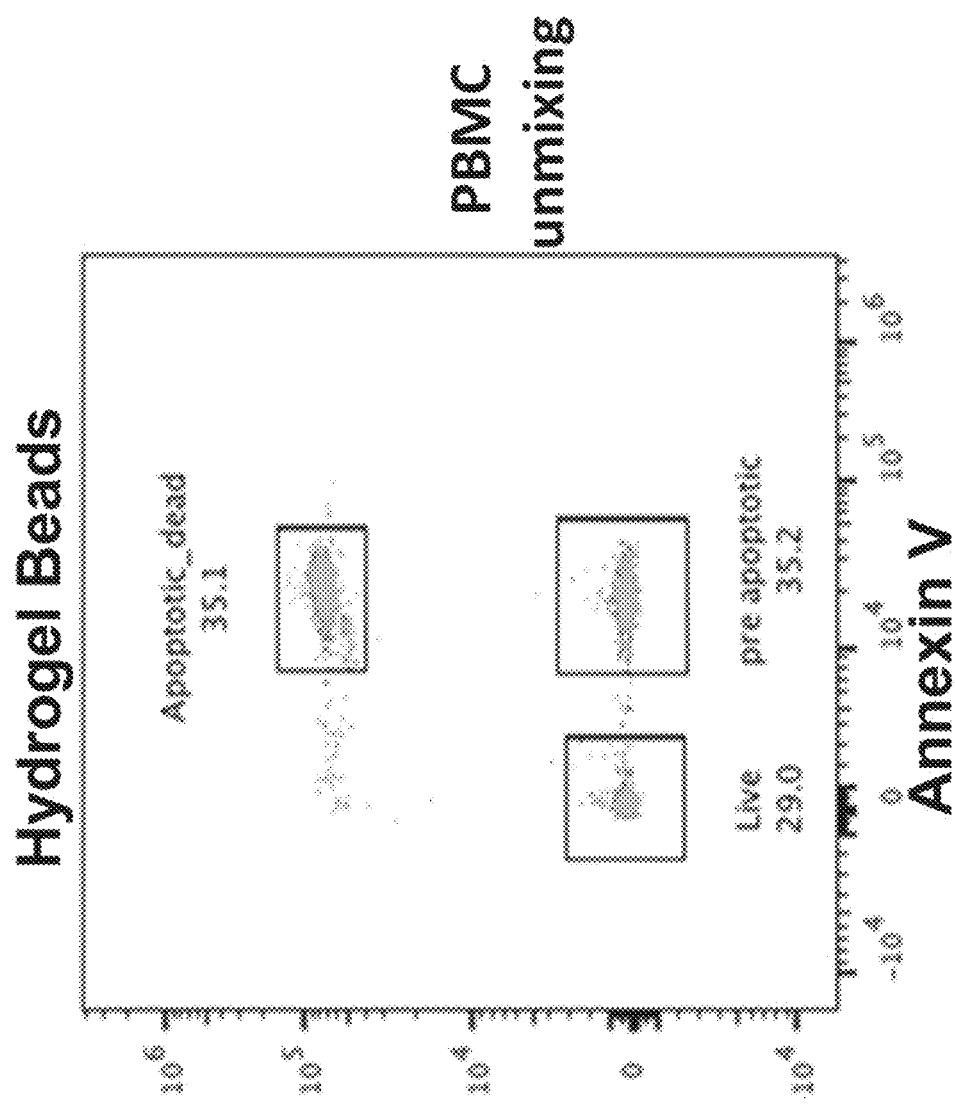
FIGS. 67-69 show binding of 7AAD and Annexin V labeled with an ALEXA FLUOR® 647 dye to a composition containing three hydrogel bead populations (FIG. 67); Jurkat cells (FIG. 68); or peripheral blood mononuclear cells (PBMCs) (FIG. 69), as measured on a CYTEK® Aurora cytometric device. Each of these compositions is described in detail in Example 8. The live cells, dead cells, and apoptotic cells (labeled "pre-apoptotic") are labeled in each figure. The fluorescence spectra of PBMCs bound to Annexin V labeled with an ALEXA FLUOR® 647 dye and/or 7AAD was used to perform spectral unmixing.
Figure 68:
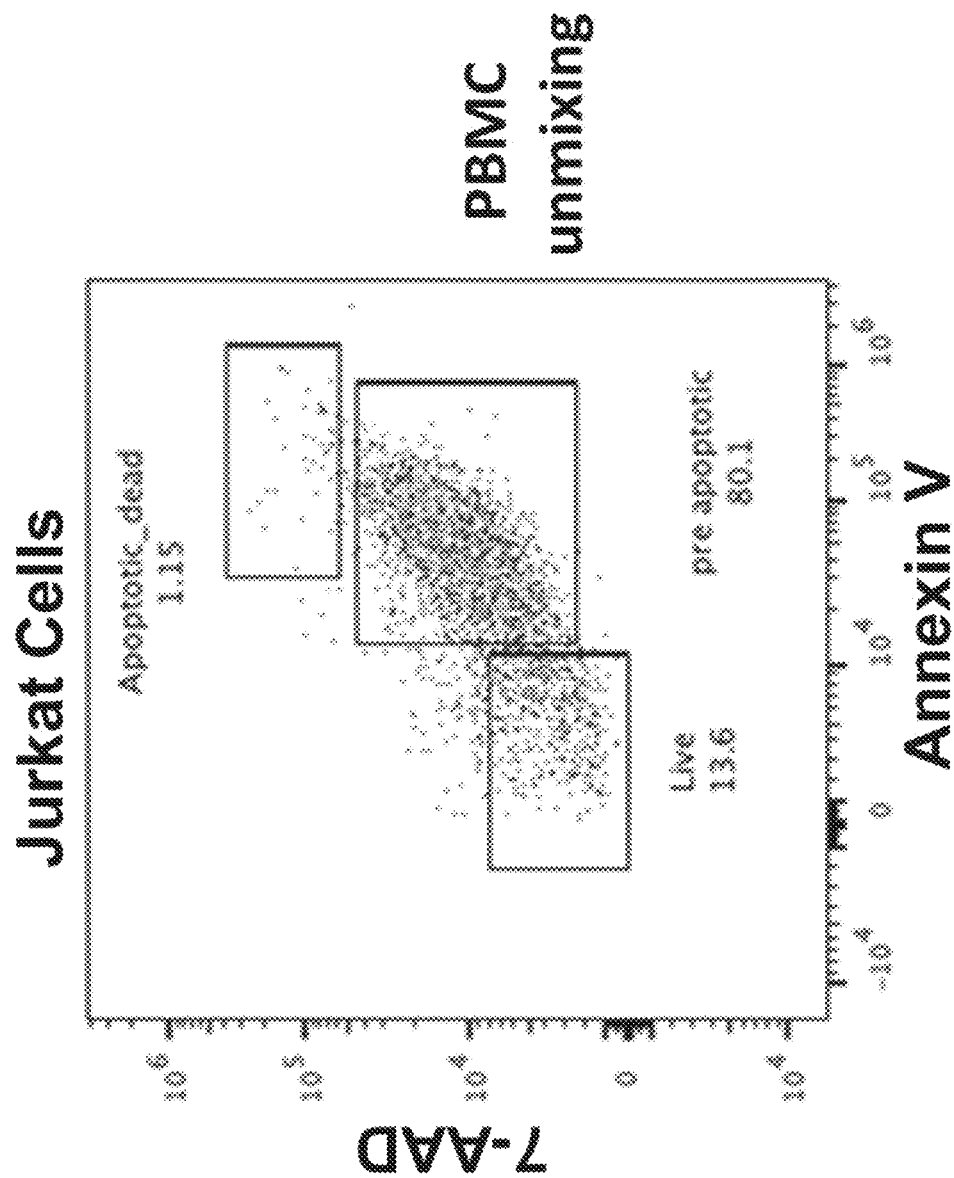
Figure 69:
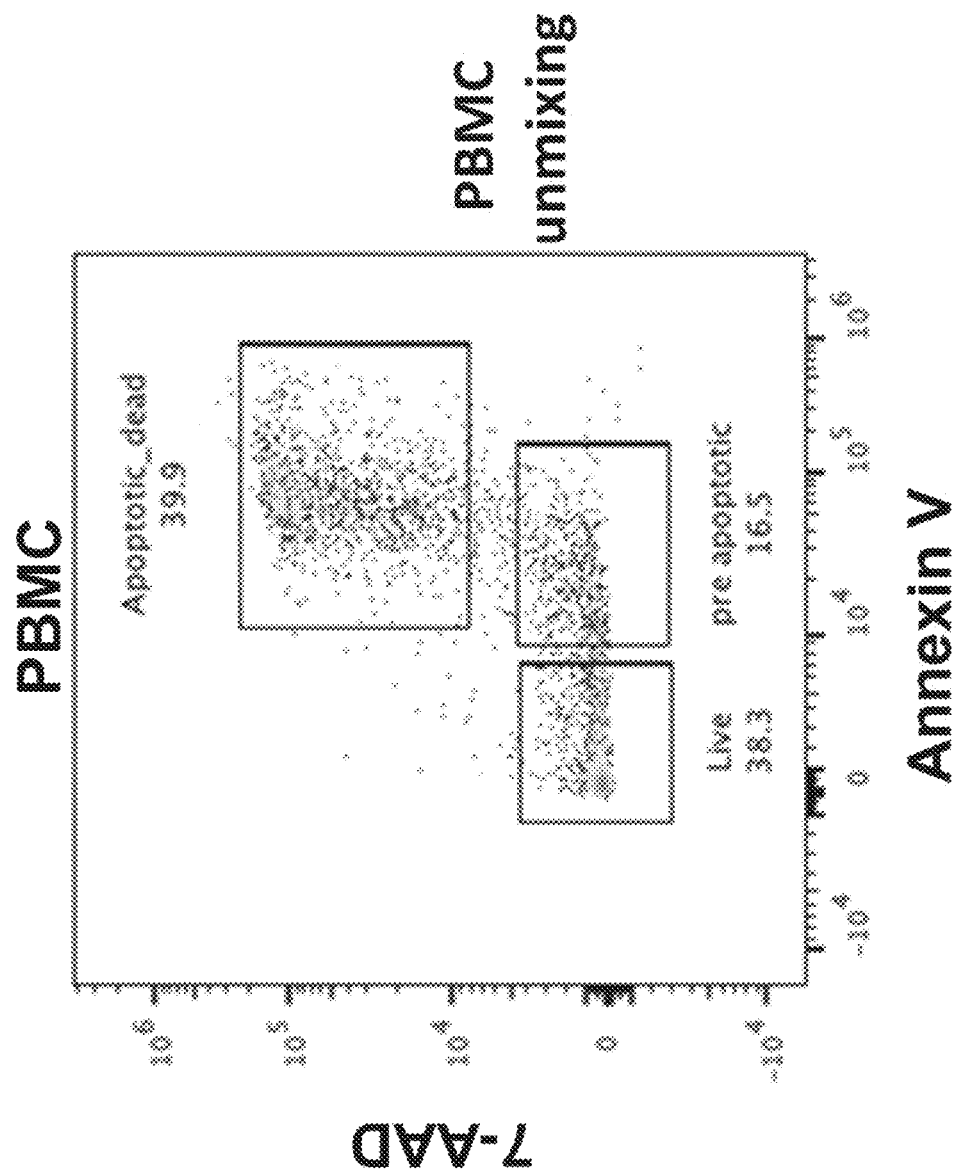
Figure 70:
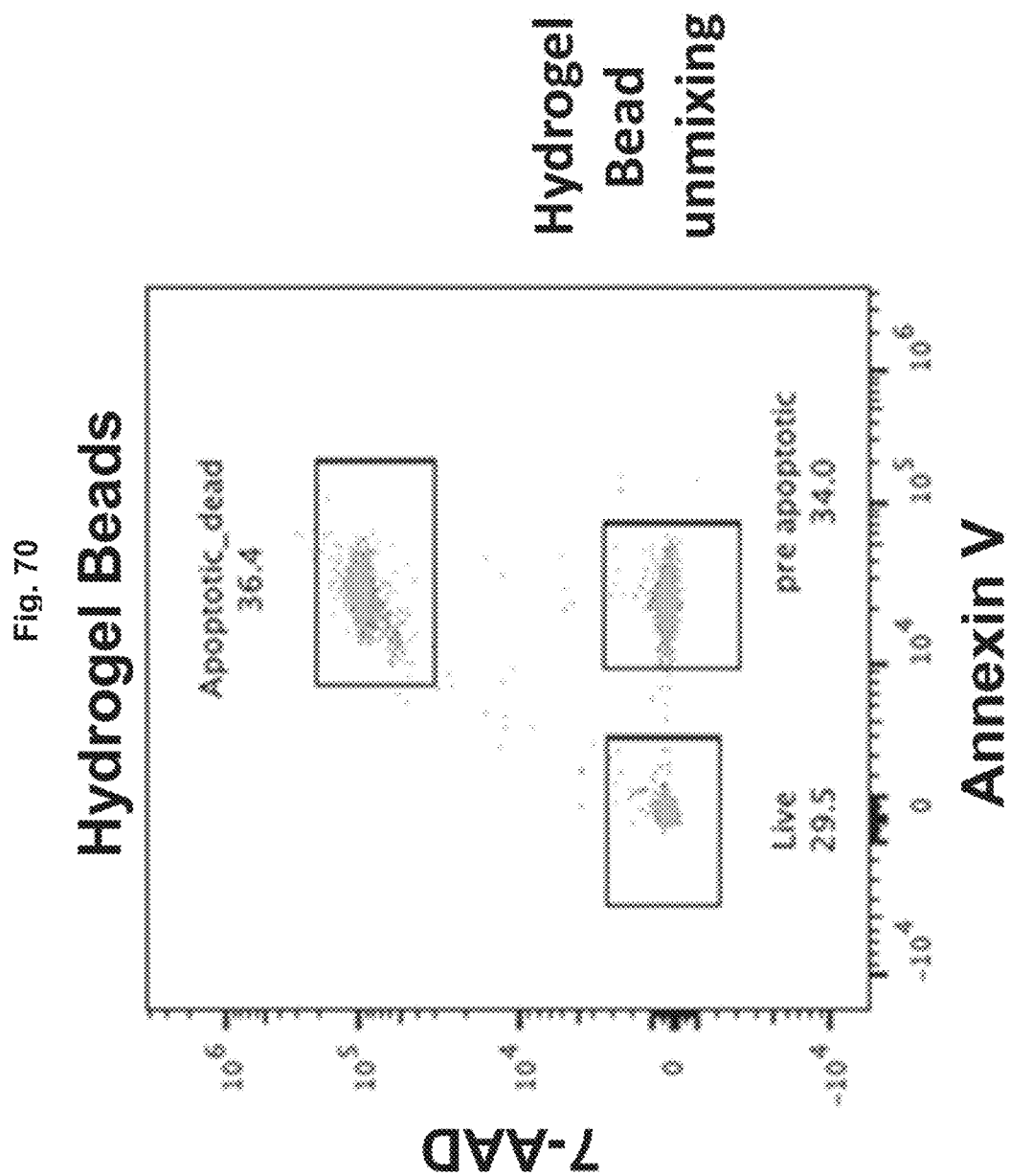
FIGS. 70-72 show binding of 7AAD and Annexin V labeled with an ALEXA FLUOR® 647 dye to a composition containing three hydrogel bead populations (FIG. 70); Jurkat cells (FIG. 71); or peripheral blood mononuclear cells (PBMCs) (FIG. 72), as measured on a CYTEK® Aurora cytometric device. Each of these compositions is described in detail in Example 8. The live cells, dead cells, and apoptotic cells (labeled "pre-apoptotic") are labeled in each figure. The fluorescence spectra of the composition containing three hydrogel bead populations bound to Annexin V labeled with an ALEXA FLUOR® 647 dye and/or 7AAD was used to perform spectral unmixing.
Figure 71:
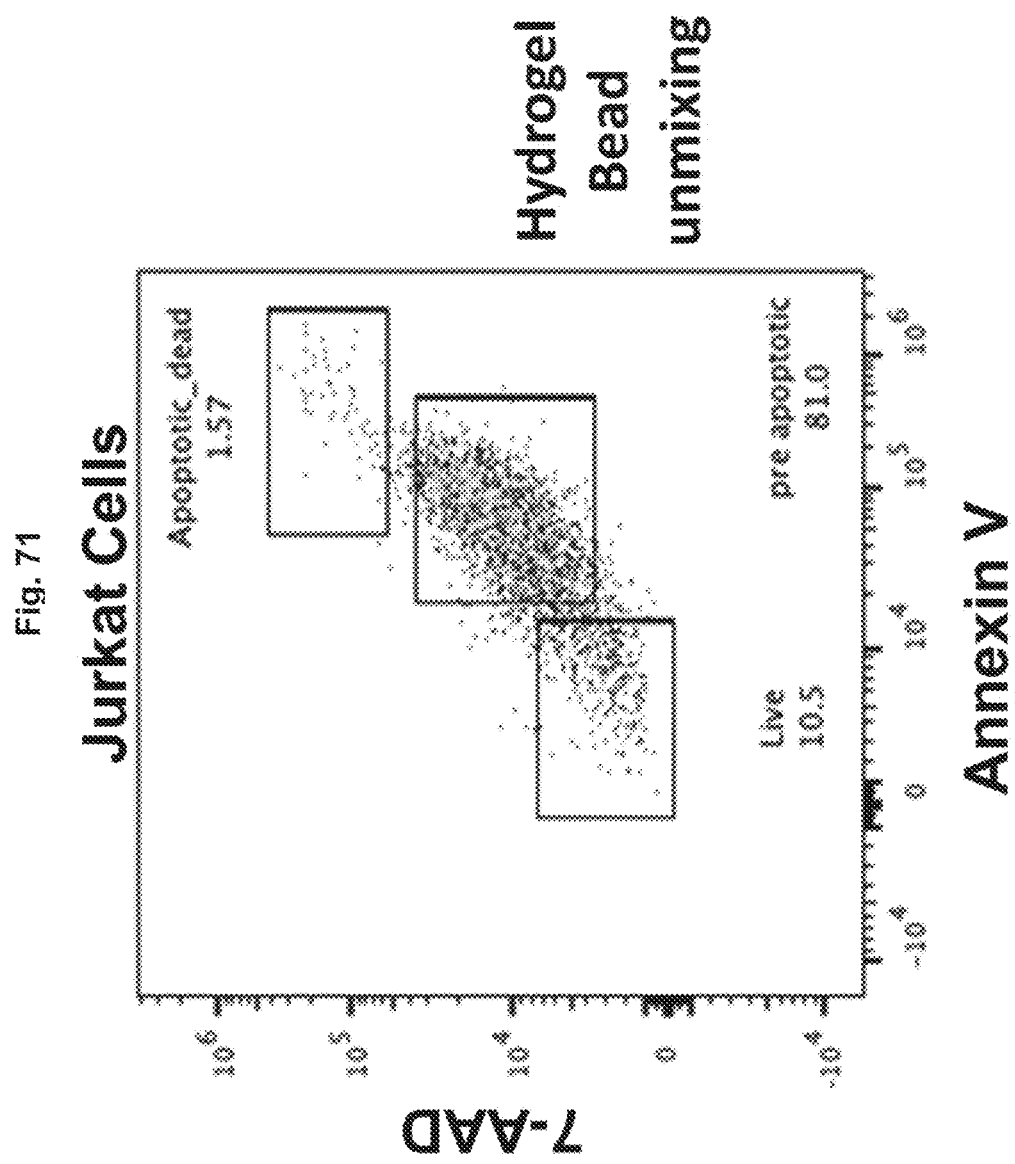
Figure 72:
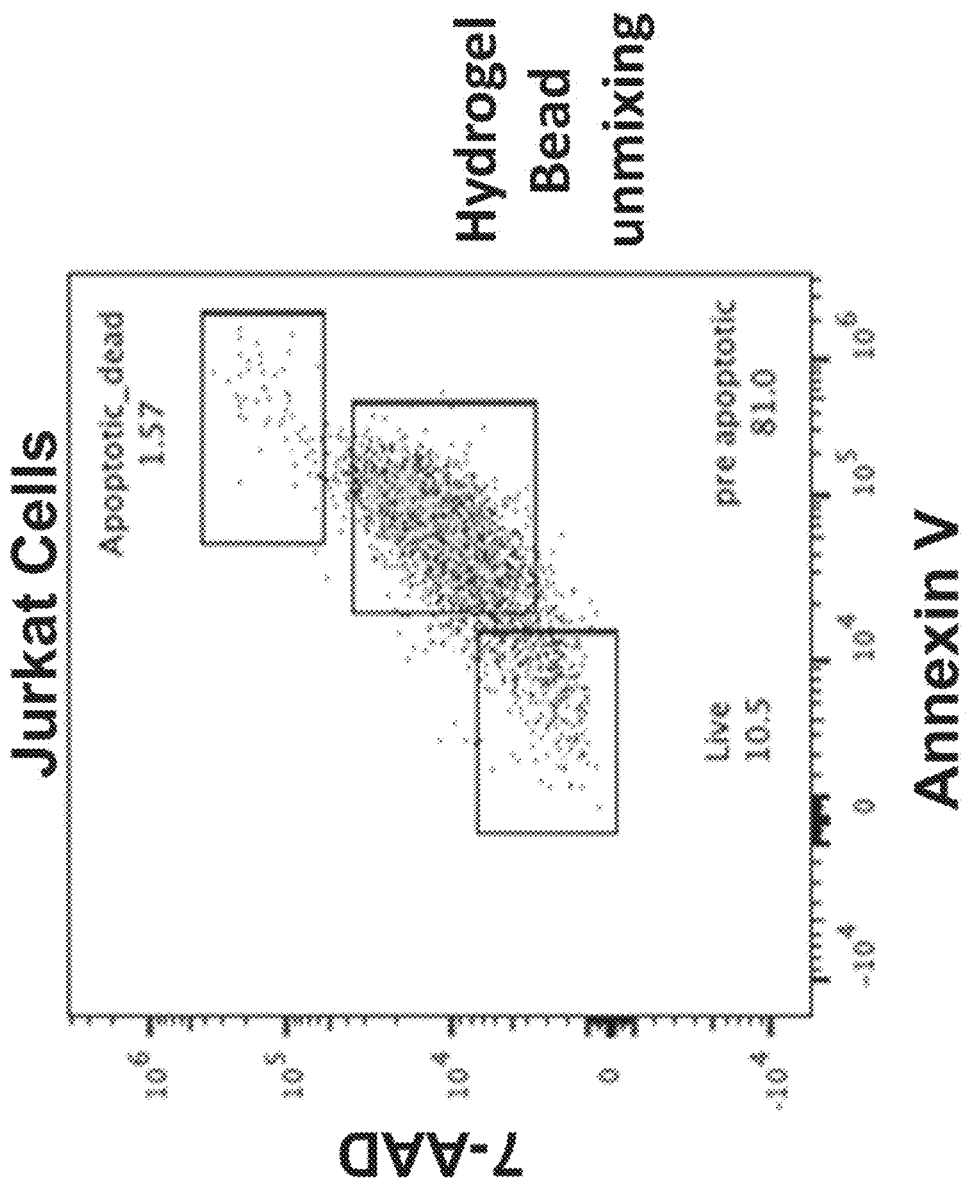

FIGS. 64-72 show binding of 7AAD and Annexin V labeled with an ALEXA FLUOR® 647 dye to (a) a composition containing three hydrogel bead populations (FIG. 64, FIG. 67, FIG. 70); (b) Jurkat cells (FIG. 65, FIG. 68, FIG. 71); or (c) peripheral blood mononuclear cells (PBMCs) (FIG. 66, FIG. 69, FIG. 72), as measured on a CYTEK® Aurora cytometric device. The live cells, dead cells, and apoptotic cells (labeled "pre-apoptotic") are labeled in each figure. The fluorescence spectra of the composition containing the three hydrogel bead populations (FIGS. 70-72), Jurkat cells (FIGS. 64-66), or PBMCs (FIGS. 67-69) bound to Annexin V labeled with an ALEXA FLUOR® 647 dye and/or 7AAD were used to perform spectral unmixing.

CONCLUSIONS

This data shows that hydrogel bead compositions can be used as gating controls, as compensation controls, and as tools for spectral unmixing.

Hydrogel bead compositions are superior to cell controls because hydrogel bead compositions stained with pre-apoptotic signal and viability dyes (e.g., Annexin V labeled with an ALEXA FLUOR® 647 dye or 7AAD) exhibit clear positive and negative bead populations. In contrast, the separation between positive and negative cell populations is less clear (compare FIG. 67 to FIG. 69).

Hydrogel bead compositions are also superior to cell controls because the number of beads that serve as live cell controls (i.e., beads from the third hydrogel bead population), dead cell controls (i.e., beads from the first hydrogel bead population), and apoptotic cell controls (i.e., beads from the second hydrogel bead population) mimics can be modulated. In contrast, the amount of dead, live, and apoptotic cells in cell populations that serve as controls for apoptosis cannot be precisely controlled. Thus, the hydrogel bead compositions can be generated which have 33% each of beads that serve as dead, live, and apoptotic cell mimics.

Figure 73:
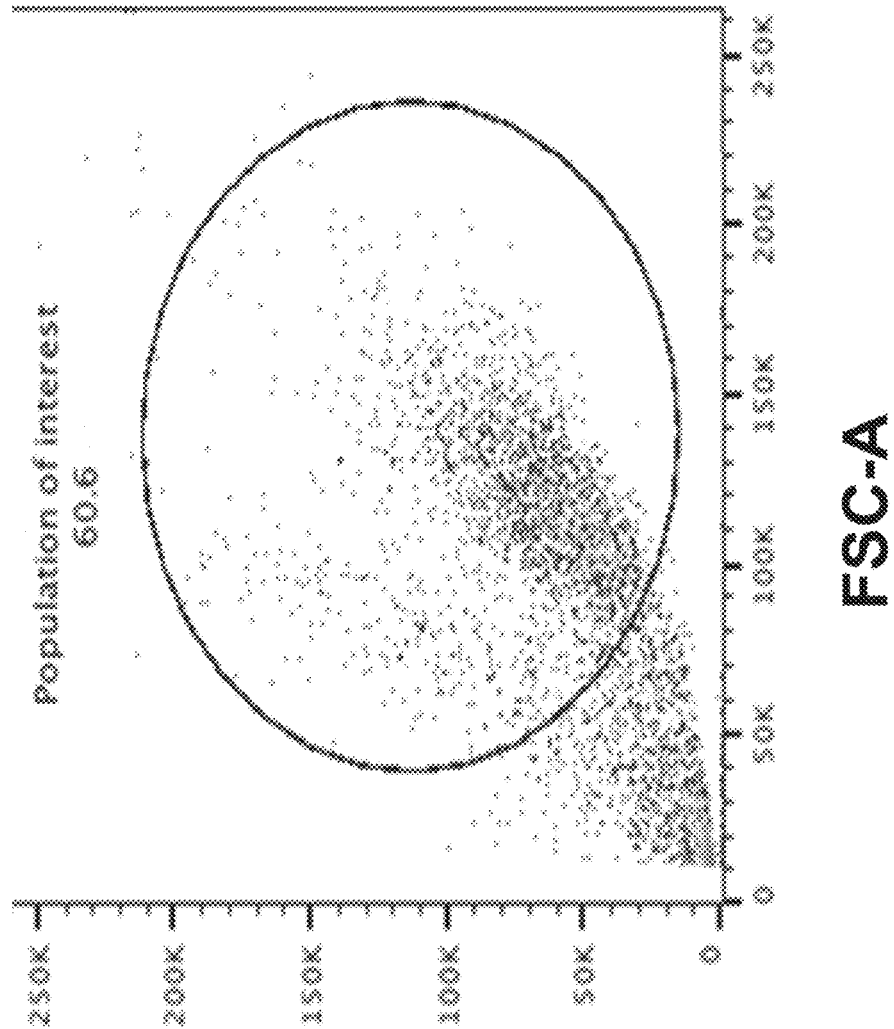
FIG. 73 shows the forward and side scatter of Jurkat cells that are five days old.

Hydrogel bead compositions also exhibit less variability than cells. Different lots of cells may exhibit different properties depending on the age of the cells. For example, the forward scatter and side scatter of Jurkat cells that are different ages is different. Compare FIG. 38, which shows the forward and side scatter of Jurkat cells that are one day old with FIG. 73, which shows the forward and side scatter of Jurkat cells that are five days old. In contrast, three replicates of hydrogel bead populations show consistent forward scatter, and mean fluorescent intensity for binding to 7AAD and Annexin V labeled with an ALEXA FLUOR® 647 dye. These replicates are overlaid in FIGS. 37, 40, 43, 46, 49, 52, 55, 58, 61, 64, and 67.

Additionally, using hydrogel bead compositions as controls is less time intensive than using cell populations as controls. Hydrogel bead compositions do not require cell culture, do not require Annexin V buffer, and do not require induction of apoptosis. Rather, hydrogel bead compositions are stable at 4° C. for 37 days and can be immediately stained with viability dyes.

NUMBERED EMBODIMENTS OF THE DISCLOSURE

Notwithstanding the appended claims, the disclosure sets forth the following numbered embodiments:

1. A hydrogel bead comprising:
   a) a polymerized monomer and a bifunctional monomer; and
   b) a pre-apoptotic signal binder.
2. A hydrogel bead comprising:
   a) a polymerized monomer and a bifunctional monomer; and
   b) a pre-apoptotic signal.
3. The hydrogel bead of embodiment 1 or 2, wherein the pre-apoptotic signal comprises a polypeptide having at least 75%, at least 80%, at least 85%, at least 90%, at least 95%, at least 98%, or 100% identity to any one of annexin V (UniProt Accession No. P08758), a polypeptide of SEQ ID NO: 103, apo-15 peptide, β2-glycoprotein1 or a fragment thereof (UniProt Accession No. D9IWP9) (e.g., domain V), prothrombin or a fragment thereof (UniProt Accession No. P00734), milk fat globule-EGF-factor 8 (MFG-E8) (UniProt Accession No. O08431), a phosphatidyl serine receptor or fragment thereof, SEQ ID NO: 102, CD36 (UniProt Accession No. P16671), an LDL-receptor related protein (UniProt Accession No. P01130), or an anti-calreticulin antibody or antigen-binding fragment thereof.
4. The hydrogel bead of embodiment 3, wherein the pre-apoptotic signal comprises a phosphatidylserine receptor or fragment thereof.
5. The hydrogel bead of embodiment 4, wherein the phosphatidylserine receptor or fragment thereof comprises a polypeptide having at least 75%, at least 80%, at least 85%, at least 90%, at least 95%, at least 98%, or 100% identity to any one of a brain-specific angiogenesis inhibitor-1 (Bai1) (UniProt Accession No. O41514), Axl (UniProt Accession No. P30530), Tyro3 (UniProt Accession No. O06418), Mer (UniProt Accession No. Q12866 or UniProt Accession No. Q50744), TIM-1 (also known as "KIM-1") (UniProt Accession No. Q96D42), TIM-4 (UniProt Accession No. Q96H15), lectin-like oxidized low-density lipoprotein receptor-1 (LOX-1) (UniProt Accession No. P78380), stabilin-1 (UniProt Accession No. Q9NY15), stabilin-2 (UniProt Accession No. Q8WWQ8), CD300a (UniProt Accession No. Q9UGN4), CD300b (UniProt Accession No. A8K4G0), CD300f (UniProt Accession No. Q8TDQ1), receptor for advanced glycosylation end products (RAGE) (UniProt Accession No. Q15109), complement component 1q (C1q) (UniProt Accession No. P02746; UniProt Accession No. P02745; or UniProt Accession No. P02747), β2-glycoprotein I (β2GPI), and integrin αVβ3/β5 (UniProt Accession No. P06756; UniProt Accession No. P05106; or UniProt Accession No. P18084).
6. The hydrogel bead of embodiment 1, wherein the pre-apoptotic signal binder comprises a polypeptide having at least 75%, at least 80%, at least 85%, at least 90%, at least 95%, at least 98%, or 100% identity to any one of a phosphatidylserine, an anti-annexin V antibody or antigen-binding fragment thereof, annexin I (UniProt Accession No. P04083), calreticulin (UniProt Accession No. Q96L12), an anti-CD36 antibody or antigen-binding fragment thereof, thrombospondin-1 (TSP-1) (UniProt Accession No. P07996), anti-β2-glycoprotein I antibody or antigen-binding fragment thereof, anti-milk fat globule-EGF-factor 8 (MFG-E8) or antigen-binding fragment thereof, anti-phosphatidylserine receptor or antigen-binding fragment thereof, and an anti-LDL-receptor related protein or antigen-binding fragment thereof.
7. The hydrogel bead of any one of embodiments 1-6, comprising:
   c) an encapsulated nucleic acid.
8. The hydrogel bead of embodiment 7, wherein the nucleic acid is double stranded DNA.
9. The hydrogel bead of any one of embodiments 2-3, 7, and 8, wherein the pre-apoptotic signal is annexin V.
10. The hydrogel bead of any one of embodiments 1, 3, 7, and 8, wherein the pre-apoptotic signal binder is phosphatidylserine.
11. The hydrogel bead of any one of embodiments 1, 3, 7, and 8, wherein the pre-apoptotic signal binder is an anti-annexin V antibody or antigen-binding fragment thereof.
12. The hydrogel bead of any one of embodiments 2-3, 7, and 8, wherein the pre-apoptotic signal is apo-15.
13. The hydrogel bead of any one of embodiments 1-12, wherein the hydrogel bead comprises an artificial optical-scatter property that is substantially similar to a corresponding optical-scatter property of a target cell optical scatter property, said artificial optical scatter property provided by: a co-monomer, a chemical sidegroup, an encapsulated material, a colloidal silica, or a ratio of acrylamide to bis-acrylamide.
14. The hydrogel bead of any one of embodiments 1-13, wherein the hydrogel bead comprises a scatter-modulating additive.
15. The hydrogel bead of embodiment 13, wherein the optical-scatter property that is substantially similar to the corresponding optical-scatter property of the target cell is side scatter (SSC).
16. The hydrogel bead of embodiment 13, wherein the optical-scatter property that is substantially similar to the corresponding optical-scatter property of the target cell is forward scatter (FSC).
17. The hydrogel bead of embodiment 14, wherein the scatter-modulating additive includes a co-monomer.
18. The hydrogel bead of embodiment 14, wherein the scatter-modulating additive includes a suspension of nanoparticles.
19. The hydrogel bead of any one of embodiments 13 and 15-18, wherein the target cell is one of a lymphocyte, a monocyte, or a granulocyte.
20. The hydrogel bead of any one of embodiments 13 and 15-18, wherein the target cell is one of a prokaryotic cell or a eukaryotic cell.
21. The hydrogel bead of any one of embodiments 13 and 15-18, wherein the target cell is a white blood cell.

22. The hydrogel bead of any one of embodiments 13 and 15-18, wherein the target cell is an immune cell.
23. The hydrogel bead of any one of embodiments 1-22, wherein the polymerized monomer is a biodegradable monomer.
24. The hydrogel bead of any one of embodiments 1-22, wherein the hydrogel bead is biodegradable.
25. The hydrogel bead of embodiment 23, wherein the biodegradable monomer is a monosaccharide, disaccharide, polysaccharide, peptide, protein, or protein domain.
26. The hydrogel bead of embodiment 23, wherein the hydrogel bead comprises a monosaccharide, disaccharide, polysaccharide, peptide, protein, or protein domain.
27. The hydrogel bead of embodiment 23, wherein the biodegradable monomer is a structural polysaccharide.
28. The hydrogel bead of embodiment 23, wherein the hydrogel bead comprises a structural polysaccharide.
29. The hydrogel bead of embodiment 23, wherein the biodegradable monomer is selected from the group consisting of agar, agarose, alginic acid, alguronic acid, alpha glucan, amylopectin, amylose, arabinoxylan, beta-glucan, callose, capsullan, carrageenan polysaccharide, cellodextrin, cellulin, cellulose, chitin, chitosan, chrysolaminarin, curdlan, cyclodextrin, alpha-cyclodextrin, dextrin, dextran, ficoll, fructan, fucoidan, galactoglucomannan, galactomannan, galactosaminoogalactan, gellan gum, glucan, glucomannan, glucorunoxylan, glycocalyx, glycogen, hemicellulose, homopolysaccharide, hypromellose, icodextrin, inulin, kefiran, laminarin, lentinan, levan polysaccharide, lichenin, mannan, mixed-linkage gluxan, paramylon, pectic acid, pectin, pentastarch, phytoglycogen, pleuran, polydextrose, polysaccharide peptide, porphyran, pullulan, schizophyllan, sinistrin, sizofiran, welan gum, xanthan gum, xylan, xyloglucan, zymosan, and a combination thereof.
30. The hydrogel bead of embodiment 23, wherein the hydrogel bead comprises agar, agarose, alginic acid, alguronic acid, alpha glucan, amylopectin, amylose, arabinoxylan, beta-glucan, callose, capsullan, carrageenan polysaccharide, cellodextrin, cellulin, cellulose, chitin, chitosan, chrysolaminarin, curdlan, cyclodextrin, alpha-cyclodextrin, dextrin, dextran, ficoll, fructan, fucoidan, galactoglucomannan, galactomannan, galactosaminoogalactan, gellan gum, glucan, glucomannan, glucorunoxylan, glycocalyx, glycogen, hemicellulose, homopolysaccharide, hypromellose, icodextrin, inulin, kefiran, laminarin, lentinan, levan polysaccharide, lichenin, mannan, mixed-linkage gluxan, paramylon, pectic acid, pectin, pentastarch, phytoglycogen, pleuran, polydextrose, polysaccharide peptide, porphyran, pullulan, schizophyllan, sinistrin, sizofiran, welan gum, xanthan gum, xylan, xyloglucan, zymosan, or a combination thereof.
31. The hydrogel bead of any one of embodiments 9, and 13-30, wherein the annexin V is from a species selected from human, rabbit, mouse, *Ailuropoda melanoleuca, Aotus nancymaae, Balaenoptera acutorostrata scammoni, Balaenoptera musculus, Bos indicus* x *Bos taurus, Bos indicus, Bos mutus, Bos taurus, Bubalus bubalis, Callithrix jacchus, Camelus bactrianus, Canis lupus familiaris, Capra hircus, Carlito syrichta, Castor canadensis,* cattle, *Cebus imitator, Cervus canadensis, Cervus elaphus, Cervus hanglu yarkandensis, Delphinapterus leucas, Dipodomys ordii, Dipodomys spectabilis, Elephas maximus indicus, Equus przewalskii, Eschrichtius robustus, Felis catus, Gorilla gorilla, Gorilla beringer, Gulo gulo luscus, Halichoerus grypus, Hyaena hyaena, Hylobates moloch, Ictidomys tridecemlineatus, Jaculus jaculus, Lagenorhynchus obliquidens, Lemur catta, Lipotes vexillifer, Loxodonta africana, Macaca fascicularis, Macaca mulatta, Mandrillus leucophaeus, Marmota flaviventris, Marmota marmota marmota, Marmota monax, Moschus berezovskii, Muntiacus muntjak, Mustela putorius furo, Neogale vison, Neomonachus schauinslandi, Nomascus leucogenys, Nyctereutes procyonoides, Odobenus rosmarus divergens, Odocoileus virginianus texanus, Orcinus orca, Ovis aries, Pan troglodytes, Papio anubis, Perognathus longimembris pacificus, Phoca vitulina, Physeter catodon, Piliocolobus tephrosceles, Propithecus coquereli, Rangifer tarandus platyrhyncus, Rhinopithecus bieti, Saimiri boliviensis boliviensis, Sciurus carolinensis, Sorex araneus, Sus scrofa, Trachypithecus francoisi, Tupaia chinensis, Tursiops truncatus, Urocitellus parryii, Ursus maritimus, Vulpes lagopus,* and *Zalophus californianus.*
32. The hydrogel bead of any one of embodiments 13, and 13-31, wherein the annexin V comprises a sequence exhibiting at least 100%, 95%, 90%, 85%, 80%, or 75% sequence identity with a sequence selected from the group consisting of SEQ ID NOS: 1-101.
33. The hydrogel bead of any one of embodiments 7-32, wherein the encapsulated nucleic acid is bound to a dye.
34. The hydrogel bead of embodiment 33, wherein the dye bound to the encapsulated nucleic acid is selected from the group consisting of 7-aminoactinomycin D (7AAD), propidium iodide, Hoechst 33258, Hoechst 33342, Hoechst 34580, 4',6-diamidino-2-phenylindole (DAPI), DRAQ5™, DRAQ7™, CytoPhase™ Violet, Helix NP™ Blue, Helix NP™ Green, Helix NP™ NIR, YOYO-1, TOTO™-1 Iodide (Thermo Fisher Scientific), TO-PRO-3®, SYTOX™ Blue, ethidium bromide, SYBR™ Gold, SYBR™ Green, SYBR™ Safe, EvaGreen®, and crystal violet.
35. The hydrogel bead of embodiment 34, wherein the dye is 7AAD.
36. The hydrogel bead of embodiment 34, wherein the dye is propidium iodide.
37. The hydrogel bead of any one of embodiments 1-36, wherein the hydrogel bead has a refractive index of greater than about 1.15.
38. The hydrogel bead of any one of embodiments 1-36, wherein the hydrogel bead has a refractive index of greater than about 1.3.
39. The hydrogel bead of any one of embodiments 1-36, wherein the hydrogel bead has a refractive index of greater than about 1.7.
40. The hydrogel bead of any one of embodiments 1-39, wherein the hydrogel bead has a diameter of less than about 100 μm.
41. The hydrogel bead of any one of embodiments 1-39, wherein the hydrogel bead has a diameter more than about 10 μm.
42. The hydrogel bead of any one of embodiments 1-39, wherein the hydrogel bead has a diameter of more than about 1 μm.
43. The hydrogel bead of any one of embodiments 14-42, wherein the scatter-modulating additive comprises polymer nanoparticles.

44. The hydrogel bead of embodiment 43, wherein the polymer nanoparticles comprise polystyrene.
45. The hydrogel bead of any one of embodiments 1-44, wherein the hydrogel bead is a chemically functionalized hydrogel particle.
46. The hydrogel bead of any one of embodiments 1-45, wherein the hydrogel bead comprises a free amine group.
47. The hydrogel bead of embodiment 46, wherein the pre-apoptotic signal binder is attached to the free amine group.
48. The hydrogel bead of any one of embodiments 1-47, wherein the hydrogel bead comprises allylamine.
49. The hydrogel bead of any one of embodiments 2-5, 7-9, and 12-48, wherein the hydrogel bead exhibits a mean fluorescence intensity (MFI) when labeled with the pre-apoptotic signal that is at least as high as the MFI of a target cell labeled with the same pre-apoptotic signal.
50. The hydrogel bead of any one of embodiments 2-5, 7-9, and 12-48, wherein the hydrogel bead exhibits a mean fluorescence intensity (MFI) when labeled with the pre-apoptotic signal that is substantially the same as the MFI of a target cell labeled with the same pre-apoptotic signal.
51. The hydrogel bead of any one of embodiments 1, 6-8, 10-11, and 13-48, wherein the hydrogel bead exhibits a mean fluorescence intensity (MFI) when labeled with the pre-apoptotic signal binder that is at least as high as the MFI of a target cell labeled with the same pre-apoptotic signal binder.
52. The hydrogel bead of any one of embodiments 1, 6-8, 10-11, and 13-48, wherein the hydrogel bead exhibits a mean fluorescence intensity (MFI) when labeled with the pre-apoptotic signal binder that is substantially the same as the MFI of a target cell labeled with the same pre-apoptotic signal binder.
53. The hydrogel bead of embodiment 50 or 52, wherein the MFI of the hydrogel bead and the MFI of the target cell is within 50%, 40%, 30%, 20%, or 10%.
54. The hydrogel bead of any one of embodiments 7-53, wherein the hydrogel bead exhibits a mean fluorescence intensity (MFI) when labeled with a DNA binding dye that is at least as high as the MFI of a target cell labeled with the same DNA binding dye.
55. The hydrogel bead of any one of embodiments 7-53, wherein the hydrogel bead exhibits a mean fluorescence intensity (MFI) when labeled with a DNA binding dye that is substantially the same as the MFI of a target cell labeled with the same DNA binding dye.
56. The hydrogel bead of embodiment 55, wherein the MFI of the hydrogel bead and the MFI of the target cell is within 50%, 40%, 30%, 20%, or 10%.
57. A kit comprising:
   a) a first population of hydrogel beads, each bead comprising:
      i) a polymerized monomer;
      ii) a pre-apoptotic signal binder; and
      iii) an encapsulated nucleic acid;
   b) a second population of hydrogel beads, each bead comprising:
      i) a polymerized monomer;
      ii) a pre-apoptotic signal binder; but
      iii) lacking the encapsulated nucleic acid of the first population of hydrogel beads; and
   c) a third population of hydrogel beads comprising:
      i) a polymerized monomer; but
      ii) lacking the pre-apoptotic signal binder of the first population of hydrogel beads; and
      iii) lacking the encapsulated nucleic acid of the first population of hydrogel beads.
58. A composition comprising:
   a) a first population of hydrogel beads, each bead comprising:
      i) a polymerized monomer;
      ii) a pre-apoptotic signal binder; and
      iii) an encapsulated nucleic acid;
   b) a second population of hydrogel beads, each bead comprising:
      i) a polymerized monomer;
      ii) a pre-apoptotic signal binder; but
      iii) lacking the encapsulated nucleic acid of the first population of hydrogel beads; and
   c) a third population of hydrogel beads comprising:
      i) a polymerized monomer; but
      ii) lacking the pre-apoptotic signal binder of the first population of hydrogel beads; but
      iii) lacking the encapsulated nucleic acid of the first population of hydrogel beads.
59. A kit comprising:
   a) a first population of hydrogel beads, each bead comprising:
      i) a polymerized monomer;
      ii) a pre-apoptotic signal; and
      iii) an encapsulated nucleic acid;
   b) a second population of hydrogel beads, each bead comprising:
      i) a polymerized monomer;
      ii) a pre-apoptotic signal; but
      iii) lacking the encapsulated nucleic acid of the first population of hydrogel beads; and
   c) a third population of hydrogel beads comprising:
      i) a polymerized monomer; but
      ii) lacking the pre-apoptotic signal of the first population of hydrogel beads; and
      iii) lacking the encapsulated nucleic acid of the first population of hydrogel beads.
60. A composition comprising:
   a) a first population of hydrogel beads, each bead comprising:
      i) a polymerized monomer;
      ii) a pre-apoptotic signal; and
      iii) an encapsulated nucleic acid;
   b) a second population of hydrogel beads, each bead comprising:
      i) a polymerized monomer;
      ii) a pre-apoptotic signal; but
      iii) lacking the encapsulated nucleic acid of the first population of hydrogel beads; and
   c) a third population of hydrogel beads comprising:
      i) a polymerized monomer; but
      ii) lacking the pre-apoptotic signal of the first population of hydrogel beads; but
      iii) lacking the encapsulated nucleic acid of the first population of hydrogel beads.
61. The kit or composition of any one of embodiments 57-60, wherein the second and third population of hydrogels do not contain any nucleic acids.
62. The kit or composition of any one of embodiments 57-60, wherein the second and third population of hydrogels do not contain any double stranded DNA.

63. The kit or composition of any one of embodiments 57-62, wherein the first, second, and third, population of hydrogel beads are at a w/w ratio of about 1:1:1.
64. The kit or composition of any one of embodiments 57-62, wherein the first, second, and third, population of hydrogel beads are at a ratio of about 1:1:1 by number of beads.
65. The kit or composition of any one of embodiments 57-62, wherein each of the first, second, and third, population of hydrogel beads represents about 10-50% of total amount of hydrogel beads in the kit or composition by weight.
66. The kit or composition of any one of embodiments 57-62, wherein each of the first, second, and third, population of hydrogel beads represents about 10-50% of total amount of hydrogel beads in the kit or composition by number of beads.
67. The kit or composition of any one of embodiments 59-66, wherein the pre-apoptotic signal comprises a polypeptide having at least 75%, at least 80%, at least 85%, at least 90%, at least 95%, at least 98%, or 100% identity to any one of annexin V (UniProt Accession No. P08758), a polypeptide of SEQ ID NO: 103, apo-15 peptide, β2-glycoprotein1 or a fragment thereof (UniProt Accession No. D9IWP9) (e.g., domain V), prothrombin or a fragment thereof (UniProt Accession No. P00734), milk fat globule-EGF-factor 8 (MFG-E8) (UniProt Accession No. 008431), a phosphatidyl serine receptor or fragment thereof, SEQ ID NO: 102, CD36 (UniProt Accession No. P16671), an LDL-receptor related protein (UniProt Accession No. P01130), or an anti-calreticulin antibody or antigen-binding fragment thereof.
68. The kit or composition of any one of embodiments 59-66, wherein the pre-apoptotic signal comprises a phosphatidylserine receptor or fragment thereof.
69. The kit or composition of embodiment 68, wherein the phosphatidylserine receptor or fragment thereof comprises a polypeptide having at least 75%, at least 80%, at least 85%, at least 90%, at least 95%, at least 98%, or 100% identity to any one of a brain-specific angiogenesis inhibitor-1 (Bai1) (UniProt Accession No. 041514), Axl (UniProt Accession No. P30530), Tyro3 (UniProt Accession No. 006418), Mer (UniProt Accession No. Q12866 or UniProt Accession No. Q50744), TIM-1 (also known as "KIM-1") (UniProt Accession No. Q96D42), TIM-4 (UniProt Accession No. Q96H15), lectin-like oxidized low-density lipoprotein receptor-1 (LOX-1) (UniProt Accession No. P78380), stabilin-1 (UniProt Accession No. Q9NY15), stabilin-2 (UniProt Accession No. Q8WWQ8), CD300a (UniProt Accession No. Q9UGN4), CD300b (UniProt Accession No. A8K4G0), CD300f (UniProt Accession No. Q8TDQ1), receptor for advanced glycosylation end products (RAGE) (UniProt Accession No. Q15109), complement component 1q (C1q) (UniProt Accession No. P02746; UniProt Accession No. P02745; or UniProt Accession No. P02747), β2-glycoprotein I (β2GPI), and integrin αVβ3/β5 (UniProt Accession No. P06756; UniProt Accession No. P05106; or UniProt Accession No. P18084).
70. The kit or composition of any one of embodiments 57-58 and 61-66, wherein the pre-apoptotic signal binder comprises a polypeptide having at least 75%, at least 80%, at least 85%, at least 90%, at least 95%, at least 98%, or 100% identity to any one of a phosphatidylserine, an anti-annexin V antibody or antigen-binding fragment thereof, annexin I (UniProt Accession No. P04083), calreticulin (UniProt Accession No. Q96L12), an anti-CD36 antibody or antigen-binding fragment thereof, thrombospondin-1 (TSP-1) (UniProt Accession No. P07996), anti-β2-glycoprotein I antibody or antigen-binding fragment thereof, anti-milk fat globule-EGF-factor 8 (MFG-E8) or antigen-binding fragment thereof, anti-phosphatidylserine receptor or antigen-binding fragment thereof, and an anti-LDL-receptor related protein or antigen-binding fragment thereof.
71. The kit or composition of any one of embodiments 57-70, comprising:
c) an encapsulated nucleic acid.
72. The kit or composition of embodiment 71, wherein the nucleic acid is double stranded DNA.
73. The kit or composition of any one of embodiments 59-69, and 71-72, wherein the pre-apoptotic signal is annexin V.
74. The kit or composition of any one of embodiments 57, 58, 61-66, and 70-72, wherein the pre-apoptotic signal binder is phosphatidylserine.
75. The kit or composition of any one of embodiments 57, 58, 61-66, and 70-72, wherein the pre-apoptotic signal binder is an anti-annexin V antibody or antigen-binding fragment thereof.
76. The kit or composition of any one of embodiments 59-69 and 71-72, wherein the pre-apoptotic signal is apo-15.
77. The kit or composition of any one of embodiments 57-76, wherein the hydrogel bead comprises an artificial optical-scatter property that is substantially similar to a corresponding optical-scatter property of a target cell optical scatter property, said artificial optical scatter property provided by: a co-monomer, a chemical side-group, an encapsulated material, a colloidal silica, or a ratio of acrylamide to bis-acrylamide.
78. The kit or composition of any one of embodiments 57-77, wherein the hydrogel bead comprises a scatter-modulating additive.
79. The kit or composition of embodiment 77 or 78, wherein the optical-scatter property that is substantially similar to the corresponding optical-scatter property of the target cell is side scatter (SSC).
80. The kit or composition of embodiment 77 or 78, wherein the optical-scatter property that is substantially similar to the corresponding optical-scatter property of the target cell is forward scatter (FSC).
81. The kit or composition of any one of embodiments 78-80, wherein the scatter-modulating additive includes a co-monomer.
82. The kit or composition of any one of embodiments 78-80, wherein the scatter-modulating additive includes a suspension of nanoparticles.
83. The kit or composition of any one of embodiments 77-82, wherein the target cell is one of a lymphocyte, a monocyte, or a granulocyte.
84. The kit or composition of any one of embodiments 77-82, wherein the target cell is one of a prokaryotic cell or a eukaryotic cell.
85. The kit or composition of any one of embodiments 77-82, wherein the target cell is a white blood cell.
86. The kit or composition of any one of embodiments 77-82, wherein the target cell is an immune cell.
87. The kit or composition of any one of embodiments 77-86, wherein the polymerized monomer is a biodegradable monomer.

88. The kit or composition of any one of embodiments 7-86, wherein the hydrogel bead is biodegradable.
89. The kit or composition of embodiment 87, wherein the biodegradable monomer is a monosaccharide, disaccharide, polysaccharide, peptide, protein, or protein domain.
90. The kit or composition of embodiment 88, wherein the hydrogel bead comprises a monosaccharide, disaccharide, polysaccharide, peptide, protein, or protein domain.
91. The kit or composition of embodiment 87, wherein the biodegradable monomer is a structural polysaccharide.
92. The kit or composition of embodiment 88, wherein the hydrogel bead comprises a structural polysaccharide.
93. The kit or composition of embodiment 87, wherein the biodegradable monomer is selected from the group consisting of agar, agarose, alginic acid, alguronic acid, alpha glucan, amylopectin, amylose, arabinoxylan, beta-glucan, callose, capsullan, carrageenan polysaccharide, cellodextrin, cellulin, cellulose, chitin, chitosan, chrysolaminarin, curdlan, cyclodextrin, alpha-cyclodextrin, dextrin, dextran, ficoll, fructan, fucoidan, galactoglucomannan, galactomannan, galactosaminoogalactan, gellan gum, glucan, glucomannan, glucorunoxylan, glycocalyx, glycogen, hemicellulose, homopolysaccharide, hypromellose, icodextrin, inulin, kefiran, laminarin, lentinan, levan polysaccharide, lichenin, mannan, mixed-linkage gluxan, paramylon, pectic acid, pectin, pentastarch, phytoglycogen, pleuran, polydextrose, polysaccharide peptide, porphyran, pullulan, schizophyllan, sinistrin, sizofiran, welan gum, xanthan gum, xylan, xyloglucan, zymosan, and a combination thereof.
94. The kit or composition of embodiment 88, wherein the hydrogel bead comprises agar, agarose, alginic acid, alguronic acid, alpha glucan, amylopectin, amylose, arabinoxylan, beta-glucan, callose, capsullan, carrageenan polysaccharide, cellodextrin, cellulin, cellulose, chitin, chitosan, chrysolaminarin, curdlan, cyclodextrin, alpha-cyclodextrin, dextrin, dextran, ficoll, fructan, fucoidan, galactoglucomannan, galactomannan, galactosaminoogalactan, gellan gum, glucan, glucomannan, glucorunoxylan, glycocalyx, glycogen, hemicellulose, homopolysaccharide, hypromellose, icodextrin, inulin, kefiran, laminarin, lentinan, levan polysaccharide, lichenin, mannan, mixed-linkage gluxan, paramylon, pectic acid, pectin, pentastarch, phytoglycogen, pleuran, polydextrose, polysaccharide peptide, porphyran, pullulan, schizophyllan, sinistrin, sizofiran, welan gum, xanthan gum, xylan, xyloglucan, zymosan, or a combination thereof.
95. The kit or composition of any one of embodiments 73 and 77-94, wherein the annexin V is from a species selected from human, rabbit, mouse, *Ailuropoda melanoleuca, Aotus nancymaae, Balaenoptera acutorostrata scammoni, Balaenoptera musculus, Bos indicus* x *Bos taurus, Bos indicus, Bos mutus, Bos taurus, Bubalus bubalis, Callithrix jacchus, Camelus bactrianus, Canis lupus familiaris, Capra hircus, Carlito syrichta, Castor canadensis, cattle, Cebus imitator, Cervus canadensis, Cervus elaphus, Cervus hanglu yarkandensis, Delphinapterus leucas, Dipodomys ordii, Dipodomys spectabilis, Elephas maximus indicus, Equus przewalskii, Eschrichtius robustus, Felis catus, Gorilla gorilla, Gorilla beringer, Gulo gulo luscus, Halichoerus grypus, Hyaena hyaena, Hylobates moloch, Ictidomys tridecemlineatus, Jaculus jaculus, Lagenorhynchus obliquidens, Lemur catta, Lipotes vexillifer, Loxodonta africana, Macaca fascicularis, Macaca mulatta, Mandrillus leucophaeus, Marmota flaviventris, Marmota marmota marmota, Marmota monax, Moschus berezovskii, Muntiacus muntjak, Mustela putorius furo, Neogale vison, Neomonachus schauinslandi, Nomascus leucogenys, Nyctereutes procyonoides, Odobenus rosmarus divergens, Odocoileus virginianus texanus, Orcinus orca, Ovis aries, Pan troglodytes, Papio anubis, Perognathus longimembris pacificus, Phoca vitulina, Physeter catodon, Piliocolobus tephrosceles, Propithecus coquereli, Rangifer tarandus platyrhyncus, Rhinopithecus bieti, Saimiri boliviensis boliviensis, Sciurus carolinensis, Sorex araneus, Sus scrofa, Trachypithecus francoisi, Tupaia chinensis, Tursiops truncatus, Urocitellus parryii, Ursus maritimus, Vulpes lagopus*, and *Zalophus californianus*.
96. The kit or composition of any one of embodiments 73 and 77-95, wherein the annexin V comprises a sequence exhibiting at least 100%, 95%, 90%, 85%, 80%, or 75% sequence identity with a sequence selected from the group consisting of SEQ ID NOS: 1-101.
97. The kit or composition of any one of embodiments 71-96, wherein the encapsulated nucleic acid is bound to a dye.
98. The kit or composition of embodiment 97, wherein the dye bound to the encapsulated nucleic acid is selected from the group consisting of 7-aminoactinomycin D (7AAD), propidium iodide, Hoechst 33258, Hoechst 33342, Hoechst 34580, 4',6-diamidino-2-phenylindole (DAPI), DRAQ5™, DRAQ7™, CytoPhase™ Violet, Helix NP™ Blue, Helix NP™ Green, Helix NP™ NIR, YOYO™-1, TOTO™-1 Iodide (Thermo Fisher Scientific), TO-PRO-3®, SYTOX™ Blue, ethidium bromide, SYBR™ Gold, SYBR™ Green, SYBR™ Safe, EvaGreen®, and crystal violet.
99. The kit or composition of embodiment 97, wherein the dye is 7AAD.
100. The kit or composition of embodiment 97, wherein the dye is propidium iodide.
101. The kit or composition of any one of embodiments 77-100, wherein the hydrogel bead has a refractive index of greater than about 1.15.
102. The kit or composition of any one of embodiments 77-100, wherein the hydrogel bead has a refractive index of greater than about 1.3.
103. The kit or composition of any one of embodiments 77-100, wherein the hydrogel bead has a refractive index of greater than about 1.7.
104. The kit or composition of any one of embodiments 77-103, wherein the hydrogel bead has a diameter of less than about 100 µm.
105. The kit or composition of any one of embodiments 77-103, wherein the hydrogel bead has a diameter more than about 10 µm.
106. The kit or composition of any one of embodiments 77-103, wherein the hydrogel bead has a diameter of more than about 1 µm.
107. The kit or composition of any one of embodiments 78-106, wherein the scatter-modulating additive comprises polymer nanoparticles.
108. The kit or composition of embodiment 107, wherein the polymer nanoparticles comprise polystyrene.

109. The kit or composition of any one of embodiments 77-108, wherein the hydrogel bead is a chemically functionalized hydrogel particle.
110. The kit or composition of any one of embodiments 77-109, wherein the hydrogel bead comprises a free amine group.
111. The kit or composition of any one of embodiments 57, 58, 61-66, and 70-72, 74-75, 77-94, and 97-110, wherein the pre-apoptotic signal binder is attached to the free amine group.
112. The kit or composition of any one of embodiments 57-111, wherein the hydrogel bead comprises allylamine.
113. The kit or composition of any one of embodiments 59-69, 71-73, 76-110, and 112, wherein the hydrogel bead exhibits a mean fluorescence intensity (MFI) when labeled with the pre-apoptotic signal that is at least as high as the MFI of a target cell labeled with the same pre-apoptotic signal.
114. The kit or composition of any one of embodiments 59-69, 71-73, 76-110, and 112, wherein the hydrogel bead exhibits a mean fluorescence intensity (MFI) when labeled with the pre-apoptotic signal that is substantially the same as the MFI of a target cell labeled with the same pre-apoptotic signal.
115. The kit or composition of any one of embodiments 57, 58, 61-66, and 70-72, 74-75, 77-94, and 97-112, wherein the hydrogel bead exhibits a mean fluorescence intensity (MFI) when labeled with the pre-apoptotic signal binder that is at least as high as the MFI of a target cell labeled with the same pre-apoptotic signal binder.
116. The kit or composition of any one of embodiments 57, 58, 61-66, and 70-72, 74-75, 77-94, and 97-112, wherein the hydrogel bead exhibits a mean fluorescence intensity (MFI) when labeled with the pre-apoptotic signal binder that is substantially the same as the MFI of a target cell labeled with the same pre-apoptotic signal binder.
117. The kit or composition of embodiment 114 or 116, wherein the MFI of the hydrogel bead and the MFI of the target cell is within 50%, 40%, 30%, 20%, or 10%.
118. The kit or composition of any one of embodiments 71-117, wherein the hydrogel bead exhibits a mean fluorescence intensity (MFI) when labeled with a DNA binding dye that is at least as high as the MFI of a target cell labeled with the same DNA binding dye.
119. The kit or composition of any one of embodiments 71-117, wherein the hydrogel bead exhibits a mean fluorescence intensity (MFI) when labeled with a DNA binding dye that is substantially the same as the MFI of a target cell labeled with the same DNA binding dye.
120. The kit or composition of embodiment 119, wherein the MFI of the hydrogel bead and the MFI of the target cell is within 50%, 40%, 30%, 20%, or 10%.
121. A method of determining if a target cell sample includes one or more dead or pre-apoptotic cells, said method comprising:
   a) providing a population of hydrogel beads according to any one of embodiments 1-56, or from the kits or compositions of any one of embodiments 57-120;
   b) contacting said population of hydrogel beads with a pre-apoptotic signal and/or a DNA dye;
   c) measuring concentration of pre-apoptotic signal and/or DNA dye in the population of hydrogel beads;
   d) measuring concentration of pre-apoptotic signal and/or DNA dye in the target cell sample; and
   e) comparing the measured concentrations of pre-apoptotic signal and/or DNA dye in the population of hydrogel beads and target cell sample; thereby determining if the target cell sample includes one or more dead or pre-apoptotic cells.
122. A method of determining if a target cell sample includes one or more dead or pre-apoptotic cells, said method comprising:
   a) providing a population of hydrogel beads according to any one of embodiments 1-56, or from the kits or compositions of any one of embodiments 57-120;
   b) contacting said population of hydrogel beads with a pre-apoptotic signal and/or a DNA dye;
   c) measuring concentration of pre-apoptotic signal and/or DNA dye in the population of hydrogel beads in a cytometric device;
   d) calibrating the cytometric device based on the measured concentration of pre-apoptotic signal and/or DNA dye of the hydrogel beads;
   e) measuring concentration of pre-apoptotic signal and/or DNA dye in the target cell sample to determine if the target cell sample includes one or more dead or pre-apoptotic cells.
123. A method of determining if a target cell sample includes one or more dead or pre-apoptotic cells, said method comprising:
   a) providing a population of hydrogel beads according to any one of embodiments 1-56, or from the kits or compositions of any one of embodiments 57-120; wherein at least a subpopulation of hydrogel beads within the population of hydrogel beads, comprises a pre-apoptotic signal and/or a DNA dye;
   b) measuring concentration of pre-apoptotic signal and/or DNA dye in the population of hydrogel beads;
   c) measuring concentration of pre-apoptotic signal and/or DNA dye in the target cell sample; and
   d) comparing the measured concentrations of pre-apoptotic signal and/or DNA dye in the population of hydrogel beads and target cell sample; thereby determining if the target cell sample includes one or more dead or pre-apoptotic cells.
124. A method of determining if a target cell sample includes one or more dead or pre-apoptotic cells, said method comprising:
   a) providing a population of hydrogel beads according to any one of embodiments 1-56, or from the kits or compositions of any one of embodiments 57-120; wherein at least a subpopulation of hydrogel beads within the population of hydrogel beads, comprises a pre-apoptotic signal and/or a DNA dye;
   b) measuring concentration of pre-apoptotic signal and/or DNA dye in the population of hydrogel beads in a cytometric device;
   c) calibrating the cytometric device based on the measured concentration of pre-apoptotic signal and/or DNA dye of the hydrogel beads;
   d) measuring concentration of pre-apoptotic signal and/or DNA dye in the target cell sample to determine if the target cell sample includes one or more dead or pre-apoptotic cells.

Additional Embodiments

Notwithstanding the appended claims, the disclosure sets forth the following additional numbered embodiments:
1. A hydrogel bead comprising:
   a) a polymerized monomer and a bifunctional monomer; and
   b) a pre-apoptotic signal binder.
2. A hydrogel bead comprising:
   a) a polymerized monomer and a bifunctional monomer; and
   b) a pre-apoptotic signal.
3. The hydrogel bead of embodiment 1 or 2, wherein the pre-apoptotic signal comprises a polypeptide having at least 75%, at least 80%, at least 85%, at least 90%, at least 95%, at least 98%, or 100% identity to any one of annexin V (UniProt Accession No. P08758), a polypeptide of SEQ ID NO: 103, apo-15 peptide, β2-glycoprotein1 or a fragment thereof (UniProt Accession No. D9IWP9) (e.g., domain V), prothrombin or a fragment thereof (UniProt Accession No. P00734), milk fat globule-EGF-factor 8 (MFG-E8) (UniProt Accession No. O08431), a phosphatidyl serine receptor or fragment thereof, SEQ ID NO: 102, CD36 (UniProt Accession No. P16671), an LDL-receptor related protein (UniProt Accession No. P01130), or an anti-calreticulin antibody or antigen-binding fragment thereof.
3.1. The hydrogel bead of embodiment 3, wherein the pre-apoptotic signal comprises a phosphatidylserine receptor or fragment thereof.
3.2. The hydrogel bead of embodiment 4, wherein the phosphatidylserine receptor or fragment thereof comprises a polypeptide having at least 75%, at least 80%, at least 85%, at least 90%, at least 95%, at least 98%, or 100% identity to any one of a brain-specific angiogenesis inhibitor-1 (Bai1), Axl, Tyro3, Mer, TIM-1 (also known as "KIM-1"), TIM-4, lectin-like oxidized low-density lipoprotein receptor-1 (LOX-1), stabilin-1, stabilin-2, CD300a, CD300b, CD300f, receptor for advanced glycosylation end products (RAGE), complement component 1q (C1q), β2-glycoprotein I (β2GPI), and integrin αVβ3/β5.
4. The hydrogel bead of embodiment 1, wherein the pre-apoptotic signal binder selected from the group consisting of a phosphatidylserine, an anti-annexin V antibody or antigen-binding fragment thereof, annexin I, calreticulin, an anti-CD36 antibody or antigen-binding fragment thereof, thrombospondin-1 (TSP-1), anti-β2-glycoprotein I antibody or antigen-binding fragment thereof, anti-milk fat globule-EGF-factor 8 (MFG-E8) or antigen-binding fragment thereof, anti-phosphatidylserine receptor or antigen-binding fragment thereof, and an anti-LDL-receptor related protein or antigen-binding fragment thereof.
5. The hydrogel bead of any one of embodiments 1-4, comprising:
   c) an encapsulated nucleic acid.
6. The hydrogel bead of embodiment 5, wherein the nucleic acid is double stranded DNA.
7. The hydrogel bead of any one of embodiments 2-3, and 6, wherein the pre-apoptotic signal is annexin V.
8. The hydrogel bead of any one of embodiments 2-3, and 6, wherein the pre-apoptotic signal binder is phosphatidylserine.
9. The hydrogel bead of any one of embodiments 1-3, and 6, wherein the pre-apoptotic signal binder is an anti-annexin V antibody or antigen-binding fragment thereof.
10. The hydrogel bead of any one of embodiments 1-3, and 6, wherein the pre-apoptotic signal is apo-15.
11. The hydrogel bead of any one of embodiments 1-10, wherein the hydrogel bead comprises an artificial optical-scatter property that is substantially similar to a corresponding optical-scatter property of a target cell optical scatter property, said artificial optical scatter property provided by: a co-monomer, a chemical side-group, an encapsulated material, a colloidal silica, or a ratio of acrylamide to bis-acrylamide.
12. The hydrogel bead of any one of embodiments 1-10, wherein the hydrogel bead comprises a scatter-modulating additive.
13. The hydrogel bead of embodiment 11, wherein the optical-scatter property that is substantially similar to the corresponding optical-scatter property of the target cell is side scatter (SSC).
14. The hydrogel bead of embodiment 11, wherein the optical-scatter property that is substantially similar to the corresponding optical-scatter property of the target cell is forward scatter (FSC).
15. The hydrogel bead of any one of embodiment 11 or 12, wherein the scatter-modulating additive includes a co-monomer.
16. The hydrogel bead of any one of embodiment 11 or 12, wherein the scatter-modulating additive includes a suspension of nanoparticles.
17. The hydrogel bead of any one of embodiments 11 and 13-16, wherein the target cell is one of a lymphocyte, a monocyte, or a granulocyte.
17.1 The hydrogel bead of any one of embodiments 11 and 13-16, wherein the target cell is one of a prokaryotic cell or a eukaryotic cell.
17.2 The hydrogel bead of any one of embodiments 11 and 13-16, wherein the target cell is a white cell.
17.3 The hydrogel bead of any one of embodiments 11 and 13-16, wherein the target cell is an immune cell.
18. The hydrogel bead of any one of embodiments 1-17, wherein the polymerized monomer is a biodegradable monomer.
18.1 The hydrogel bead of any one of embodiments 1-17, wherein the hydrogel is biodegradable.
19. The hydrogel bead of embodiment 18, wherein the biodegradable monomer is a monosaccharide, disaccharide, polysaccharide, peptide, protein, or protein domain.
19.1 The hydrogel bead of embodiment 18, wherein the hydrogel comprises a monosaccharide, disaccharide, polysaccharide, peptide, protein, or protein domain.
20. The hydrogel bead of embodiment 18, wherein the biodegradable monomer is a structural polysaccharide.
20.1 The hydrogel bead of embodiment 18, wherein the hydrogel comprises a structural polysaccharide.
21. The hydrogel bead of embodiment 18, wherein the biodegradable monomer is selected from the group consisting of agar, agarose, alginic acid, alguronic acid, alpha glucan, amylopectin, amylose, arabinoxylan, beta-glucan, callose, capsullan, carrageenan polysaccharide, cellodextrin, cellulin, cellulose, chitin, chitosan, chrysolaminarin, curdlan, cyclodextrin, alpha-cyclodextrin, dextrin, dextran, ficoll, fructan, fucoidan, galactoglucomannan, galactomannan, galactosaminogalactan, gellan gum, glucan, glucomannan, glucorunoxylan, glycocalyx, glycogen, hemicellulose, homopolysaccharide, hypromellose, icodextrin, inulin, kefiran, laminarin, lentinan, levan polysaccharide, lichenin, mannan, mixed-linkage gluxan, paramylon, pectic acid, pectin, pentastarch, phytoglycogen, pleuran, polydextrose, polysaccharide peptide, porphyran, pullulan, schizophyllan, sinistrin, sizofiran, welan gum, xanthan gum, xylan, xyloglucan, zymosan, and a combination thereof.

21.1 The hydrogel bead of embodiment 18, wherein the hydrogel comprises agar, agarose, alginic acid, alguronic acid, alpha glucan, amylopectin, amylose, arabinoxylan, beta-glucan, callose, capsullan, carrageenan polysaccharide, cellodextrin, cellulin, cellulose, chitin, chitosan, chrysolaminarin, curdlan, cyclodextrin, alpha-cyclodextrin, dextrin, dextran, ficoll, fructan, fucoidan, galactoglucomannan, galactomannan, galactosaminoogalactan, gellan gum, glucan, glucomannan, glucorunoxylan, glycocalyx, glycogen, hemicellulose, homopolysaccharide, hypromellose, icodextrin, inulin, kefiran, laminarin, lentinan, levan polysaccharide, lichenin, mannan, mixed-linkage gluxan, paramylon, pectic acid, pectin, pentastarch, phytoglycogen, pleuran, polydextrose, polysaccharide peptide, porphyran, pullulan, schizophyllan, sinistrin, sizofiran, welan gum, xanthan gum, xylan, xyloglucan, zymosan, or a combination thereof.

22. The hydrogel bead of any one of embodiments 7, and 11-22.1, wherein the annexin V is from a species selected from human, rabbit, mouse, *Ailuropoda melanoleuca, Aotus nancymaae, Balaenoptera acutorostrata scammoni, Balaenoptera musculus, Bos indicus* x *Bos taurus, Bos indicus, Bos mutus, Bos taurus, Bubalus bubalis, Callithrix jacchus, Camelus bactrianus, Canis lupus familiaris, Capra hircus, Carlito syrichta, Castor canadensis, cattle, Cebus imitator, Cervus canadensis, Cervus elaphus, Cervus hanglu yarkandensis, Delphinapterus leucas, Dipodomys ordii, Dipodomys spectabilis, Elephas maximus indicus, Equus przewalskii, Eschrichtius robustus, Felis catus, Gorilla gorilla, Gorilla beringer, Gulo gulo luscus, Halichoerus grypus, Hyaena hyaena, Hylobates moloch, Ictidomys tridecemlineatus, Jaculus jaculus, Lagenorhynchus obliquidens, Lemur catta, Lipotes vexillifer, Loxodonta africana, Macaca fascicularis, Macaca mulatta, Mandrillus leucophaeus, Marmota flaviventris, Marmota marmota marmota, Marmota monax, Moschus berezovskii, Muntiacus muntjak, Mustela putorius furo, Neogale vison, Neomonachus schauinslandi, Nomascus leucogenys, Nyctereutes procyonoides, Odobenus rosmarus divergens, Odocoileus virginianus texanus, Orcinus orca, Ovis aries, Pan troglodytes, Papio anubis, Perognathus longimembris pacificus, Phoca vitulina, Physeter catodon, Piliocolobus tephrosceles, Propithecus coquereli, Rangifer tarandus platyrhyncus, Rhinopithecus bieti, Saimiri boliviensis boliviensis, Sciurus carolinensis, Sorex araneus, Sus scrofa, Trachypithecus francoisi, Tupaia chinensis, Tursiops truncatus, Urocitellus parryii, Ursus maritimus, Vulpes lagopus,* and *Zalophus californianus*.

23. The hydrogel bead of any one of embodiments 7, and 11-22, wherein the annexin V comprises a sequence exhibiting at least 100%, 95%, 90%, 85%, 80%, or 75% sequence identity with a sequence selected from the group consisting of SEQ ID NOS: 101.

23.1. The hydrogel bead of any one of embodiments 7, and 11-22, wherein the annexin V comprises a sequence exhibiting at least 100%, 95%, 90%, 85%, 80%, or 75% sequence identity with a sequence of SEQ ID NO: 1.

24. The hydrogel bead of any one of embodiments 5-23, wherein the encapsulated DNA is bound to a dye.

25. The hydrogel bead of embodiment 24, wherein the dye bound to the encapsulated DNA is selected from the group consisting of 7-aminoactinomycin D (7AAD), propidium iodide, Hoechst 33258, Hoechst 33342, Hoechst 34580, 4',6-diamidino-2-phenylindole (DAPI), DRAQ5™, DRAQ7™, CytoPhase™ Violet, Helix NP™ Blue, Helix NP™ Green, Helix NP™ NIR, YOYO™-1, TOTO™-1 Iodide (Thermo Fisher Scientific), TO-PRO-3®, SYTOX™ Blue, ethidium bromide, SYBR™ Gold, SYBR™ Green, SYBR™ Safe, EvaGreen®, and crystal violet.

26. The hydrogel bead of embodiment 25, wherein the dye is 7AAD.

26.1 The hydrogel bead of embodiment 25, wherein the dye is propidium iodide.

27. The hydrogel bead of any one of embodiments 1-26.1, wherein the hydrogel bead has a refractive index of greater than about 1.15.

28. The hydrogel bead of any one of embodiments 1-26.1, wherein the hydrogel bead has a refractive index of greater than about 1.3.

29. The hydrogel bead of any one of embodiments 1-26.1, wherein the hydrogel bead has a refractive index of greater than about 1.7.

30. The hydrogel bead of any one of embodiments 1-29, wherein the hydrogel bead has a diameter of less than about 100 µm.

31. The hydrogel bead of any one of embodiments 1-29, wherein the hydrogel bead particle has a diameter more than about 10 µm.

32. The hydrogel bead of any one of embodiments 1-29, wherein the hydrogel bead particle has a diameter of more than about 1 µm.

33. The hydrogel bead of any one of embodiments 11-32, wherein the scatter-modulating additive comprises polymer nanoparticles.

34. The hydrogel bead of embodiment 33, wherein the polymer nanoparticles comprise polystyrene.

35. The hydrogel bead of any one of embodiments 11-34, wherein the hydrogel bead is a chemically functionalized hydrogel particle.

36. The hydrogel bead of any one of embodiments 1-35, wherein the hydrogel bead comprises a free amine group.

36.1 The hydrogel bead of embodiment 36, wherein the apoptotic signal binder is attached to the free amine group.

37. The hydrogel bead of any one of embodiments 1-35, wherein the hydrogel bead comprises allylamine.

38 The hydrogel bead of any one of embodiments 1 and 3-37, wherein the hydrogel exhibits a mean fluorescence intensity (MFI) when labeled with the pre-apoptotic signal that is at least as high as the MFI of a target cell labeled with the same pre-apoptotic signal.

39. The hydrogel bead of any one of embodiments 1 and 3-37, wherein the hydrogel exhibits a mean fluorescence intensity (MFI) when labeled with the pre-apoptotic signal that is substantially the same as the MFI of a target cell labeled with the same pre-apoptotic signal.

40. The hydrogel bead of embodiment 39, wherein the MFI of the hydrogel and the MFI of the target cell is within 50%, 40%, 30%, 20%, or 10%, 41 The hydrogel bead of any one of embodiments 5-40, wherein the hydrogel exhibits a mean fluorescence intensity (MFI) when labeled with the a DNA binding dye that is at least as high as the MFI of a target cell labeled with the same DNA binding dye.
42. The hydrogel bead of any one of embodiments 5-40, wherein the hydrogel exhibits a mean fluorescence intensity (MFI) when labeled with the pre-apoptotic signal that is substantially the same as the MFI of a target cell labeled with the same pre-apoptotic signal.
43. The hydrogel bead of embodiment 42, wherein the MFI of the hydrogel and the MFI of the target cell is within 50%, 40%, 30%, 20%, or 10%.
44. A kit comprising:
   a) a first population of hydrogel beads, each bead comprising:
      i) a polymerized monomer;
      ii) a pre-apoptotic signal binder; and
      iii) an encapsulated nucleic acid;
   b) a second population of hydrogel beads, each bead comprising:
      i) a polymerized monomer;
      ii) a pre-apoptotic signal binder; but
      iii) lacking the encapsulated nucleic acid of the first population of hydrogel beads; and
   c) a third population of hydrogel beads comprising:
      i) a polymerized monomer; but
      ii) lacking the pre-apoptotic signal binder of the first population of hydrogel beads; but
      iii) lacking the encapsulated nucleic acid of the first population of hydrogel beads.
45. A composition comprising:
   a) a first population of hydrogel beads, each bead comprising:
      i) a polymerized monomer;
      ii) a pre-apoptotic signal binder; and
      iii) an encapsulated nucleic acid;
   b) a second population of hydrogel beads, each bead comprising:
      i) a polymerized monomer;
      ii) a pre-apoptotic signal binder; but
      iii) lacking the encapsulated nucleic acid of the first population of hydrogel beads; and
   c) a third population of hydrogel beads comprising:
      i) a polymerized monomer; but
      ii) lacking the pre-apoptotic signal binder of the first population of hydrogel beads; but
      iii) lacking the encapsulated nucleic acid of the first population of hydrogel beads.
46. A composition comprising:
   a) a first population of hydrogel beads, each bead comprising:
      i) a polymerized monomer;
      ii) a pre-apoptotic signal; and
      iii) an encapsulated nucleic acid;
   b) a second population of hydrogel beads, each bead comprising:
      i) a polymerized monomer;
      ii) a pre-apoptotic signal; but
      iii) lacking the encapsulated nucleic acid of the first population of hydrogel beads; and
   c) a third population of hydrogel beads comprising:
      i) a polymerized monomer; but
      ii) lacking the pre-apoptotic signal of the first population of hydrogel beads; but
      iii) lacking the encapsulated nucleic acid of the first population of hydrogel beads.
47. The kit or composition of any one of embodiments 44-46, wherein the second and third population of hydrogels do not contain any nucleic acids.
48. The kit or composition of any one of embodiments 44-46, wherein the second and third population of hydrogels do not contain any double stranded DNA.
49. The kit or composition of any one of embodiments 44-48, wherein the first, second, and third, population of hydrogel beads are at a w/w ratio of about 1:1:1.
50. The kit or composition of any one of embodiments 44-48, wherein the first, second, and third, population of hydrogel beads are at a ratio of about 1:1:1 by number of beads.
51. The kit or composition of any one of embodiments 44-48, wherein each of the first, second, and third, population of hydrogel beads represents about 10-50% of total amount of hydrogel beads in the kit or composition by weight.
52. The kit or composition of any one of embodiments 44-48, wherein each of the first, second, and third, population of hydrogel beads represents about 10-50% of total amount of hydrogel beads in the kit or composition by number of beads.
53. A method of determining if a target cell sample includes one or more dead or pre-apoptotic cells, said method comprising:
   a) providing a population of hydrogel beads according to any one of embodiments 1-43, or from the kits or compositions of any one of embodiments 44-52;
   b) contacting said population of hydrogel beads with a pre-apoptotic signal and/or a DNA dye;
   c) measuring concentration of pre-apoptotic signal and/or DNA dye in the population of hydrogel beads;
   d) measuring concentration of pre-apoptotic signal and/or DNA dye in the target cell sample; and
   e) comparing the measured concentrations of pre-apoptotic signal and/or DNA dye in the population of hydrogel beads and target cell sample; thereby determining if the target cell sample includes one or more dead or pre-apoptotic cells.
54. A method of determining if a target cell sample includes one or more dead or pre-apoptotic cells, said method comprising:
   a) providing a population of hydrogel beads according to any one of embodiments 1-43, or from the kits or compositions of any one of embodiments 44-52;
   b) contacting said population of hydrogel beads with a pre-apoptotic signal and/or a DNA dye;
   c) measuring concentration of pre-apoptotic signal and/or DNA dye in the population of hydrogel beads in a cytometric device;
   d) calibrating the cytometric device based on the measured concentration of pre-apoptotic signal and/or DNA dye of the hydrogel beads; and
   e) measuring concentration of pre-apoptotic signal and/or DNA dye in the target cell sample to determine if the target cell sample includes one or more dead or pre-apoptotic cells.

55. A method of determining if a target cell sample includes one or more dead or pre-apoptotic cells, said method comprising:
   a) providing a population of hydrogel beads according to any one of embodiments 1-43, or from the kits or compositions of any one of embodiments 44-52; wherein at least a subpopulation of hydrogel beads within the population of hydrogel beads, comprises a pre-apoptotic signal and/or a DNA dye;
   b) measuring concentration of pre-apoptotic signal and/or DNA dye in the population of hydrogel beads;
   c) measuring concentration of pre-apoptotic signal and/or DNA dye in the target cell sample; and
   d) comparing the measured concentrations of pre-apoptotic signal and/or DNA dye in the population of hydrogel beads and target cell sample; thereby determining if the target cell sample includes one or more dead or pre-apoptotic cells.

56. A method of determining if a target cell sample includes one or more dead or pre-apoptotic cells, said method comprising:
   a) providing a population of hydrogel beads according to any one of embodiments 1-43, or from the kits or compositions of any one of embodiments 44-52; wherein at least a subpopulation of hydrogel beads within the population of hydrogel beads, comprises a pre-apoptotic signal and/or a DNA dye;
   b) measuring concentration of pre-apoptotic signal and/or DNA dye in the population of hydrogel beads in a cytometric device;
   c) calibrating the cytometric device based on the measured concentration of pre-apoptotic signal and/or DNA dye of the hydrogel beads; and
   d) measuring concentration of pre-apoptotic signal and/or DNA dye in the target cell sample to determine if the target cell sample includes one or more dead or pre-apoptotic cells.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world. Further, U.S. Pat. No. 9,915,598, issued on Mar. 13, 2018, and entitled: Hydrogel Particles with Tunable Optical Properties, is hereby incorporated by reference for all purposes. Further, U.S. Pat. No. 9,714,897, issued on Jul. 25, 2017, and entitled: Hydrogel Particles with Tunable Optical Properties and Methods for Using the Same, is hereby incorporated by reference for all purposes. Further, U.S. Pat. No. 11,313,782, issued on Apr. 26, 2022, and entitled: Compositions and Methods for Cell-Like Calibration Particles, is hereby incorporated by reference for all purposes. Further, U.S. Publication No. 2023/0067460 published on Mar. 2, 2023, and entitled: Hydrogel Particles as Feeder Cells and Synthetic Antigen Presenting Cells, is hereby incorporated by reference for all purposes. Further, International Application No. PCT/US2023/066684, filed on May 5, 2023, and entitled: Engineered Particles as Red Blood Cell Mimics and Compositions Containing Same for Hematology, is hereby incorporated by reference for all purposes. Further, International Publication No. WO2021/226036, published on Nov. 11, 2021, and entitled: Compositions and Methods for Passive Optical Barcoding for Multiplexed Assays, is hereby incorporated by reference for all purposes.

SEQUENCE LISTING

```
Sequence total quantity: 104
SEQ ID NO: 1            moltype = AA  length = 320
FEATURE                 Location/Qualifiers
source                  1..320
                        mol_type = protein
                        organism = Homo sapiens
SEQUENCE: 1
MAQVLRGTVT DFPGFDERAD AETLRKAMKG LGTDEESILT LLTSRSNAQR QEISAAFKTL   60
FGRDLLDDLK SELTGKFEKL IVALMKPSRL YDAYELKHAL KGAGTNEKVL TEIIASRTPE  120
ELRAIKQVYE EEYGSSLEDD VVGDTSGYYQ RMLVVLLQAN RDPDAGIDEA QVEQDAQALF  180
QAGELKWGTD EEKFITIFGT RSVSHLRKVF DKYMTISGFQ IEETIDRETS GNLEQLLLAV  240
VKSIRSIPAY LAETLYYAMK GAGTDDHTLI RVMVSRSEID LFNIRKEFRK NFATSLYSMI  300
KGDTSGDYKK ALLLLCGEDD                                              320

SEQ ID NO: 2            moltype = AA  length = 320
FEATURE                 Location/Qualifiers
source                  1..320
                        mol_type = protein
                        organism = Pan troglodytes
SEQUENCE: 2
MAQVLRGTVT DFPGFDERAD AETLRKAMKG LGTDEESILT LLTSRSNAQR QEISAAFKTL   60
FGRDLLDDLK SELTGKFEKL IVALMKPSRL YDAYELKHAL KGAGTNEKVL TEIIASRTPE  120
ELRAIKQVYE EEYGSSLEDD VVGDTSGYYQ RMLVVLLQAN RDPDAGIDEA QVEQDAQALF  180
QAGELKWGTD EEKFITIFGT RSVSHLRKVF DKYMTISGFQ IEETIDRETS GNLEQLLLAV  240
VKSIRSIPAY LAETLYYAMK GAGTDDHTLI RVMVSRSEID LFNIRKEFRK NFATSLYSMI  300
KGDTSGDYKK ALLLLCGEDD                                              320

SEQ ID NO: 3            moltype = AA  length = 321
FEATURE                 Location/Qualifiers
source                  1..321
                        mol_type = protein
                        organism = synthetic construct
SEQUENCE: 3
```

```
MAQVLRGTVT DFPGFDERAD AETLRKAMKG LGTDEESILT LLTSRSNAQR QEISAAFKTL    60
FGRDLLDDLK SELTGKFEKL IVALMKPSRL YDAYELKHAL KGAGTNEKVL TEIIASRTPE   120
ELRAIKQVYE EEYGSSLEDD VVGDTSGYYQ RMLVVLLQAN RDPDAGIDEA QVEQDAQALF   180
QAGELKWGTD EEKFITIFGT RSVSHLRKVF DKYMTISGFQ IEETIDRETS GNLEQLLLAV   240
VKSIRSIPAY LAETLYYAMK GAGTDDHTLI RVMVSRSEID LFNIRKEFRK NFATSLYSMI   300
KGDTSGDYKK ALLLLCGEDD D                                            321

SEQ ID NO: 4            moltype = AA  length = 320
FEATURE                 Location/Qualifiers
source                  1..320
                        mol_type = protein
                        organism = Gorilla gorilla
SEQUENCE: 4
MAQILRGTVT DFPGFDERAD AETLRKAMKG LGTDEESILT LLTSRSNAQR QEISAAFKTL    60
FGRDLLDDLK SELTGKFEKL IVALMKPSRL YDAYELKHAL KGAGTNEKVL TEIIASRTPE   120
ELRAIKQVYE EEYGSSLEDD VVGDTSGYYQ RMLVVLLQAN RDPDAGIDEA QVEQDAQALF   180
QAGELKWGTD EEKFITIFGT RSVSHLRKVF DKYMTISGFQ IEETIDRETS GNLEQLLLAV   240
VKSIRSIPAY LAETLYYAMK GAGTDDHTLI RVMVSRSEID LFNIRKEFRK NFATSLYSMI   300
KGDTSGDYKK ALLLLCGEDD                                              320

SEQ ID NO: 5            moltype = AA  length = 320
FEATURE                 Location/Qualifiers
source                  1..320
                        mol_type = protein
                        organism = synthetic construct
SEQUENCE: 5
MAQVLRGTVT DFPGFDERAD AETLRKAMKG LGTDEESILT LLTSRSNAQR QEISAAFKTL    60
FGRDLLDDLK SELTGKFEKL IVALMKPSRL YDAYELKHAL KGAGTNEKVL TEIIASRTPE   120
ELRAIKQVYE EEYGSSLEDD VVGDTSGYYQ RMLVVLLQAN RDPDAGIDEA QVEQDAQALF   180
QAGELKWGTD EEKFITIFGT RSVSHLRKVF DKYMTISGFQ IEETIDRETS GNLEQLLLAV   240
VKSIRSIPAY LAETLYYAMK GAGTDDHTLI RVMVSRSEID LFNIRKEFRK NFATSLYSMI   300
KGDTSGDYKK ALLMLCGEDD                                              320

SEQ ID NO: 6            moltype = AA  length = 331
FEATURE                 Location/Qualifiers
source                  1..331
                        mol_type = protein
                        organism = Homo sapiens
SEQUENCE: 6
MGAQVLRGTV TDFPGFDERA DAETLRKAMK GLGTDEESIL TLLTSRSNAQ RQEISAAFKT    60
LFGRDLLDDL KSELTGKFEK LIVALMKPSR LYDAYELKHA LKGAGTNEKV LTEIIASRTP   120
EELRAIKQVY EEEYGSSLED DVVGDTSGYY QRMLVVLLQA NRDPDAGIDE AQVEQDAQAL   180
FQAGELKWGT DEEKFITIFG TRSVSHLRKV FDKYMTISGF QIEETIDRET SGNLEQLLLA   240
VVKSIRSIPA YLAETLYYAM KGAGTDDHTL IRVMVSRSEI DLFNIRKEFR KNFATSLYSM   300
IKGDTSGDYK KALLLLCGED DHHHHHHHHH H                                 331

SEQ ID NO: 7            moltype = AA  length = 320
FEATURE                 Location/Qualifiers
source                  1..320
                        mol_type = protein
                        organism = Homo sapiens
SEQUENCE: 7
MAQVLRGTVT DFPGFDERAD AETLRKAMKG LGTDEESILT LLTSRSNAQR QEISAAFKTL    60
FGRDLLDDLK SELTGKFEKL IVALMKPSRL YDAYELKHAL KGAGTNEKVL TEIIASRTPE   120
ELRAIKQVYE EEYGSSLEDD VVGDTSGYYQ RMLVVLLQAN RDPDAGIDEA QVEQDAQALF   180
QAGELKWGTD EEKFITIFGT RSVSHLRKVF DKYMTISGFQ IEETIDRETS GNLEQLLLAV   240
VKSIRSIPAY LAETLYYAMK GAGTDDHTLI RVMVSRSETD LFNIRKEFRK NFATSLYSMI   300
KGDTSGDYKK ALLLLCGEDD                                              320

SEQ ID NO: 8            moltype = AA  length = 319
FEATURE                 Location/Qualifiers
source                  1..319
                        mol_type = protein
                        organism = Homo sapiens
SEQUENCE: 8
AQVLRGTVTD FPGFDERADA ETLRKAMKGL GTDEESILTL LTSRSNAQRQ EISAAFKTLF    60
GRDLLDDLKS ELTGKFEKLI VALMKPSRLY DAYELKHALK GAGTNEKVLT EIIASRTPEE   120
LRAIKQVYEE EYGSSLEDDV VGDTSGYYQR MLVVLLQAND PDAGIDEAQ VEQDAQALFQ    180
AGELKWGTDE EKFITIFGTR SVSHLRKVFD KYMTISGFQI EETIDRETSG NLEQLLLAVV   240
KSIRSIPAYL AETLYYAMKG AGTDDHTLIR VMVSRSEIDL FNIRKEFRKN FATSLYSMIK   300
GDTSGDYKKA LLLLCGEDD                                               319

SEQ ID NO: 9            moltype = AA  length = 400
FEATURE                 Location/Qualifiers
source                  1..400
                        mol_type = protein
                        organism = synthetic construct
SEQUENCE: 9
MEAGEDCDCG SPANPCCDAA TCKLLPGAEC ESGPCCRNCK FLKEGTICKR ARGDDMDDYC    60
```

```
NGKTCDCPRN PHKGPATGGG GAQVLRGTVT DFPGFDERAD AETLRKAMKG LGTDEESILT    120
LLTSRSNAQR QEISAAFKTL FGRDLLDDLK SELTGKFEKL IVALMKPSRL YDAYELKHAL    180
KGAGTNEKVL TEIIASRTPE ELRAIKQVYE EEYGSSLEDD VVGDTSGYYQ RMLVVLLQAN    240
RDPDAGIDEA QVEQDAQALF QAGELKWGTD EEKFITIFGT RSVSHLRKVF DKYMTISGFQ    300
IEETIDRETS GNLEQLLLAV VKSIRSIPAY LAETLYYAMK GAGTDDHTLI RVMVSRSEID    360
LFNIRKEFRK NFATSLYSMI KGDTSGDYKK ALLLLCGEDD                          400

SEQ ID NO: 10              moltype = AA   length = 320
FEATURE                    Location/Qualifiers
source                     1..320
                           mol_type = protein
                           organism = Homo sapiens
SEQUENCE: 10
MAQVLRGTVT DFPGFDERAD AETLRKAMKG LGTDEESILT LLTSRSNAQR QEISAAFKTL    60
FGRDLLDDLK SELTGKFEKL IVALMKPSRL YDAYELKHAL KGAGTNEKVL TEIIASRTPE    120
ELRAIKQVYE EEYGLSLEDD VVGDTSGYYQ RMLVVLLQAN RDPDAGIDEA QVEQDAQALF    180
QAGELKWGTD EEKFITIFGT RSVSHLRKVF DKYMTISGFQ IEETIDRETS GNLEQLLLAV    240
VKSIRSIPAY LAETLYYAMK GAGTDDHTLI RVMVSRSEID LFNIRKEFRK NFATSLYSMI    300
KGDTSGDYKK ALLLLCGEDD                                                320

SEQ ID NO: 11              moltype = AA   length = 319
FEATURE                    Location/Qualifiers
source                     1..319
                           mol_type = protein
                           organism = Homo sapiens
SEQUENCE: 11
AQVLRGTVTD FPGFDERADA ETLRKAMKGL GTDEESILTL LTSRSNAQRQ EISAAFKTLF    60
GRDLLDDLKS ELTGKFQKLI VALMKPSRLY DAYELKHALK GAGTNEKVLT EIIASRTPEE    120
LRAIKQVYEE EYGSSLEDDV VGDTSGYYQR MLVVLLQANR DPDAGIDEAQ VEQDAQALFQ    180
AGELKWGTDE EKFITIFGTR SVSHLRKVFD KYMTISGFQI EETIDRETSG NLEQLLLAVV    240
KSIRSIPAYL AETLYYAMKG AGTDDHTLIR VMVSRSEIDL FNIRKEFRKN FATSLYSMIK    300
GDTSGDYKKA LLLLCGEDD                                                 319

SEQ ID NO: 12              moltype = AA   length = 319
FEATURE                    Location/Qualifiers
source                     1..319
                           mol_type = protein
                           organism = Homo sapiens
SEQUENCE: 12
AQVLRGTVTD FPGFDGRADA ETLRKAMKGL GTDEESILTL LTSRSNAQRQ EISAAFKTLF    60
GRDLLDDLKS ELTGKFEKLI VALMKPSRLY DAYELKHALK GAGTNEKVLT EIIASRTPEE    120
LRAIKQVYEE EYGSSLEDDV VGDTSGYYQR MLVVLLQANR DPDAGIDEAQ VEQDAQALFQ    180
AGELKWGTDE EKFITIFGTR SVSHLRKVFD KYMTISGFQI EETIDRETSG NLEQLLLAVV    240
KSIRSIPAYL AETLYYAMKG AGTDDHTLIR VMVSRSEIDL FNIRKEFRKN FATSLYSMIK    300
GDTSGDYKKA LLLLCGEDD                                                 319

SEQ ID NO: 13              moltype = AA   length = 320
FEATURE                    Location/Qualifiers
source                     1..320
                           mol_type = protein
                           organism = Lipotes vexillifer
SEQUENCE: 13
MAQALRGTVT DFPGFDERAD AETLRKAMKG LGTDEESILT LLTSRSNAQR QEIAVAFKTL    60
FGRDLLDDLK SELTGKFEKL IVALMKPSRL YDAYELKHAL KGAGTNEKVL TEIIASRTPE    120
ELRAIKQVYE EEYGSSLEDD VVGDTSGYYQ RMLVVLLQAN RDPDAGIDEA QVEQDAQALF    180
QAGELKWGTD EEKFITIFGT RSVSHLRRVF DKYMTISGFQ IEETIDRETS GNLEQLLLAV    240
VKSIRSIPAY LAETLYYAMK GAGTDDHTLI RVMVSRSEID LFNIRKEFRK NFATSLYSMI    300
KGDTSGDYKK ALLLLCGEDD                                                320

SEQ ID NO: 14              moltype = AA   length = 319
FEATURE                    Location/Qualifiers
source                     1..319
                           mol_type = protein
                           organism = Homo sapiens
SEQUENCE: 14
AQVLRGTVTD FPGFDGRADA ETLRKAMKGL GTDEESILTL LTSRSNAQRQ EISAAFKTLF    60
GRDLLDDLKS ELTGKFQKLI VALMKPSRLY DAYELKHALK GAGTNEKVLT EIIASRTPEE    120
LRAIKQVYEE EYGSSLEDDV VGDTSGYYQR MLVVLLQANR DPDAGIDEAQ VEQDAQALFQ    180
AGELKWGTDE EKFITIFGTR SVSHLRKVFD KYMTISGFQI EETIDRETSG NLEQLLLAVV    240
KSIRSIPAYL AETLYYAMKG AGTDDHTLIR VMVSRSEIDL FNIRKEFRKN FATSLYSMIK    300
GDTSGDYKKA LLLLCGEDD                                                 319

SEQ ID NO: 15              moltype = AA   length = 320
FEATURE                    Location/Qualifiers
source                     1..320
                           mol_type = protein
                           organism = Hylobates moloch
SEQUENCE: 15
MAQVLRGTVT DFPGFDERAD AETLRKAMKG LGTDEESILT LLTSRSNAQR QEISAAFKTL    60
```

```
FGRDLLDDLK SELTGKFEKL IVALMKPSRL YDAYELKHAL KGAGTNEKVL TEIIASRTPE    120
ELRAIKQVYE EEYGSSLEDD VVGDTSGYYQ RMLVVLLQAN RDPDAGIDEA QVEQDAQALF    180
QAGELKWGTD EEKFITIFGT RSVSHLRKVL DKYMTISGFQ IEETIDRETS GNLEQLLLAV    240
VKSIRSIPAY LAETLYYAMK GAGTDDHTLI RVMVSRSEID LFNIRKEFRK NFATSLYSMI    300
KGDTSGDYKK ALLLLCGGED                                                320

SEQ ID NO: 16              moltype = AA   length = 320
FEATURE                    Location/Qualifiers
source                     1..320
                           mol_type = protein
                           organism = Orcinus orca
SEQUENCE: 16
MAQALRGTVT DFPGFDERAD AETLRKAMKG LGTDEESILT LLTSRSNAQR QEIAMAFKTL     60
FGRDLLDDLK SELTGKFEKL IVALMKPSRL YDAYELKHAL KGAGTNEKVL TEIIASRTPE    120
ELRAIKQVYE EEYGSSLEDD VVGDTSGYYQ RMLVVLLQAN RDPDAGIDEA QVEQDAQALF    180
QAGELKWGTD EEKFITIFGT RSVSHLRRVF DKYMTISGFQ IEETIDRETS GNLEQLLLAV    240
VKSIRSIPAY LAETLYYAMK GAGTDDHTLI RVMVSRSEID LFNIRKEFRK NFATSLYSMI    300
KGDTSGDYKK ALLLLCGEED                                                320

SEQ ID NO: 17              moltype = AA   length = 364
FEATURE                    Location/Qualifiers
source                     1..364
                           mol_type = protein
                           organism = Lagenorhynchus obliquidens
SEQUENCE: 17
MESPESSCVE RSLPASLPAL CAAALPEVQV WSCINHLLLT WAVAMAQALR GTVTDFPGFD     60
ERADAETLRK AMKGLGTDEE SILTLLTSRS NAQRQEIAMA FKTLFGRDLL DDLKSELTGK    120
FEKLIVALMK PSQLYDAYEL KHALKGAGTN EKVLTEIIAS RTPEELRAIK QVYEEEYGSS    180
LEDDVVGDTS GYYQRMLVVL LQANRDPDAG IDEAQVEQDA QALFQAGELK WGTDEEKFIT    240
IFGTRSVSHL RRVFDKYMTI SGFQIEETID RETSGNLEQL LLAVVKSIRS IPAYLAETLY    300
YAMKGAGTDD HTLIRVVVSR SEIDLFNIRK EFRKNFATSL YSMIKGDTSG DYKKALLLLC    360
GEDD                                                                 364

SEQ ID NO: 18              moltype = AA   length = 320
FEATURE                    Location/Qualifiers
source                     1..320
                           mol_type = protein
                           organism = Tursiops truncatus
SEQUENCE: 18
MAQALRGTVT DFPGFDERAD AETLRKAMKG LGTDEESILT LLTSRSNAQR QEIAMAFKTL     60
FGRDLLDDLK SELTGKFEKL IVALMKPSRL YDAYELKHAL KGAGTNEKVL TEIIASRTPE    120
ELRAIKQVYE EEYGSSLEDD VVGDTSGYYQ RMLVVLLQAN RDPDAGIDEA QVEQDAQALF    180
QAGELKWGTD EEKFITIFGT RSVSHLRRVF DKYMTISGFQ IEETIDRETS GNLEQLLLAV    240
VKSIRSIPAY LAETLYYAMK GAGTDDHTLI RVVVSRSEID LFNIRKEFRK NFATSLYSMI    300
KGDTSGDYKK ALLLLCGEDD                                                320

SEQ ID NO: 19              moltype = AA   length = 320
FEATURE                    Location/Qualifiers
source                     1..320
                           mol_type = protein
                           organism = Papio anubis
SEQUENCE: 19
MAQVLRGTVT DFPGFDERAD AETLRKAMKG LGTDEESILT LLTSRSNAQR QEISAAFKTL     60
FGRDLLDDLK SELTGKFEKL IVALMKPSRL YDAYELKHAL KGAGTNEKVL TEIIASRTPE    120
ELRAIKEVYE EEYGSSLEDD VVGDTSGYYQ RMLVVLLQAN RDPDAGIDEA QVEQDAQALF    180
QAGELKWGTD EEKFITIFGT RSVSHLRKVF DKYMTISGFQ IEETIDRETS GNLEQLLLAV    240
VKSIRSIPAY LAETLYYAMK GAGTDDHTLI RVMVSRSEID LLNIRKEFRK NFATSLYSMI    300
KGDTSGDYKK ALLLLCGGED                                                320

SEQ ID NO: 20              moltype = AA   length = 320
FEATURE                    Location/Qualifiers
source                     1..320
                           mol_type = protein
                           organism = Nomascus leucogenys
SEQUENCE: 20
MAQVLRGTVT DFPGFDERAD AETLRKAMKG LGTDEESILT LLTSRSNAQR QEISAAFKTL     60
FGRDLLDDLK SELTGKFEKL IVALMKPSRL YDAYELKHAL KGAGTNEKVL TEIIASRTPE    120
ELRAIKQVYE EEYGSSLEDD VVEDTSGYYQ RMLVVLLQAN RDPDAGIDEA QVEQDAQALF    180
QAGELKWGTD EEKFITIFGT RSVSHLRKVL DKYMTISGFQ IEETIDRETS GNLEQLLLAV    240
VKSIRSIPAY LAETLYYAMK GAGTDDHTLI RVMVSRSEID LFNIRKEFRK NFATSLYSMI    300
KGDTSGDYKK ALLLLCGGED                                                320

SEQ ID NO: 21              moltype = AA   length = 321
FEATURE                    Location/Qualifiers
source                     1..321
                           mol_type = protein
                           organism = Saimiri boliviensis
SEQUENCE: 21
MAQVLRGTVT DFPGFDERAD AETLRKAMKG LGTDEESILT LLTSRSNAQR QKISEAFKTL     60
```

```
FGRDLLDDLK SELTGKFEKL IVALMKPSRL YDAYELKHAL KGAGTDEKVL TEIIASRTPE    120
ELRAIKQVYE EEYGSSLEDD VVGDTSGYYQ RMLVVLLQAN RDPDAGIDEA QVEQDAQALF    180
QAGELKWGTD EEKFITIFGT RSVSHLRKVF DKYMTISGFQ IEETIDRETS GNLEQLLLAV    240
VKSIRSIPAY LAETLYYAMK GAGTDDHTLI RVMVSRSEID LFNIRKEFRK NFATSLYSMV    300
KGDTSGDYKK ALLLLCGGED D                                              321

SEQ ID NO: 22              moltype = AA  length = 320
FEATURE                    Location/Qualifiers
source                     1..320
                           mol_type = protein
                           organism = Macaca fascicularis
SEQUENCE: 22
MAQVLRGTVT DFPGFDERAD AETLRKAMKG LGTDEESILT LLTSRSNAQR QEISAAFKTL    60
FGRDLLDDLK SELTGKFEKL IVALMKPSRL YDAYELKHAL KGAGTDEKVL TEIIASRTPE    120
ELRAIKEVYE EEYGSSLEDD VVGDTSGYYQ RMLVVLLQAN RDPDAGIDEA QIEQDAQALF    180
QAGELKWGTD EEKFITIFGT RSVSHLRKVF DKYMTISGFQ IEETIDRETS GNLEQLLLAV    240
VKSIRSIPAY LAETLYYAMK GAGTDDHTLI RVMVSRSEID LLNIRKEFRK NFATSLYSMI    300
KGDTSGDYKK ALLLLCGGED                                                320

SEQ ID NO: 23              moltype = AA  length = 320
FEATURE                    Location/Qualifiers
source                     1..320
                           mol_type = protein
                           organism = Piliocolobus tephrosceles
SEQUENCE: 23
MAQVLRGTVT DFPGFDERAD AETLRKAMKG LGTDEESILT LLTSRSNAQR QEISAAFKTL    60
FGRDLLDDLK SELTGKFEKL IVALMKPSQL YDAYELKHAL KGAGTDEKVL TEIIASRTPE    120
ELRAIKEVYE EEYGSSLEDD VVGDTSGYYQ RMLVVLLQAN RDPDAGIDEA QVEQDAQALF    180
QAGELKWGTD EEKFITIFGT RSVSHLRKVF DKYMTISGFQ IEETIDRETS GNLEQLLLAV    240
VKSIRSIPAY LAETLYYAMK GAGTDDHTLI RVMVSRSEID LLNIRKEFRK NFATSLYSMI    300
KGDTSGDYKK ALLLLCGGED                                                320

SEQ ID NO: 24              moltype = AA  length = 370
FEATURE                    Location/Qualifiers
source                     1..370
                           mol_type = protein
                           organism = Delphinapterus leucas
SEQUENCE: 24
MLPDQSGERL NGNEACKEVP SLNQEVLVEL DHWGAMPEGR GPWKPAFLLM VSQALRGTVT    60
DFPGFDERAD AETLRKAMKG LGTDEESILT LLTSRSNAQR QEIAMAFKTL FGRDLLDDLK    120
SELTGKFEKL IVALMKPSRL YDAYELKHAL KGAGTNEKVL TEIIASRTPE ELRAIKQVYE    180
EEYGSSLEDD VVGDTSGYYQ RMLVVLLQAN RDPDAGIDEA QVEQDAQALF QAGELKWGTD    240
EEKFITIFGT RSVSHLRRVF DKYMTISGFQ IEETIDRETS GNLEQLLLAV VKSIRSIPAY    300
LAETLYYAMK GAGTDDHTLI RVVVSRSEID LFNIRKEFRK NFATSLYSMI KGDTSGDYKK    360
ALLLLCGEDD                                                           370

SEQ ID NO: 25              moltype = AA  length = 321
FEATURE                    Location/Qualifiers
source                     1..321
                           mol_type = protein
                           organism = Aotus nancymaae
SEQUENCE: 25
MAQVLRGTVT DFPGFDERAD AETLRKAMKG LGTDEESILT LLTSRSNAQR QKISEAFKTL    60
FGRDLLDDLK SELTGKFEKL IVALMKPSRL YDAYELKHAL KGAGTDEKVL TEIIASRTPE    120
ELRAIKQVYE EEYGSSLEDD VVGDTSGYYQ RMLVVLLQAN RDPDAGIDEA QVEQDAQALF    180
QAGELKWGTD EEKFITIFGT RSVSHLRKVF DKYMTISGFQ IEETIDRETS GNLEQLLLAV    240
VKSIRSIPAY LAETLYYAMK GAGTDDHTLI RVMVSRSEID LFNIRKEFRK NFATSLYSMV    300
KGDTSGDYKK ALLLLCGGAD D                                              321

SEQ ID NO: 26              moltype = AA  length = 320
FEATURE                    Location/Qualifiers
source                     1..320
                           mol_type = protein
                           organism = Mandrillus leucophaeus
SEQUENCE: 26
MAQVLRGTVT DFPGFDERAD AETLRKAMKG LGTDEESILT LLTSRSNAQR QEISAAFKTL    60
FGRDLLDDLK SELTGKFEKL IVALMKPSRF YDAYELKHAL KGAGTDEKVL TEIIASRTPE    120
ELRAIKEVYE EEYGSSLEDD VVGDTSGYYQ RMLVVLLQAN RDPDAGIDEA QVEQDAQALF    180
QAGELKWGTD EEKFITIFGT RSVSHLRKVF DKYMTISGFQ IEETIDRETS GNLEQLLLAV    240
VKSIRSIPAY LAETLYYAMK GAGTDDHTLI RVMVSRSEID LLNIRKEFRK NFATSLYSMI    300
KGDTSGDYKK ALLLLCGGED                                                320

SEQ ID NO: 27              moltype = AA  length = 321
FEATURE                    Location/Qualifiers
source                     1..321
                           mol_type = protein
                           organism = Cebus imitator
SEQUENCE: 27
MAKVLRGTVT DFPGFDERAD AETLRKAMKG LGTDEESILT LLTSRSNAQR QKISEAFKTL    60
```

```
FGRDLLDDLK SELTGKFEKL IVALMKPSRL YDAYELKHAL KGAGTDEKVL TEIIASRTPE    120
ELRAIKQVYE EEYGSSLEDD VVGDTSGYYQ RMLVVLLQAN RDPDAGIDEA QVEQDAQALF    180
QAGELKWGTD EEKFITIFGT RSVSHLRKVF DKYMTISGFQ IEETIDRETS GNLEQLLLAV    240
VKSIRSIPAY LAETLYYAMK GAGTDDHTLI RVMVSRSEID LFNIRKEFRK NFATSLYSMV    300
KGDTSGDYKK ALLLLCGGED D                                              321

SEQ ID NO: 28          moltype = AA   length = 320
FEATURE                Location/Qualifiers
source                 1..320
                       mol_type = protein
                       organism = Rhinopithecus bieti
SEQUENCE: 28
MAQVLRGTVT DFPGFDERAD AETLRKAMKG LGTDEESILT LLTSRSNAQR QEISAAFKTL     60
FGRDLLDDLK SELTGKFEKL IVALMKPSRL YDAYELKHAL KGAGTDEKVL TEIIASRTPE    120
ELRAIKEVYE EEYGSSLEDD VVGDTSGYYQ RMLVVLLQAN RDPDAGIDEA QVEQDAQALF    180
QAGELKWGTD EEQFITIFGT RSVSHLRKVF DKYMTISGFQ IEETIDRETS GNLEQLLLAV    240
VKSIRSIPAY LAETLYYAMK GAGTEDHTLI RVMVSRSEID LLNIRKEFRK NFATSLYSMI    300
KGDTSGDYKK ALLLLCGGED                                                320

SEQ ID NO: 29          moltype = AA   length = 320
FEATURE                Location/Qualifiers
source                 1..320
                       mol_type = protein
                       organism = Balaenoptera musculus
SEQUENCE: 29
MAQALRGTVT DFPGFDERAD AETLRNAMKG LGTDEESILT LLTSRSNAQR QEIAAAFKTL     60
FGRDLLDDLK SELTGKFEKL IVALMKPSRL YDAYELKHAL KGAGTNEKVL TEIIASRTPG    120
ELRAIKQVYE EEYGSSLEDD VVGDTSGYYQ RMLVVLLQAN RDPDAGIDEA QVEQDAQALF    180
QAGELKWGTD EEKFITIFGT RSVSHLRRVF DKYMTISGFQ IEETIDRETS GNLEQLLLAV    240
VKSIRSIPAY LAETLYYAMK GAGTDDHTLI RVVVSRSEID LCNIKKEFRK NFATSLYSMI    300
KGDTSGDYKK ALLLLCGEDD                                                320

SEQ ID NO: 30          moltype = AA   length = 321
FEATURE                Location/Qualifiers
source                 1..321
                       mol_type = protein
                       organism = Nyctereutes procyonoides
SEQUENCE: 30
MAQVLKGTVT PFPGFDERAD AEVLRKAMKG LGTDEESILT LLTSRSNAQR QEIAAAFKTL     60
FGRDLLDDLK SELTGKFEKL IVALMKPSRL YDAYELKHAL KGAGTNEKVL TEIIASRTPE    120
ELRAIKQVYE EEYGSSLEDD VVGDTSGYYQ RMLVVLLQAN RDPDAGIDEA QVEQDAQALF    180
QAGELKWGTD EEKFITIFGT RSVSHLRRVF DKYMTISGFQ IEETIDRETS GNLEQLLLAV    240
VKSIRSIPAY LAETLYYAMK GAGTDDHTLI RVVVSRSEID LFNIRKEFRK NFATSLYSMI    300
KGDTSGDYKK ALLLLCGGED D                                              321

SEQ ID NO: 31          moltype = AA   length = 321
FEATURE                Location/Qualifiers
source                 1..321
                       mol_type = protein
                       organism = Rangifer tarandus
SEQUENCE: 31
MAQVLRGTVT DFPGFDERAD AETLRKAMKG LGTDEESILT LLTSRSNAQR QEIAVAFKTL     60
FGRDLLDDLK SELTGKFEKL IVALMKPSRL YDAYELKHAL KGAGTNEKVL TEIIASRTPE    120
ELRAIKQVYE EEYGSSLEDD VVGDTSGYYQ RMLVVLLQAN RDPDARIDEA QVEQDAQALF    180
QAGELKWGTD EEKFITIFGT RSVSHLRRVF DKYMTISGFQ IEETIDRETS GNLEQLLLAV    240
VKSIRSIPAY LAETLYYAMK GAGTDDHTLI RVVVSRSEID LYNIRKEFRK NFATSLYSMI    300
KGDTSGDYKK ALLLLCGGED D                                              321

SEQ ID NO: 32          moltype = AA   length = 321
FEATURE                Location/Qualifiers
source                 1..321
                       mol_type = protein
                       organism = Canis lupus
SEQUENCE: 32
MAQVLKGTVT PFPGFDERAD AEVLRKAMKG LGTDEESILT LLTSRSNAQR QEIAAAFKTL     60
FGRDLLDDLK SELTGKFEKL IVALMKPSRL YDAYELKHAL KGAGTNEKVL TEIIASRTPE    120
ELRAIKQVYE EEYGSSLEDD VVGDTSGYYQ RMLVVLLQAN RDPDAGIDEA QVEQDAQALF    180
QAGELKWGTD EEKFITIFGT RSVSHLRRVF DKYMTISGFQ IEETIDRETS GNLEQLLLAV    240
VKSIRSIPAY LAETLYYAMK GAGTDDHTLI RVVVSRSEID LFNIRKEFRK NFATSLYSMI    300
KGDTSGDYKK ALLMLCGGED D                                              321

SEQ ID NO: 33          moltype = AA   length = 444
FEATURE                Location/Qualifiers
source                 1..444
                       mol_type = protein
                       organism = Cervus canadensis
SEQUENCE: 33
MASSLHEGQT FPGALGSRDP SVLQSSGGQA PPRRRGLRAA AHAGALRPE AVGGAQGRCG      60
PRPAGLGWAG PDRAAVFPLP GAASKQRPQR PPLTLAGSAR PAAFPAVRVW SCVAHLLLTW    120
```

```
AGAMAQVLRG TVTDFPGFDE RADAETLRKA MKGLGTDEES ILTLLTSRSN AQRQEIAVAF    180
KTLFGRDLLD DLKSELTGKF EKLIVALMKP SRLYDAYELK HALKGAGTNE KVLTEIIASR    240
TPEELRAIKK VYEEEYGSSL EDDVVGDTSG YYQRMLVVLL QANRDPDTRI DEAQVEQDAQ    300
ALFQAGELKW GTDEEKFITI FGTRSVSHLR RVFDKYMTIS GFQIEETIDR ETSGNLEQLL    360
LAVVKSIRSI PAYLAETLYY AMKGAGTDDH TLIRVMVSRS EIDLYNIRKE FRKNFATSLY    420
SMIKGDTSGD YKKALLLLCG GEDD                                          444

SEQ ID NO: 34            moltype = AA  length = 320
FEATURE                  Location/Qualifiers
source                   1..320
                         mol_type = protein
                         organism = Balaenoptera acutorostrata
SEQUENCE: 34
MAQALRGTVT DFPGFDERAD AETLRNAMKG LGTDEESILT LLTSRSNAQR QEIAAAFKTL    60
FGRDLLDDLK SELTGKFEKL IVALMKPSRL YDAYELKHAL KGAGTNEKIL TEIIASRTPG    120
ELRAIKQVYE EEYGSSLEDD VVGDTSGYYQ RMLVVLLQAN RDPDAGIDEA QVEQDAQALF    180
QAGELKWGTD EEKFITIFGT RSVSHLRRVF DKYMTISGFQ IEETIDRETS GNLEQLLLAV    240
VKSIRSIPAY LAETLYYAMK GAGTDDHTLI RVVVSRSEID LCNIKKEFRK NFATSLYSMI    300
KGDTSGDYKK ALLLLCGEDD                                                320

SEQ ID NO: 35            moltype = AA  length = 321
FEATURE                  Location/Qualifiers
source                   1..321
                         mol_type = protein
                         organism = Moschus berezovskii
SEQUENCE: 35
MAQVLRGTVA DFPGFDERAD AETLRKAMKG LGTDEESILT LLTSRSNAQR QEIAVAFKTL    60
FGRDLLDDLK SELTGKFEKL IVALMKPSRL YDAYELKHAL KGAGTDEKVL TEIIASRTPE    120
ELRAIKQVYE EEYGSSLEDD VVGDTSGYYQ RMLVVLLQAN RDPDAGIDEA QVEQDAQALF    180
QAGELKWGTD EEKFITIFGT RSVSHLRRVF DKYMTISGFQ IEETIDRETS GNLEQLLLAV    240
VKSIRSIPAY LAETLYYAMK GAGTDDHTLI RVVVSRSEID LYNIRKEFRK NFATSLYSMI    300
KGDTSGDYKK ALLLLCGGED D                                              321

SEQ ID NO: 36            moltype = AA  length = 321
FEATURE                  Location/Qualifiers
source                   1..321
                         mol_type = protein
                         organism = Sus scrofa
SEQUENCE: 36
MAQVLRGTVT DFPGFDERAD AETLRKAMKG LGTDEESILT LLTSRSNAQR QEIAVAFKTL    60
FGRDLLDDLK SELTGKFEKL IVALMKPSRL YDAYELKHAL KGAGTDEKIL TEIIASRTPE    120
ELRAIKQVYE EEYGSSLEDD VVGDTSGYYQ RMLVVLLQAN RDPDGRIDEA QVEQDAQALF    180
QAGELKWGTD EEKFITIFGT RSVSHLRRVF DKYMTISGFQ IEETIDRETS GNLEQLLLAV    240
VKSIRSIPAY LAETLYYAMK GAGTDDHTLI RVMVSRSEID LFNIRKEFRK NFATSLYSMI    300
KGDTSGDYKK ALLLLCGGED D                                              321

SEQ ID NO: 37            moltype = AA  length = 321
FEATURE                  Location/Qualifiers
source                   1..321
                         mol_type = protein
                         organism = Sciurus carolinensis
SEQUENCE: 37
MAQALRGTVT DFPGFDERAD AETLRKAMKG LGTDEETILT LLTSRSNAQR QEIAEAFKTL    60
FGRDLLDDLK SELTGKFEKL IVALMKPSRL YDAYELKHAL KGAGTDEKVL TEIIASRTPE    120
ELRAIKQVYE EEYGSSLEDD VVGDTSGYYQ RMLVVLLQAN RDPDAGIDEA QVEQDAQALF    180
QAGELKWGTD EEKFITIFGT RSVSHLRRVF DKYMTISGFQ IEETIDRETS GNLEQLLLAV    240
VKSIRSIPAY LAETLYYAMK GAGTDDHTLI RVVVSRSEID LFNIRKEFRK NFATSLYSMI    300
KGDTSGDYKK ALLLLCGGED D                                              321

SEQ ID NO: 38            moltype = AA  length = 320
FEATURE                  Location/Qualifiers
source                   1..320
                         mol_type = protein
                         organism = Physeter catodon
SEQUENCE: 38
MAQALRGTVT DFPGFDERAD AETLRKAMKG LGTDEDSILT LLTSRSNAQR QEIAAAFKTL    60
FGRDLLDDLK SELTGKFEKL IVALMKPSRL YDAYELKHAL KGAGTNEKVL TEIIASRTPE    120
ELRAIKQVYE EEYGSSLEDD VVGDTSGYYQ RMLVVLLQAN RDPDARIDEA QVEQDAQALF    180
QAGELKWGTD EEKFITIFGT RSVSHLRRVF DKYMTISGFQ IEETIDRETS GNLEQLLLAV    240
VKSIRSVPAY LAETLYYAMK GAGTDDHTLI RVVVSRSEID LFKIREEFRK NFATSLYSMI    300
KGDTSGDYKK ALLLLCGEED                                                320

SEQ ID NO: 39            moltype = AA  length = 317
FEATURE                  Location/Qualifiers
source                   1..317
                         mol_type = protein
                         organism = Macaca mulatta
SEQUENCE: 39
VLRGTVTDFP GFDERADAET LRKAMKGLGT DEESILTLLT SRSNAQRQEI SAAFKTLFGR    60
```

```
DLLDDLKSEL TGKFEKLIVA LMKPSRLYDA YELKHALKGA GTDEKVLTEI IASRTPEELR    120
AIKEVYEEEY GSSLEDDVVG DTSGYYQRML VVLLQANRDP DAGIDEAQVE QDAQALFQAG    180
ELKWGTDEEK FITIFGTRSV SHLRKVFDKY MTISGFQIEE TIDRETSGNL EQLLLAVVKS    240
IRSIPAYLAE TLYYAMKGAG TDDHTLIRVM VSRSEIDLLN IRKEFRKNFA TSLYSMIKGD    300
TSGDYKKALL LLCGGED                                                   317

SEQ ID NO: 40              moltype = AA   length = 321
FEATURE                    Location/Qualifiers
source                     1..321
                           mol_type = protein
                           organism = Odocoileus virginianus
SEQUENCE: 40
MAQVLRGTVT DFPGFDERAD AETLRKAMKG LGTDEESILT LLTSRSNAQR QEIAVAFKTL    60
FGRDLLDDLK SELTGKFEKL IVALMKPSRL YDAYELKHAL KGAGTNEKVL TEIIASRTPE    120
ELRAIKQVYE EEYGSSLEDD VVGDTSGYYQ RMLVVLLQAN RDPDTRIDEA QVEQDAQALF    180
QAGELKWGTD EEKFITIFGT RSVSHLRRVF DKYMTISGFQ IEETIDRETS GNLEQLLLAV    240
VKSIRSIPAY LAETLYYAMK GAGTDDHTLI RVVVSRSEID LYNIRKEFRK NFATSLYSMI    300
KGDTSGDYKK ALLLLCGGED D                                              321

SEQ ID NO: 41              moltype = AA   length = 320
FEATURE                    Location/Qualifiers
source                     1..320
                           mol_type = protein
                           organism = Homo sapiens
SEQUENCE: 41
MAQVLRGTVT DFXGFDERAD AETLRKAMKG LGTDEESILT LLTSRSNAQR QEISAAFKTL    60
FGRDLLDDLK SELTGKFEKL IVALMKXSRL YDAYELKHAL KGAGTNEKVL TEIIASRTXE    120
ELRAIKQVYE EEYGSSLEDD VVGDTSGYYQ RMLVVLLQAN RDXDAGIDEA QVEQDAQALF    180
QAGELKWGTD EEKFITIFGT RSVSHLRKVF DKYMTISGFQ IEETIDRETS GNLEQLLLAV    240
VKSIRSIXAY LAETLYYAMK GAGTDDHTLI RVMVSRSEID LFNIRKEFRK NFATSLYSMI    300
KGDTSGDYKK ALLLLCGEDD                                                320

SEQ ID NO: 42              moltype = AA   length = 321
FEATURE                    Location/Qualifiers
source                     1..321
                           mol_type = protein
                           organism = Callithrix jacchus
SEQUENCE: 42
MAQVPRGTVT DFPGFDERAD AETLRKAMKG LGTDEESILT LLTSRSNAQR QKISEAFKTL    60
FGRDLLDDLK SELTGKFEKL IVALMKPSRL YDAYELKHAL KGAGTDEKVL TEIIASRTPE    120
ELRAIKQVYE EEYGSSLEDD VVGDTSGYYQ RMLVVLLQAN RDPDARIDEA QVEQDAQALF    180
QAGELKWGTD EEKFITIFGT RSVSHLRKVF DKYMTISGFQ IEETIDRETS GNLEQLLLAV    240
VKSIRSIPAY LAETLYYAMK GAGTDDHTLI RVMVSRSEID LFNIRKEFRK NFATSLYSMV    300
KGDTSGDYKK ALLLLCGGED D                                              321

SEQ ID NO: 43              moltype = AA   length = 463
FEATURE                    Location/Qualifiers
source                     1..463
                           mol_type = protein
                           organism = Marmota monax
SEQUENCE: 43
MALGGVREFL LQGSTHPCKS APPGTHPPQV RAGERLSLCS SSIAPAQPAA REAPWACPLS    60
QDRAPRAASR SPRDCPAQAP GPARRRAPRR RAEPRAEGVA EGVAGPAGPC RAFPLRTPLG    120
RCPAARAAPL PAGSVASPTS RAMAQALRGT VTDFPGFDDR ADAETLRKAM KGLGTDEESI    180
LTLLTSRSNA QRQEIAEAFK TLFGRDLLDD LKSELTGKFE KLIVAVMKPS RLYDAYELKH    240
ALKGAGTKEK VLTEIIASRT PEELRAIKQV YEEEYGSSLE DDVVGDTSGY YQRMLVVLLQ    300
ANRDPDAGID EAQVEQDAQA LFQAGELKWG TDEEKFITIF GTRSVSHLRR VFDKYMTISG    360
FQIEETIDRE TSGHLEQLLL AVVKSIRSIP AYLAETLYYA MKGAGTDDHT LIRVVVSRSE    420
IDLSNIRKEF RKNFATSLYS MIKGDTSGDY KKALLLLCGG EDD                      463

SEQ ID NO: 44              moltype = AA   length = 321
FEATURE                    Location/Qualifiers
source                     1..321
                           mol_type = protein
                           organism = Lemur catta
SEQUENCE: 44
MAQVPKGTVS DFPGFDERAD AETLRKAMKG LGTDEESILT LLTSRSNAQR QEISAAFKTL    60
FGRDLLDDLK SELTGKFEKL IVALMKPSRL YDAYELKHAL KGAGTNEKVL TEIIASRTPE    120
ELRAIKQVYE EEYGSSLEDD VVGDTSGYYQ RMLVVLLQAN RDPDAGIDEA QVEQDAQALF    180
QAGELKWGTD EEKFITIFGT RSVSHLRRVF DKYMTISGFQ IEETIDRETS GNLEQLLLAV    240
VKSIRSIPAY LAETLYYAMK GAGTDDHTLI RVIVSRSEVD LFNIRKEFRK NFATSLYSMI    300
KSDTSGDYKK ALLRLCGGED D                                              321

SEQ ID NO: 45              moltype = AA   length = 321
FEATURE                    Location/Qualifiers
source                     1..321
                           mol_type = protein
                           organism = Camelus bactrianus
SEQUENCE: 45
```

```
MAQVLRGTVT SFPGFDERAD AETLRKAMKG LGTDEESILT LLTSRSNAQR QEIAVAFKTL      60
FGRDLLDDLK SELTGKFEKL IVALMKPSRL YDAYELKHAL KGAGTDEKVL TEIIASRTPE     120
ELRAIKQVYE EEYGSSLEDD VVGDTSGYYQ RMLVVLLQAN RDPDAGIDEA QVEQDAQALF     180
QAGELKWGTD EEKFITIFGT RSVSHLRRVF DKYMTISGFQ IEETIDRETS GNLEKLLLAV     240
VKSIRSIPAY LAETLYYAMK GAGTDDHTLI RVLVSRSEID LYNIRKEFRK NFATSLYSMI     300
KGDTSGDYKK ALLLLCGGED D                                               321

SEQ ID NO: 46           moltype = AA  length = 423
FEATURE                 Location/Qualifiers
source                  1..423
                        mol_type = protein
                        organism = Cervus elaphus
SEQUENCE: 46
MFQSSGGRAP PRRRGLGAAA AHAGALRPEA VGGAQGRCGP RPAGLGWAGP DRAAVFPLPG      60
AASKQRPQRP PLTLAGSARP AAFPAVRVWS CVAHLLLTWA GAMAQVLRGT VTDFPGFDER     120
ADAETLRKAM KGLGTDEESI LTLLTSRSNA QRQEIAVAFK TLFGRDLLDD LKSELTGKFE     180
KLIVALMKPS RLYDAYELKH ALKGAGTNEK VLTEIIASRT PEELRAIKKV YEEEYGSSLE     240
DDVVGDTSGY YQRMLVVLLQ ANRDPDTRID EAQVEQDAQA LFQAGELKWG TDEEKFITIF     300
GTRSVSHLRR VFDKYMTISG FQIEETIDRE TSGNLEQLLL AVVKSIRSIP AYLAETLYYA     360
MKGAGTDDHT LIRVVVSRSE IDLYNIRKEF RKNFATSLYS MIKGDTSGDY KKALLLLCGG     420
EDD                                                                   423

SEQ ID NO: 47           moltype = AA  length = 321
FEATURE                 Location/Qualifiers
source                  1..321
                        mol_type = protein
                        organism = Vulpes lagopus
SEQUENCE: 47
MAQVLKGTVT PFPGFDERAD AEVLRKAMKG LGTDEESILT LLTSRSNAQR QEIAAAFKTL      60
FGRDLLDDLK SELTGKFEKL IVALMKPSRL YDAYELKHRAL KGAGTNEKVL TEIIASRTPE    120
ELRAIKQVYE EEYGSSLEDD VVGDTSGYYQ RMLVVLLQAN RDPDAGIDEA QVEQDAQALF     180
QAGELKWGTD EEKFITIFGT RSVSHLRRVF DKYMTISGFQ IEETIDRETS GNLEQLLLAV     240
VKSIRSIPAY LAETLYYAMK GTGTDDHTLI RVVVSRSEID LFNIRKEFRK NFATSLYSMI     300
KDDTSGDYKK ALLLLCGGED D                                               321

SEQ ID NO: 48           moltype = AA  length = 320
FEATURE                 Location/Qualifiers
source                  1..320
                        mol_type = protein
                        organism = Trachypithecus francoisi
SEQUENCE: 48
MAQVLRGTVT DFPGFDERAD AETLRKAMKG LGTDEESILT LLTSRSNAQR QEISAAFKTL      60
FGRDLLDDLK SELTGKFEKL IVALMKPSRL YDTDELKHAL KGAGTDKKVL TEIIASRTPE     120
ELRAIKEVYE EEYGSSLEDD VVGDTSGYYQ RMLVVLLQAN RDPDAGIDEA QVEQDAQALF     180
QAGELKWGTD EEKFITIFGT RSVSHLRKVF DKYMTISGFQ IEETIDRETS GNLEQLLLAV     240
VKSIRSIPAY LAETLYYAMK GAGTDDHTLI RVMVSRSETD LLNIRKEFRK NFATSLYSMI     300
KGDTSGDYKK ALLLLCGGED                                                 320

SEQ ID NO: 49           moltype = AA  length = 417
FEATURE                 Location/Qualifiers
source                  1..417
                        mol_type = protein
                        organism = Tupaia chinensis
SEQUENCE: 49
MVKGVLSLAS DFVSPYENNL PKALSLCPRP RLLQQEGGGP PVPKPGVLDS SSWPSSRARQ      60
SAPQGSQGAA PPPGSNRAAA GPHPVLHRVA LTRQVAMAEV LKGTVTDFPG FDERADAETL     120
RKAMKGLGTD EDSILTLLTS RSNAQRQEIT GAFKTLFGRD LLDDLKSELT GKFEKLIVAL     180
MKPSRLYDAY ELKHALKGAG TDEKVLTEII ASRTPEELRA IKEVYEEEYG SSLEDDVVGD     240
TSGYYQRMLV VLLQANRDPD ARINEAQVEQ DAQALFQAGE LKWGTDEEKF ITIFGTRSVS     300
HLRKVFDKYM TISGFQIEET IDRETSGNLE QLLLAVVKSI RSIPAYLAET LYYAMKGAGT     360
DDHTLIRILV SRSEIDLFNI RKEFRKNFAT SLYSMIKGDT SGDYKKALLL LCGGEDD        417

SEQ ID NO: 50           moltype = AA  length = 321
FEATURE                 Location/Qualifiers
source                  1..321
                        mol_type = protein
                        organism = Carlito syrichta
SEQUENCE: 50
MAQVLRGTVT NFPGFDERAD AETLRKAMKG LGTDEESVLT LLTSRSNAQR QEITVAFKTL      60
YGRDLMDDLK SELTGKFEKL IVAMMKPSRL YDAYELKHAL KGAGTNEKVL TEIIASRTPE     120
ELRAIKQVYE EEYGSSLEDD VVGDTSGYYQ RMLVVLLQAN RDPDAGISEA QVEQDAQALF     180
QAGELKWGTD EEKFITIFGT RSVSHLRRVF DKYMTISGFQ IEETIDRETS GNLEQLLLAV     240
VKSIRSIPAY LAEVLYYAMK GAGTDDHTLI RVVVSRSEID LYNIRKEFRK NFATSLYSMI     300
KGDTSGDYKK ALLLLCGGED D                                               321

SEQ ID NO: 51           moltype = AA  length = 321
FEATURE                 Location/Qualifiers
source                  1..321
                        mol_type = protein
```

```
                         organism = Marmota marmota
SEQUENCE: 51
MSQALRGTVT DFPGFDDRAD AETLRKAMKG LGTDEESILT LLTSRSNAQR QEIAEAFKTL      60
FGRDLLDDLK SELTGKFEKL IVALMKPSRL YDAYELKHAL KGAGTKEKVL TEIIASRTPE     120
ELRAIKQVYE EEYGSSLEDD VVGDTSGYYQ RMLVVLLQAN RDPDAGIDEA QVEQDAQALF     180
QAGELKWGTD EEKFITIFGT RSVSHLRRVF DKYMTISGFQ IEETIDRETS GHLEQLLLAV     240
VKSIRSIPAY LAETLYYAMK GAGTDDHTLI RVVVSRSEID LFNIRKEFRK NFATSLYSMI     300
KGDTSGDYKK ALLLLCGGED D                                               321

SEQ ID NO: 52           moltype = AA   length = 335
FEATURE                 Location/Qualifiers
source                  1..335
                        mol_type = protein
                        organism = Eschrichtius robustus
SEQUENCE: 52
MPEGRGPWKP AFLLMVSQAL RGTVTDFPGF DERADAETLR NAMKGLGTDE ESILTLLTSR      60
SNAQRQEIAA AFKTLFGRDL LDDLKSELTG KFEKLIVALM KPSRLYDAYE LKHALKGAGT     120
NEKVLTEIIA SRTPGELRAI KQVYEEEYGS SLEDDVVGDT SGYYQRMLVV LLQANRDPDA     180
GIDEPQVEQD AQALFQAGEL KWGTDEEKFI TIFGTRSVSH LRRVFDKYMT ISGFQIEETI     240
DRETSGNLEQ LLLAVVKSIR SIPAYLAETL YYAMKGAGTD DHTLIRVVVS RSEIDLCNIK     300
KEFRKNFATS LYSMIKGDTS GDYKKALLLL CGEDD                                335

SEQ ID NO: 53           moltype = AA   length = 321
FEATURE                 Location/Qualifiers
source                  1..321
                        mol_type = protein
                        organism = Bos taurus
SEQUENCE: 53
MAQVLRGTVA DFPGFDERAD AETLRKAMKG LGTDEESILT LLTSRSNAQR QEIAVAFKTL      60
FGRDLLDDLK SELTGKFEKL IVALMKPSRL YDAYELKHAL KGAGTDEKVL TEIIASRTPE     120
ELRAIKQVYE EEYGSSLEDD VVGDTSGYYQ RMLVVLLQAN RDPDARIDEA QVEQDAQALF     180
QAGELKWGTD EEKFITIFGT RSVSHLRRVF DKYMTISGFQ IEETIDRETS GNLEQLLLAV     240
VKSIRSIPAY LAETLYYAMK GAGTDDHTLI RVVVSRSEID LYNIRKEFRK NFGTSLYSMI     300
KGDTSGDYKK ALLLLCGGED D                                               321

SEQ ID NO: 54           moltype = AA   length = 325
FEATURE                 Location/Qualifiers
source                  1..325
                        mol_type = protein
                        organism = Nyctereutes procyonoides
SEQUENCE: 54
MAKELLIVLK GTVTPFPGFD ERADAEVLRK AMKGLGTDEE SILTLLTSRS NAQRQEIAAA      60
FKTLFGRDLL DDLKSELTGK FEKLIVALMK PSRLYDAYEL KHALKGAGTN EKVLTEIIAS     120
RTPEELRAIK QVYEEEYGSS LEDDVVGDTS GYYQRMLVVL LQANRDPDAG IDEAQVEQDA     180
QALFQAGELK WGTDEEKFIT IFGTRSVSHL RRVFDKYMTI SGFQIEETID RETSGNLEQL     240
LLAVVKSIRS IPAYLAETLY YAMKGAGTDD HTLIRVVVSR SEIDLFNIRK EFRKNFATSL     300
YSMIKGDTSG DYKKALLLLC GGEDD                                           325

SEQ ID NO: 55           moltype = AA   length = 320
FEATURE                 Location/Qualifiers
source                  1..320
                        mol_type = protein
                        organism = Homo sapiens
SEQUENCE: 55
XAQVLRGTVT DFPGFDERAD AETLRKAXKG LGTDEESILT LLTSRSNAQR QEISAAFKTL      60
FGRDLLDDLK SELTGKFEKL IVALXKPSRL YDAYELKHAL KGAGTNEKVL TEIIASRTPE     120
ELRAIKQVYE EEYGSSLEDD VVGDTSGYYQ RXLVVLLQAN RDPDAGIDEA QVEQDAQALF     180
QAGELKWGTD EEKFITIFGT RSVSHLRKVF DKYXTISGFQ IEETIDRETS GNLEQLLLAV     240
VKSIRSIPAY LAETLYYAXK GAGTDDHTLI RVXVSRSEID LFNIRKEFRK NFATSLYSXI     300
KGDTSGDYKK ALLLLCGEDD                                                 320

SEQ ID NO: 56           moltype = AA   length = 323
FEATURE                 Location/Qualifiers
source                  1..323
                        mol_type = protein
                        organism = Cervus hanglu
SEQUENCE: 56
MFPCQVLRGT VTDFPGFDER ADAETLRKAM KGLGTDEESI LTLLTSRSNA QRQEIAVAFK      60
TLFGRDLLDD LKSELTGKFE KLIVALMKPS RLYDAYELKH ALKGAGTNEK VLTEIIASRT     120
PEELRAIKKV YEEEYGSSLE DDVVGDTSGY YQRMLVVLLQ ANRDPDTRID EAQVEQDAQA     180
LFQAGELKWG TDEEKFITIF GTRSVSHLRR VFDKYMTISG FQIEETIDRE TSGNLEQLLL     240
AVVKSIRSIP AYLAETLYYA MKGAGTDDHT LIRVMVSRSE IDLYNIRKEF RKNFATSLYS     300
MIKGDTSGDY KKALLLLCGG EDD                                             323

SEQ ID NO: 57           moltype = AA   length = 321
FEATURE                 Location/Qualifiers
source                  1..321
                        mol_type = protein
                        organism = Capra hircus
```

```
SEQUENCE: 57
MAQVLRGTVT DFPGFDERAD AETLRKAMKG LGTDEESILT LLTSRSNAQR QEIAVAFKTL    60
FGRDLLDDLK SELTGKFEKL IVALMKPSRL YDAYELKHAL KGAGTDEKVL TEIIASRTPE   120
ELRAIKQVYE EEYGSSLEDD VVGDTSGYYQ RMLVVLLQAN RDPDARIDEA QVEQDAQALF   180
QAGELKWGTD EEKFITIFGT RSVSHLRRVF DKYMTISGFQ IEETIDRETS GNLEQLLLAV   240
VKSIRSIPAY LAETLYYAMK GAGTDDHTLI RVVVSRSEID LYNIRKEFRK NFGTSLYSMI   300
KGDTSGDYKK TLLLLCGGED D                                            321

SEQ ID NO: 58              moltype = AA  length = 321
FEATURE                    Location/Qualifiers
source                     1..321
                           mol_type = protein
                           organism = Ailuropoda melanoleuca
SEQUENCE: 58
MAQVLKGTVS ASPGFDERAD AEALRKAMKG LGTDEESILT LLTSRSNAQR QEIAVAFKTL    60
FGRDLLDDLK SELTGKFEKL IVALMKPSRI YDAYELKHAL KGAGTDEKVL TEIIASRTPE   120
ELRAIKQVYE EEYGSSLEDD VVGDTSGYYQ RMLVVLLQAN RDPDAGIDEA QVEQDAQALF   180
QAGELKWGTD EEKFITIFGT RSVSHLRRVF DKYMTISGFQ IEETIDRETS GNLEQLLLAV   240
VKSIRSIPAY LAETLYYAMK GAGTDDHTLI RVMVSRSEID LFNIRKEFRK NFATSLYSMI   300
KGDTSGDYKK ALLLLCGGED D                                            321

SEQ ID NO: 59              moltype = AA  length = 382
FEATURE                    Location/Qualifiers
source                     1..382
                           mol_type = protein
                           organism = Bubalus bubalis
SEQUENCE: 59
MRMHRDVRAL GEAHVPAATE RRNIPHAKLG VPHCSRRPPR CTKARLSQSC VAQLLLTWAG    60
AMAQVLRGTV TDFPGFDERA DAETLRKAMK GLGTDEESIL TLLTSRSNAQ RQEIAVAFKT   120
LFGRDLLDDL KSELTGKFEK LIVALMKPSR LYDAYELKHA LKGAGTDEKV LTEIIASRTP   180
EELRAIKQVY EKEYGSSLED DVVGDTSGYY QRMLVVLLQA NRDPDTRIDE AQVEQDAQAL   240
FQAGELKWGT DEEKFITIFG TRSVSHLRRV FDKYMTISGF QIEETIDRET SGNLEQLLLA   300
VVKSIRSIPA YLAETLYYAM KGAGTDDHTL IRVVVSRSEI DLYNIRKEFR KNFGTSLYSM   360
IKGDTSGDYK KALLLLCGGE DD                                           382

SEQ ID NO: 60              moltype = AA  length = 321
FEATURE                    Location/Qualifiers
source                     1..321
                           mol_type = protein
                           organism = Castor canadensis
SEQUENCE: 60
MAQVLRGTVT DFPGFDDRGD AETLRNAMKG LGTDEESILT LLTSRSNAQR QEIAEAFKTL    60
FGRDLLDDLK SELTGKFEKL IVALMKPSRL YDAYELKHAL KGAGTNEKVL TEIIASRTPE   120
QLRAIKQVYE EEYGSSLEDD VXGDTSGYYQ RMLVVLLQAN RDPDAAIDEA QVEQDAQALF   180
QAGELKWGTD EEKFITIFGT RSVSHLRRVF DKYMTISGFQ IEETIDRETS GNLEQLLLAV   240
VKSIRSIPAY LAETLYYAMK GAGTDDHTLI RVMVSRSEID LFNIRKEFRK NFATSLYSMI   300
KGDTSGDYKK TLLLLCGGED D                                            321

SEQ ID NO: 61              moltype = AA  length = 321
FEATURE                    Location/Qualifiers
source                     1..321
                           mol_type = protein
                           organism = Perognathus longimembris
SEQUENCE: 61
MAQVLRGTVS DFPGFDDRAD AETLRKAMKG LGTDEESILT LLTSRSNAQR QEIAVAFKTL    60
FGRDLLDDLK SELTGKFEKL IVALMKPARL YDAYELKHAL KGAGTDEKVL TEIIASRTPE   120
QLRAIKQVYE EEYGSSLEDD VVGDTSGFYQ RMLVVLLQAN RDPDAAIDEA QVEQDAQALF   180
QAGELKWGTD EEKFITIFGT RSVSHLRRVF DKYMTISGFQ IEETIDRETS GNLEQLLLAV   240
VKSIRSIPAY LAETLYYAMK GAGTDDHTLI RVVVSRSEID LFNIRKEFRK NFATSLYSMI   300
KGDTSGDYKK ALLLLCGGED D                                            321

SEQ ID NO: 62              moltype = AA  length = 321
FEATURE                    Location/Qualifiers
source                     1..321
                           mol_type = protein
                           organism = Neogale vison
SEQUENCE: 62
MAQVLRGTVT AFPGFDERAD AETLRKAMKG LGTDEDSILT LLTSRSNAQR QEIAVAFKTL    60
FGRDLLDDLK SELTGKFEKL IVALMKPSRL YDAYELKHAL KGAGTDEKVL TEIIASRTPE   120
ELRAIKQVYE EEYGSSLEDD VVGDTSGYYQ RMLVVLLQAN RDPDAGIDEA QVEQDAQALF   180
QAGELKWGTD EEKFITIFGT RSVSHLRRVF DKYMTISGFQ IEETIDRETS GNLEQLLLAV   240
VKSIRSIPAY LAETLYYAMK GAGTDDHTLI RVVVSRSEID LYNIRKEFRK NFSTSLYSMI   300
KGDTSGDYKK ALLRLCGGED D                                            321

SEQ ID NO: 63              moltype = AA  length = 320
FEATURE                    Location/Qualifiers
source                     1..320
                           mol_type = protein
                           organism = Hyaena hyaena
```

```
SEQUENCE: 63
MAQVKGTVTA FPGFDERADA ETLRKAMKGL GTDEESILTL LTSRSNAQRQ EIAAAFKTLF   60
GRDLLDDLKS ELTGKFEKLI VALMKPSRLY DAYELKHALK GAGTNEKVLT EIIASRTPEE  120
LRAIKQVYEE EYGSSLEDDV VGDTSGYYQR MLVVLLQANR DPDGRIDEAQ VEQDAQALFQ  180
AGELKWGTDE EKFITIFGTR SVSHLRRVFD KYMTISGFQI EETIDRETSG NLEQLLLAVV  240
KSIRSIPAYL AETLYYAMKG AGTDDHTLIR VMVSRSEIDL FNIRKEFRKN FATSLYSMIK  300
GDTSGDYKKA LLLLCGGEDD                                             320

SEQ ID NO: 64            moltype = AA  length = 358
FEATURE                  Location/Qualifiers
source                   1..358
                         mol_type = protein
                         organism = Marmota flaviventris
SEQUENCE: 64
MGRVFPGGEP VERLSLVGSS GRSCPAGQQD VDDSTVLLSQ ALRGTVTDFP GFDDRADAET   60
LRKAMKGLGT DEESILTLLT SRSNAQRQEI AEAFKTLFGR DLLDDLKSEL TGKFEKLIVA  120
LMKPSRLYDA YELKHALKGA GTKEKVLTEI IASRTPEELR AIKQVYEEEY GSSLEDDVVG  180
DTSGYYQRML VVLLQANRDP DAGIDEAQVE QDAQALFQAG ELKWGTDEEK FITIFGTRSV  240
SHLRRVFDKY MTISGFQIEE TIDRETSGHL EQLLLAVVKS IRSIPAYLAE TLYYAMKGAG  300
TDDHTLIRVL VSRSEIDLFN IRKEFRKNFA TSLYSMIKGD TSGDYKKALL LCGGEDD     358

SEQ ID NO: 65            moltype = AA  length = 321
FEATURE                  Location/Qualifiers
source                   1..321
                         mol_type = protein
                         organism = Urocitellus parryii
SEQUENCE: 65
MAQALRGTVT AFPGFDDRAD AETLRKAMKG LGTDEESILT LLTSRSNAQR QQIAEAFKTL   60
FGRDLLDDLK SELTGKFEKL IVALMKPSRL YDAYELKHAL KGAGTNEKVL TEIIASRTPE  120
ELRAIKQVYE EEYGSSLEDD VVADTSGYYQ RMLVVLLQAN RDPDAGIDEA QVEQDAQALF  180
QAGELKWGTD EEKFITIFGT RSVSHLRRVF DKYMTISGFQ IEETIDRETS GHLEQLLLAV  240
VKSIRSIPAY LAETLYYAMK GAGTDDHTLI RVVVSRSEID LFNIRKEFRK NFATSLYSMI  300
KGDTSGDYKK ALLLLCGGED D                                           321

SEQ ID NO: 66            moltype = AA  length = 321
FEATURE                  Location/Qualifiers
source                   1..321
                         mol_type = protein
                         organism = Ovis aries
SEQUENCE: 66
MAQVLRGTVT DFPGFNERAD AETLRKAMKG LGTDEESILT LLTSRSNAQR QEIAVAFKTL   60
FGRDLLDDLK SELTGKFEKL IVALMKPSRL YDAYELKHAL KGAGTDEKVL TEIIASRTPE  120
ELRAIKQVYE EEYGSSLEDD VVGDTSGYYQ RMLVVLLQAN RDPDARIDEA QVEQDAQALF  180
QAGELKWGTD EEKFITIFGT RSVSHLRRVF DKYMTISGFQ IEETIDRETS GNLEQLLLAV  240
VKSIRSIPAY LAETLYYAMK GAGTDDHTLI RVVVSRSEID LYNIRKEFRK NFGTSLYSMI  300
KGDTSGDYKK TLLLLCGGED D                                           321

SEQ ID NO: 67            moltype = AA  length = 321
FEATURE                  Location/Qualifiers
source                   1..321
                         mol_type = protein
                         organism = Bos taurus
SEQUENCE: 67
MAQVLRGTVA DFPGFDERAD AETLRKAMKG LGTDEESILT LLTSRSNAQR QEIAVAFKTL   60
FGRDLLDDLK SELTGKFEKL IVALMKPSRL YDAYELKHAL KGAGTDEKVL TEIIASRTPE  120
ELRAIKQVYE EEYGTSLEDD VVGDTSGYYQ RMLVVLLQAN RDPDARIDEA QVEQDAQALF  180
QAGELKWGTD EEKFITIFGT RSVSHLRRVF DKYMTISGFQ IEETIDRETS GNLEQLLLAV  240
VKSIRSIPAY LAETLYYAMK GAGTDDHTLI RVVVSRSEID LYNIRKEFRK NFGTSLYSMI  300
KGDTSGDYKK ALLLLCGGED D                                           321

SEQ ID NO: 68            moltype = AA  length = 323
FEATURE                  Location/Qualifiers
source                   1..323
                         mol_type = protein
                         organism = Rangifer tarandus
SEQUENCE: 68
MLGIGVLRGT VTDFPGFDER ADAETLRKAM KGLGTDEESI LTLLTSRSNA QRQEIAVAFK   60
TLFGRDLLDD LKSELTGKFE KLIVALMKPS RLYDAYELKH ALKGAGTNEK VLTEIIASRT  120
PEELRAIKQV YEEEYGSSLE DDVVGDTSGY YQRMLVVLLQ ANRDPDARID EAQVEQDAQA  180
LFQAGELKWG TDEEKFITIF GTRSVSHLRR VFDKYMTISG FQIEETIDRE TSGNLEQLLL  240
AVVKSIRSIP AYLAETLYYA MKGAGTDDHT LIRVVVSRSE IDLYNIRKEF RKNFATSLYS  300
MIKGDTSGDY KKALLLLCGG EDD                                         323

SEQ ID NO: 69            moltype = AA  length = 321
FEATURE                  Location/Qualifiers
source                   1..321
                         mol_type = protein
                         organism = Bubalus bubalis
SEQUENCE: 69
```

```
MAQVLRGTVT DFPGFDERAD AETLRKAMKG LGTDEESILT LLTSRSNAQR QEIAVAFKTL    60
FGRDLLDDLK SELTGKFEKL IVALMKPSRL YDAYELKHAL KGAGTDEKVL TEIIASRTPE   120
ELRAIKQVYE KEYGSSLEDD VVGDTSGYYQ RMLVVLLQAN RDPDTRIDEA QVEQDAQALF   180
QAGELKWGTD EEKFITIFGT RSVSHLRRVF DKYMTISGFQ IEETIDRETS GNLEQLLLAV   240
VKSIRSIPAY LAETLYYAMK GAGTDDHTLI RVVVSRSEID LYNIRKEFRK NFGTSLYSMI   300
KGDTSGDYKK ALLLLCGGED D                                            321

SEQ ID NO: 70            moltype = AA   length = 321
FEATURE                  Location/Qualifiers
source                   1..321
                         mol_type = protein
                         organism = Dipodomys ordii
SEQUENCE: 70
MAQVLRGTVS DFPGFDDRAD AETLRKAMKG LGTDEESILT LLTSRSNAQR QEIAEAFKTL    60
FGRDLLDDLK SELTGKFEKL IVALMKPARL YDAYELKHAL KGAGTDEKVL TEIIASRTPE   120
QLRAIKQVYE EEYGSSLEDD VVGDTSGYYQ RMLVVLLQAN RDPDTAIDEA QVEQDAQALF   180
QAGELKWGTD EEKFITIFGT RSVSHLRRVF DKYMTISGFQ IEETIDRETS GNLEQLLLAV   240
VKSIRSIPAY LAETLYYAMK GAGTDDHTLI RVVVSRSEID LFNIRKEFRK NFATSLYSMI   300
KGDTSGDYKK ALLLLCGGED D                                            321

SEQ ID NO: 71            moltype = AA   length = 321
FEATURE                  Location/Qualifiers
source                   1..321
                         mol_type = protein
                         organism = Bos indicus
SEQUENCE: 71
MAQVLRGTVA DFPGFDERAD AETLRKAMKG LGTDEEXILT LLTSRSNAQR QEIAVAFKTL    60
FGRDLLDDLK SELTGKFEKL IVALMKPSRL YDAYELKHAL KGAGTDEKVL TEIIASRTPE   120
ELRAIKQVYE EEYGSSLEDD VVGDTSGYYQ RMLVVLLQAN RDPDARIDEA QVEQDAQALF   180
QAGELKWGTD EEKFITIFGT RSVSHLRRVF DKYMTISGFQ IEETIDRETS GNLEQLLLAV   240
VKSIRSIPAY LAETLYYAMK GAGTDDHTLI RVVVSRSEID LYNIRKEFRK NFGTSLYSMI   300
KGDTSGDYKK ALLLLCGGED D                                            321

SEQ ID NO: 72            moltype = AA   length = 318
FEATURE                  Location/Qualifiers
source                   1..318
                         mol_type = protein
                         organism = Muntiacus muntjak
SEQUENCE: 72
VLRGTVTDFP GFDERADAET LRKAMKGLGT DEESILTLLT SRSNAQRQEI AVAFKTLFGR    60
DLLDDLKSEL TGKFEKLIVA LMKPSRLYDA YELKHALKGA GTNEKVLTEI IASRTPEELR   120
AIKQVYEEEY GSSLEDDVVG DTSGYYQRML VVLLQANRDP DTRIDEAQVE QDAQALFQAG   180
ELKWGTDEEK FITIFGTRSV SHLRRVFDKY MTISGFQIEE TIDRETSGNL EQLLLAVVKS   240
IRSIPAYLAE TLYYAMKGAG TDDHTLIRVV VSRSEIDLYN IRKEFRKNFA TSLYSMIKGD   300
TSGDYKKALL LLCGGEDD                                                318

SEQ ID NO: 73            moltype = AA   length = 321
FEATURE                  Location/Qualifiers
source                   1..321
                         mol_type = protein
                         organism = Marmota monax
SEQUENCE: 73
MAQALRGTVT DFPGFDDRAD AETLRKAMKG LGTDEESILT LLTSRSNAQR QEIAEAFKTL    60
FGRDLLDDLK SELTGKFEKL IVALMKPSRL YDAYELKHAL KGAGTKEKVL TEIIASRTPE   120
ELRAIKQVYE EEYGSSLEDD VVGDTSGYYQ RMLVVLLQAN RDPDAGIDEA QVEQDAQALF   180
QAGELKWGTD EEKFITIFGT RSVSHLRRVF DKYMTISGFQ IEETIDRETS GHLEQLLLAV   240
VKSIRSIPAY LAETLYYAMK GAGTDDHTLI RVVVSRSEID LSNIRKEFRK NFATSLYSMI   300
KGDTSGDYKK ALLLLCGGED D                                            321

SEQ ID NO: 74            moltype = AA   length = 321
FEATURE                  Location/Qualifiers
source                   1..321
                         mol_type = protein
                         organism = Bos taurus
SEQUENCE: 74
MAQVLRGTVA DFPGFDERAD AETLRKAMKG LGTDEESILT LLTSRSNAQR QEIAVAFKTL    60
FGRDLLDDLK SELTGKFEKL IVALMKPSRL YDAYELKHAL KGAGTDEKVL TEIIASRTPE   120
ELRAIEQVYE EEYGSSLEDD VVGDTSGYYQ RMLVVLLQAN RDPDARIDEA QVEQDAQALF   180
QAGELKWGTD EEKFITIFGT RSVSHLRRVF DKYMTISGFQ IEETIDRETS GNLEQLLLAV   240
VKSIRSIPAY LAETLYYAMK GAGTDDHTLI RVVVSRSEID LYNIRKEFRK NFGTSLYSMI   300
KGDTSGDYKK ALLLLCGGED D                                            321

SEQ ID NO: 75            moltype = AA   length = 321
FEATURE                  Location/Qualifiers
source                   1..321
                         mol_type = protein
                         organism = Odobenus rosmarus
SEQUENCE: 75
MAQALKGTVV AFPGFDERAD AETLRKAMKG LGTDEESILT LLTSRSNAQR QEIAVAFKTL    60
```

```
FGRDLLDDLK SELTGKFEKL IMALMKPSRL YDAYELKHAL KGAGTDEKVL TEIIASRTPE   120
ELRAIKQVYE EEYGSSLEDD VVGDTSGYYQ RMLVVLLQAN RDPDAGIDEA QVEQDAQALF   180
QAGELKWGTD EEKFITIFGT RSVSHLRRVF DKYMTISGFQ IEETIDRETS GNLEQLLLAV   240
VKSIRSIPAY LAETLYYAMK GAGTDDHTLI RIVVSRSEID LFNIRKEFRK NFATSLYSMI   300
KGDTSGDYKK ALLLLCGGEN D                                            321

SEQ ID NO: 76           moltype = AA   length = 321
FEATURE                 Location/Qualifiers
source                  1..321
                        mol_type = protein
                        organism = Tupaia chinensis
SEQUENCE: 76
MAEVLKGTVT DFPGFDERAD AETLRKAMKG LGTDEDSILT LLTSRSNAQR QEITGAFKTL   60
FGRDLLDDLK SELTGKFEKL IVALMKPSRL YDAYELKHAL KGAGTDEKVL TEIIASRTPE   120
ELRAIKEVYE EEYGSSLEDD VVGDTSGYYQ RMLVVLLQAN RDPDARINEA QVEQDAQALF   180
QAGELKWGTD EEKFITIFGT RSVSHLRKVF DKYMTISGFQ IEETIDRETS GNLEQLLLAV   240
VKSIRSIPAY LAETLYYAMK GAGTDDHTLI RILVSRSEID LFNIRKEFRK NFATSLYSMI   300
KGDTSGDYKK ALLLLCGGED D                                            321

SEQ ID NO: 77           moltype = AA   length = 353
FEATURE                 Location/Qualifiers
source                  1..353
                        mol_type = protein
                        organism = Cervus canadensis
SEQUENCE: 77
MCEREPSRKP RVAGVRTKAS EANAFLFSFD LILFSVLRGT VTDFPGFDER ADAETLRKAM   60
KGLGTDEESI LTLLTSRSNA QRQEIAVAFK TLFGRDLLDD LKSELTGKFE KLIVALMKPS   120
RLYDAYELKH ALKGAGTNEK VLTEIIASRT PEELRAIKVV YEEEYGSSLE DDVVGDTSGY   180
YQRMLVVLLQ ANRDPDTRID EAQVEQDAQA LFQAGELKWG TDEEKFITIF GTRSVSHLRR   240
VFDKYMTISG FQIEETIDRE TSGNLEQLLL AVVKSIRSIP AYLAETLYYA MKGAGTDDHT   300
LIRVMVSRSE IDLYNIRKEF RKNFATSLYS MIKGDTSGDY KKALLLLCGG EDD          353

SEQ ID NO: 78           moltype = AA   length = 320
FEATURE                 Location/Qualifiers
source                  1..320
                        mol_type = protein
                        organism = Bos taurus
SEQUENCE: 78
AQVLRGTVAD FPGFDERADA ETLRKAMKGL GTDEESILTL LTSRSNAQRQ EIAVAFKTLF   60
GRDLLDDLKS ELTGKFEKLI VALMKPSRLY DAYELKHALK GAGTDEKVLT EIIASRTPEE   120
LRAIKQVYEE EYGSSLEDDV VGDTSGYYQR MLVVLLQANR DPDARIDEAQ VEQDAQALFQ   180
AGELKWGTDE EKFITIFGTR SVSHLRRVFD KYMTISGFQI EETIDRETSG NLEQLLLAVV   240
KSIRSIPAYL AETLYYAMKG AGTDDHTLIR VVVSRSEIDL YNIRKEFRKN FGTSLYSMIK   300
GDTSGDYKKA LLLLCGGEDD                                              320

SEQ ID NO: 79           moltype = AA   length = 321
FEATURE                 Location/Qualifiers
source                  1..321
                        mol_type = protein
                        organism = Neomonachus schauinslandi
SEQUENCE: 79
MAQVLKGTVV AFPGFDERAD AETLRKAMKG LGTDEESILT LLTSRSNAQR QEIAVAFKTL   60
FGRDLLDDLK SELTGKFEKL IVALMKPSRL YDAYELKHAL KGAGTDEKVL TEIIASRTPE   120
ELRAIKQVYE EEYGSSLEDD VVGDTSGFYQ RMLVVLLQAN RDPDAGIDEA QVEQDAQALF   180
QAGELKWGTD EEKFITIFGT RSVSHLRRVF DKYMTISGFQ IEETIDRETS GNLEQLLLAV   240
VKSIRSIPAY LAETLYYAMK GAGTDDHTLI RVVVSRSEID LFNIRKEFRK NFATSLYSMI   300
KDDTSGDYKK ALLLLCGGEN D                                            321

SEQ ID NO: 80           moltype = AA   length = 321
FEATURE                 Location/Qualifiers
source                  1..321
                        mol_type = protein
                        organism = Mustela putorius
SEQUENCE: 80
MAQVLRGTVA AFPGFDERAD AETLRKAMKG LGTDEDSILT LLTSRSNAQR QEIAVAFKTL   60
FGRDLLDDLK SELTGKFEKL IVALMKPSRL YDAYELKHAL KGAGTDEKVL TEIIASRTPE   120
ELRAIKQVYE EEYGSSLEDD VVGDTSGYYQ RMLVVLLQAN RDPDAGIDEA QVEQDAQALF   180
QAGELKWGTD EEKFITIFGT RSVSHLRRVF DKYMTISGFQ IEETIDRETS GNLEQLLLAV   240
VKSIRSIPAY LAETLYYAMK GAGTDDHTLI RVVVSRSEID LYNIRKEFRK NFSTSLYSMI   300
KGDTSGDYKK ALLRLCGGED D                                            321

SEQ ID NO: 81           moltype = AA   length = 320
FEATURE                 Location/Qualifiers
source                  1..320
                        mol_type = protein
                        organism = Felis catus
SEQUENCE: 81
MAQVKGTVTP FPGFDERADA ETLRKAMKGL GTDEESILTL LTSRSNAQRQ EIATAFKTLF   60
GRDLLDDLKS ELTGKFEKLI VALMKPSRLY DAYELKHALK GAGTNEKVLT EIIASRTPEE   120
```

```
LRAIKQVYEE EYGSSLEDDV VGDTSGYYQR MLVVLLQANR DPDARIDEAQ VEQDAQALFQ    180
AGELKWGTDE EKFITIFGTR SVSHLRRVFD KYMTISGFQI EETIDRETSG NLEQLLLAVV    240
KSIRSIPAYL AETLYYAMKG AGTDDHTLIR VVVSRSEIDL FNIRKEFRKN FATSLYSMIK    300
GDTSGDYKKA LLLLCGGEDD                                                320

SEQ ID NO: 82           moltype = AA  length = 321
FEATURE                 Location/Qualifiers
source                  1..321
                        mol_type = protein
                        organism = Equus przewalskii
SEQUENCE: 82
MAQVLKGTVT DFPGFDERAD AEVLRKAMKG LGTDEESILT LLTSRSNAQR QEIAVAFKTL    60
FGRDLLDDLK SELTGKFEKL IVALMKPSRL YDAYELKHAL KGAGTNEKVL TEIIASRTPA    120
ELRAIKQVYE EEYGSNLEDD VVADTSGFYY RMLVVLLQAN RDPDAGIDEA QVEQDAQTLF    180
QAGELKWGTD EEKFITIFGT RSVSHLRRVF DKYMTISGFQ IEETIDRETS GNLEQLLLAV    240
VKSIRSIPAY LAETLYYAMK GAGTDDHTLI RVVVSRSEID LFNIRKEFRK NFATSLYSMI    300
KSDTSGDYKK ALLLLCGGED D                                              321

SEQ ID NO: 83           moltype = AA  length = 321
FEATURE                 Location/Qualifiers
source                  1..321
                        mol_type = protein
                        note = Bos indicus x Bos taurus
                        organism = unidentified
SEQUENCE: 83
MAQVLRGTVA DFPGFDERAD AETLRKAMKG LGTDEETILT LLTSRSNAQR QEIAVAFKTL    60
FGRDLLDDLK SELTGKFEKL IVALMKPSRL YDAYELKHAL KGAGTDEKVL TEIIASRTPE    120
ELRAIEQVYE EEYGSSLEDD VVGDTSGYYQ RMLVVLLQAN RDPDARIDEA QVEQDAQALF    180
QAGELKWGTD EEKFITIFGT RSVSHLRRVF DKYMTISGFQ IEETIDRETS GNLEQLLLAV    240
VKSIRSIPAY LAETLYYAMK GAGTDDHTLI RVVVSRSEID LYNIRKEFRK NFGTSLYSMI    300
KGDTSGDYKK ALLLLCGGED D                                              321

SEQ ID NO: 84           moltype = AA  length = 453
FEATURE                 Location/Qualifiers
source                  1..453
                        mol_type = protein
                        organism = Ictidomys tridecemlineatus
SEQUENCE: 84
MAPEPAVQKT ELWEGGGGRE LASGSGAWDS SQAPACGGSA SDFSDLSSVT LIHRTGSGAC    60
WEVEKPPTES PQMDTSQRAL LLLLLLISWH DFQIDVTVQG FNSVESSMEC TGSQQRLLLL    120
CWSQDVDDST VLLSQALRGT VTAFPGFDDR ADAETLRKAM KGLGTDEESI LTLLTSRSNA    180
QRQQIAEAFK TLFGRDLLDD LKSELTGKFE KLIVALMKPS RLYDAYELKH ALKGAGTNEK    240
VLTEIIASRT PEELRAIKQV YEEEYGSSLE DDVVADTSGY YQRMLVVLLQ ANRDPDAGID    300
EAQVEQDAQA LFQAGELKWG TDEEKFITIF GTRSVSHLRR VFDKYMTISG FQIEETIDRE    360
TSGHLEQLLL AVVKSIRSIP AYLAETLYYA MKGAGTDDHT LIRVVVSRSE IDLFNIRKEF    420
RKNFATSLYS MIKGDTSGDY KKALLLLCGG EDD                                 453

SEQ ID NO: 85           moltype = AA  length = 321
FEATURE                 Location/Qualifiers
source                  1..321
                        mol_type = protein
                        organism = Dipodomys spectabilis
SEQUENCE: 85
MAQVLRGTVS DFPGFDDRAD AETLRKAMKG LGTDEESILT LLTSRSNAQR QEIAEAFKTL    60
FGRDLLDDLK SELTGKFEKL IVALMKPARL YDAYELKHAL KGAGTDEKVL TEIIASRTPE    120
QLRVIKQVYE EEYGSSLEDD VVGDTSGYYQ RMLVVLLQAN RDPDTAIDEA QVEQDAQALF    180
QAGELKWGTD EEKFITIFGT RSVSHLRRVF DKYMTISGFQ IEETIDRETS GNLEQLLLAV    240
VKSIRSIPAY LAETLYYAMK GAGTDDHTLI RVVVSRSEID LFNIRKEFRK NFATSLYSMI    300
KGDTSGDYKK ALLLLCGGED D                                              321

SEQ ID NO: 86           moltype = AA  length = 321
FEATURE                 Location/Qualifiers
source                  1..321
                        mol_type = protein
                        organism = Elephas maximus
SEQUENCE: 86
MAQVLRGTVT DFPGFDERAD AETLRKAMKG LGTDEETILT LLTSRSNAQR QEIIAAFKTL    60
FGRDLLDDLK SELTGKFEKL IVALMKPSQL YDAYELKHAL KGAGTNEKVL TEIIASRTPE    120
ELRAVKQVYE EEYGSSLEDD VVGDTSGYYQ RMLVVLLQAN RDPDARIDEA QVELDAQALF    180
QAGELKWGTD EEKFITIFGT RSVSHLRRVF DKYMTISGFQ IEETIDRETC GNLEQLLLAV    240
VKSIRSIPAY LAETLYYAMK GAGTDDHTLI RVVVSRSEID LFNIRKEFRK NFATSLYSMI    300
KSDTSGDYKK ALLLLCGGED D                                              321

SEQ ID NO: 87           moltype = AA  length = 321
FEATURE                 Location/Qualifiers
source                  1..321
                        mol_type = protein
                        organism = Gulo gulo
SEQUENCE: 87
```

```
MAQVLRGTVA APFGFDERAD AETLRKAMKG LGTDEDSILT LLTSRSNAQR QEIAVAFKTL    60
FGRDLLDDLK SELTGKFEKL IVALMKPSRL YDAYELKHAL KGAGTDEKVL TEIIASRTPE   120
ELRAIKQVYE EEYGSSLEDD VVGDTSGYYQ RMLVVLLQAN RDPDAGIDEA QVEQDAQALF   180
QAGELKWGTD EEKFITIFGT RSVSHLRRVF DKYMTISGFQ IEETIDRETS GNLEQLLLAV   240
VKSIRSVPAY LAETLYYAMK GAGTDDHTLI RVVVSRSEID LYNIRKEFRK NFSTSLYSMI   300
KGDTSGDYKK ALLRLCGGED D                                            321

SEQ ID NO: 88           moltype = AA  length = 321
FEATURE                 Location/Qualifiers
source                  1..321
                        mol_type = protein
                        organism = Zalophus californianus
SEQUENCE: 88
MAQALKGTVV APFGFDERAD AEALRKAMKG LGTDEESILT LLTSRSNAQR QEIAVAFKTL    60
FGRDLLDDLK SELTGKFEKL IMALMKPSRL YDAYELKHAL KGAGTDEKVL TEIIASRTPE   120
ELRAIKQVYE EEYGSSLEDD VVGDTSGYYQ RMLVVLLQAN RDPDAGIDEA QVEQDAQALF   180
QAGELKWGTD EEKFITIFGT RSVSHLRRVF DKYMTISGFQ IEETIDRETS GNLEQLLLAV   240
VKSIRSIPAY LAETLYYAMK GAGTDDHTLI RIVVSRSEID LFNIRKEFRK NFATSLYSMI   300
KGDTSGDYKK ALLLLCGGEN D                                            321

SEQ ID NO: 89           moltype = AA  length = 321
FEATURE                 Location/Qualifiers
source                  1..321
                        mol_type = protein
                        organism = Phoca vitulina
SEQUENCE: 89
MAQVLKGTVV APFGFDERAD AETLRKAMKG LGTDEESILT LLTSRSNAQR QEIAVAFKTL    60
FGRDLLDDLK SELTGKFEKL IVALMKPSRL YDAYELKHAL KGAGTDEKVL TEIIASRTPE   120
ELRAIKQVYE EEYGSSLEDD VVGDTSGFYQ RMLVVLLQAN RDPDAGIDEA QVEQDAQALF   180
QAGELKWGTD EEKFITIFGT RSVSHLRRVF DKYMTISGFQ IEETIDRETS GNLEQLLLAV   240
VKSIRSIPSY LAETLYYAMK GAGTDDHTLI RVVVSRSEID LFNIRKEFRK NFATSLYSMI   300
KDDTSGDYKK ALLLLCGGEN D                                            321

SEQ ID NO: 90           moltype = AA  length = 353
FEATURE                 Location/Qualifiers
source                  1..353
                        mol_type = protein
                        organism = Cervus elaphus
SEQUENCE: 90
MCEREPSRKP RVAGVRTKAS EANAFLFSFD LILFSVLRGT VTDFPGFDER ADAETLRKAM    60
KGLGTDEESI LTLLTSRSNA QRQEIAVAFK TLFGRDLLDD LKSELTGKFE KLIVALMKPS   120
RLYDAYELKH ALKGAGTNEK VLTEIIASRT PEELRAIKKV YEEEYGSSLE DDVVGDTSGY   180
YQRMLVVLLQ ANRDPDTRID EAQVEQDAQA LFQAGELKWG TDEEKFITIF GTRSVSHLRR   240
VFDKYMTISG FQIEETIDRE TSGNLEQLLL AVVKSIRSIP AYLAETLYYA MKGAGTDDHT   300
LIRVVVSRSE IDLYNIRKEF RKNFATSLYS MIKGDTSGDY KKALLLLCGG EDD          353

SEQ ID NO: 91           moltype = AA  length = 321
FEATURE                 Location/Qualifiers
source                  1..321
                        mol_type = protein
                        organism = Bos mutus
SEQUENCE: 91
MAQVLRGTVA DFPGFDERAD AETLRKAMKG LGTDEESILT LLTSHSNAQR QEIAVAFKTL    60
FGRDLLDDLK SELTGKFEKL IVALMKPSRL YDAYELKHAL KGAGTDEKVL TEIIASRTPE   120
ELRAIKQVYE EEYGSSLEDD VVGDTSGYYQ RMLVVLLQAN RDPDARIDEA QVEQDAQALF   180
QAGELKWGTD EEKFITIFGT RSVSHLRRVF DKYMTISGFQ IEETIDRETS GNLEQLLLAV   240
VKSIRSIPAY LAETLYYAMK GAGTDDHTLI RVVVSRSEID LYNIRKEFRN NFGTSLYSMI   300
KGDTSGDYKK ALLLLCGGED D                                            321

SEQ ID NO: 92           moltype = AA  length = 321
FEATURE                 Location/Qualifiers
source                  1..321
                        mol_type = protein
                        organism = Loxodonta africana
SEQUENCE: 92
MAQVLRGTVT DFPGFDERAD AETLRKAMKG LGTDEETILT LLTSRSNAQR QEIIAFKTL     60
YGRDLLDDLK SELTGKFEKL IVALMKPSQL YDAYELKHAL KGAGTNEKVL TEIIASRTPE   120
ELRAVKQVYE EEYGSSLEDD VVGDTSGYYQ RMLVVLLQAN RDPDARIDEA QVELDAQALF   180
QAGELKWGTD EEKFITIFGT RSVSHLRRVF DKYMTISGFQ IEETIDRETC GNLEQLLLAV   240
VKSIRSIPAY LAETLYYAMK GAGTDDHTLI RVVVSRSEID LFNIRKEFRK NFATSLYSMI   300
KSDTSGDYKK ALLLLCGGED D                                            321

SEQ ID NO: 93           moltype = AA  length = 321
FEATURE                 Location/Qualifiers
source                  1..321
                        mol_type = protein
                        organism = Propithecus coquereli
SEQUENCE: 93
MEQLRKGTVS DFPGFDERAD AETLRKAMKG LGTDEESILT LLTSRSNAQR QEIAAAFKTL    60
```

```
FGRDLLDDLK SELTGKFEKL IVALMKPSRL YDAYELKHAL KGAGTNEKVL TEIIASRTPE   120
ELRAIKEVYE EEYGSSLEDA VVGDTSGYYQ RMLVVLLQAN RDPDAGIDEA QVEQDAQALF   180
QAGELKWGTD EEKFITIFGT RSVSHLRRVF DKYMTISGFQ IEETIDRETS GNLEQLLLAV   240
VKSIRSIPAY LAETLYYAMK GAGTDDHTLI RVMVSRSEVD LFNIRKEFRK NFATSLYSMI   300
KSDTSGDYKK ALLRLCGGED D                                            321

SEQ ID NO: 94           moltype = AA  length = 321
FEATURE                 Location/Qualifiers
source                  1..321
                        mol_type = protein
                        organism = Ovis aries
SEQUENCE: 94
MAQVLRGTVT DFPGFNERAD AETLRKAMKG LGTDEESILT LLTSRSNAQR QEIAVAFKTL    60
FGRDLLDDLK SELTGKCEKL IVALMKPSRL YDAYELKHAL KGAGTDEKVL TEIIASRTPE   120
ELRAIKQVYE EEYGSSLEDD VVGDTSGYYQ RMLVVLLQAN RDPDARIDEA QVEQDAQALF   180
QAGELKWGTD EEKFITIFGT RSVSHLRRVF DKYMTISGFQ IEETIDRETS GNLEQLLLAV   240
VKSIRSIPAY LAETLYYAMK GAGTDDHTLI RVVVSRSEID LYNIRKEFRK NFGTSLYSMI   300
KGDTSGDYKK TLLLLCGGED D                                            321

SEQ ID NO: 95           moltype = AA  length = 321
FEATURE                 Location/Qualifiers
source                  1..321
                        mol_type = protein
                        organism = Sorex araneus
SEQUENCE: 95
MAQGLRGTVT DFPGFDERAD AETLRKAMKG LGTDEESILT LLTSRSNAQR QEIAVAFKTL    60
FGRDLLDDLK SELTGKFEKL IVALMKPSQL YDAYELKHAL KGAGTDEKVL TEIIASRTPA   120
ELTAIKQVYE EEYGSSLEDD VVGDTSGYYQ RMLVVLLQAN RDPDAGIDEA LVEQDAQALF   180
QAGELKWGTD EEKFITIFGT RSVSHLRRVF DKYMTISGFQ IEETIDRETS GNLEQLLLAV   240
VKSIRSIPAY LAETLLYYAMK GAGTDDHTLI RVVVSRSEID LFNIRKEFRK NFATSLYSMI  300
KGDTSGDYKK ALLLLCGGED D                                            321

SEQ ID NO: 96           moltype = AA  length = 341
FEATURE                 Location/Qualifiers
source                  1..341
                        mol_type = protein
                        organism = Capra hircus
SEQUENCE: 96
MFPSQVLRGT VTDFPGFDER ADAETLRKAM KGLGTDEESI LTLLTSRSNA QRQEIAVAFK    60
TLFGRDLLDD LKSELTGKFE KLIVALMKPS RLYDAYELKH ALKGAGTDEK VLTEIIASRT   120
PEELRAIKQV YEEEYGSSLE DDVVGDTSGY YQRMLVVLLQ ANRDPDTRID EAQVEQDAQA   180
LFQAGELKWG TDEEKFITIF GTRSVSHLRR VFDKYMTISG FQIEETIDRE TSGNLEQLLL   240
AVVKSIRSIP AYLAETLYYA MKGAGTDDHT LIRVVVSRSE IDLYNIRKEF RKNFGTSLYS   300
MIKGDTSGDY KKTLLLLCGG EDDSCEPAET PHTIEITEKL M                      341

SEQ ID NO: 97           moltype = AA  length = 333
FEATURE                 Location/Qualifiers
source                  1..333
                        mol_type = protein
                        organism = Vulpes lagopus
SEQUENCE: 97
MLFYPSAARE RNGLVVLKGT VTPFPGFDER ADAEVLRKAM KGLGTDEESI LTLLTSRSNA    60
QRQEIAAAFK TLFGRDLLDD LKSELTGKFE KLIVALMKPS RLYDAYELKH ALKGAGTNEK   120
VLTEIIASRT PEELRAIKQV YEEEYGSSLE DDVVGDTSGY YQRMLVVLLQ ANRDPDAGID   180
EAQVEQDAQA LFQAGELKWG TDEEKFITIF GTRSVSHLRR VFDKYMTISG FQIEETIDRE   240
TSGNLEQLLL AVVKSIRSIP AYLAETLYYA MKGTGTDDHT LIRVVVSRSE IDLFNIRKEF   300
RKNFATSLYS MIKDDTSGDY KKALLLLCGG EDD                               333

SEQ ID NO: 98           moltype = AA  length = 321
FEATURE                 Location/Qualifiers
source                  1..321
                        mol_type = protein
                        organism = Jaculus jaculus
SEQUENCE: 98
MAQALRGTVT DFPGFDDRVD AETLRKAMKG LGTDEESILT LLTSRSNVQR QQIAEAFKTL    60
FGRDLLDDLK SELTGKFEKL IVALMKPSRL YDAYELKHAL KGAGTDEKVL TEIIASRTPE   120
ELRAIKEVYE EEYGSSLEDD VVGDTSGYYQ RMLVVLLQAN RDPDAAIDEA QVELDAQALF   180
QAGELKWGTD EEKFITIFGT RSVSHLRRVF DKYMTISGFQ IEETIDRETS GNLEQLLLAV   240
VKSIRSIPAY LAETLYYAMK GAGTDDHTLI RVMVSRSEID LFNIRKEFRK NFATSLYSMI   300
KGDTSGDYKK ALLLLCGGED D                                            321

SEQ ID NO: 99           moltype = AA  length = 321
FEATURE                 Location/Qualifiers
source                  1..321
                        mol_type = protein
                        organism = Halichoerus grypus
SEQUENCE: 99
MAQVLKGTVV AFPGFDERAD AETLRKAMKG LGTDEESILT LLTSRSNAQR QEIAVAFKTL    60
FGRDLLDDLK SELTGKFXKL IVALMKPSRL YDAYELKHAL KGAGTDEKVL TEIIASRTPE   120
```

```
ELRAIKQVYE EEYGSSLEDD VVGDTSGFYQ RMLVVLLQAN RDPDAGIDEA QVEQDAQALF    180
QAGELKWGTD EEKFITIFGT RSVSHLRRVF DKYMTISGFQ IEETIDRETS GNLEQLLLAV    240
VKSIRSIPAY LAETLYYAMK GAGTDDHTLI RVVVSRSEID LFNIRKEFRK NFATSLYSMI    300
KDDTSGDYKK ALLLLCGGEN D                                             321

SEQ ID NO: 100          moltype = AA  length = 320
FEATURE                 Location/Qualifiers
source                  1..320
                        mol_type = protein
                        organism = Bos taurus
SEQUENCE: 100
AQVLRGTVAD FPGFDERADA ETLRKAMKGL GTDEETILTL LTSRSNAQRQ EIAVAFKTLF     60
GRDLLDDLKS ELTGKFEKLI VALMKPSRLY DAYELKHALK GAGTDEKVLT EIIASRTPEE    120
LRAIEQVYEE EYGSSLEDDV VGDTSGYYQR MLVVLLQANR DPDARIDEAQ VEQDAQALFQ    180
AGELKWGTDE EKFITIFGTR SVSHLRRVFD KYMTISGFQI EETIDRETSG NLEQLLLAVV    240
KSIRSIPAYL AETLYYAMKG AGTDDHTLIR VVVSRSEIDL YNIRKEFRKN FGTSLYSMIK    300
GDTSGDYKKA LLLLCGGEDD                                                320

SEQ ID NO: 101          moltype = AA  length = 321
FEATURE                 Location/Qualifiers
source                  1..321
                        mol_type = protein
                        organism = Ursus maritimus
SEQUENCE: 101
MAQVLKGTVS AFPGFDERAD AEALRKAMKG LGTDEESILT LLTSRSNAQR QEIAVAFKTL     60
FGRDLLDDLK SELTGKFEKL IVALMKPSRI YDAYELKHAL KGAGTDEKVL TEIIASRTPE    120
ELRAIKQVYE EEYGSSLEDD VVGDTSGYYQ RMLVVLLQAN RDPDGRIDEA QVEQDAQALF    180
QAGELKWGTD EEKFITIFGT RSVSHLRRVF DKYMTISGFQ IEETIDRETS GNLEQLLLAV    240
VKSIRSIPAY LAETLYYAMK GAGTDDHTLI RVVVSRSEID LFNIRKEFRK NFATSLYSMI    300
KGDTSGDYKK ALLLLCGGED D                                              321

SEQ ID NO: 102          moltype = AA  length = 15
FEATURE                 Location/Qualifiers
source                  1..15
                        mol_type = protein
                        organism = Homo sapiens
SEQUENCE: 102
SRLYDAYELK HALKG                                                     15

SEQ ID NO: 103          moltype = AA  length = 5
FEATURE                 Location/Qualifiers
source                  1..5
                        mol_type = protein
                        organism = synthetic construct
REGION                  1..5
                        note = circular peptide
SEQUENCE: 103
RKKWF                                                                5

SEQ ID NO: 104          moltype = AA  length = 7
FEATURE                 Location/Qualifiers
source                  1..7
                        mol_type = protein
                        organism = synthetic construct
REGION                  1..7
                        note = circular peptide
SEQUENCE: 104
GRKKWFW                                                              7
```

The invention claimed is:

1. A kit comprising:
   a) a first population of hydrogel beads, each hydrogel bead comprising:
      i) a polymerized monomer;
      ii) annexin V; and
      iii) double stranded DNA;
   b) a second population of hydrogel beads, each hydrogel bead comprising:
      i) a polymerized monomer;
      ii) annexin V; but
      iii) lacking the double stranded DNA of the first population of hydrogel beads;
   c) a third population of hydrogel beads, each hydrogel population comprising:
      i) a polymerized monomer; but
      ii) lacking the annexin V of the first population of hydrogel beads and the second population of hydrogel beads; and
      iii) lacking the double stranded DNA of the first population of hydrogel beads;
   wherein the annexin V of the first and/or second population of hydrogel beads comprises SEQ ID NO: 102.

2. The kit of claim 1, wherein the hydrogel beads of the first and/or second population of hydrogel beads comprise an artificial optical-scatter property that is substantially similar to a corresponding optical-scatter property of a target biological cell.

3. The kit of claim 2, wherein the artificial optical-scatter property that is substantially similar to the corresponding optical-scatter property of the target biological cell is side scatter (SSC).

4. The kit of claim 2, wherein the artificial optical-scatter property that is substantially similar to the corresponding optical-scatter property of the target biological cell is forward scatter (FSC).

5. The kit of claim 2, wherein the target biological cell is a lymphocyte, a monocyte, or a granulocyte.

6. The kit of claim 1, wherein the double stranded DNA of the first population of hydrogel beads is bound to a dye.

7. The kit of claim 6, wherein the dye is a DNA intercalating dye.

8. The kit of claim 6, wherein the dye bound to the double stranded DNA is selected from the group consisting of 7-aminoactinomycin D (7AAD), propidium iodide, Hoechst 33258, Hoechst 33342, Hoechst 34580, 4',6-diamidino-2-phenylindole (DAPI), ethidium bromide, and crystal violet.

9. The kit of claim 6, wherein the dye bound to the double stranded DNA is 7-aminoactinomycin D (7AAD) or propidium iodide.

10. The kit of claim 1, wherein the annexin V of the first and/or second population of hydrogel beads is bound to a dye.

11. The kit of claim 10, wherein the dye is selected from the group consisting of 6-carboxy-4',5'-dichloro-2',7'-dimethoxyfluorescein succinimidyl ester; 5-(6)-carboxyeosin; 5-carboxyfluorescein; 6-carboxyfluorescein; 5-(6)-carboxyfluorescein; 5-carboxyfluorescein-bis-(5-carboxymethoxy-2-nitrobenzyl) ether, 3-alanine-carboxamide, or succinimidyl ester; 5-carboxy fluorescein succinimidyl ester; 6-carboxyfluorescein succinimidyl ester; 5-(6)-carboxyfluorescein succinimidyl ester; 5-(4,6-dichlorotriazinyl) amino fluorescein; 2',7'-difluoro fluorescein; eosin-5-isothiocyanate; erythrosin5-isothiocyanate; 6-(fluorescein-5-carboxamido) hexanoic acid or succinimidyl ester; 6-(fluorescein-5-(and -6)-carboxamido) hexanoic acid or succinimidyl ester; fluorescein-S-EX succinimidyl ester; fluorescein-5-isothiocyanate; fluorescein-6-isothiocyanate; bis-(4-carboxypiperidinyl) sulfone rhodamine or di (succinimidyl ester); 5-(6) carboxynaphtho fluorescein; 5-(6) carboxynaphthofluorescein succinimidyl ester; 5-carboxyrhodamine 6G hydrochloride; 6-carboxyrhodamine 6G hydrochloride, 5-carboxyrhodamine 6G succinimidyl ester; 6-carboxyrhodamine 6G succinimidyl ester; 5-(6)-carboxyrhodamine 6G succinimidyl ester; 5-carboxy-2',4',5',7'-tetrabromosulfonefluorescein succinimidyl ester or bis-(diisopropylethylammonium) salt; 5-carboxytetramethylrhodamine; 6-carboxytetramethylrhodamine; 5-(6)-carboxytetramethylrhodamine; 5-arboxytetramethylrhodamine succinimidyl ester; 6-carboxytetramethylrhodamine succinimidyl ester; 5-(6)-carboxytetramethylrhodamine succinimidyl ester; 6-carboxy-X-rhodamine; 5-carboxy-X-rhodamine succinimidyl ester; 6-carboxy-X-rhodamine succinimidyl ester; 5-(6)-carboxy-X-rhodamine succinimidyl ester; 5-carboxy-X-rhodamine triethylammonium salt; malachite green; isothiocyanate; 6-(tetramethylrhodamine-5-(and -6)-carboxamido) hexanoic acid or succinimidyl ester; tetramethylrhodamine-5-isothiocyanate; tetramethylrhodamine-6-isothiocyanate; tetramethylrhodamine-5-(6)-isothiocyanate; X-rhodamine-5-(6) isothiocyanate; 6-dibromo-4,4-difluoro-5,7-dimethyl-4-bora-3a,4a-diaza-s-indacene-3-propionic acid or succinimidyl ester; 4,4-difluoro-4-bora-3a,4a-diaza-s-indacene-3,5-dipropionic acid; 4,4-difluoro-5,7-dimethyl-4-bora-3a,4a-diaza-s-indacene-3-pentanoic acid; 4,4-difluoro-5,7-dimethyl-4-bora-3a,4a-diaza-s-indacene-3-pentanoic acid or succinimidyl ester; 4,4-difluoro-5,7-dimethyl-4-bora-3a,4a-diaza-s-indacene-3propionic acid; 4,4-difluoro-5,7-dimethyl-4-bora-3a,4a-diaza-s-indacene-3-propionic acid or succinimidyl ester; 4,4-difluoro-5,7-dimethyl-4-bora-3a,4a-diaza-s-indacene-3propionic acid, sulfosuccinimidyl ester, or sodium salt; 6-((4,4-difluoro-5,7-dimethyl-4-bora-3a,4a-diaza-s-indacene-3propionyl) amino) hexanoicacid; 6-((4,4-difluoro-5,7-dimethyl-4-bora-3a,4a-diaza-s-indacene-3-propionyl) amino) hexanoic acid or succinimidyl ester; N-(4,4-difluoro-5,7-dimethyl-4-bora-3a,4a-diaza-s-indacene-3-propionyl) cysteic acid, succinimidyl ester, or triethylammonium salt; 6-4,4-difluoro-1,3-dimethyl-5-(4-methoxyphenyl)-4-bora-3a,4a-4,4-difluoro-5,7-diphenyl-4-bora-3a,4a-diaza-s-indacene-3-propionic acid; 4,4-difluoro-5,7-diphenyl-4-bora-3a,4a-diaza-s-indacene-3-propionic acid or succinimidyl ester; 4,4-difluoro-5-phenyl-4-bora-3a,4a-diaza-s-indacene-3-propionic acid or succinimidyl ester; 6-((4,4-difluoro-5-phenyl-4-bora-3a,4a-diaza-s-indacene-3-propionyl) amino) hexanoic acid or succinimidyl ester; 4,4-difluoro-5-(4-phenyl-1,3butadienyl)-4-bora-3a,4a-diaza-s-indacene-3-propionic acid or succinimidyl ester; 4,4-difluoro-5-(2-pyrrolyl)-4-bora-3a,4a-diaza-s-indacene-3-propionic acid or succinimidyl ester; 6-(((4,4-difluoro-5-(2-pyrrolyl)-4-bora-3a,4a-diaza-s-indacene-3-yl) styryloxy) acetyl) aminohexanoic acid or succinimidyl ester; 4,4-difluoro-5-styryl-4-bora-3a,4a-diaza-s-indacene-3-propionic acid; 4,4-difluoro-5-styryl-4-bora-3a,4a-diaza-s-indacene-3-propionic acid or succinimidyl ester; 4,4-difluoro-1,3,5,7-tetramethyl-4-bora-3a,4a-diaza-s-indacene-8-propionic acid; 4,4-difluoro-1,3,5,7-tetramethyl-4-bora-3a,4a-diaza-s-indacene-8-propionic acid or succinimidyl ester; 4,4-difluoro-5-(2-thienyl)-4-bora-3a,4a-diaza-s-indacene-3-propionic acid or succinimidyl ester; 6-(((4-(4,4-difluoro-5-(2-thienyl)-4-bora-3a,4a-diaza-s-indacene-3-yl) phenoxy) acetyl) amino) hexanoic acid or succinimidyl ester; 6-(((4, 4-difluoro-5-(2-thienyl)-4-bora-3a,4a-diaza-s-indacene-3-yl) styryloxy) acetyl) aminohexanoic acid or succinimidyl ester; Cy3 NHS ester; Cy5 NHS ester; Cy5.5 NHS ester; and Cy7 NHS ester.

12. The kit of claim 10, wherein the dye is attached to the annexin V of the first and/or second population of hydrogel beads via a noncovalent interaction.

13. The kit of claim 1, wherein the annexin V of the first and/or second population of hydrogel beads is attached to a free amine group, a biotin, a streptavidin, an avidin, a carboxyl group, or a hydroxyl group of the hydrogel beads.

14. The kit of claim 1, wherein the annexin V of the first and/or second population of hydrogel beads is attached to the hydrogel beads via a noncovalent interaction.

15. The kit of claim 1, wherein the annexin V of the first and/or second population of hydrogel beads is attached to the hydrogel beads via a functionalized linker.

16. The kit of claim 15, wherein the functionalized linker is a phosphatidyl serine or an anti-annexin V antibody.

17. The kit of claim 1, wherein the polymerized monomer of the first, and/or second population of hydrogel beads is selected from the group consisting of agar, agarose, alginic acid, alguronic acid, alpha glucan, amylopectin, amylase, arabinoxylan, beta-glucan, callose, capsulan, carrageenan polysaccharide, cellodextrin, cellulin, cellulose, chitin, chitosan, chrysolaminarin, curdlan, cyclodextrin, alpha-cyclodextrin, dextrin, dextran, ficoll, fructan, fucoidan, galactoglucomannan, galactomannan, galactosaminogalactan, gellan gum, glucan, glucomannan, glucuronoxylan, glycocalyx, glycogen, hemicellulose, homopolysaccharide, hypromellose, icodextrin, inulin, kefiran, laminarin, lentinan, levan polysaccharide, lichenin, mannan, mixed-linkage gluxan, paramylon, pectic acid, pectin, pentastarch, phytoglycogen, pleuran, polydextrose, polysaccharide peptide, porphyran, pullulan, schizophyllan, sinistrin, sizofiran, welan gum, xanthan gum, xylan, xyloglucan, zymosan, and a combination thereof.

18. The kit of claim 1, wherein the polymerized monomer of one or more of the first, second, and third populations of hydrogel beads comprises polyacrylamide.

19. The kit of claim 1, wherein the hydrogel beads of one or more of the first, second, and third population of hydrogel beads further comprise bis-acrylamide.

20. The kit of claim 1, wherein the hydrogel beads of one or more of the first, second, and third population of hydrogel beads have a refractive index of greater than about 1.15.

21. The kit of claim 1, The kit of claim 1, wherein the hydrogel beads of one or more of the first, second, and third population of hydrogel beads have a diameter of less than about 100 µm.

22. The kit of claim 1, wherein the hydrogel beads of one or more of the first, second, and third population of hydrogel beads have a diameter of more than about 10 µm.

23. The kit of claim 1, wherein the hydrogel beads of one or more of the first, second, and third population of hydrogel beads have a diameter of more than about 1 µm.

24. The kit of claim 1, wherein the first, second, and third population of hydrogel beads are present at a w/w ratio of about 1:1:1.

25. The kit of claim 1, wherein the first, second, and third population of hydrogel beads are present at a ratio of about 1:1:1 by number of beads.

* * * * *